(12) United States Patent
Ellis et al.

(10) Patent No.: US 8,968,156 B2
(45) Date of Patent: Mar. 3, 2015

(54) METHODS FOR DETERMINING WORKOUT PLANS AND SESSIONS

(71) Applicant: adidas AG, Herzogenaurach (DE)

(72) Inventors: Michael D. Ellis, Boulder, CO (US); Caron Schwartz, Boulder, CO (US)

(73) Assignee: adidas AG, Herzogenaurach (DE)

( * ) Notice: Subject to any disclaimer, the term of this patent is extended or adjusted under 35 U.S.C. 154(b) by 239 days.

(21) Appl. No.: 13/791,190

(22) Filed: Mar. 8, 2013

(65) Prior Publication Data

US 2014/0107817 A1    Apr. 17, 2014

Related U.S. Application Data

(60) Continuation of application No. 13/789,266, filed on Mar. 7, 2013, now Pat. No. 8,652,009, which is a continuation of application No. 12/617,871, filed on Nov. 13, 2009, which is a division of application No. 10/645,713, filed on Aug. 20, 2003, now Pat. No. 7,670,263, which is a continuation of application No. PCT/US02/04947, filed on Feb. 20, 2002.

(60) Provisional application No. 60/270,400, filed on Feb. 20, 2001.

(51) Int. Cl.
*A63B 24/00* (2006.01)

(52) U.S. Cl.
USPC ......... 482/8; 482/1; 482/9; 482/901; 434/247

(58) Field of Classification Search
USPC .......................... 482/1–9, 900–902; 434/247
See application file for complete search history.

(56) References Cited

U.S. PATENT DOCUMENTS

| 2,223,544 | A | 3/1941 | McKinley |
| 3,699,672 | A | 10/1972 | Sims |
| 3,702,999 | A | 11/1972 | Gradisar |

(Continued)

FOREIGN PATENT DOCUMENTS

| DE | 197 12 672 A1 | 7/1998 |
| EP | 1 018 832 A2 | 7/2000 |

(Continued)

OTHER PUBLICATIONS

Barber Jr., Thomas J., "BodyLAN: A Low-Power Communications System," Thesis submitted to the Massachusetts Institute of Technology Department of Electrical Engineering and Computer Science, pp. 1-75 (Feb. 1996).

(Continued)

*Primary Examiner* — Glenn Richman
(74) *Attorney, Agent, or Firm* — Sterne, Kessler, Goldstein & Fox P.L.L.C.

(57) ABSTRACT

We have disclosed methods of determining workout plans and sessions for an individual. The methods may include receiving input from the individual, determining a first type of workout based on the input, determining a plurality of workout sessions for the first type of workout for a workout plan, determining a second type of workout that is different than the first type of workout based on input from the individual, determining a plurality of workout sessions for the second type of workout for the workout plan, and storing data describing the workout plan, including data describing the workout sessions for the for the first and second types of workouts, in a memory accessible by a server computer system.

35 Claims, 111 Drawing Sheets

(56) References Cited

U.S. PATENT DOCUMENTS

| | | |
|---|---|---|
| 3,840,726 A | 10/1974 | Harrison |
| 3,972,038 A | 7/1976 | Fletcher et al. |
| 3,974,491 A | 8/1976 | Sipe |
| 4,019,030 A | 4/1977 | Tamiz |
| 4,120,052 A | 10/1978 | Butler |
| 4,175,446 A | 11/1979 | Crowninshield et al. |
| 4,247,908 A | 1/1981 | Lockhart, Jr. et al. |
| 4,371,945 A | 2/1983 | Karr et al. |
| 4,402,147 A | 9/1983 | Wu |
| 4,408,183 A | 10/1983 | Willis |
| 4,409,992 A | 10/1983 | Sidorenko et al. |
| 4,485,529 A | 12/1984 | Blum |
| 4,499,394 A | 2/1985 | Koal |
| 4,510,704 A | 4/1985 | Johnson |
| 4,578,769 A | 3/1986 | Frederick |
| 4,637,536 A | 1/1987 | Wong |
| 4,649,552 A | 3/1987 | Yukawa |
| 4,651,446 A | 3/1987 | Yukawa et al. |
| 4,652,141 A | 3/1987 | Arai |
| 4,675,960 A | 6/1987 | Higgins, Jr. |
| 4,745,564 A | 5/1988 | Tennes et al. |
| 4,757,714 A | 7/1988 | Purdy et al. |
| 4,761,835 A | 8/1988 | Chen |
| 4,763,287 A | 8/1988 | Gerhaeuser et al. |
| 4,771,394 A | 9/1988 | Cavanagh |
| 4,774,679 A | 9/1988 | Carlin |
| 4,803,487 A | 2/1989 | Willard et al. |
| 4,814,661 A | 3/1989 | Ratzlaff et al. |
| 4,817,306 A | 4/1989 | Bayer |
| 4,823,426 A | 4/1989 | Bragga |
| 4,829,540 A | 5/1989 | Waggener, Sr. et al. |
| 4,830,021 A | 5/1989 | Thornton |
| 4,855,942 A | 8/1989 | Bianco |
| 4,867,442 A | 9/1989 | Matthews |
| 4,897,947 A | 2/1990 | Kass-Pious |
| 4,932,914 A | 6/1990 | Aranda |
| 4,956,628 A | 9/1990 | Furlong |
| 4,962,469 A | 10/1990 | Ono et al. |
| 5,029,183 A | 7/1991 | Tymes |
| 5,033,013 A | 7/1991 | Kato et al. |
| 5,059,126 A | 10/1991 | Kimball |
| 5,063,690 A | 11/1991 | Slenker |
| 5,063,782 A | 11/1991 | Kellett |
| 5,148,002 A | 9/1992 | Kuo et al. |
| 5,186,062 A | 2/1993 | Roost |
| 5,241,542 A | 8/1993 | Natarajan et al. |
| 5,243,659 A | 9/1993 | Stafford et al. |
| 5,269,081 A | 12/1993 | Gray |
| 5,285,586 A | 2/1994 | Goldston et al. |
| 5,291,301 A | 3/1994 | Lee |
| 5,311,679 A | 5/1994 | Birch, Sr. |
| 5,313,719 A | 5/1994 | Koethe |
| 5,323,650 A | 6/1994 | Fullen et al. |
| 5,335,188 A | 8/1994 | Brisson |
| 5,343,445 A | 8/1994 | Cherdak |
| 5,357,696 A | 10/1994 | Gray et al. |
| 5,361,778 A | 11/1994 | Seitz |
| 5,391,080 A | 2/1995 | Bernacki et al. |
| 5,404,577 A | 4/1995 | Zuckennan et al. |
| 5,416,779 A | 5/1995 | Barnes et al. |
| 5,422,628 A | 6/1995 | Rodgers |
| 5,437,289 A | 8/1995 | Liverance et al. |
| 5,452,269 A | 9/1995 | Cherdak |
| 5,471,405 A | 11/1995 | Marsh |
| 5,474,083 A | 12/1995 | Church et al. |
| 5,479,441 A | 12/1995 | Tymes et al. |
| 5,485,163 A | 1/1996 | Singer et al. |
| 5,485,402 A | 1/1996 | Smith et al. |
| 5,502,903 A | 4/1996 | Barker |
| 5,516,334 A | 5/1996 | Easton |
| 5,517,073 A | 5/1996 | Ohkuma |
| 5,524,637 A | 6/1996 | Erickson |
| 5,526,290 A | 6/1996 | Kanzaki |
| 5,539,706 A | 7/1996 | Takenaka et al. |
| 5,541,860 A | 7/1996 | Takei et al. |
| 5,541,976 A | 7/1996 | Ghisler |
| 5,566,477 A | 10/1996 | Mathis et al. |
| 5,581,492 A | 12/1996 | Janik |
| 5,583,776 A | 12/1996 | Levi et al. |
| 5,596,821 A | 1/1997 | Solo |
| 5,606,728 A | 2/1997 | Keba et al. |
| 5,608,412 A | 3/1997 | Welles et al. |
| 5,610,387 A | 3/1997 | Bard et al. |
| 5,623,944 A | 4/1997 | Nashner |
| 5,625,882 A | 4/1997 | Vook et al. |
| 5,631,421 A | 5/1997 | Ohgke et al. |
| 5,636,146 A | 6/1997 | Flentov et al. |
| 5,655,028 A | 8/1997 | Soll et al. |
| 5,664,346 A | 9/1997 | Barker |
| 5,668,694 A | 9/1997 | Sato et al. |
| 5,668,880 A | 9/1997 | Alajajian |
| 5,673,501 A | 10/1997 | Mathews |
| 5,684,918 A | 11/1997 | Abecassis |
| 5,719,743 A | 2/1998 | Jenkins et al. |
| 5,720,200 A | 2/1998 | Anderson et al. |
| 5,721,539 A | 2/1998 | Goetzl |
| 5,721,783 A | 2/1998 | Anderson |
| 5,724,265 A | 3/1998 | Hutchings |
| 5,728,032 A | 3/1998 | Glass |
| 5,729,590 A | 3/1998 | Dimitriadis et al. |
| 5,743,269 A | 4/1998 | Okigami et al. |
| 5,775,011 A | 7/1998 | Reitano, Jr. |
| 5,781,913 A | 7/1998 | Felsenstein et al. |
| 5,794,164 A | 8/1998 | Beckert et al. |
| 5,810,736 A | 9/1998 | Pail |
| 5,813,009 A | 9/1998 | Johnson et al. |
| 5,825,327 A | 10/1998 | Krasner |
| 5,832,296 A | 11/1998 | Wang et al. |
| 5,838,226 A | 11/1998 | Houggy et al. |
| 5,844,824 A | 12/1998 | Newman et al. |
| 5,884,198 A | 3/1999 | Kese et al. |
| 5,890,074 A | 3/1999 | Rydbeck et al. |
| 5,891,042 A | 4/1999 | Sham et al. |
| 5,897,457 A | 4/1999 | Mackovjak |
| 5,898,831 A | 4/1999 | Hall et al. |
| 5,899,963 A | 5/1999 | Hutchings |
| 5,906,004 A | 5/1999 | Lebby et al. |
| 5,908,464 A | 6/1999 | Kishigarni et al. |
| 5,909,183 A | 6/1999 | Borgstahl et al. |
| 5,910,799 A | 6/1999 | Carpenter et al. |
| 5,913,163 A | 6/1999 | Johansson |
| 5,919,239 A | 7/1999 | Fraker et al. |
| 5,921,890 A | 7/1999 | Miley |
| 5,925,001 A | 7/1999 | Hoyt et al. |
| 5,930,920 A | 8/1999 | Arnold |
| 5,948,040 A | 9/1999 | DeLorme et al. |
| 5,955,667 A | 9/1999 | Fyfe |
| 5,963,891 A | 10/1999 | Walker et al. |
| 5,976,083 A | 11/1999 | Richardson et al. |
| 5,987,018 A | 11/1999 | Freeburg et al. |
| 5,989,200 A | 11/1999 | Yoshimura et al. |
| 6,000,000 A | 12/1999 | Hawkins et al. |
| 6,002,918 A | 12/1999 | Heiman et al. |
| 6,002,982 A | 12/1999 | Fry |
| 6,013,007 A | 1/2000 | Root et al. |
| 6,018,705 A | 1/2000 | Gaudet et al. |
| 6,028,853 A | 2/2000 | Haartsen |
| 6,032,108 A | 2/2000 | Seiple et al. |
| 6,038,542 A | 3/2000 | Ruckdashel |
| 6,038,935 A | 3/2000 | Fullen et al. |
| 6,041,023 A | 3/2000 | Lakhansingh |
| 6,041,114 A | 3/2000 | Chestnut |
| 6,042,549 A | 3/2000 | Amano et al. |
| 6,047,301 A | 4/2000 | Bjorklund et al. |
| 6,050,924 A | 4/2000 | Shea |
| 6,052,654 A | 4/2000 | Gaudet et al. |
| 6,078,825 A | 6/2000 | Hahn et al. |
| 6,080,690 A | 6/2000 | Lebby et al. |
| 6,094,844 A | 8/2000 | Potts |
| 6,108,197 A | 8/2000 | Janik |
| 6,122,340 A | 9/2000 | Darley et al. |
| 6,128,290 A | 10/2000 | Carvey |
| 6,135,951 A | 10/2000 | Richardson et al. |
| 6,140,981 A | 10/2000 | Kuenster et al. |

(56) References Cited

U.S. PATENT DOCUMENTS

| | | | |
|---|---|---|---|
| 6,145,551 A | 11/2000 | Jayaraman et al. |
| 6,154,642 A | 11/2000 | Dumont et al. |
| 6,157,533 A | 12/2000 | Sallam et al. |
| 6,157,824 A | 12/2000 | Bailey |
| 6,157,935 A | 12/2000 | Tran et al. |
| 6,164,541 A | 12/2000 | Dougherty et al. |
| 6,169,905 B1 | 1/2001 | Fukuda |
| 6,175,608 B1 | 1/2001 | Pyles et al. |
| 6,198,431 B1 | 3/2001 | Gibson |
| 6,210,771 B1 | 4/2001 | Post et al. |
| 6,212,469 B1 | 4/2001 | Knepper |
| 6,229,454 B1 | 5/2001 | Heikkilä et al. |
| 6,236,674 B1 | 5/2001 | Morelli et al. |
| 6,243,573 B1 | 6/2001 | Jacklin |
| 6,246,362 B1 | 6/2001 | Tsubata et al. |
| 6,249,427 B1 | 6/2001 | Carroll |
| 6,272,359 B1 | 8/2001 | Kivela et al. |
| 6,282,362 B1 | 8/2001 | Murphy et al. |
| 6,301,964 B1 | 10/2001 | Fyfe et al. |
| 6,304,459 B1 | 10/2001 | Toyosato et al. |
| 6,305,221 B1 | 10/2001 | Hutchings |
| 6,314,091 B1 | 11/2001 | LaRowe, Jr. et al. |
| 6,315,009 B1 | 11/2001 | Jayaraman et al. |
| 6,321,158 B1 | 11/2001 | DeLorme et al. |
| 6,324,053 B1 | 11/2001 | Kamijo |
| 6,331,972 B1 | 12/2001 | Harris et al. |
| 6,336,126 B1 | 1/2002 | Bjorklund et al. |
| 6,347,290 B1 | 2/2002 | Bartlett |
| 6,351,629 B1 | 2/2002 | Altschul et al. |
| 6,356,856 B1 | 3/2002 | Damen et al. |
| 6,357,147 B1 | 3/2002 | Darley et al. |
| 6,385,434 B1 | 5/2002 | Chuprun et al. |
| 6,388,613 B1 | 5/2002 | Nagatsuma et al. |
| 6,401,085 B1 | 6/2002 | Gershman et al. |
| 6,427,063 B1 | 7/2002 | Cook et al. |
| 6,447,424 B1 | 9/2002 | Ashby et al. |
| 6,449,583 B1 | 9/2002 | Sakumoto et al. |
| 6,450,922 B1 | 9/2002 | Henderson et al. |
| 6,477,117 B1 | 11/2002 | Narayanaswami et al. |
| 6,513,532 B2 | 2/2003 | Mault et al. |
| 6,519,207 B1 | 2/2003 | Lukacsko |
| 6,536,139 B2 | 3/2003 | Darley et al. |
| 6,560,651 B2 | 5/2003 | Katz et al. |
| 6,594,370 B1 | 7/2003 | Anderson |
| 6,601,016 B1 | 7/2003 | Brown et al. |
| 6,605,038 B1 | 8/2003 | Teller et al. |
| 6,611,789 B1 | 8/2003 | Darley |
| 6,650,629 B1 | 11/2003 | Takahashi et al. |
| 6,669,600 B2 | 12/2003 | Warner |
| 6,678,535 B1 | 1/2004 | Narayanaswami |
| 6,685,634 B1 | 2/2004 | Fry |
| 6,736,759 B1 | 5/2004 | Stubbs et al. |
| 6,741,864 B2 | 5/2004 | Wilcock et al. |
| 6,771,213 B2 | 8/2004 | Durst et al. |
| 6,790,178 B1 | 9/2004 | Mault et al. |
| 6,872,077 B2 | 3/2005 | Yeager |
| 6,876,845 B1 | 4/2005 | Tabata et al. |
| 6,934,461 B1 | 8/2005 | Strub et al. |
| 6,947,571 B1 | 9/2005 | Rhoads et al. |
| 7,162,392 B2 | 1/2007 | Vock et al. |
| 7,203,721 B1 | 4/2007 | Ben-Efraim et al. |
| 7,220,220 B2 | 5/2007 | Stubbs et al. |
| 7,229,385 B2 | 6/2007 | Freeman et al. |
| 7,261,564 B2 | 8/2007 | Sutula, Jr. |
| 7,428,471 B2 | 9/2008 | Darley et al. |
| 7,428,472 B2 | 9/2008 | Darley et al. |
| 7,549,947 B2 | 6/2009 | Hickman et al. |
| 8,678,979 B2 * | 3/2014 | Stark et al. ............ 482/8 |
| 2001/0003542 A1 | 6/2001 | Kita |
| 2001/0027375 A1 | 10/2001 | Machida et al. |
| 2001/0049470 A1 | 12/2001 | Mault et al. |
| 2002/0000470 A1 | 1/2002 | Lanzaro et al. |
| 2002/0022551 A1 | 2/2002 | Watterson et al. |
| 2002/0049535 A1 | 4/2002 | Rigo |
| 2002/0055419 A1 | 5/2002 | Hinnebusch |
| 2002/0091843 A1 | 7/2002 | Vaid |
| 2002/0094776 A1 | 7/2002 | Pulver |
| 2002/0094845 A1 | 7/2002 | Inasaka |
| 2002/0102988 A1 | 8/2002 | Myllymaki |
| 2002/0107433 A1 | 8/2002 | Mault |
| 2003/0000053 A1 | 1/2003 | Rooney et al. |
| 2003/0091964 A1 | 5/2003 | Yeager |
| 2003/0100315 A1 | 5/2003 | Rankin |
| 2003/0208409 A1 | 11/2003 | Mault |
| 2005/0113650 A1 | 5/2005 | Pacione et al. |
| 2011/0312470 A1 * | 12/2011 | Hickman ............ 482/4 |
| 2012/0264570 A1 * | 10/2012 | Watterson et al. ....... 482/8 |
| 2013/0217543 A1 * | 8/2013 | Shea .............. 482/8 |

FOREIGN PATENT DOCUMENTS

| | | |
|---|---|---|
| EP | 1 050 793 A2 | 11/2000 |
| GB | 2 350 749 A | 12/2000 |
| JP | 5-249899 A | 9/1993 |
| WO | WO 87/05229 A2 | 9/1987 |
| WO | WO 98/38820 A2 | 9/1998 |
| WO | WO 00/36900 A2 | 6/2000 |
| WO | WO 01/00281 A2 | 1/2001 |

OTHER PUBLICATIONS

Barber, Jr. et al., "Designing for Wireless LAN Communications," Circuits and Devices, vol. 12, No. 4, Jul. 1996, pp. 29-33.

Bhagwat et al., "A Routing Vector Method (RVM) for Routing in Bluetooth Scatternets," Mobile Multimedia Communications, Nov. 1999, pp. 375-379.

Bukhres et al., "Mobile Computing in Military Ambulatory Care," 10th IEEE Symposium on Computer-Based Medical Systems, Jun. 1997, pp. 58-63.

Hum, "Fabric area network—a new wireless communications infrastructure to enable ubiquitous networking and sensing on intelligent clothing," Computer Networks, vol. 35, Issue 4, Mar. 2001, pp. 391-399.

Jones et al., "A Protocol for Automatic Sensor Detection and Identification in a Wireless Biodevice Network," 11th IEEE Symposium on Computer-Based-Medical Systems, Jun. 1998, pp. 311-316.

Mann, Steve, "Wearable Computing: A First Step Toward Personal Imaging," Computer, vol. 30, No. 2, Feb. 1997, 11 pages.

Santos, Roy, "FitSense. The FS-1 Pro promises highly accurate speed and distance readings for runners," copyright 2004, website address: http://www.g4tv.com/articles/17027/fun-fitness-tech/.

Sayer, Peter, "New wired clothing line comes with personal network," Aug. 18, 2000, CNN.com; website address: http://archives.cnn.com/2000/TECH/computing/08/18/wired.jacket.idg/index.html.

Website, Bluetooth, The Official Bluetoothe® Wireless Info Site, regarding Bluetooth enabled devices, copyright 2004; website address: http://www.bluetooth.com/index.asp.

Website, Digiman, human-computer interface research, copyright 2003; website address: http://www.digiman.org/html/main.html.

Website, FitSense Technology, "FS-1, Speedometer. One Watch. Total Feedback. Speed, Distance & Heart Rate Monitoring System for Runners and Walkers," copyright 2003; website address: http://fitsense.com.

Website, Institute of Electrical and Electronics Engineers, Inc., IEEE 802.11™ Wireless Local Area Networks- The Working Group for WLAN Standards, copyright 2004 IEEE; website address: http://grouper.ieee.org/groups/802/11/.

Website, ViA Inc., Computers that fit people, Jan. 2004, website address: http://www.via.pc.com/index.html.

Website article, "Visions of wearable Internet ware," Jun. 26, 2000, CNN.com; website address: http://archives.cnn.com/2000/STYLE/fashion/06/26/wearable.computers/index.html.

* cited by examiner

| ID | Manufacturer |
|---|---|
| 0 | Unknown/Unassigned |
| 1 | Mfg. A |
| 2 | Mfg. B |
| 3 | Mfg. C |

| ID | Model/Mfg. A |
|---|---|
| 0 - 255 | Unassigned |
| 256 | Model A |
| 257 | Model B |
| 258 | Model C |

| ID | Device Type | |
|---|---|---|
| 236 ⌇ 0 - 255 | Unknown/Unassigned Output | ⎫ |
| 256 | Display | ⎬ 232 |
| 257 | Audio Output | ⎭ |
| . | . | |
| 238 ⌇ . | . | |
| 32768-33023 | Unknown/Unassigned Input | ⎫ |
| 33024 | Push Button Input | ⎬ 234 |
| 33025 | Audio Input | ⎭ |
| . | . | |
| . | . | |
| . | . | |

Device Type 257

| Capability | Type | Range | 242 |
|---|---|---|---|
| 1 | Stereo | Yes/No | ⌇ 244 |
| 2 | Volume Control | Yes/No | |
| 3 | Volume Level | Number of Levels | ⌇ 246 |

301 — Msg Type: Identity Request
Network ID: — 303
Network Address: — 304
Controller ID: — 305
Error Detection/Correction: — 302

301 — Msg Type: Component Identity
Network ID: — 311
Network Address: — 312
Component ID: — 313
Manufacturer ID: — 314
Model ID: — 315
Device Type: — 316
Capability List: — 317
Error Detection/Correction: — 302

301 — Msg Type: Net Address Assignment
Controller ID: — 305
Network ID: — 321
Network Address: — 322
Component ID: — 313
Security Code: — 323
Error Detection/Correction: — 302

301 — Msg Type: Network Ack
Component ID: — 313
Network ID: — 321
Network Address: — 322
Error Detection/Correction: — 302

Msg Type: Output Data Request
301
Network ID: 321
Network Address: 322
Request Serial Number: 341
Device Type: 316
Capability Type: 317
Data to Output (dependent on Device Type): 342
Error Detection/Correction: 302

Msg Type: Output Ack
301
Network ID: 321
Network Address: 322
Request Serial Number: 341
Ack Code: 351
Error Detection/Correction: 302

Msg Type: Input Data Request
301
Network ID: 321
Network Address: 322
Request Serial Number: 361
Device Type: 316
Capability Type: 317
Error Detection/Correction: 302

| Network Address | Component ID | Manufacturer | Model | Device Type | Capability | Active |
|---|---|---|---|---|---|---|
| 1 | 55555 | 2 | 506 | 701 | 1 / 4 | Yes |
| 2 | 66666 | 2 | 510 | 42163 | 1 / 1 , 2 / 0 | No |
| 3 | 77777 | 4 | 1062 | 891 | 1 / 10 | Yes |
| . | . | . | . | . | . | . |
| . | . | . | . | . | . | . |
| . | . | . | . | . | . | . |
| . | . | . | . | . | . | . |

410 — Network Address
420 — Component ID
430 — Manufacturer
440 — Model
450 — Device Type
460 — Capability
470 — Active

400

700

1200

1300

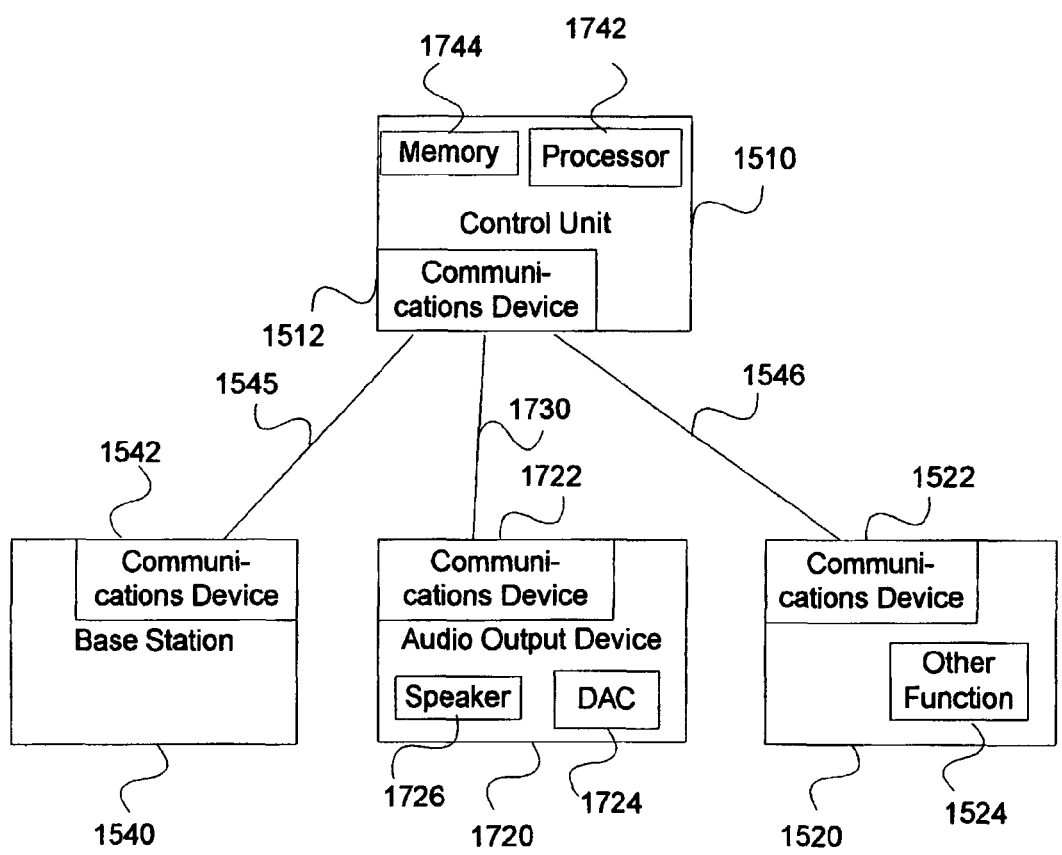

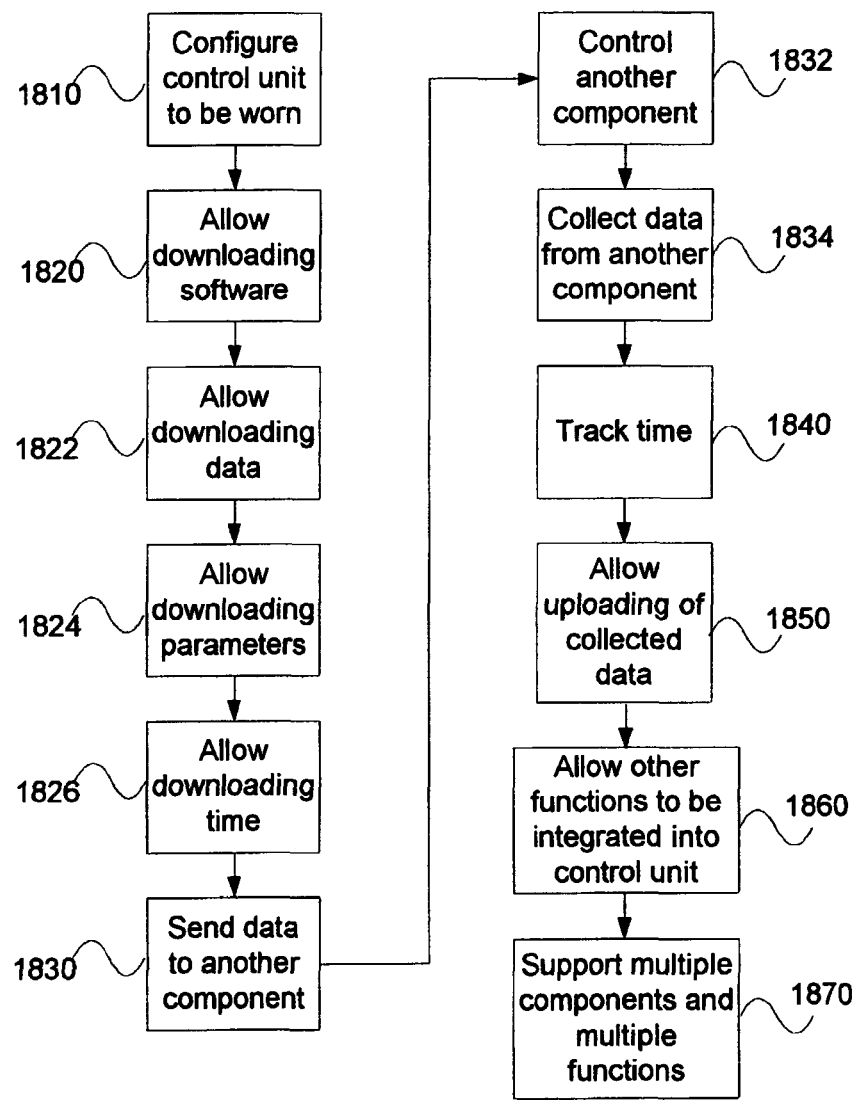

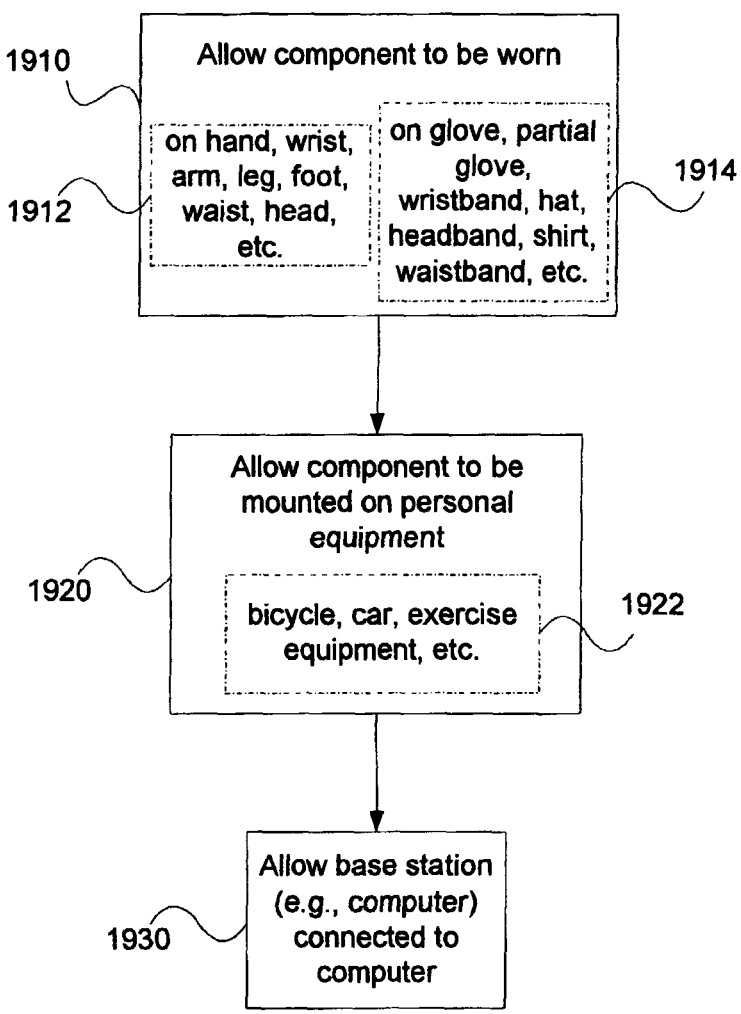

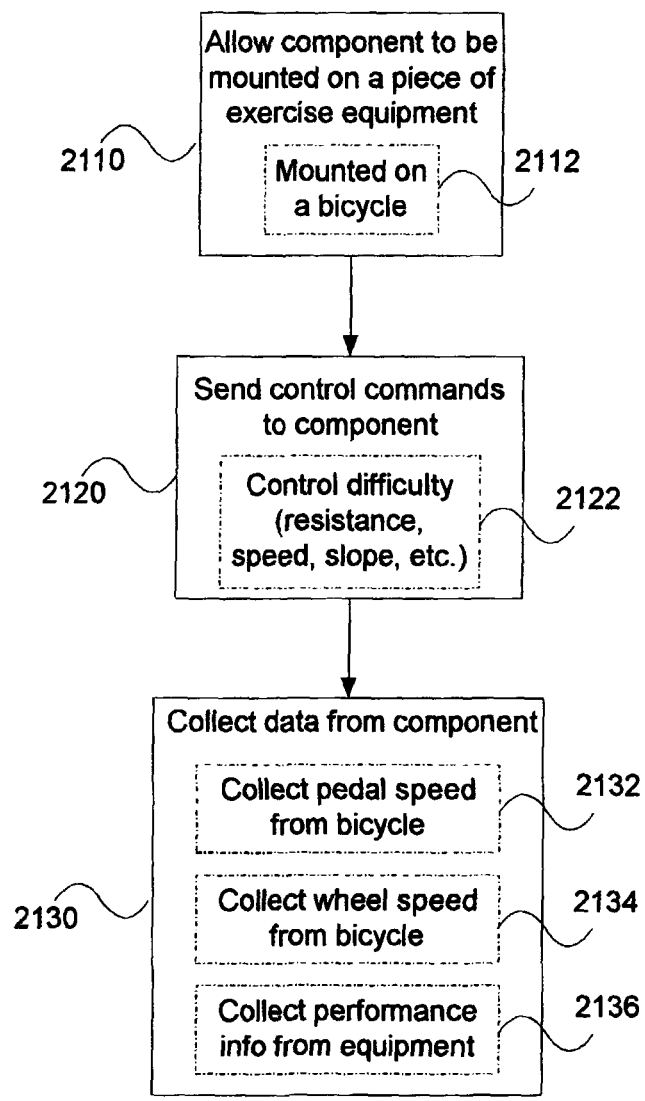

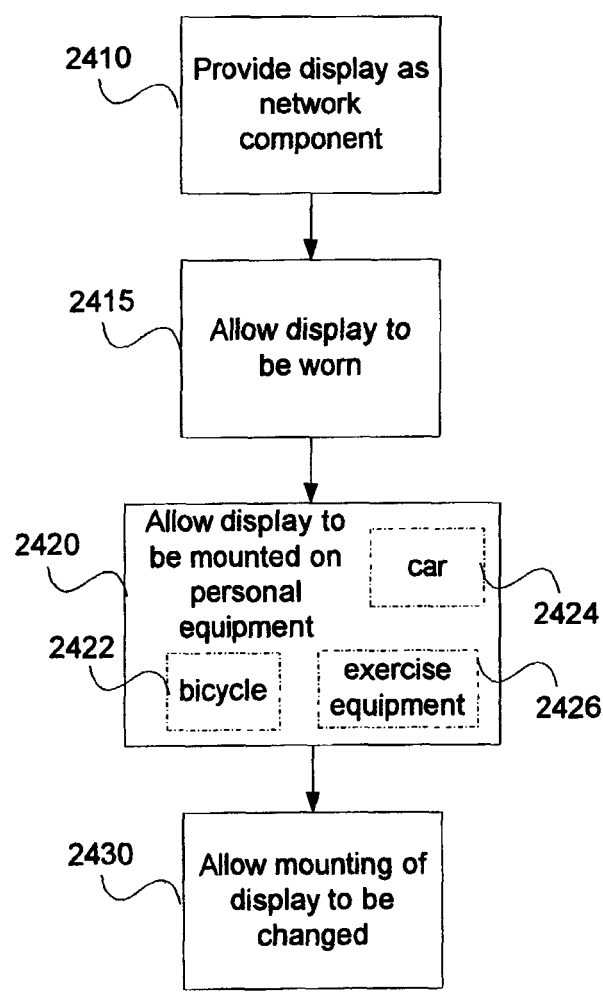

3500

3700

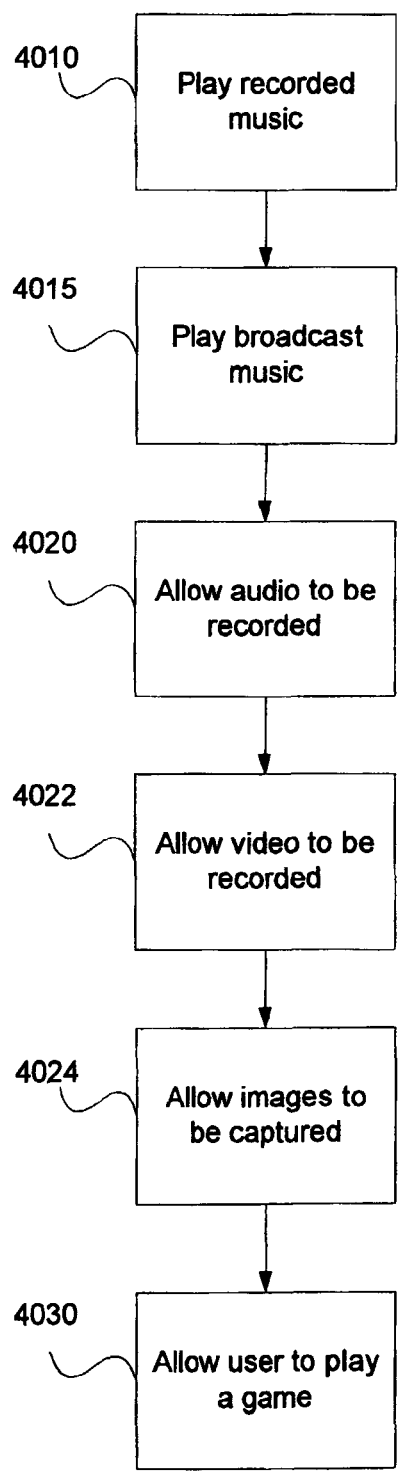
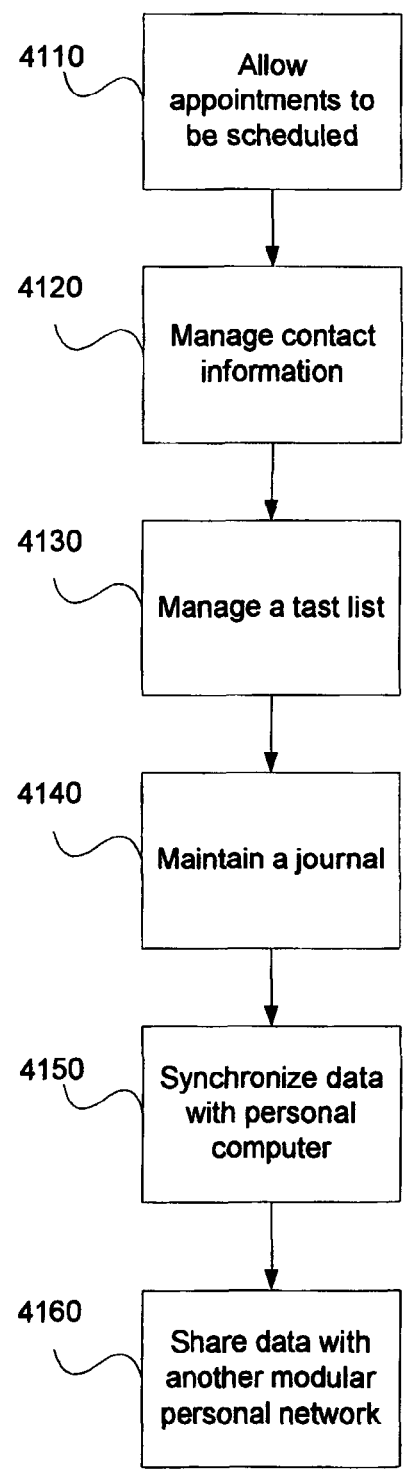

4400

ELEV
5280 ft

POS
LAT 40.0
LONG -105.3

SPD
6.2 MPH

ELEV GAIN
+20 ft/min

HR
94 bpm

TURN RIGHT

CADENCE
54/min

STRIDE
0.85 m

12:34 PM
JUN 6

TOTAL SESSION 6
2:46:07
SPLIT 2
0:32:57

REPEAT 2
SEG 4
REMAIN
4:26

FASTER!

5910
Number of SuperSections: 3

SuperSection 1:
- Number of sections: 1 — 5921
- Repeats: 1 — 5922
- Section A:
  - Duration: 15 min 0 sec — 5926
  - Main Parameter: HR — 5921
  - Curve: Linear
    Starting: 100 BPM  Ending: 125 BPM — 5928
  - Secondary Parameter: Cadence: 90 RPM — 5929
  - Control By: User audio prompt — 5930

5920 { 5925 {

SuperSection 2:
- Number of sections: 2 — 5941
- Repeats: 2 — 5942
- Section B:
  - Duration: 5 min 0 sec — 5946
  - Main Parameter: HR — 5947
  - Curve: Range: 150 – 160 BPM — 5948
  - Secondary Parameter: Cadence: 90 RPM — 5949
  - Control By: Resistance Setting — 5950
- Section C:
  - Duration: 1 min 30 sec — 5956
  - Main Parameter: Speed — 5957
  - Curve: Range: < 15 MPH — 5958
  - Secondary Parameter: Resistance: Easy — 5959
  - Control By: User audio prompt — 5960

5940 { 5945 {
5960 { 5955 {

SuperSection 3:
- Number of sections: 1 — 5961
- Repeats: 1 — 5962
- Section D:
  - Duration: 15 min 0 sec — 5976
  - Main Parameter: HR — 5977
  - Curve: Constant: 110 BPM — 5978
  - Secondary Parameter: Cadence: 90 RPM — 5979
  - Control By: User audio prompt — 5980

```
6380
  |
File    Device    System    User    Security    Help          _ ☐ X
User Information:

Name:    [ Ketzel Coattle ]
                           6310

Age:  [ 26 ]      Weight:  [ 115 ]  lb
            6320                        6330

○ Male
Gender:                  6340
          ● Female

Height:  [ 5 ] ft  [ 6 ] in
                              6350

Heart    [ 55 ] BPM    [ 194 ] BPM
Rate:
         Resting 6360   Maximum 6370
```

6300

6410

6420

6430

6440

6450

6460

FIG 67
3:45:20.45  6705
3:45:20.94  6710
3:45:21.43  6715
3:45:21.91  6720
3:45:24.87  6725
3:45:25.35  6730
3:45:25.86  6735
3:45:26.35  6740
6700

FIG 68A        FIG 68B

| | | |
|---|---|---|
| 122 | | 122 |
| 124 } 6805 | | 124 |
| 126 | | 126 |
| 128 | | 128 |

| | | |
|---|---|---|
| 0 | | 128.8 |
| 0 } 6810 | | 129.6 } 6835 |
| 0 | | 130.4 |
| 0 | | 131.2 |

| | | |
|---|---|---|
| 132 | | 132 |
| 133 } 6815 | | 133 |
| 134 | | 134 |
| 135 | | 135 |

| | | |
|---|---|---|
| 250 | | 134.2 |
| 250 | | 133.3 |
| 250 } 6820 | | 132.5 } 6840 |
| 250 | | 131.7 |
| 250 | | 130.8 |

| | | |
|---|---|---|
| 130 | | 130 |
| 129 } 6825 | | 129 |
| 128 | | 128 |
| 127 | | 127 |

9920 { Time: 9:01:46　　9910
　　　　HR = 122 BPM
　　　　SPEED = 6.4 MPH
　　　　ELEV = 5472 FT 9940 { Time: 9:01:47　　9930
　　　　HR = 123 BPM
　　　　SPEED = 6.4 MPH
　　　　ELEV = 5472 FT
　　　　IMAGE = I20020407090147.JPG　　9950

9970 { Time: 9:01:48　　9960
　　　　HR = 122 BPM
　　　　SPEED = 6.3 MPH
　　　　ELEV = 5472 FT

9900

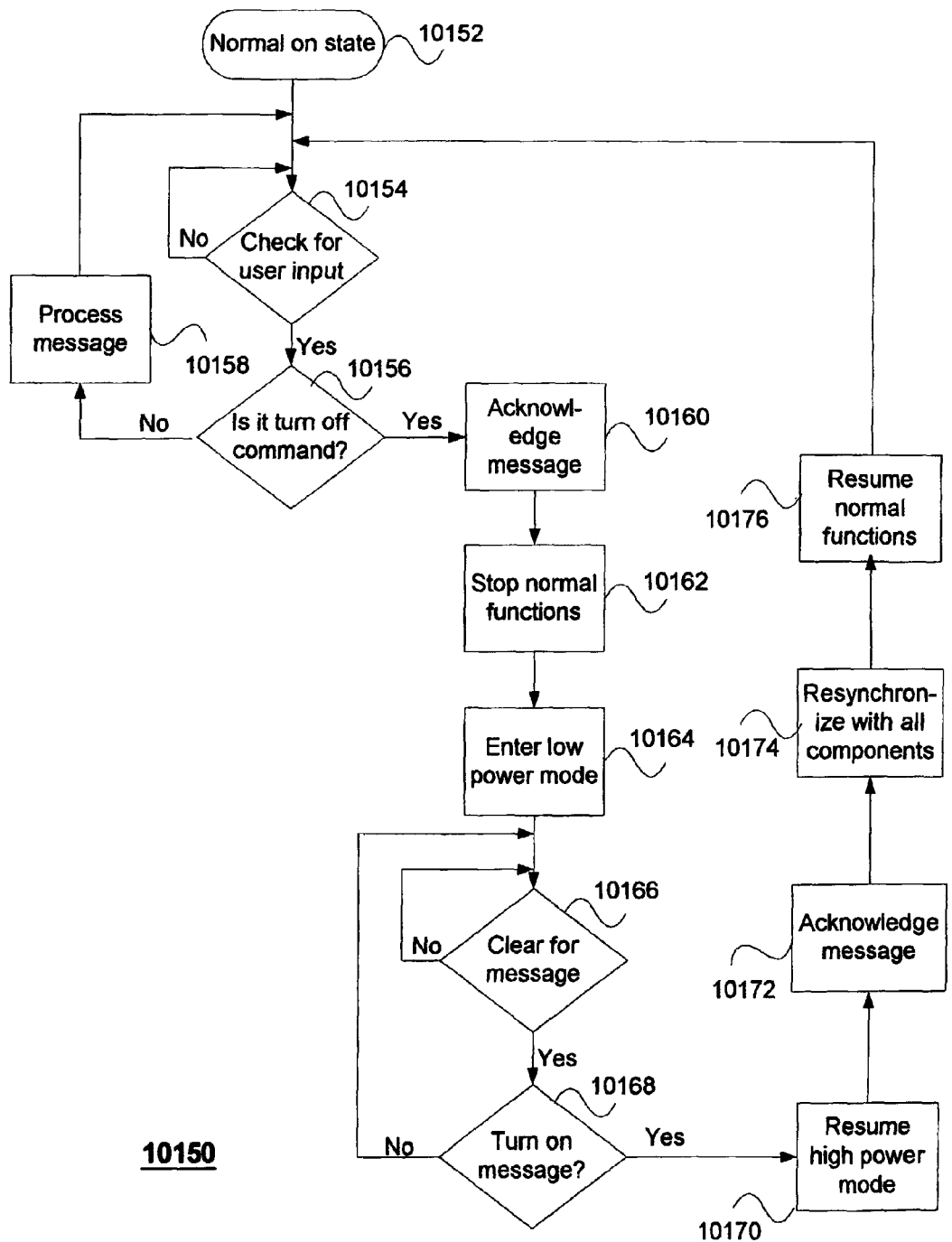

METHODS FOR DETERMINING WORKOUT PLANS AND SESSIONS

CROSS-REFERENCE TO RELATED APPLICATIONS

This application is a continuation of U.S. application Ser. No. 13/789,266, filed Mar. 7, 2013, which is a continuation of U.S. application Ser. No. 12/617,871, filed Nov. 13, 2009, which is a divisional of U.S. application Ser. No. 10/645,713, filed Aug. 20, 2003, which is a continuation of International App. No. PCT/US02/04947, filed Feb. 20, 2002, which claims the benefit of U.S. Provisional App. No. 60/270,400, filed Feb. 20, 2001. The contents of each of these applications are expressly incorporated herein by reference thereto in their entireties.

BACKGROUND OF THE INVENTION

1. Field of Invention

Our invention relates to modular personal network systems and methods. In particular this invention relates to wireless networks of individual components that can be easily added to or removed from the network to change its functions, and in which the individual components are worn, carried, or used on or about the person of the user.

2. Background Art

A number of individual portable personal devices are available today. Such personal devices provide specific functions to a person, in a number of different fields of use. For example, there are mobile phones, personal digital assistants, medical monitoring devices, personal entertainment systems, and athletic monitoring systems. These and other portable electronic devices have significantly improved the convenience of many activities.

However, each of these functions is provided individually. None of these individual devices can combine with any of the other devices to provide improved functions. If a user wishes to upgrade the capabilities of any of these devices, a new, expensive device must be purchased and the old device discarded.

What is needed is a system in which individual portable device modules can be combined in a multitude of ways to provide an infinite variety of functions. A portable system is needed in which new functions can be added by simply adding or replacing a single component. A portable system is needed in which the functions can be modified simply by downloading new software or other parameters. A system is needed in which functions in different fields of use can be easily combined. And a system is needed in which the economies of scale and scope of building devices across multiple fields of use can be used to benefit users of devices in all of the fields of use.

Wireless communication protocols have been defined. Bluetooth and IEEE 802.15 are two examples of protocols that may be used with personal portable devices. What is needed is a system that provides the advantages of a modular personal network, and that uses a standard wireless communication protocol such as one of these.

U.S. Pat. No. 6,047,301 (2000) and U.S. Pat. No. 6,336,126 (2002) both to Bjorklund, et al., disclose a wearable computer that communicates with a display device using an optical link, and with a local area network using a radio communications link. However, the system described is not modular, nor is it extensible.

U.S. Pat. No. 6,324,053 (2001) to Kamijo discloses a wearable data processing system. However, this system depends on a network of wiring stitched into the clothing of the user.

U.S. Pat. No. 6,108,197 (2000) to Janik discloses a flexible wearable computer. However, this disclosure does not envision the needed extensibility.

U.S. Pat. No. 5,781,913 (1998) to Felsenstein, et al., discloses a wearable hypermedium system. It is designed to allow a user to access a large amount of electronic information using a hands-free system, but does not include provisions for extending to other unanticipated uses.

A personal area network has been disclosed. For example, U.S. Pat. No. 6,331,972 (2001) to Harris, et al., discloses a circuit and method for personalizing an electronic device through a personal area network. U.S. Pat. No. 6,314,091 (2001) to LaRowe, Jr., et al., discloses a wireless personal area network with a plurality of peripheral devices, wherein a hub device provides attachment and detachment of peripheral devices. U.S. Pat. No. 6,128,290 (2000) to Carvey discloses a personal data network that uses low duty cycle pulsed radio frequency energy to communicate and provide synchronization. U.S. Pat. No. 5,909,183 (1999) to Borgstahl, et al., discloses a method for programming an appliance by a controller in a personal area network. U.S. Pat. No. 5,898,831 (1999) to Hall, et al., discloses a method for including an appliance in a personal area network and programming security criteria. However, none of these systems provides the needed flexibility of our modular personal network (MPN). For example, each of them requires a controller to be one of the devices in the personal area network. These systems do not anticipate the needed methods for downloading data to a personal area network from a personal computer or other system, nor for retrieving data from a personal area network to a personal computer or other system. And the wide variety of components, configurations, and uses has not been anticipated.

Users need more flexibility in display devices, such as how they are worn so that they may be easily viewed during different activities. Users need display devices that can be easily modified in their position and orientation. Users need a variety of mounting options for individual components in an MPN. Users need an audio device that can be easily worn during various activities, that can be heard during activities with ambient noise, and that won't disturb other nearby people. Users need a system that provides multiple types of audio output in an intelligent fashion. Users need a variety of input devices for different types of activities, and which can be easily accessed during those activities.

Users need to be able to reuse the same components for multiple purposes. These purposes may include time keeping. Users need a network that allows communication with other individuals, who may or may not have their own MPNs. Users need a network that provides entertainment features, including playing music, playing games, and capturing audio and video. Users need a portable system that combines personal organization functions with other functions. Users need a mobile journal system that can be customized for different types of uses, such as travel, athletics, healthcare, or other purposes. Users need a system that provides guidance features, and combines them with other features, such as audio and video annotations, collection of personal data, and athletic workouts.

Users need a system that can provide a variety of athletic functions, such as downloading workout control parameters as well as uploading results of a workout. Users need a system that can interface with exercise equipment, bicycles, and other personal equipment. They need a system that collects performance data, detects and corrects errors in the collected data, and estimates secondary data, based on the collected primary data. Athletes need a mobile system to measure cadence and stride length. Some athletes need reminders to consume water, sodium, and food. Swimmers need a system to measure and log lap-swimming workouts. Runners and other athletes need a mobile system to provide form feedback. Athletes need a system that can work with another system to provide a competition between multiple athletes.

Physical therapist, doctors, and other healthcare professionals need a system that can provide a variety of functions, such as measuring user capabilities, monitoring changes, keeping a medical journal, measuring metabolic parameters, detecting medical problems, providing treatments, and providing medical databases. A system is needed that allows components to be ingested, injected, or implanted, as well as worn, carried, or mounted on personal equipment. A system is needed that provides alternate input, output, and mounting for a disabled user.

Travelers and outdoor users need a system that provides a variety of integrated features. For example, a system is needed that combines translation, travel information repository, wildlife recognition, weather, route guidance, local entertainment, and orienteering functions. A system is needed that can provide user identification functions and that can use that identification to provide other services, such as transfer of money and product purchasing and discounts. Users need a system that can provide personal security features, such as audible alerts, transmitted alerts, and storing emergency information. A system is also needed that can support military needs.

BRIEF SUMMARY OF THE INVENTION

Our invention satisfies these and other needs by providing a modular personal network (MPN). A main aspect of our invention is a system that allows multiple individual network components (INCs), each with one or more primary functions, to be used in a wireless personal network, and that INCs may be added and removed modularly to add or remove functions of the MPN. This includes the ability to add INCs that were not anticipated when the MPN was first assembled. INCs are personal, in that they may be worn, carried, mounted on personal equipment, or otherwise used in proximity to the person associated with the MPN. Another aspect of our invention is that it supports INCs from different manufacturers, of different models, of different types, and with different capabilities. Another aspect is the ability to download software, data, settings, and other information into an INC to control functions of the MPN, and to upload data from an INC. Yet another aspect of our invention is the use of a common network identifier among the INCs of the MPN, to prevent interference between INCs that may be part of different MPNs, and to prevent the unauthorized use of an INC. Still another aspect of our invention is a single turn on or turn off command to turn on or off all INCs in an MPN.

Another aspects of our invention is a control unit, which may be an INC containing a processor and memory for controlling other INCs in the MPN. Alternatively, there may be no control unit, and each INC may provide its own control. A base station or personal computer may interact with the MPN, to download software, data, and settings, and to upload data that may have been collected by the MPN. The MPN may interact with a wide area network, such as the Internet, using the base station or personal computer in another aspect.

Another aspect of our invention is that one of the INCs may function as a display device. A display INC may be mounted on the back of the wrist in a manner similar to a wristwatch, it may be worn on the side of the wrist or hand, or it may be worn in any other suitable location. The orientation of the display may be changed to suit the needs of the user. In another aspect of our invention, the display INC or other INCs may be worn using a reconfigurable mount that allows easy repositioning and replacement of the INC.

Another aspect of our invention is that one of the INCs may function as an audio output device, which may provide audio cues, voice, music or other types of audio information. The audio output INC may include headphones, ear inserts, or speakers that mount in a hat or headband. If multiple types of audio output are supported, one audio signal may be paused or muted while the other is generated.

Another aspect of our invention is that one of the INCs may function as a user input device, and may include a device such as a button or pressure sensor, a touch pad and stylus, or a voice input. Pressure sensors may be worn on the hand, fingers, foot, or waist, where they may be easily operated by tapping.

Another aspect of our invention is that it may be used for one or many purposes, and that the purposes may be changed as INCs are added or removed, as software or data is downloaded, or as a user changes activities. Purposes may include time-related, communications, entertainment, personal organization, guidance, athletic, physical therapy, medical, disability-related, travel-related, outdoor-related, identification, security, military, or other purposes or combinations of purposes.

Time-related purposes of our invention may include providing the current time, multiple time zones, stopwatch functions, and interval timing functions, and may also be used to synchronize other functions of the MPN. Communications functions may include communicating with another MPN to provide games, competitions, and to transfer personal information, software, music, and other information. Other communications functions may include telephone, paging, instant messaging, and electronic mail. Entertainment functions may include playing recorded music or radio, recording audio or video, or playing a game. Audio, video and images recorded by the user may be linked to other personal data that may have been simultaneously collected by the MPN. Personal organization functions may include scheduling appointments, managing contacts, managing a task list, and keeping an electronic journal. An electronic journal may support text, audio, sketch, image, and video entries, may automatically tag journal entries with time or location, may allow journal entries to be linked to database entries, and may allow journal entries to be uploaded to a personal computer and converted to a standard file format. Guidance functions may include providing position, elevation, and speed information, providing route guidance, and collecting and annotating position information with text, audio, video, and personal data. Guidance functions may also include recommending an athletic training route based on desired workout parameters, and comparing personal data collected during multiple sessions.

Athletic functions may include controlling a workout, including controlling individual sections of a workout, and collecting results from a workout. A coaching interface may provide creation and monitoring of a workout plan. Both music and audio athletic cues may be provided. An INC of the MPN may control a setting on a piece of exercise equipment, or may collect data from a piece of exercise equipment. The MPN may measure distance, speed, heart rate, cadence, stride length, and other athletic data. Errors in collected data may be corrected. Secondary performance parameters may be estimated based on collected data and other stored information.

An athlete may be reminded to consume water, sodium, food, or other consumables. Two athletes with MPNs may be provided a competition. The MPN may provide lap counts, workout logging, and other lap swimming functions. The MPN may provide form feedback to an athlete. An athletic journal may also be provided.

Physical therapy functions may include measuring range of motion, doing gait analysis and form feedback, testing muscle strength, monitoring changes in physical capabilities, and providing a physical therapy journal. Medical functions may include measuring a metabolic value, detecting a medical problem, controlling a treatment device or taking other medical actions, providing emergency communications, providing storage of medical databases, and providing a medical journal. INCs may be worn or carried by a doctor, patient, or nurse, mounted on equipment such as a wheelchair, or implanted, injected, or ingested into a patient. Functions for a disabled user may include alternate output methods, alternate input devices, and mounting an INC on a wheelchair or other equipment.

Travel-related functions may include language translation, currency conversion, time zone conversion, route guidance, local information, guidebook functions, wildlife recognition, a travel journal, weather information, transit information, local entertainment information, and expense tracking Outdoor-related functions may include direction, position, elevation, route, and weather features. Identity functions may use a smart card, personal code, or biometric information to identify a user to another person or system, and may provide exchange of money, product discounts, and purchasing features. Security functions may include an audible alert, an alert message to a public safety facility, and storing emergency contact and emergency medical information. Military functions may include communications, global positioning, guidance, and weather functions.

An MPN is a set of INCs that communicate using a wireless network. These INCs use a common communications protocol, such as the Bluetooth protocol or the IEEE 802.15 standard, to send messages between themselves. Using a common protocol means that the same electronic components and software can be used in each of them, keeping the cost low.

A common protocol also allows new INCs to be added more easily. This invention is "modular," in that new INCs can be added at any time. This may change the function of the overall system. As INCs are added, the system's capabilities will grow. As one INC replaces another, the functions of the system change accordingly. The system will continue to function, with reduced capabilities, as INCs are removed. INCs may be built by various manufacturers, and may have different capabilities.

Our invention is also "personal." This means that the MPN is small in size, roughly encompassing one person's "personal space." INCs may be worn by the user, they may be carried by the user, or they may just be in close proximity, for example mounted on personal equipment. Also "personal" is the fact that MPNs provide exactly the functions that the individual wants, because the combination of INCs is virtually limitless.

The MPN may be changed at any time, and the functions of the system may change correspondingly. For example, a new INC may be added, and a new function may be enabled by the system. An INC may be removed, and a function of the system may be disabled. The system may automatically detect a change in the MPN, and correspondingly change the functions. Alternatively, a user may enter a changed configuration, for example into a base station, control unit, or personal computer.

Another advantage of our invention is that it is extensible. This means that an INC can be added at any later time, even though that specific INC and its functions may not have been anticipated at the time the system was first put together. Each new INC uses the same communications methods and protocols to send and receive data and commands. The functions of the system are controlled by downloaded software. This means that new software can be downloaded to support the unanticipated new INC.

Software may be downloaded into an INC in the MPN, such as a "control unit." The control unit may include memory for holding software and data, and a processor. The control unit may send commands and data to some INCs and retrieve data from other INCs. By modifying the software in the control unit, the system may support previously unanticipated INCs. Software may also be downloaded into any other INC.

Software may be downloaded into an INC of the MPN by a personal computer. Software on the personal computer may control what is downloaded. The software on the personal computer may allow extensions to support unanticipated functions and INCs. The software extensions may allow the user to specify software modules to download, to configure parameters for the unanticipated INCs, or to perform other functions related to additional INCs and functions.

One of the INCs in the MPN may be a "base station." This base station may used to download information, such as software, data, setup options, and time, into at least one of the other INCs, such as the control unit. The base station may, for example, be connected to a personal computer. The base station, in that embodiment, may provide wireless connectivity to one or more of the other INCs, while the personal computer provides storage and a user interface for manipulating the information sent to and from the INCs in the MPN. The base station may communicate with the personal computer over a standard connection, such as a universal serial bus (USB), serial port, Ethernet, wireless network, infrared, PC Card interface, or over a direct connection to the personal computer's bus.

The personal computer may provide a user interface for controlling the INCs in the MPN. For example, the computer may allow the user to specify what functions are to be enabled by the system, which may then determine what software to download. The user may set configuration parameters that would then be downloaded to the INC(s) in the MPN.

The base station or personal computer may also have a wide area network connection, such as an Internet connection. This may allow another person to control functions of the system. This could include a healthcare professional, if the system is being used for medical purposes. It might include a coach if the system is being used for athletic purposes. It might include a manufacturer or distributor of any of the INCs in the MPN, who may wish to download software and parameters into the system to support the INC.

The base station, personal computer, and/or computer over a network connection may also be used to upload data from any of the INCs in the MPN, such as a control unit or data collection INC. This data may be stored, modified, analyzed, displayed, or otherwise used on one of those other stations.

All of the INCs within a single MPN may be assigned a single unique identifier. This identifier may be downloaded, for example, from a base station or personal computer to each of the INCs. All communications between INCs may be tagged with this unique identifier. This will prevent interference between the two MPNs used by two different people. INCs in each system will only listen to messages tagged with that MPN's own identifier.

The unique identifier can also be used to deter theft and other misuse of any INC. Each INC can be programmed to not accept a different unique identifier without explicit authorization from the authorized user, for example on a base station or personal computer. The INCs may also be configured so that the unique identifier they use cannot be extracted to program into a different INC.

All of the INCs in a single MPN may be turned off or on with a single command. For example, a user may press a button or speak a command, which may be received by one of the INCs. The command to turn off may be sent to all of the INCs in the MPN. When any INC receives the turn off command, it may cease any data collection or control functions, stop sending any wireless communications, go into a low-power mode, and otherwise minimize power use. Other than periodically checking for a turn on message, the INC may cease all communications. The user input INC may continue monitoring for a turn on indication from the user. When the turn on command is received, the INC may resume its full capabilities. This feature may be useful to conserve power, as well as to minimize radio frequency interference in environments, such as on a commercial airliner, where wireless communication may cause interference.

Our invention may be controlled by a single module configured as a control unit. This may be an INC that is worn on the person like the other INCs in the MPN. The control unit may have the facility to allow software to be downloaded into it. The control unit may interface with and control the other INCs in the MPN over the wireless network, based on the downloaded software. This allows the functions of the system to be easily modified, simply by downloading different software. If desired, there may be no control unit, and some or all of the INCs may support software download. In addition to software or firmware, the control unit (or any other INCs in the MPN) may also allow the download of data, setup options and other configuration data, current time, or any other information. The control unit, or other INCs, may also allow the uploading of data to a base station or personal computer.

The control unit, if present, may be a separate INC, or it may be combined with another of the INCs, such as a display. In some cases, it may be more efficient to combine the functions of any two of the INCs into a single INC that provides multiple functions. Alternatively, any individual function may be provided by a single INC. The control unit, for example, may be a separate unit, worn on a waistband.

The control unit, if present, preferably has memory and a processor, in addition to its communication device. This memory and processor support downloading of information and software, as well as control of other INCs in the MPN.

For example, one of the INCs may be a display device. Traditionally, displays worn by a person have been in the form of a wrist display, such as a wristwatch. However, users of our invention can choose the type of display that best suits their needs. This may be a display worn on a wristband, carried in the hand or pocket, mounted on a piece of exercise equipment, mounted on a bicycle or in an automobile, or any other suitable method of carrying by the user. In fact, the user may have multiple display INCs, and pick the desired one at any time based on a specific activity.

Traditionally, a wristwatch-type display is worn on the back of the wrist. However, our invention allows the display to be worn or carried in any manner. For example, a runner who does not wish to turn the wrist to view the display may prefer a display that is mounted on the side of the wrist or hand, that can be viewed while maintaining proper running form. The display may be configured so that it can be worn on either the left or right side. It may be configured so that the top of the display is oriented toward the thumb, toward the back of the wrist, or at an angle between the two. Alternatively, it may allow the user to configure the orientation of the display by choosing between one or more options.

Our invention may provide a reusable wearable mount for a display INC or other INCs. This mount may allow the user to easily change one INC for another, to move the INC, or to reorient the INC.

Wrist displays today, such as wristwatches, typically have input controls and audio outputs built-in. These input controls are often tiny and difficult to use. These audio outputs, since they are located far from the user's ear, are often difficult to hear. Our invention does not require that these controls and outputs be integrated into the wrist display. In fact, our invention encourages each function to be placed where it is most usable. For example, the controls may be a set of switches, buttons, or other pressure-sensitive devices worn at convenient points on the body. For example, one sensor can be worn at the tip of each finger in a glove or partial glove. The user can then operate the system by tapping with different fingers or tapping specific sequences to enter different commands to the system. Alternatively, the sensors may be worn at different locations on a waistband, allowing the user to control the system by tapping different locations on the waist. The sensors may be worn on a foot, so that the system can be operated by tapping a foot. The controls may be mounted on a bicycle or piece of exercise equipment. Any other suitable types of controls may be used, including dials, levers, keyboards, voice inputs, touch pads and any suitable combination of multiple types of inputs.

Similarly, an audio output may be provided separately from the display and other INCs. For example, headphones or earphones may be used. Alternatively, one or more speakers may be worn inside a hat or headband, providing sound via conduction through the skull. Such embodiments allow the audio feedback to be loud enough to be easily heard by the user, even in poor conditions such as being on a busy street, while keeping the sounds quiet enough to not disturb other nearby people.

The system with an audio output INC may provide an audio output function. For example, music may be stored in a digital form in memory in the control unit or another INC with a storage capability and sent to the audio output INC. An INC may also generate audio feedback related to other functions provided by the system. For example, if the system is being used for athletic monitoring, audio feedback may be used to prompt the user to work out harder or easier, to provide performance information, or to inform the user what workout zone he or she is in.

The system may provide different audio outputs to signify different situations or conditions. For example, different sounds may be generated for different situations. Alternatively, different sound sequences may be generated for different conditions. As yet another embodiment, sound may be sent to different speakers for different conditions. Voice may also be synthesized. Any of these techniques may be combined.

The system may also provide both music and audio feedback. This is an example of one system providing multiple functions. In this case, the music may be paused, muted, or the volume may be lowered while the audio feedback is provided.

Our invention may be used for a wide variety of purposes or combination of purposes. If desired, one MPN may support different purposes at different times, as INCs are added or removed, as different software and data are downloaded, as the user performs different activities, etc.

One of the INCs in the MPN may be a clock. The time may be automatically downloaded to the clock from a base station or personal computer. The clock may support functions such as a stopwatch, an interval timer, a multiple event timer, a split timer, etc. The clock may also support other timing functions in the system, such as measuring speed, cadence, rate of elevation change, heart rate, etc. A clock may also be used to synchronize functions of the MPN.

The MPN may provide communication functions. For example, multiple MPNs may be used to send data from one user to another. This may be done, for example, with the same wireless transmitters and receivers used to communicate between INCs in a single MPN, as long as the users are close enough to each other. Alternatively, a stationary device may coordinate communications between two or more users.

Data sent between two systems may enable two or more users to play a game, for example, by sending commands, moves, results, etc. from one user to another. Data may allow two or more users to engage in an athletic competition, for example, by transmitting performance data between athletes. Personal data may also be sent between users, for example, name, contact information, etc. Users may also exchange recorded music, software, or any other data.

Our invention may be used to support personal communications. INCs may include a wireless telephone INC or a paging INC. INCs may support instant messaging, electronic mail, and other types of text communications. INCs may support voice communications or video communications. INCs may support transmission and receipt of any type of data, including image data, video data, audio data, and text data.

Our invention may be used for entertainment purposes. This may include allowing a user to play a game, to play music or view other media.

The MPN may allow collection of media data. For example, INCs may include a microphone or a video input. INCs may also include memory or another storage device to store media. The media collected, such as audio, video, or still images, may be replayed for the user by one of the INCs. The media may be uploaded to a base station or personal computer.

The MPN collecting media data may also collect other personal data. For example, the system may collect position data, heart rate data, athletic data such as speed, or other data. The media and personal data may be sent using the wireless network to a base station, and into a personal computer. The media data may be interpreted by a media interpretation unit or algorithm, such as a speech recognition system. The interpreted media data may be used to change the personal data collection functions.

A relationship may be defined when the media and personal data are collected. For example, the media data may be associated with the personal data collected at about the same time as the media was collected. That relationship may be noted in the data, and maintained as the data is uploaded to a base station or stored in a personal computer. For example, a voice note or a picture may be tagged as associated with data collected at a specific time during an athletic workout or other session.

An MPN may provide personal organizer functions. For example, the system may provide appointment scheduling, task management, and contact management. The system may also provide a mobile electronic journal. A journal may allow a user to create text or audio entries, and to annotate them with video, still images, audio, or sketches. The entries may be automatically tagged with the time and location. The user may be able to link a journal entry to an element in an application specific database, such as a medical database, a health database, a travel database, a music database, a work database, a school database, or a database related to any other suitable application. The MPN may support uploading the journal entries and related data to a personal computer, and converting them to a standard file format for viewing, editing, or printing on the personal computer. The journal may also include any other functions or features related to a specific application, such as medical features, health features, travel features, music features, work features, school features, or any other suitable application features.

Our invention may support guidance features. The MPN may include INCs such as a global positioning system monitor, an elevation monitor, or a compass. The system may display current location, direction, elevation, speed, or other related information. The system may provide route guidance, using downloaded map data. The system may collect location, direction, elevation, or speed data. The user may be allowed to annotate the collected data with audio, video, image, or other types of information. The system may automatically annotate the collected data with simultaneously collected personal information, such as heart rate data. The collected data and annotations may be uploaded to a personal computer, where they may be displayed. The data may be compared with map data. Data from multiple sessions may be compared. The system may use collected data to recommend a route in a later athletic session, based on a desired distance, elevation profile, or difficulty, and the user may be automatically guided through the recommended route. The system may also simulate a previous route.

Our invention may provide other athletic functions. For example, a workout plan may be created on an athlete's computer or a coach's computer. The plan may have a specific athletic or health goal, and may be used to define individual workout sessions. Individual workout sessions may include multiple sections, each of which may have an individual goal and individual control characteristics, such a parameter to control, a desired range of values for the parameter, data to collect, and duration. The control characteristics for a workout session may be downloaded into an INC of the MPN, and the system may use them to control aspects of the workout. Control may be accomplished by prompting the athlete, by sending a command to a piece of exercise equipment, or other suitable method. The system may use a servo algorithm to control the parameter. Results, such as speed, distance, heart rate, data from a piece of exercise equipment or bicycle, and other performance data, may be collected during the workout. Errors may be detected in the collected data, for example based on recognizing invalid sample values. Replacement data may be substituted for the invalid values, for example by interpolation. Secondary data, such as cadence, stride length, $VO_2$ max, oxygen uptake, maximum heart rate, percent of maximum heart rate, percent of heart rate reserve, energy consumed, power exerted, or lactate threshold may be derived based on the collected personal data and other personal data. The collected data or the derived secondary data may be displayed for the user during a workout, and it may be used to modify a workout. The data may be uploaded to the athlete's computer, coach's computer, or other suitable location, where it may be stored, displayed, compared between sessions, or otherwise analyzed. The collected or uploaded data may be used to modify future workouts. Progress may be measured against the goal of the workout plan. Workout data, and other information, may be maintained in a mobile athletic journal supported by the MPN.

Our invention may provide consumable reminders to an athlete. For example, the athlete may be reminded to drink water or a sports drink or to take a sodium supplement, based on metabolic measurements taken of the athlete, measurements of the amount of consumable carried, the time since the most recent reminder, the amount of the consumable carried by the athlete, or other suitable factors.

One MPN may interface with one or more other MPNs to allow multiple athletes to compete.

The MPN may be configured to provide lap swimming information. By using one or more monitors worn by the swimmer, the MPN may count laps, distinguish between different strokes, calculate the swimmer's speed, estimate total distance, and provide a log of an entire lap-swimming workout.

Our invention may be configured to monitor the form of the athlete, such as an athlete's running, walking, swimming, bicycling, or rowing form, and provide feedback, either during a training session or afterwards. The form feedback may be based on collecting accelerometer data during the training session and comparing it with data representing ideal form.

Our invention may provide physical therapy features. The form feedback described above may be used to provide gait analysis and other types of activity monitoring. The system may also be used to measure range of motion, test muscle strength, measure and record changes in physical capabilities, provide a therapy journal, or provide other suitable functions.

Medical features may also be supported by our invention. The system may monitor metabolic parameters, such as heart rate, blood oxygen, blood pressure, temperature, and blood sugar. The monitored parameters and other data may be used to estimate or predict a medical problem. The system may also control a medical device such as a syringe pump or defibrillator. It may also provide emergency medical communication, provide storage of medical databases, provide a mobile electronic medical journal, or other suitable medical functions. INCs may be worn or carried by a doctor, patient, or nurse, or mounted on equipment such as a wheelchair. In addition, an INC may be implanted or injected into a patient, or ingested by a patient. Our invention may also be configured to support a disabled user. This may include alternate output methods, alternate input devices, and mounting an INC on a wheelchair or other equipment.

Our invention may provide travel-related functions. These may include language translation, currency conversion, time zone conversion, route guidance, local information, guidebook functions, weather information, transit information, local entertainment information, and expense tracking Our invention may provide a mobile travel journal. It may also provide automated or semi-automated wildlife recognition. Our invention may support users who enjoy outdoor activities. Functions for an outdoor user may include providing orientation (e.g., compass directions), determining position, displaying elevation, and providing route guidance. The system may provide weather features, such as environmental temperature, humidity, and barometric pressure.

Our invention may provide identity functions. The system may identify a user to another person or system. It may use a smart card, personal code, biometric information, or another suitable method to identify the user. Based on the identification, the system may provide exchange of money, product discounts, and purchasing features. The identification may also be used to prevent unauthorized use of the MPN or any of its INCs. Other personal security features may be provided. For example, the MPN may provide an audible alert or an alert message to a public safety facility. An INC of the MPN may store emergency contact or emergency medical information, and provide that information when needed. Our invention may also support military functions. These may include communications, global positioning, route guidance, and weather functions.

Our invention may support multiple purposes within a single MPN. For example, one INC may support a function related to athletics, and another INC may support a function related to personal organization. A single INC may be used for multiple purposes. Each user may easily configure his or her own MPN with exactly the INCs that are needed to meet that user's individual needs. This minimizes cost to each user by allowing him or her to acquire just the INCs that are desired. Also, because similar INCs are used to serve multiple purposes across several different types of users, the cost of INCs can be held down. In addition, because many INCs may use some of the same electronic components, such as power sources and radio frequency transceivers, the cost to manufacture INCs can be minimized.

BRIEF DESCRIPTION OF THE FIGURES

Further features of our invention, its nature and various advantages will become more apparent upon consideration of the following detailed description, taken in conjunction with the accompanying drawings, in which like reference characters refer to like parts throughout, and in which:

FIG. 2A is an illustrative table of manufacturers of INCs of MPNs;

FIG. 2B is an illustrative table of models of INCs;

FIG. 2C is an illustrative table of device types of INCs;

FIG. 2D is an illustrative table of capability types of INCs;

FIGS. 3A through 3J are illustrative message definitions of a communications protocol that may be used within an MPN;

FIG. 4 is an illustrative data structure that may be used to track INCs in an MPN;

FIG. 17 is a block diagram of a portion of an MPN showing the use of a control unit;

FIG. 18 is a flow chart of an illustrative process for using a control unit as an INC of an MPN;

FIG. 19 is a flow chart of an illustrative process for providing personal components in an MPN;

FIG. 21 is a flow chart of an illustrative process for using an INC mounted on a piece of exercise equipment in an MPN;

FIGS. 24A and 24B are flow charts of an illustrative process for providing a display device as an INC of an MPN;

FIG. 40 is a flow chart of an illustrative process for using an MPN with an entertainment function;

FIG. 41 is a flow chart of an illustrative process for using an MPN with personal organization features;

FIG. 59 is an illustrative data structure that may be used to store information about a workout session to be controlled using an MPN;

FIG. 63 is an illustrative display screen that may be displayed to allow the entry of personal data to be used with an MPN;

FIG. 67 is an example of heart beat data that may have been collected by an MPN;

FIGS. 68A and 68B show an example of collected heart rate data with invalid samples and an example of replacement data;

FIG. 99 is an illustrative data structure that may be used to store personal data and related media data;

FIGS. 101A and 101B are flow charts of an illustrative process for turning off and turning on an MPN.

DETAILED DESCRIPTION OF THE INVENTION

Figure 100:
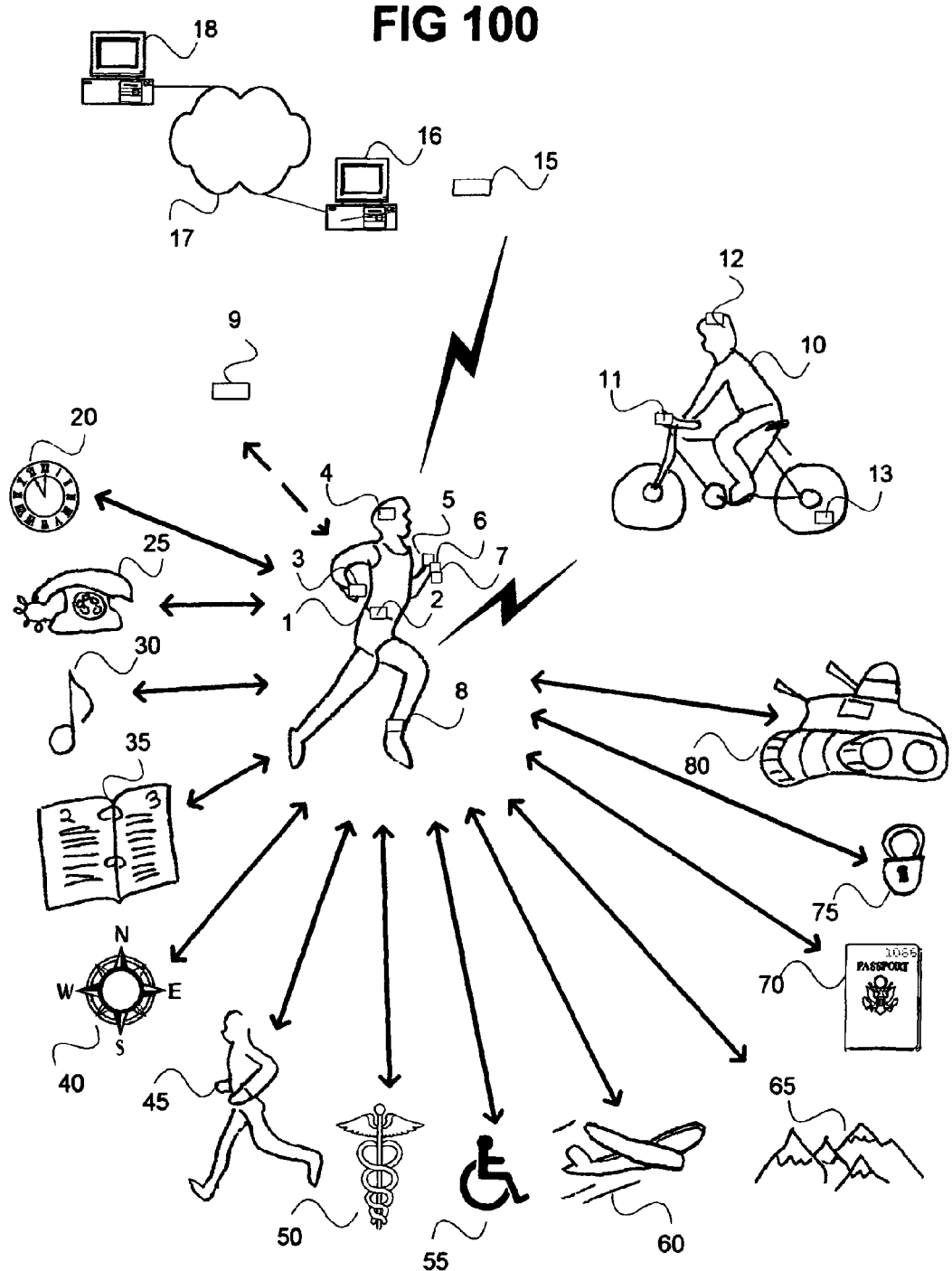
FIG. 100 is an illustrative overview of the MPN.

FIG. 100 shows an overview of how an illustrative modular personal network (MPN) may be used. The MPN is associated with a user 1. The MPN may include multiple individual network components (INCs), each of which may have one or more primary functions. Each INC may include a wireless transceiver for communicating with other INCs in the MPN. The wireless network may be associated with user 1, for example, within a few meters of the user. Each INC may be worn or carried by user 1, or otherwise in the user's immediate vicinity. For example, INC 2, which may be worn on the user's waist, may be a control unit that includes a processor and memory, to store and run software to control other INCs in the MPN. INC 3, which may be worn on the user's hand or wrist, may be a display device. If desired, a variety of mountings may be provided to allow the display to be seen optimally in variety of circumstances, such as mounting on the side of the hand or wrist. If desired, a reusable mount may allow a display or other INC to be easily repositioned, reoriented, and replaced. INC 4, which may be a headset or may be worn in a headband or hat, may be an audio output device. One or more speakers may be worn in the ear, or may be worn against the skin near the ear. The audio output device may support output of tones, music, or voice. Audio cues of various types may be generated. If desired, the audio output device may provide multiple types of audio output. One output may be paused or muted while the other is provided. INCs 5, 7, and 7 may be user input devices. Any suitable type of user input may be provided, such as voice input, buttons, a portable keyboard, or a stylus. As shown, pressure sensors are worn in the fingertips of a glove, and are operated by tapping with the fingers. Different commands may be indicated by tapping with different fingers or in different sequences. If desired, such pressure sensors may be worn on the hand, at the waist, on the foot, or in any other suitable manner. INC 8 may provide another function for the user, such as an input function, an output function, a storage function, or a control function. As many or as few INCs may be included in the MPN as desired. If desired, one or more INCs may be removed from the MPN to remove functions, and one or more INCs, such as INC 9, may be added to add other functions. The changed configuration may be determined dynamically or the changes may be indicated by the user.

Second user 10 may have a second MPN. For example, second user 10 may be riding a bicycle. INC 11 may be mounted on the handlebars of the bicycle and may include display functions, user input functions, and control unit functions. INC 12 may be an audio output device, mounted on second user 10's helmet. INC 13 may be a sensor mounted on the bicycle to measure its speed. When second user 10 comes into range of first user 1's MPN, there is no interference. Each INC in either MPN is programmed with a network identifier that is common to all INCs in the MPN but unique among different MPNs. Each message sent from one INC in an MPN to another INC in the same MPN may be tagged with the common network identifier or with a unique component identifier of the target INC, so that no unintended INCs process the message. In addition, the network identifier may be stored in secure memory in each INC, so that the INC cannot be used in a different MPN without explicit authorization from the user who programmed the network identifier.

The MPN may interface with a more stationary device, such as base station 15 or personal computer 16. Base station 15 may act as part of the MPN when the MPN is within range. Base station 15 may include a wireless communication device to communicate with one or more of the INCs in the MPN. Alternatively, base station 15 may communicate with one of the INCs using another means, such as a serial cable, USB, a docking station, infrared, or other connection. Personal computer 16 may communicate with base station 15. Alternatively, personal computer 16 may communicate directly with one or more INCs, acting as a base station. Personal computer 16 or base station 15 may download software, data, settings, and other information to one or more INCs. For example, software may be downloaded to control one or more INCs, or to implement one or more features. As unanticipated INCs are added to the MPN, new software modules may be downloaded to control and interface with them, and an application on personal computer 16 may be used to configure settings related to the new INCs. Personal computer 16 and base station 15 may be used to program the common network identifier into each INC in the MPN. Data may be uploaded from one or more INCs to personal computer 16 to be stored, displayed, or analyzed. If desired, personal computer 16 may communicate with another computer 18 over a wide area network 17, such as the Internet. Software, data, settings, and other information may be sent from computer 18 to personal computer 16 for use with the MPN, and data from the MPN may be sent from personal computer 16 to computer 18.

An MPN may be used for one or more purposes. For example, the MPN may support a global turn on or turn off feature, in which all active devices may be disabled or re-enabled with a single command to a single INC. The MPN may provide clock functions 20, such as providing the current time and date, supporting multiple time zones, providing stopwatch features, and synchronizing other features of the MPN. The MPN may provide communication functions 25, such as communicating with another MPN to support games, competitions, and other types of data transfers, telephone features, paging features, instant messaging, and electronic mail. The MPN may provide entertainment functions 30, such as playing music, recording audio and video media, and games. The MPN may provide personal organization functions 35, such as scheduling appointments, managing contacts, tracking tasks, and maintaining a mobile electronic journal. The MPN may support guidance functions 40, such as showing current position, speed, and elevation, providing route guidance, collecting and annotating position and speed data, and recommending an athletic training route. The MPN may support athletic functions 45, such as supporting a workout plan, supporting workout definition, controlling a workout, communicating with exercise equipment, collecting athletic data, detecting and correcting errors in collected data, estimating secondary data based on collected data, providing competition between users of multiple MPNs, logging lap swim workouts, providing form feedback, and providing an athletic training journal.

The MPN may support physical therapy and medical functions 50, such as measuring range of motion, gait analysis, measuring muscle strength, measuring changes in physical therapy, monitoring a metabolic value, detecting a medical problem, controlling a treatment device, providing emergency communication, storing medical databases, providing an electronic medical journal, and supporting INCs that may be injected, ingested, or implanted. The MPN may provide disabled access 55, such as alternate input devices, alternate output devices, and alternate INC mounting means. The MPN may support travel functions 60, such as language translation, currency conversion, time zone conversion, route guidance, local information, guidebook features, wildlife recognition, a mobile electronic travel journal, weather information, local transit and entertainment schedules, and expense tracking. The MPN may support outdoor functions 65, such as compass direction, geographical location, route guidance, elevation reporting, and weather features. The MPN may support identity functions 70, such as identifying a user to another user or another system, providing exchange of money, providing product discounts, and providing product purchasing. The MPN may support personal security functions 75, such as an audible alert, an alert message to a public safety facility, and storage of emergency information. The MPN may support military functions 80, such as communications, geographical position, route guidance, and weather features. The MPN may support combinations of functions, and its functions may vary over time as INCs are added or removed, as different software or data is downloaded, or as the user's needs change.

Figure 1A:
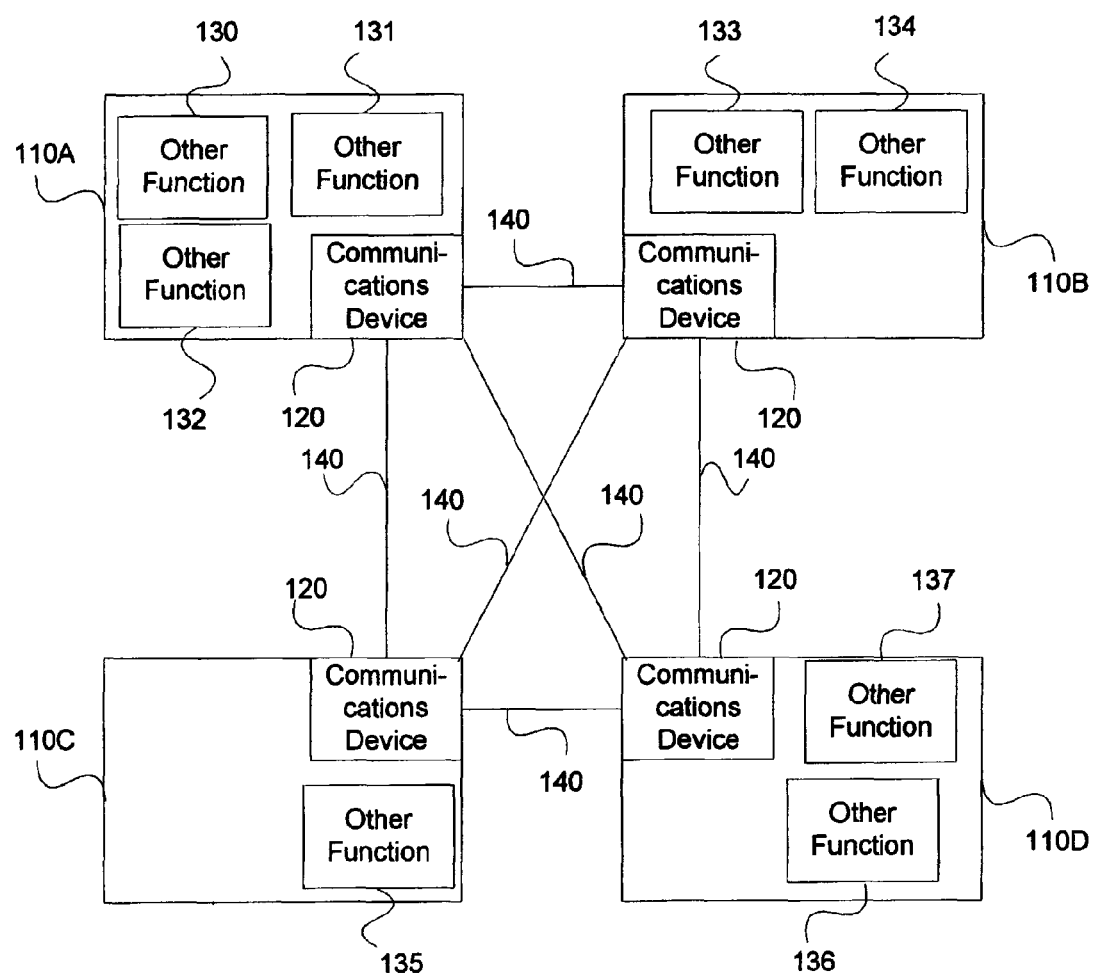
FIGS. 1A and 1B are block diagrams of an illustrative MPN.

FIG. 1A shows a block diagram of illustrative MPN 100A. This MPN includes INCs 110A, 110B, 110C, and 110/d. Each INC includes communication device 120, for communicating with other INCs over wireless communication path 140. Communication device 120 may be, for example, a standard radio frequency wireless transceiver with a range appropriate for a personal network (e.g., between six feet and sixty feet). Communication device 120 may also include hardware and software implementing a standard wireless protocol, such as Bluetooth or IEEE 802.15. An antenna may be included. If desired, transmitter and receiver may be separate devices. Not shown in each INC is a power source.

Each INC also includes one or more other functions 130-137. These other functions may be provided by hardware and/or software incorporated into the INC. The software may be firmware provided with the INC, or it may be downloaded into the INC over communication path 140 or using other means.

Figure 1B:
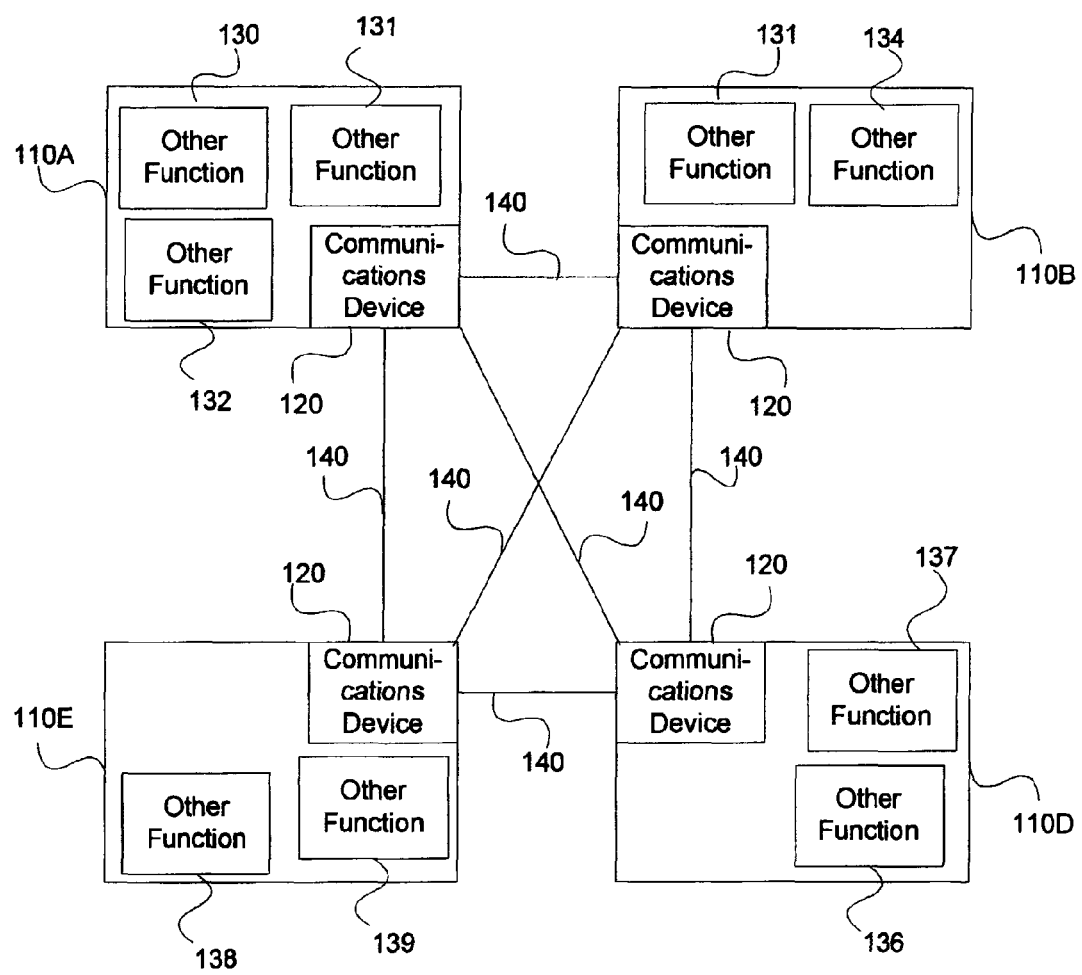

FIG. 1B shows how MPN 100A may be modified to become MPN 100B. In the modified MPN, INC 110C has been removed, and INC 110E has been added. Correspondingly, other function 135 associated with INC 110C is no longer available, and other functions 138 and 139 associated with INC 110E are now available.

Different manufacturers may manufacture INCs. Each manufacturer may be assigned a unique manufacturer identifier, as shown in table 210 of FIG. 2A. Each manufacturer may provide various types of INCs, each of which may be assigned a model identifier by the manufacturer, as shown in table 220 of FIG. 2B. The model identifier may be unique for a specific manufacturer.

There may also be defined a set of device types, as shown in table 230 of FIG. 2C. The device type identifiers may be standard across all manufacturers and models. For example, Model 3 by Manufacturer 2 may have the same device type as Model 7 by Manufacturer 12. Device types may be divided into a range for input devices 234 and a range for output devices 232. It may also have ranges 236 and 238 for manufacturers to use when a standard device type has not yet been assigned. An INC may have multiple device types, if it has multiple functions 130-139 (FIG. 1).

For each device type, there may be a standard set of defined capabilities, which may or may not be supported by any specific INC with that device type. For example, as shown in table 240 of FIG. 2D, device type 257, which may be an audio output INC, may have three standard capabilities, any of which may or may not be supported by any particular audio output INC. Capability 242 may be the ability to output stereo audio. Capability 244 may be the ability to control the output volume of the audio. Capability 246 may specify the number of volume increments supported by a particular INC. These capabilities are merely illustrative.

The manufacturer identifier, model identifier, one or more device types, and any supported device capabilities and values may be stored in read-only memory in the INC, and provided over communication path 140 (FIG. 1), to allow the INC to be identified by another INC.

FIGS. 3A through 3J illustrate an exemplary communications protocol that may be used between INCs in an MPN. The protocol may include a defined set of messages that may be sent from one INC to another. This message protocol may be encapsulated in one or more lower-level protocols, such as Bluetooth or IEEE 801.15. If desired, this protocol may function on different lower-level protocols in different environments.

As shown in FIG. 3A, each message may include message type 301 and error detection/correction fields 302. Message type 301 may indicate to the receiving INC how to process the message. Error detection/correction may include parity, checksums, cyclic redundancy checks (CRCs), or other mechanisms for detecting that a received message has one or more errors, and possibly correcting the error(s).

Identity request message 300 of FIG. 3A may be sent by an INC (such as a control unit or base station) wishing to determine the identity and characteristics of one or more other INCs in the MPN. For example, this message may be broadcast and all other INCs in the MPN may respond. Identity request message 300 may include a unique network identifier 303 common to all INCs in the MPN. It may include a network address 304 of the INC sending the request. Each INC in the MPN may have a network address that is unique among all INCs in the MPN. Identity request message 300 may also include controller identifier 305. This may be an identifier that is unique across all INCs, and it may correspond to the control unit, base station, or other INC that is sending the message.

Component identity message 310 of FIG. 3B may be sent by an INC in response to identity request message 300. It may include network identifier 311 of the INC sending the message. Network identifier 311 may be the same as the network identifier 303 in the requesting message, if both INCs are part of the same MPN. It may be blank if this INC has not yet been assigned to an MPN. It may be different if this INC belongs to a different MPN. If this INC has been assigned to an MPN, component identity message 310 may also include network address 312.

Component identity message 310 may also include information about the type of INC and its capabilities that may be stored in read-only memory in the INC. For example, the message may include component identifier 313, which may be the identifier for this INC that is unique across all INCs. The message may also include manufacturer identifier 314, model identifier 315, one or more device types 316, and capability list 317.

Net address assignment message 320 of FIG. 3C may be sent by a control unit, base station, or other INC to configure a newly detected INC to function within the MPN. It may include controller identifier 305. It may include the new network identifier 321 and network address 322 to be programmed into the INC. It may include component identifier 313 to ensure that the correct INC processes the message. It may also include security code 323 to ensure that unauthorized personnel do not change the network identifier and network address.

On processing net address assignment message 320, the INC may respond with network acknowledgement message 330 of FIG. 3D. This message may repeat component identifier 313, network identifier 321, and network address 322, to inform the controller that the operation was successful. Alternatively, the message may include a field indicating success or failure of the operation, and the reason for failure if it was not successful.

Output data request message 340 of FIG. 3E may be sent to an INC that is capable of outputting. It may include the network identifier 321 and network address 322 of the INC that is to perform the output function. The message may include request serial number 341. This number may be used by the requesting INC and the outputting INC to keep track of multiple pending requests. Output data request message 340 may include device type 316 and capability type 317 to inform an INC that supports multiple output functions how to process the data. Output data request message 340 may also include the data to output 342. The format of this data may depend on the type of INC receiving the data and how it is to be processed.

After processing output data request message 340, the output INC may respond with output acknowledgement message 350 of FIG. 3F. This message may include network identifier 321, network address 322, and request serial number 341 to allow the controller to determine which request this acknowledgement corresponds to. It may also include acknowledgement code 351, which may indicate whether the request was processed correctly, and if not successful may include a reason for the failure.

Input data request message 360 of FIG. 3G may be sent to an INC that is capable of inputting. It may include the network identifier 321 and network address 322 of the INC that is to perform the input function. The message may include request serial number 361. This number may be used by the requesting INC and the inputting INC to keep track of multiple pending requests. Input data request message 360 may include device type 316 and capability type 317 to inform an INC that supports multiple input functions how to process the data.

Figure 3H:
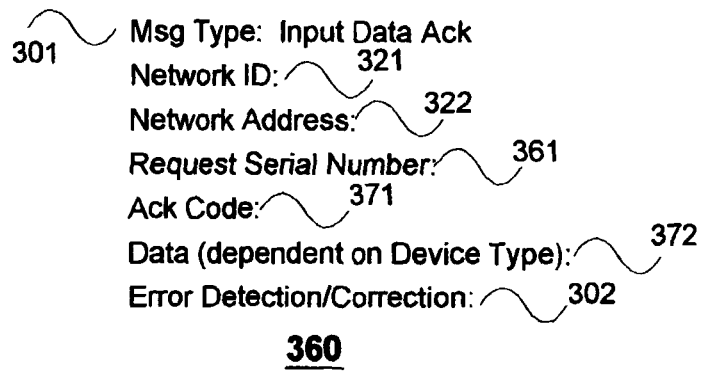

After processing input data request message 360, the input INC may respond with input acknowledgement message 370 of FIG. 3H. This message may include network identifier 321, network address 322, and request serial number 361 to allow the controller to determine which request this acknowledgement corresponds to. It may include acknowledgement code 371, which may indicate whether the request was processed correctly, and if not successful may include a reason for the failure. It may also include the requested data 372, formatted as appropriate for the device and data type.

Figure 3I:
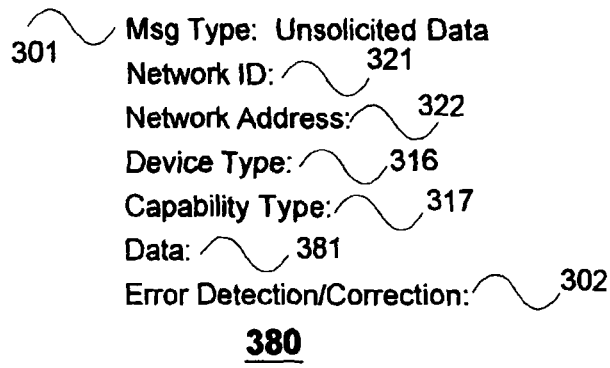

An INC may also send unsolicited data message 380 of FIG. 3I. This message may be sent when the INC has acquired some data for which there may be an ongoing request, or when the INC has entered a state, such as an error condition, that needs to be reported to a control unit, base station, or other INC. This message may include the network identifier 321 and network address 322 of the INC. It may include device type 316 and capability type 317 to allow the receiving INC to know how to process the data. It may also include data 381, formatted as appropriate for the device type and capability type.

Figure 3J:
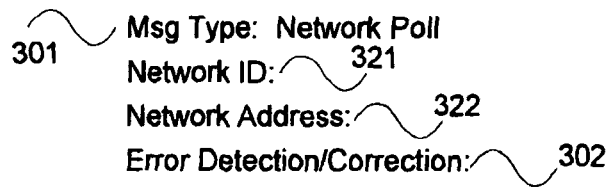

A control unit, base station, or other INC may periodically send out network poll message 390 of FIG. 3J. This message is sent to determine whether an INC is still present on the MPN. It may include network identifier 321 and network address 322 of the INC being polled. The polled INC may respond with component identity message 310 or other suitable message.

The message types shown in FIGS. 3A through 3J are merely illustrative. Other types of messages may be defined and sent between INCs in the MPN. For example, a command may be sent to turn on an INC or to turn off an INC. If desired, a command may be broadcast to all INCs in an MPN, rather than addressed to a specific INC.

Table 400 of FIG. 4 shows an illustrative data structure that may be maintained by a control unit, base station, or other INC to track INCs on the MPN. If desired, multiple INCs in the MPN may maintain such information. Column 410 may hold the network address of each INC. Column 420 may hold the component identifier of each INC. Column 430 may hold the manufacturer identifier of the INC. Column 440 may hold the model identifier of the INC. Column 450 may hold the device type of each INC. Multiple device types may be stored for a single INC if desired. Column 460 may hold a list of capability types for each device type listed for each INC. Column 460 may also hold specific values related to each capability type. Column 470 may hold a flag indicating whether the INC is currently active. For example, if an INC has not recently responded to a network poll message 390 (FIG. 3J), flag 470 may be changed to indicate that the INC is no longer active. If an INC responds to an identity request message 300 (FIG. 3A), the INC may be added to table 400 if it is not already present, and flag 470 may be set indicating that the INC is active.

Table 400 is merely illustrative. Other columns may be included. Other data structures may be used. If desired, this information may be stored in multiple data structures.

Figure 5:
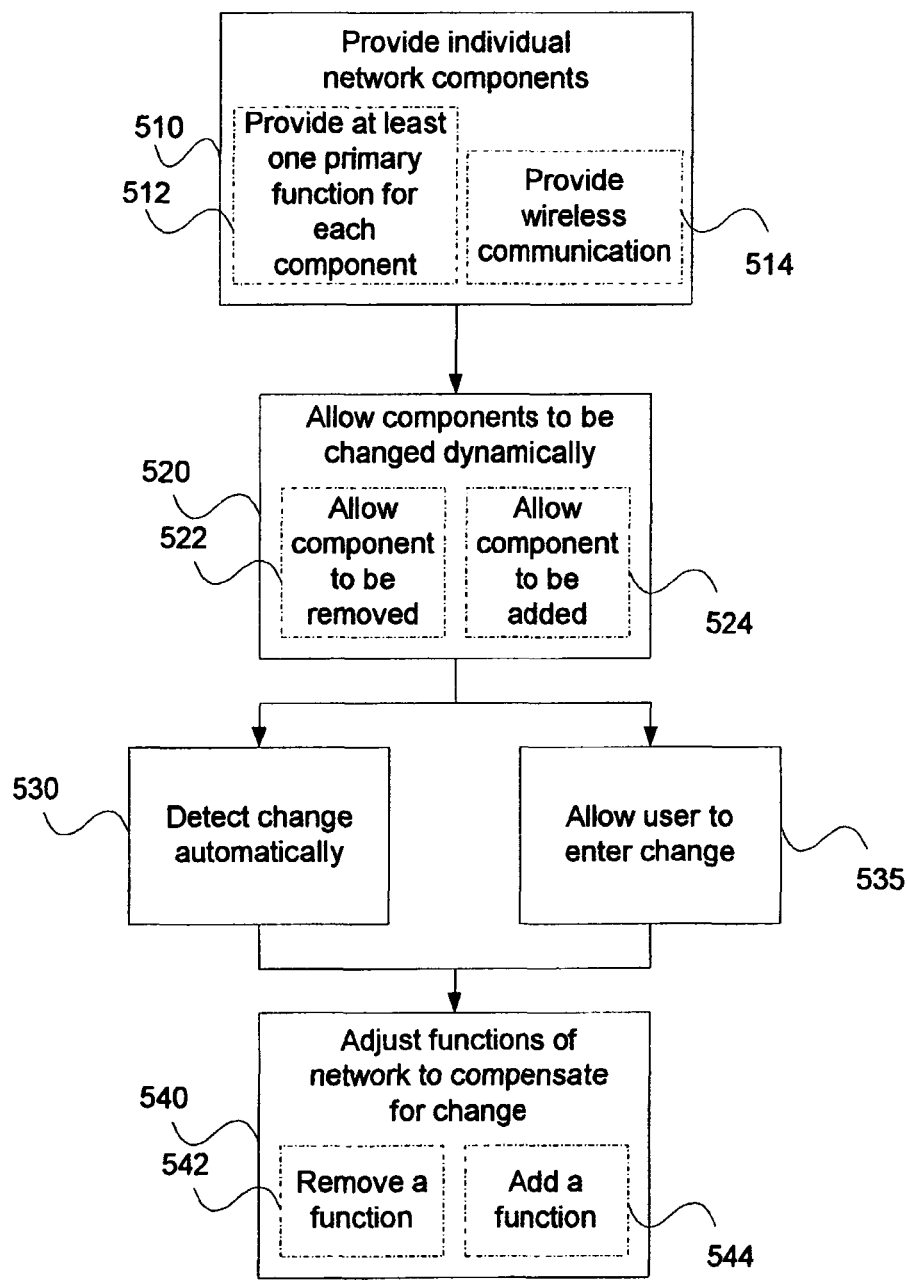
FIG. 5 shows a flow chart of an illustrative process for providing an MPN.

FIG. 5 shows flow chart 500 of an illustrative process for providing an MPN. All steps are optional and may be performed in any suitable order. In step 510, multiple INCs may be provided. This may include substep 514 of providing wireless communications with each INC. It may also include substep 512 of providing at least one primary function for each INC. The primary function may correspond to other function 130-139 (FIGS. 1A and 1B). If desired, an INC may include multiple primary functions. Alternatively, an INC may include a primary function, a secondary function, etc.

In step 520, INCs may be changed dynamically. This may include substep 522 in which an INC may be removed. It may also include substep 524 in which a new INC may be added. In step 530, the change may be detected automatically, for example using messages 300 through 390 of the communications protocol of FIGS. 3A through 3J. The system may alternatively allow a user to enter information about the change in step 535. For example, a user may add or remove an entry for an INC from a configuration screen on a personal computer.

In step 540, the functions of the MPN may be adjusted to compensate for the change. In substep 542, this may include removing a function from the MPN that may have been provided (or partly provided) by the removed INC. In substep 544, this may also include adding a function to the MPN that may be at least partly supported by the new INC.

Figure 6A:
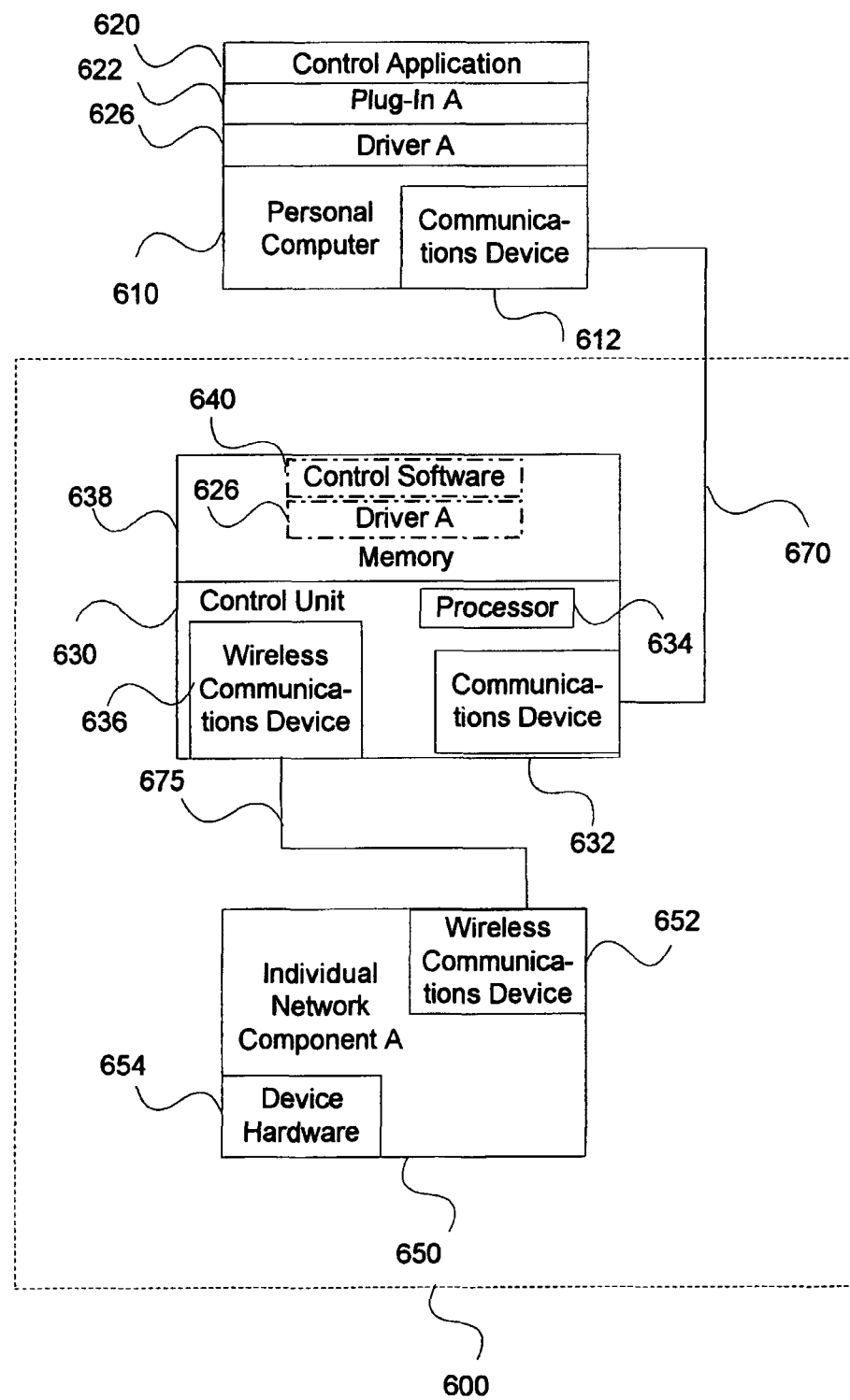
FIGS. 6A and 6B are block diagrams of an illustrative MPN showing how INCs may be added and removed.

FIG. 6A shows illustrative MPN 600 showing how software may be downloaded to control INCs. MPN 600 may interface with personal computer 610 to control downloading and configuration functions.

Personal computer 610 may include control application 620, which may be configured to control downloading to an MPN and configuring various aspects of MPN functions. Control application 620 may support plug-ins for different types of INCs. For example, plug-in A 622 may support downloading code to support INC A 650. Plug-in A 622 may support loading driver A 626, for example from local storage such as a compact disk or over the Internet, as well as downloading driver A 626. It may also support configuring INC A 650, as well as downloading data to and uploading data from INC A 650.

Personal computer 610 may include communications device 612 for communicating with one of the INCs, such as a control unit 630, using communication path 670. Control unit 630 may include communications device 632 for communicating with personal computer 610. Communications device 612, communications device 632, and communication path 670 may be, for example: a docking station and connector; a Universal Serial Bus (USB) port; infrared transmitters and receivers; serial ports; Ethernet connectors; radio frequency (RF) transceivers; or any other suitable communications means. If desired, communications may be performed wirelessly, and communications device 632 may be the same as wireless communications device 636 used to communicate between control unit 630 and other INCs.

One of the INCs may be a control unit 630. Control unit 630 may include processor 634 and memory 638, as well as communications device 632 for communicating with personal computer 610, and wireless communications device 636 for communicating with other INCs over wireless communication path 675. Memory 638 may hold control software 640 which may include firmware, operating system, boot software, communication software, and the like. Memory 638 may also hold downloaded driver A 626 for controlling INC A 650.

MPN 600 may also include INC A 650. This component may include wireless communications device 652 for communicating with control unit 630 and other INCs over wireless communication path 675. INC A 650 may also include device hardware and firmware 654 for performing one or more primary functions of the INC.

In operation, a user may run control application 620 on personal computer 610. The user may load and run plug-in A 622 to configure MPN 600 to function with INC 650. The user may load driver A 626 and download it to control unit 630. Control unit 630 may subsequently use downloaded driver A 626 to control the functions of INC A 650. The user may also use plug-in A 622 to configure aspects of INC A 650, to download data to the INC, to upload data that may have been collected by the INC, or to perform other functions related to INC A 650.

Figure 6B:
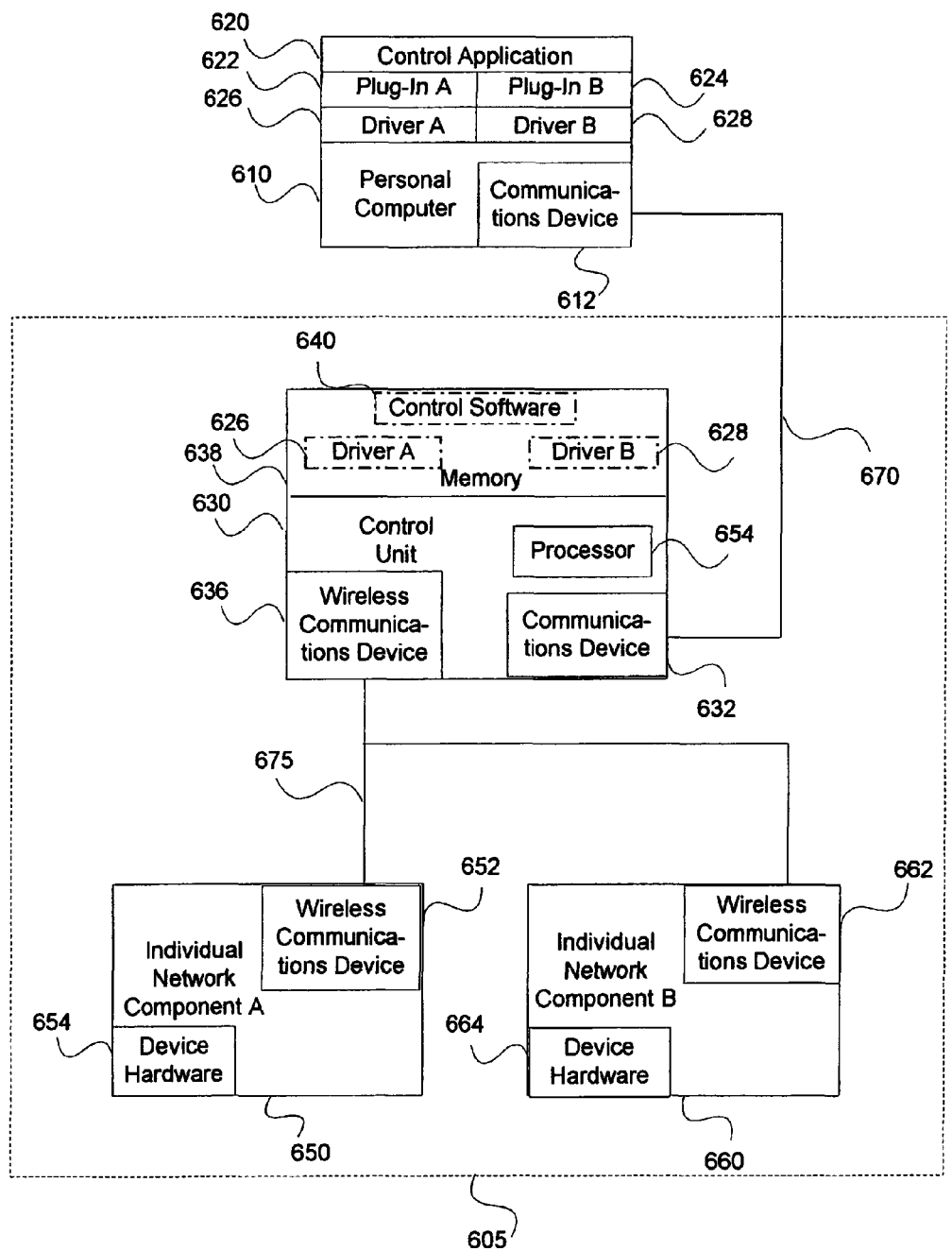

In FIG. 6B, INC B 660 has been added to MPN, creating new MPN configuration 605. INC B 660 may include wireless communications device 662 for communicating with control unit 630 and other INCs over wireless communication path 675. It may also include device hardware and firmware 664 for performing one or more primary functions associated with INC B 660.

Plug-in B 624 may be loaded into control application 620 on personal computer 610, for controlling aspects of INC B 660. Driver B 628 may be loaded into personal computer 610 and downloaded into control unit 630 for subsequently controlling INC B 660.

Although FIGS. 6A and 6B show drivers being downloaded into a control unit, software may alternatively be downloaded into any of the INCs, for example, if control unit 630 is not present.

Figure 7:
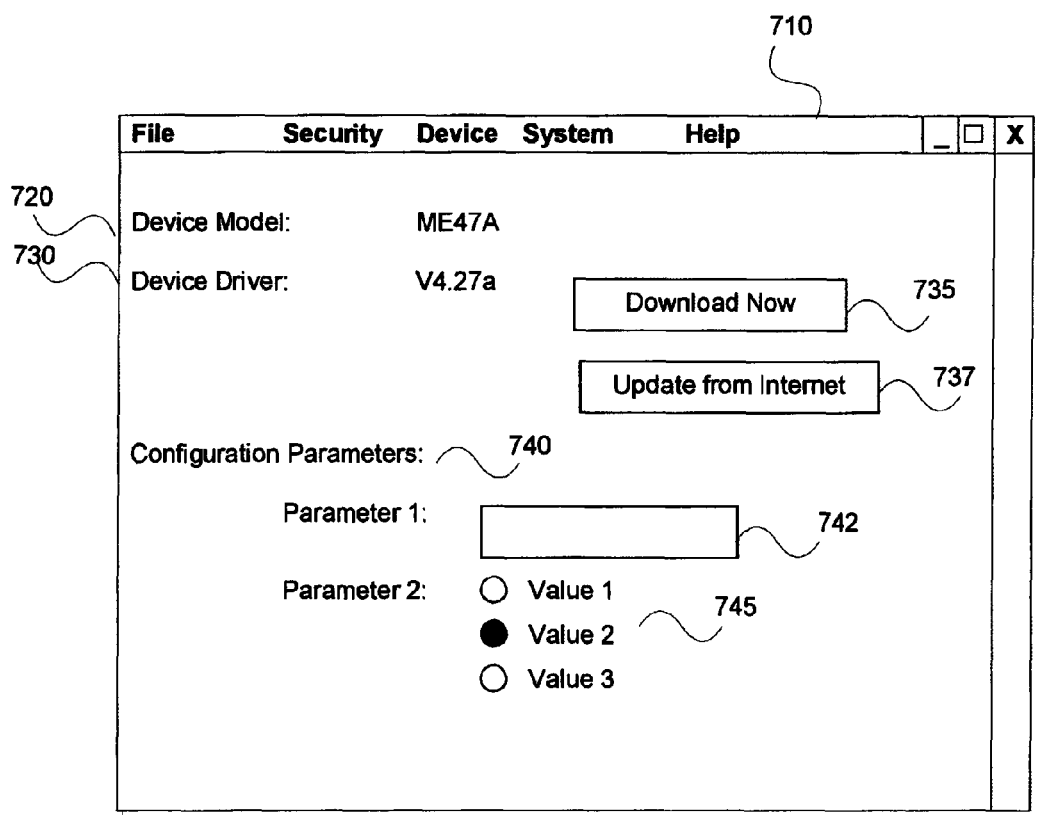
FIG. 7 is an illustrative display screen that may be used in configuring an INC of the MPN.

FIG. 7 shows illustrative screen 700 of MPN 600 (FIG. 6A) that may be displayed by control application 620 and plug-in A 622 on personal computer 610. Menu bar 710 may allow the user to access various application functions, such as file functions, security functions, device functions, system functions, help functions, and the like. Item 720 may display information about the INC, such as the name of the manufacturer, the model number, capabilities, and other suitable information. Item 730 may display the version number of the device plug-in currently loaded on personal computer 610. Button 735 may allow the user to download the selected driver to control unit 630 or other INC. Button 737 may allow the user to load a more recent driver from the Internet. Region 740 may allow the user to set various configuration parameters associated with the INC. For example, region 742 may allow the user to enter text for a first parameter. Selection 745 may allow the user to select from a set of options for a second parameter. This screen is purely illustrative and may be configured and designed in any suitable manner.

Figure 8:
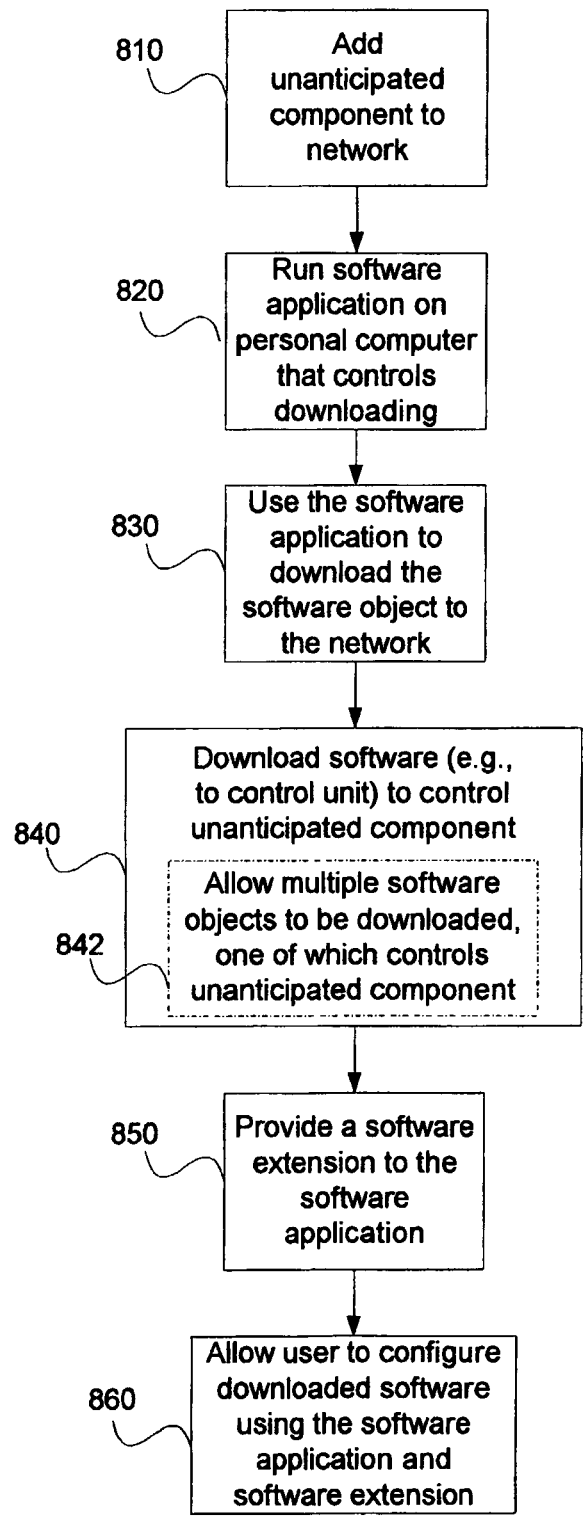
FIG. 8 is a flow chart of an illustrative process showing how an unanticipated INC may be added to an MPN.

FIG. 8 shows flow chart 800 of an illustrative process to allow an unanticipated INC to be added to the MPN. For example, after a user has several INCs of an MPN, a new INC with a new capability may be manufactured. The user does not need to discard any existing INCs; they can continue to be used just as they have been. The unanticipated INC can be added to the MPN and the capabilities of the MPN will be expanded to encompass the capabilities of the new INC.

All steps are optional and may be performed in any suitable order. In step 810, the unanticipated INC may be added to the MPN. The system may detect the INC using an identity request message 300 (FIG. 3A). In step 820, a software application may be run, for example on a personal computer, which controls downloading software objects to INCs. In step 830, that application may be used to download the specific software object to control the unanticipated INC. In step 840, software may be downloaded to control the unanticipated INC. The software may be downloaded, for example, to a control unit. Alternatively, the software may be downloaded to the unanticipated INC itself. In substep 842, multiple software objects may be downloaded, one of which may control the unanticipated INC. Other software objects may be used to control other INCs, or to perform other MPN functions. In step 850, a software extension, such as a plug-in, may be provided to the software application. In step 860, the user may be allowed to configure the new INC and the downloaded software object, using the software application and the software extension.

Figure 9:
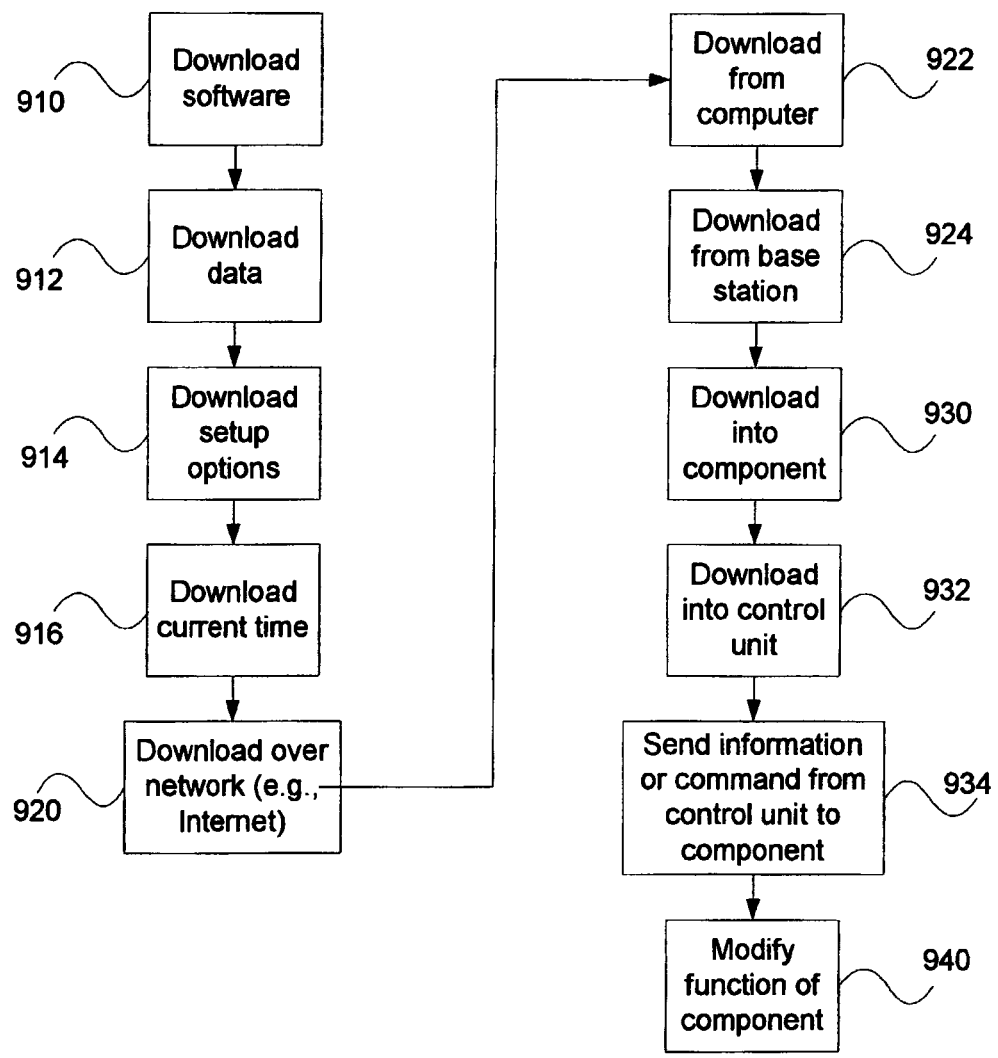
FIG. 9 is a flow chart of an illustrative process showing how data may be downloaded to an INC of an MPN.

Flow chart 900 of FIG. 9 shows an illustrative process for downloading data to control an INC. All steps are optional and may be performed in any suitable order. In step 910, software may be downloaded. In step 912, data may be downloaded. In step 914, setup options may be downloaded. In step 916, the current time may be downloaded. If desired, other suitable types of data may be downloaded as well.

In step 920, data may be downloaded over a network, such as the Internet. For example, software or other data may be downloaded from an Internet site into a personal computer. In step 922, data may be downloaded from a computer, such as a personal computer. In step 924, data may be downloaded from a base station. A base station may be a stationary device that communicates with one or more INCs. The base station may be independent, or it may be connected to a personal computer. In step 930, the data may be downloaded into the INC to be controlled. In step 932, the data may be downloaded into a control unit. The control unit may be an INC configured with a processor and memory to control aspects of other INCs in the MPN. The control unit may send information or commands to the INC in step 934. In step 940, the downloaded data may be used to modify one or more functions of the INC.

Software and other data may also be downloaded, for example into a control unit, to coordinate the functions of multiple INCs.

Figure 10:
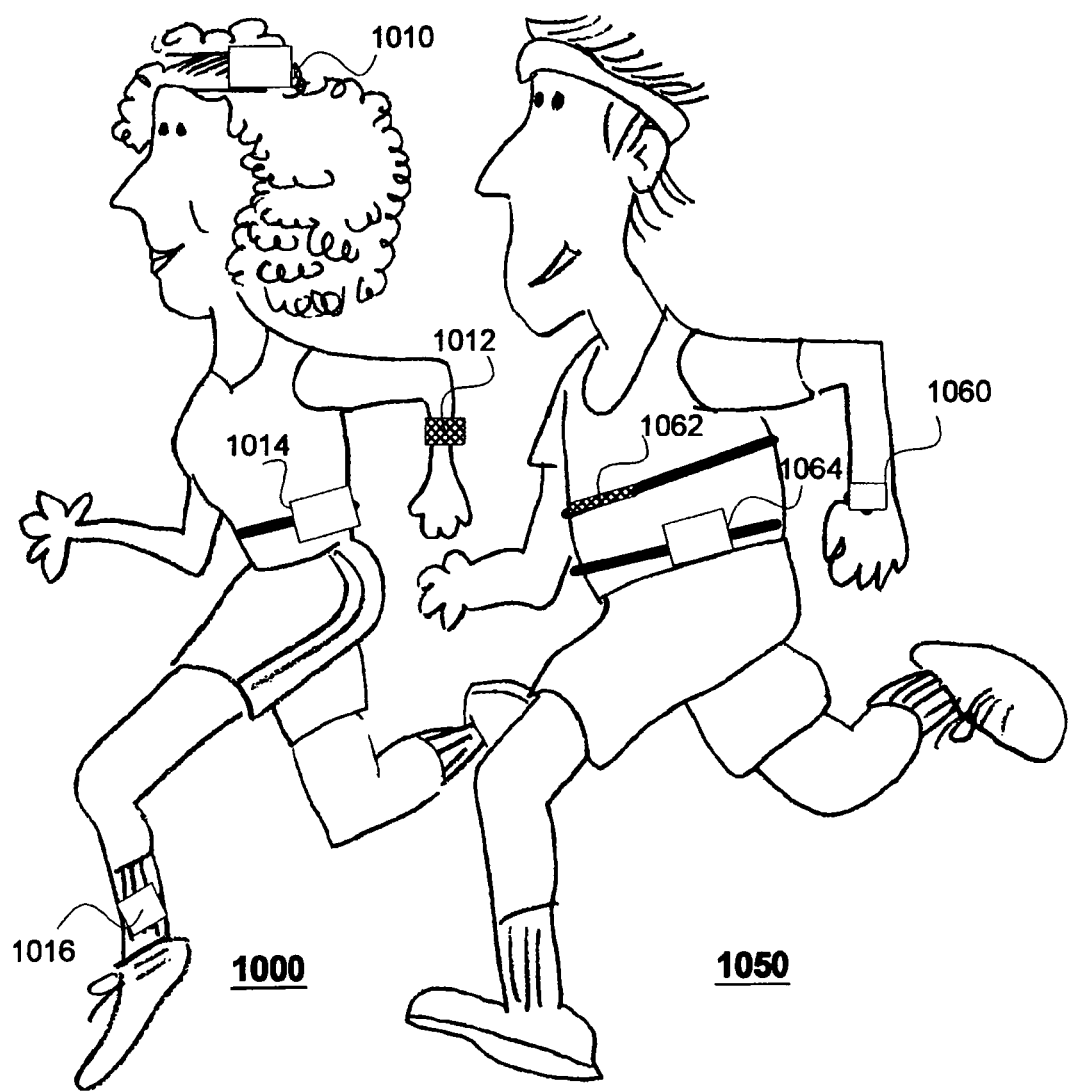
FIG. 10 is an illustration showing how two illustrative MPNs may interact.

FIG. 10 shows how two MPNs 1000 and 1050 may interact. First MPN 1000 may include audio output INC 1010, display INC 1012, control unit 1014, and accelerometer 1016. Second MPN 1050 may include display 1060, heart rate sensor 1062, and control unit 1064. Any of the INCs of either MPN may send a message intended for one or more INCs of the same MPN. The INCs of the other MPN may need to ignore the message. For example, control unit 1014 may send data to display 1012 to be displayed. Display 1060 will ignore the message, because it did not originate within second MPN 1050. Similarly, heart rate monitor 1062 may send heart rate data to control unit 1064 for processing. Control unit 1014 will ignore the data, as it did not originate within first MPN 1000. The configuration of these two MPNs is merely illustrative, and all INCs are optional.

Figure 11:
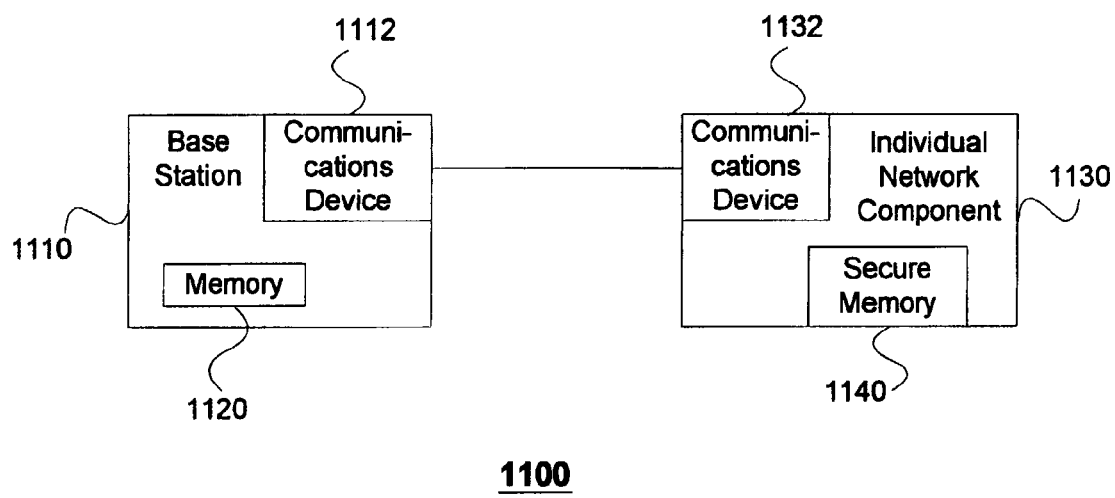
FIG. 11 is a block diagram of an illustrative MPN showing how an INC may be programmed with a common network identifier.

FIG. 11 shows illustrative partial MPN 1100, illustrating how an INC 1130 may be programmed with a common network identifier using a base station 1110. Base station 1110 may be a personal computer, a card installed in a personal computer, a docking station connected to a personal computer over a connection such as USB, a standalone device, or any other suitable configuration. Base station 1110 may include memory 1120, which may be random access memory, a hard disk, or other suitable memory. Base station 1110 may also include communications device 1112, which may be a wireless communications device similar to the communications device in each of the other INCs, or may be any other wired or wireless connection.

Memory 1120 may be used to hold a common network identifier to be used within all INCs of a single MPN. It may also be used to hold information about the various INCs that have been configured using base station 1110.

INC 1130 may be a new INC, which has not yet been assigned a network identifier. Alternatively, it may already have been assigned a network identifier, which may be stored in secure memory 1140. Secure memory 1140 may be memory that can only be read or written by INC 1130, and cannot be accessed without a security code.

A user of base station 1110 may indicate that INC 1130 is to be programmed with the base station's network identifier. The user may make this indication by, for example, bringing INC 1130 into proximity of base station 1110, making a physical connection between base station 1110 and INC 1130, pressing a button on base station 1110, making a menu selection on base station 1110 (for example, if base station 1110 is a personal computer or is connected to a personal computer), or by taking other suitable actions. The user may also be required to enter a personal code, or to invoke other security measures to ensure his or her proper identity. Base station 1110 may then send a message to INC 1130 with the new common network identifier and the proper security code. If INC 1130 is a new INC, it may store the security code and the network identifier in secure memory 1140. If it has previously been programmed with a network identifier, it may compare its stored security code with the security code it just received, and if they match may store the new network identifier.

If desired, INC 1130 may also incorporate an algorithm to prevent a large number of consecutive attempts at changing the network identifier. For example, if INC 1130 receives more than three unsuccessful attempts to change the network identifier within a ten-minute period, it may lock out any further attempts for the next thirty minutes.

Using this configuration a user may assign any new INC into his or her MPN. A user may also move an INC from one MPN to another, but only with the authorization of the original owner of the INC.

Figure 12:
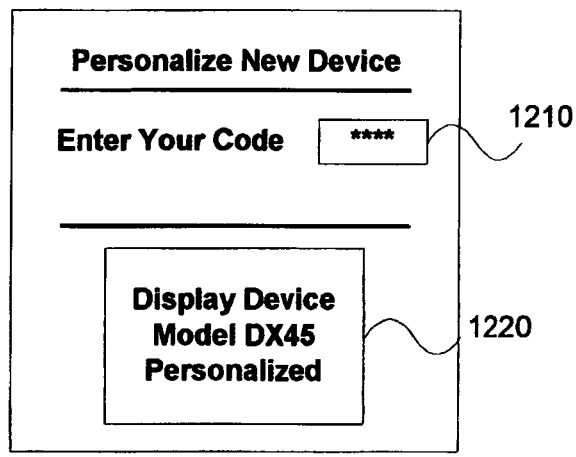
FIGS. 12 and 13 are illustrative display screens that may be used in the programming of a common network identifier into an INC of an MPN.

FIG. 12 shows illustrative screen 1200 that may be shown by base station 1110 (FIG. 11) or personal computer to allow an INC 1130 to be personalized with the user's network identifier. The user may be allowed to enter a security code in screen region 1210. When the security code has been verified, and the security code and network identifier have been successfully sent to the INC 1130, the system may display overlay 1220.

Figure 13:
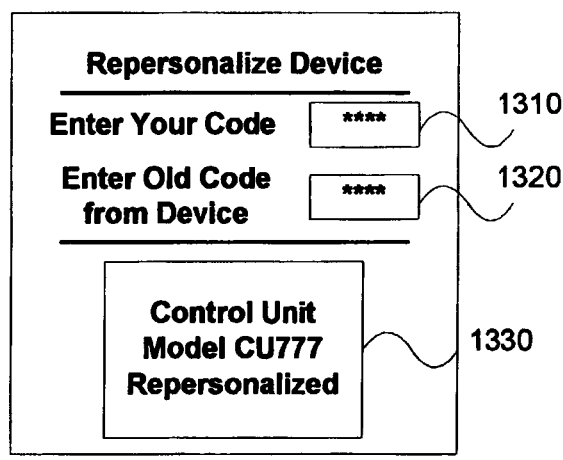

FIG. 13 shows illustrative screen 1300 that may be shown by base station 1110 (FIG. 11) or personal computer to allow INC 1130 to be programmed with a different network identifier when it already has a network identifier stored in secure memory 1140. The user may be prompted for a security code in screen region 1310, as well as the old security code used to program INC 1130 with the previous network identifier in region 1320. When the security codes have been verified, and the security code and network identifier have been successfully sent to the INC 1130, the system may display overlay 1330.

These screens are purely illustrative and may be configured and designed in any suitable manner.

Figure 14:
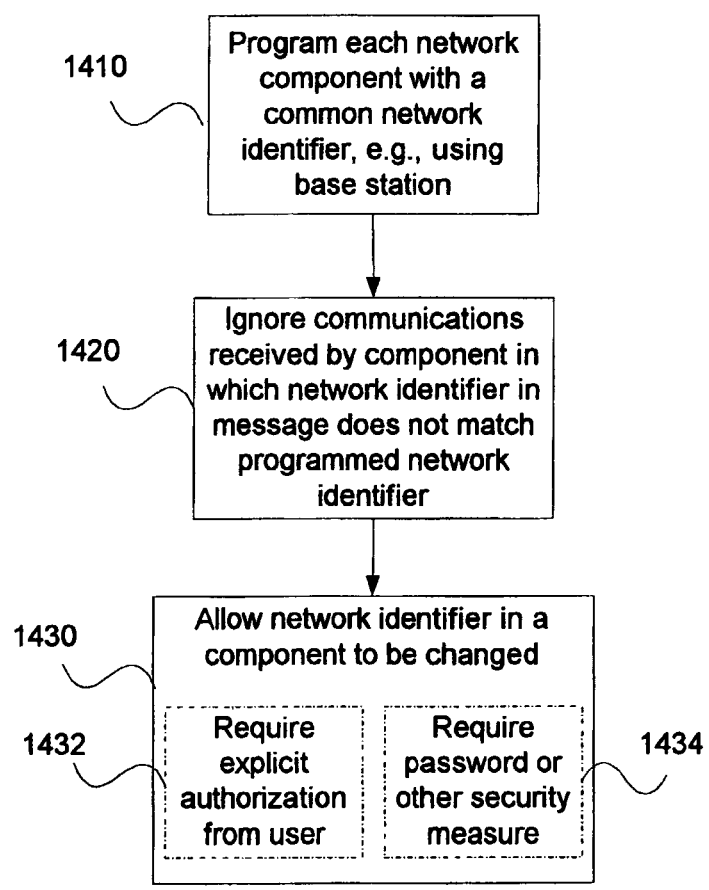
FIG. 14 is a flow chart of an illustrative process for using a common network identifier within an MPN.

FIG. 14 shows flow chart 1400 of an illustrative process to use a common network identifier among INCs in an MPN. All steps are optional and may be performed in any suitable order. In step 1410, each INC may be programmed with a common network identifier. This may be done with a base station, personal computer, or other device. The programming may use appropriate security to ensure that an unauthorized user cannot reprogram the network identifier in any INC.

In step 1420, any messages sent from a first INC in the MPN to a second INC in the same MPN may contain the network identifier stored within the first INC. The second INC, on receiving the message, may compare the network identifier within the message to the network identifier stored in the secure memory in the second INC. If the two identifiers are different, the message may be ignored. If the two identifiers are the same, the second INC may assume that the message originated from an INC within the same MPN, and may process the message if appropriate.

In step 1430, an INC may be moved from one MPN to another. This may involve changing the network identifier stored in the INC to a new value. To do this may require explicit authorization from a user, in substep 1432. It may also require the entry of a password or code or another security measure to ensure that the user is authorized to make the change, in substep 1434.

Figure 15:
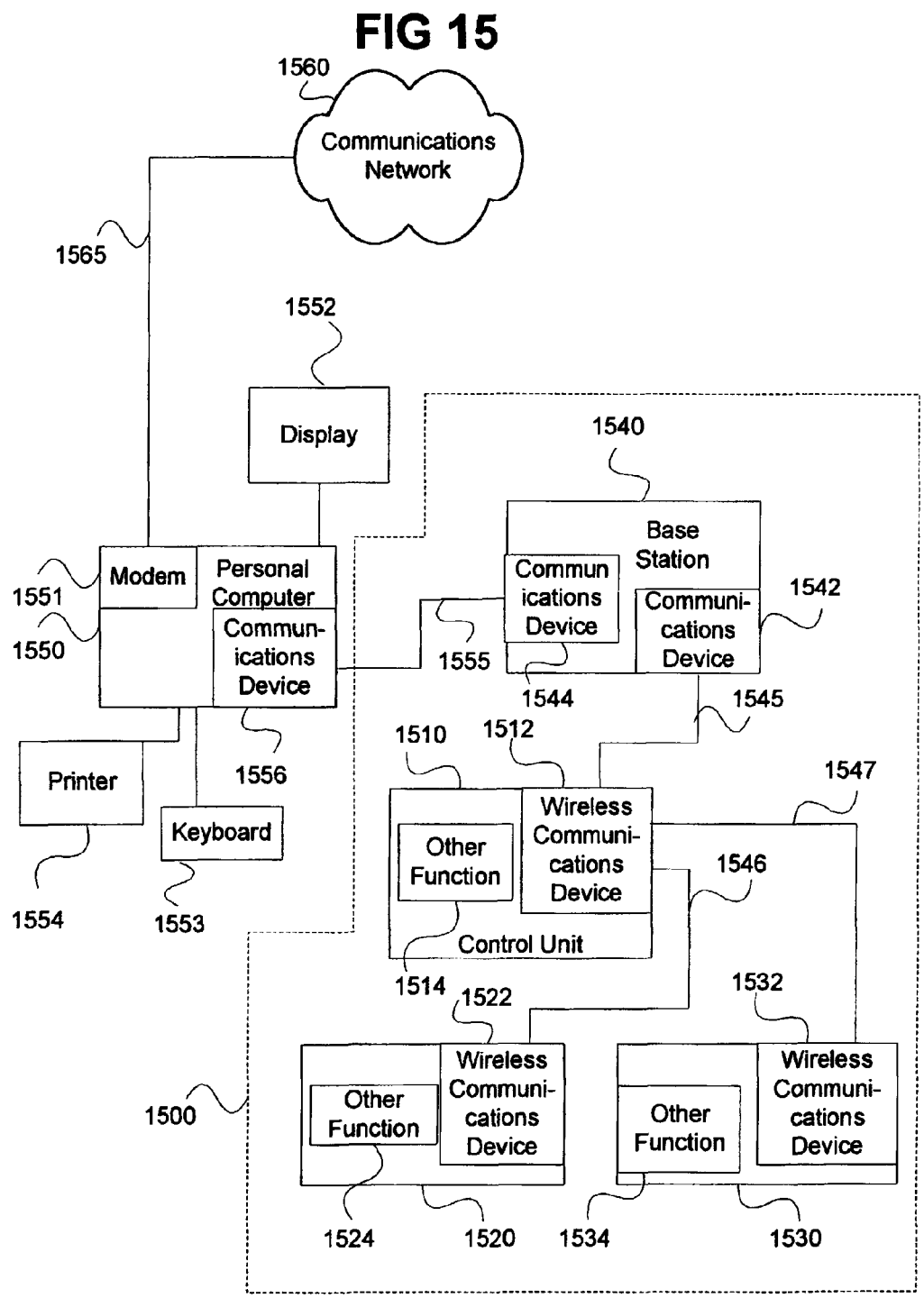
FIG. 15 is a block diagram showing how an MPN may communicate with a base station and a personal computer.

FIG. 15 shows extended MPN 1500. This block diagram shows how an MPN may interface with other systems. MPN 1500 may include control unit 1510. The use of control unit 1510 is merely illustrative. Any other suitable INC may be used. Control unit 1510 may include wireless communications device 1512 for communicating over wireless communications paths 1546 and 1547 with other INCs within the MPN. Control unit 1510 may also include one or more other functions 1514, which may include a processor and memory for controlling other INCs in the MPN. MPN 1500 may also include INCs 1520 and 1530. These INCs may include wireless communications devices 1522 and 1532, respectively. Each may include one or more other functions 1524 and 1534, respectively.

Control unit 1510, and other INCs, may communicate over communication path 1545 with base station 1540. As shown, communications path 1545 may be a wireless communications path. Alternatively, base station 1540 may communication with one or more INCs using any suitable wired path. Base station 1540 may include communications device 1542 for communicating with control unit 1510 and other INCs, and a second communications device 1544 for communicating over communication path 1555 with personal computer 1550. If desired, communications device 1542 and communications device 1544 may be the same device. Communications device 1544 may communicate with communications device 1556 on personal computer 1550 using any suitable physical and logical protocol. This may include a serial port, USB, infrared, radio frequency, a docking station, or other means.

In addition to communications device 1556, personal computer 1550 may have display 1552, keyboard 1553, mouse, printer 1554, and modem 1551. Modem 1551 may be any suitable type of connection to a wide area network, and may include a telephone modem, a digital subscriber line modem, a cable modem, an Ethernet hub, and Ethernet router, or other suitable equipment. Personal computer 1550 may connect using path 1565 to wide area communications network 1560, which may be the Internet. Personal computer 1550 may be configured to send or receive information from another computer using wide area network 1560.

Figure 16:
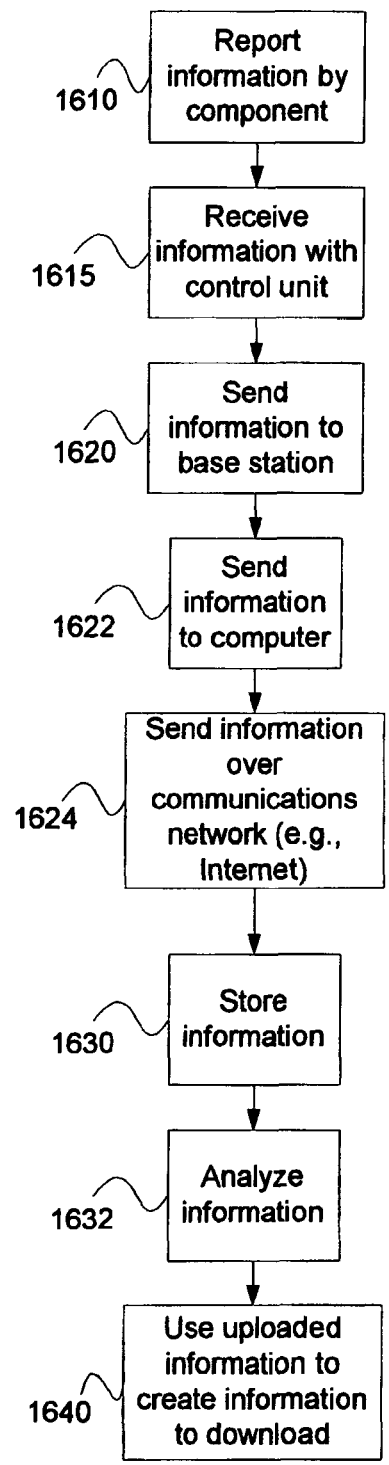
FIG. 16 is a flow chart of an illustrative process for uploading information from an INC of an MPN.

FIG. 16 shows flow chart 1600 of an illustrative process for uploading information from an INC. All steps are optional and may be performed in any suitable order. In step 1610, information may be reported by an INC. That information may have been collected by the INC, for example using a sensor within the INC. Alternatively, the information may have been generated by the INC. In step 1615, the information may be received by a control unit, which may be another INC within the same MPN. The information may be sent from the control unit, or any other suitable INC, to a base station in step 1620, and to a personal computer in step 1622. If desired, any of the control unit, base station, and personal computer may be omitted, or their functions may be combined in any suitable manner. If desired, the collected information may be sent over a communications network, such as the Internet, in step 1624, and received by another computer.

In step 1630, the information may be stored, for example by the base station, the personal computer, or by another computer accessed over the communications network. The information may be displayed for a user. The information may be analyzed, in step 1632. In step 1640, the uploaded information may be used, at least in part, to create information to download. This derived information may be downloaded to the same INC that originated the uploaded data, to the control unit, or to another INC in the MPN. Refer to the description of FIG. 9 above for steps related to downloading of data.

FIG. 17 shows a more detailed block diagram 1700 of a portion of MPN 1500 of FIG. 15. Base station 1540, control unit 1510, and INC 1520 are shown. It can be seen that control unit 1510 includes processor 1742 and memory 1744. INC 1720, which is an audio output INC, is also shown. Audio output INC 1720 includes wireless communications device 1722 for communicating over wireless communication path 1730 with control unit 1510 and other INCs. Audio output INC 1720 also includes digital-to-analog converter 1724, for converting digital audio data to an analog audio signal, and speaker 1726 for playing the analog audio signal audibly. The INCs shown are merely illustrative.

FIG. 18 shows flow chart 1800 of illustrative process for using an INC that is a control unit in an MPN. All steps are optional and may be performed in any suitable order. In step 1810, the control unit may be configured to be worn. It may be attached, for example, to a waistband, a wristband, an armband, or other worn in another suitable location. If desired, the control unit may alternatively be carried, mounted on personal equipment, or otherwise associated with the user. Information may be downloaded to the control unit, for example from a base station or personal computer. In step 1820, software may be downloaded to the control unit. In step 1822, data may be downloaded to the control unit. In step 1824, configuration parameters may be downloaded to the control unit. In step 1826, the date and/or time may be downloaded to the control unit.

In step 1830, data may be sent from the control unit to another INC within the MPN. For example, any of the data sent to the control unit in steps 1820, 1822, 1824, or 1826 may be sent to another INC. The control unit may also send information to another INC that is derived from downloaded data, from data collected from other INCs, or other suitable data.

In step 1832, the control unit may control a function of another INC. The control unit may accomplish this by sending one or more messages to the other INC, and possibly by receiving messages in response. The control may be based on downloaded software, downloaded data, downloaded parameters, time, or any derived data.

In step 1834, the control unit may collect data from another INC. The control unit may request the data by sending a message to the other INC. Alternatively, the other INC may send the data unsolicited. The data may be a single item, or it may consist of several samples collected over a period of time. The control unit may process the data, combine data samples, combine data from multiple INCs, or otherwise modify the collected data. In step 1850, data may be uploaded from the control unit, for example to a base station or personal computer. This may included collected data, derived data, or data generated by the control unit.

In step 1860, functions of the control unit may be integrated with other functions. For example, the control unit may also have a display or a user input device. The control unit may also include clock functions, in step 1840, and it may track time to coordinate functions of the MPN, to schedule actions, and to tag collected data. The control unit may treat the other integrated functions as though they were in another INC, without the need to send and receive wireless messages to communicate with them.

In step 1870, the control unit may support multiple other INCs with multiple functions. Some may be input INCs, some may be output INCs, and some may be a combination. Some INCs may be wholly contained without external input or output, such as a storage INC or a data processing INC. The control unit may maintain a table of active INCs, and communicate with the other INCs as required. The control unit may automatically detect when an INC is added to the MPN or removed from the MPN. When an INC is added to the MPN, the control unit may ignore it until it receives downloaded software or data related to the new INC. Alternatively, it may automatically make use of the capabilities of the new INC. When a INC is removed from the MPN, the control unit may wait for a period of time to make sure that communications with the INC were not temporarily lost. The control unit may continue functioning with reduced functions. In addition or alternatively it may generate an alert to the user.

If desired, an MPN need not include a control unit. Some or all of the functions of a control unit may be incorporated into one or more of the other INCs. If desired, each INC may provide its own control. If desired, software, data, configuration settings, and other information may be downloaded directly into some or all of the INCs by a base station or personal computer prior to mobile use.

FIG. 19 shows flow chart 1900 of an illustrative process for providing personal INCs in an MPN. All steps are optional and may be performed in any suitable order. In step 1910, the user may wear an INC. For example, in substep 1912, the user may wear an INC on a hand, wrist, arm, leg, foot, waist, head, or other suitable part of the body. The INC may be worn on an article of clothing in substep 1914, such as a glove, a partial glove, a wristband, an armband, a hat, a headband, a shirt, a waistband, a shoe, or other suitable item of clothing.

In step 1920, the INC may be mounted on personal equipment that may be used by the user. For example, in substep 1922, the INC may be mounted on a bicycle, a car, a piece of exercise equipment, or other suitable personal equipment. The INC may provide an input or output function associated with the personal equipment.

In step 1930, the MPN may also include a relatively stationary INC, such as a base station or personal computer. The base station or personal computer may function as part of the MPN while the user is in proximity to the device. The communications connection with the stationary device may be the same wireless network used to communicate between the INCs, or it may be another type of connection. The other type of communication may be a docking station or other fixed method, USB or other wired method, or infrared or other wireless method. The stationary device may only support communications with one of the mobile INCs, such as a control unit, or it may support communications with several or substantially all of the INCs.

Figure 20A:
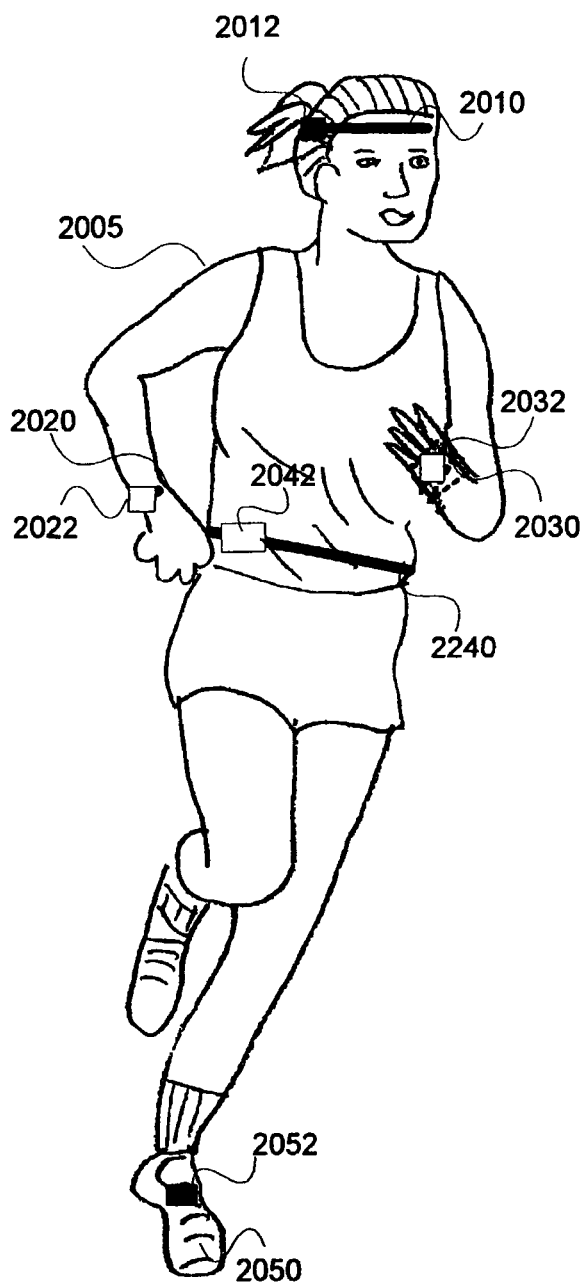
FIGS. 20A through 20C show illustrative mounting means for INCs in an MPN.
Figure 20B:
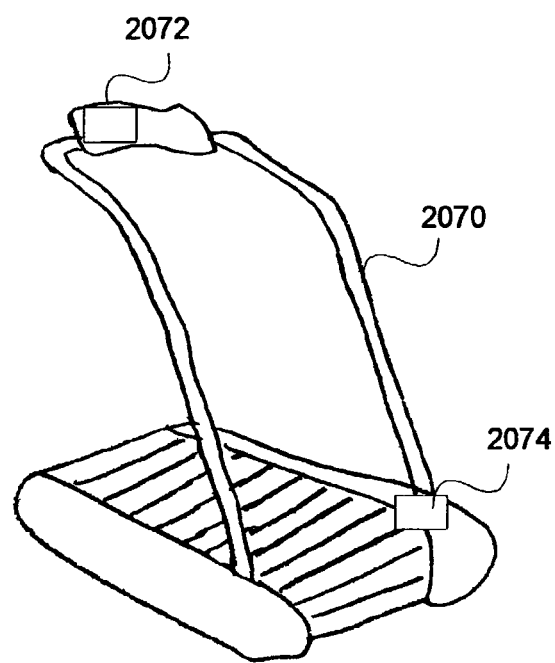
Figure 20C:
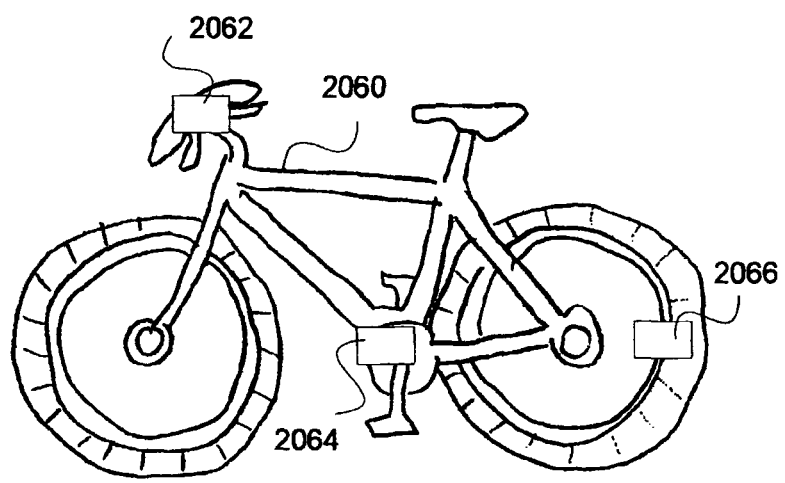

FIGS. 20A through 20C show several illustrative methods for mounting INCs. For example, FIG. 20A shows some options for allowing a user 2005 to wear INCs. INC 2012, which may be an audio output INC, may be mounted on headband 2010. INC 2022, which may be a display, may be mounted on wristband 2020. INC 2032, which may be a user control, may be mounted on glove 2030. INC 2042, which may be a control unit, may be mounted on waistband 2040. INC 2052, which may be an accelerometer, may be mounted on shoe 2050. These INCs and options for wearing are merely illustrative. Other options may be used if desired. The user 2005 may decide what functions will be provided simply by choosing to wear a specific set of INCs at any given time.

FIG. 20B shows some options for mounting INCs on a piece of exercise equipment 2070. For example, INC 2074 may be an input sensor to read data associated with the exercise equipment, or may be an output INC to control aspects of the exercise equipment. INC 2072 may be a display INC, or may be configured to communicate with a processor embedded within the exercise equipment. These INCs may function as part of the MPN when the user is on or near the device.

FIG. 20C shows options for mounting INCs on a bicycle 2060. For example, INC 2062 may be a display INC. INC 2064 may be a sensor for measuring pedaling cadence. INC 2066 may be a sensor for measuring wheel speed. These INCs may function as part of the MPN when the user is on or near the bicycle.

The options shown in FIGS. 20A through 20C are merely illustrative. Other types of INCs, other types of mounting, and other types of personal equipment may be supported if desired.

FIG. 21 shows flow chart 2100 of an illustrative process for using an INC mounted on a piece of exercise equipment. All steps are optional and may be performed in any suitable order. In step 2110, the INC may be mounted on a piece of exercise equipment. In substep 2112, the INC may be mounted on a bicycle. The INC may function as part of the user's MPN when the user is near or on the exercise equipment. In step 2120, control commands may be sent to the INC mounted on the exercise equipment. The INC may control the function of the exercise equipment directly, or it may send a command to the exercise equipment, for example using a serial port or radio frequency transmitter. As shown in substep 2122, the command may be to control the difficulty of the exercise, such as by changing a resistance setting, a speed setting, a slope setting, or the like. The control command may also be to a display INC or other user output INC mounted on the exercise equipment. In step 2130, data may be collected from the INC. The INC may measure the collected data directly, or it may retrieve the data from the exercise equipment, for example using a serial port or radio frequency receiver. The data may be, for example, pedal speed of a bicycle in substep 2132 or wheel speed of a bicycle in substep 2134. In substep 2136, other performance information may be collected from the exercise equipment, such as speed, power, or heart rate. The data may be collected, for example, using a sensor attached to the exercise equipment or bicycle, or by communicating with a processor embedded in the exercise equipment. The collected data may be stored, it may be displayed, and it may be used to modify a workout. If desired, the collected data may be uploaded to a base station or personal computer, where it may be stored, displayed, or analyzed.

An INC may function as a display INC. A display INC may be worn or carried by the user or mounted on a piece of personal equipment. A display INC may be combined with other functions, such as user controls, audio output, or a control unit, or the INC may function solely as a display INC. A single display INC may be used to display different types of information at different times, depending on the other INCs in the MPN. The display INC may not need to be changed to provide new types of information display. Rather this may be accomplished by adding a new INC with a new function, downloading new software into the display INC or a control unit, or otherwise modifying other parts of the MPN. In addition, the user may switch to a different style of display INC without changing any other part of the MPN, and maintain all preexisting MPN settings and functions.

The display INC may include a wireless communications device for communicating with other INCs in the MPN. For example, the display INC may receive display commands and data from one of the other INCs, such as a control unit. The display INC may incorporate any appropriate display technology, such as liquid crystal displays (LCDs), light emitting diodes (LEDs), etc. It may also include means for mounting the INC to the user's body. If desired, a display INC may accept different types of input for display, such as text, bitmap or other graphics, video data, instructions to turn on or off specific visual indicators, instructions to turn on or off various display modes, or other suitable display items and instructions.

Figure 22A:
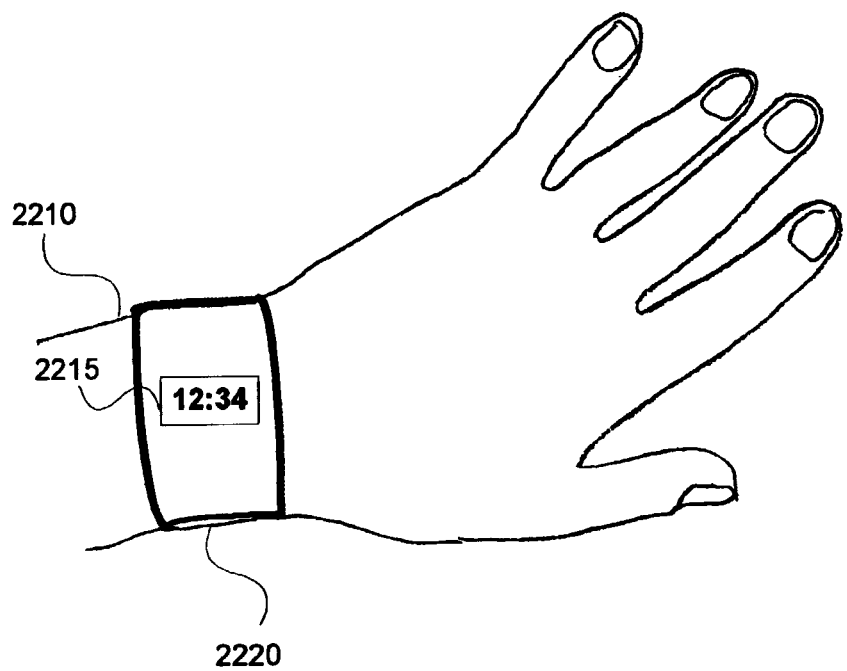
FIGS. 22A through 22C show illustrative means for mounting a display device which is an INC in an MPN.
Figure 22B:
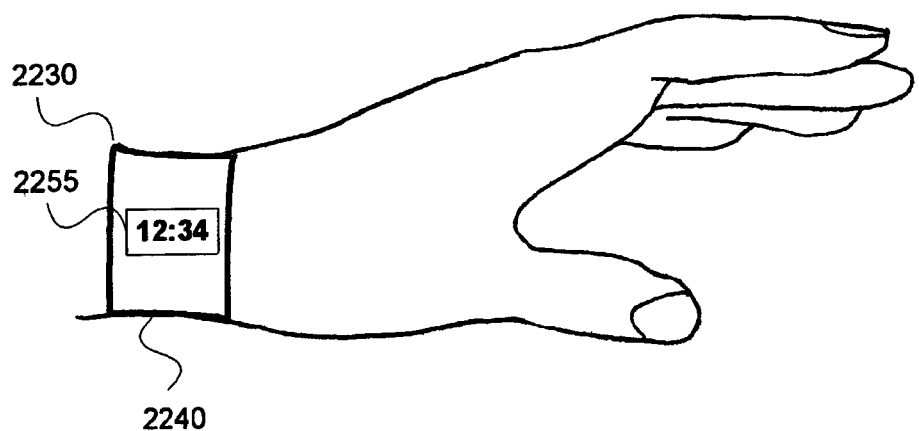
Figure 22C:
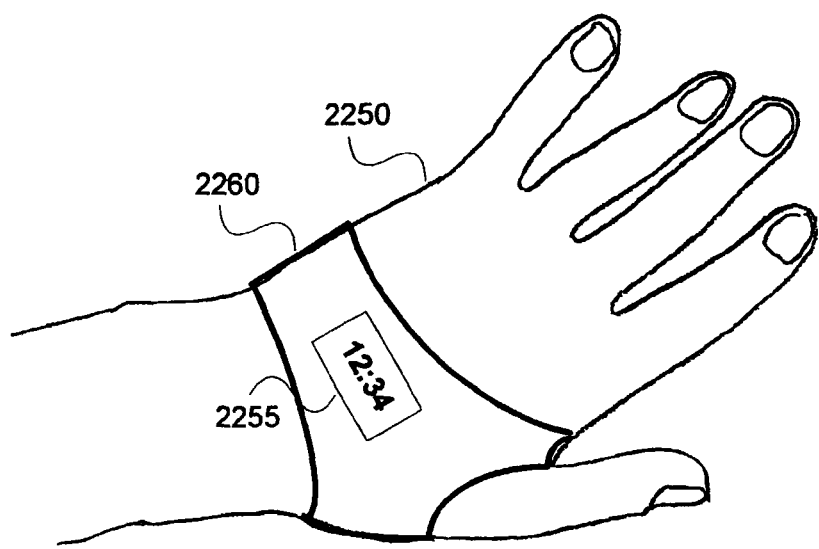

In a mounting similar to a wristwatch, a display INC 2215 may be mounted on the back of a wrist 2210, using wristband 2220, as shown in FIG. 22A. FIG. 22B shows a variation, in which display INC 2235 is mounted on the side of wrist 2230, using wristband 2240. In another variation shown in FIG. 22C, display INC 2255 may be mounted on the back of hand 2250 using partial glove 2260. In these examples, the display INCs are shown to display time. However, any suitable information appropriate to the functions provided by the INCs of the MPN may be shown on the display INC.

Figure 23A:
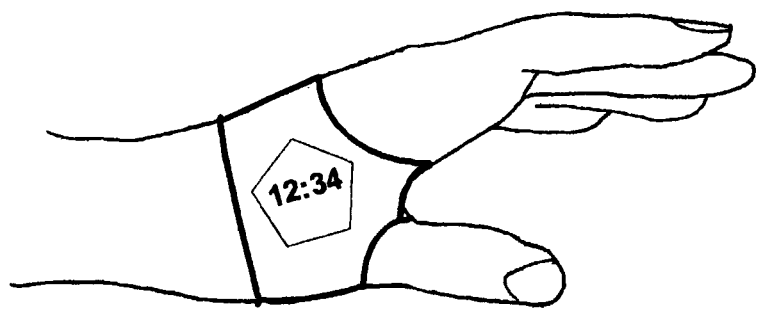
FIGS. 23A through 23F show additional illustrative means for mounting a display device which is an INC in an MPN.
Figure 23B:
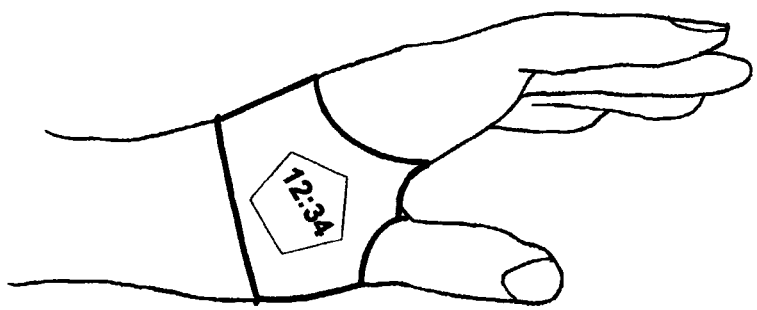
Figure 23C:
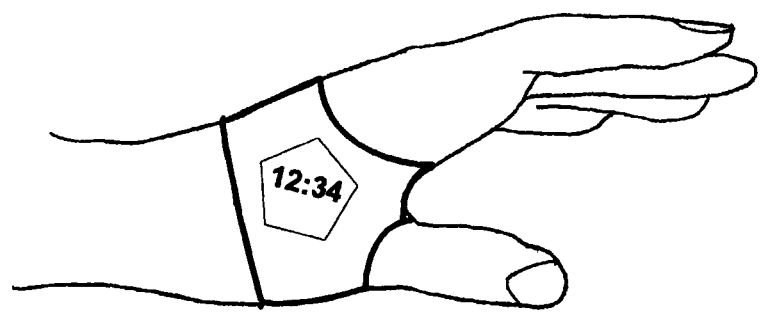
Figure 23D:
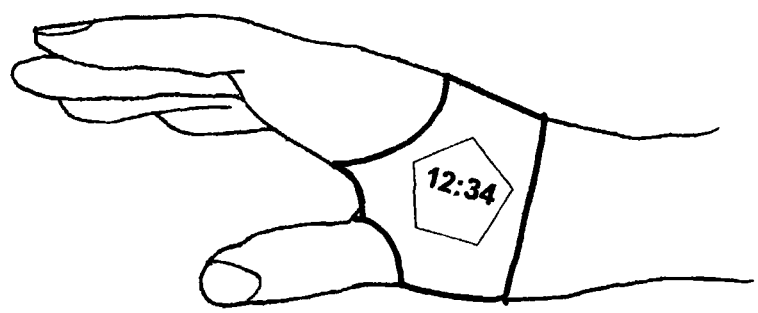
Figure 23E:
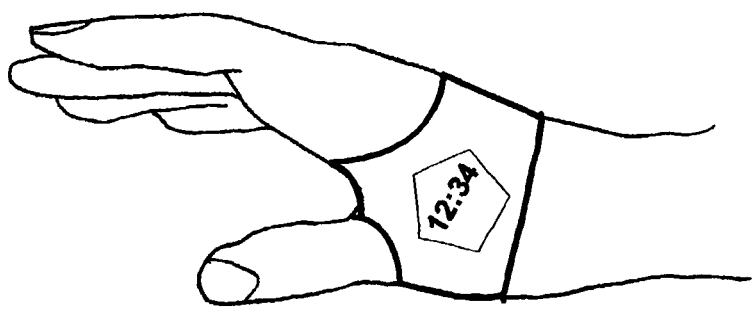
Figure 23F:
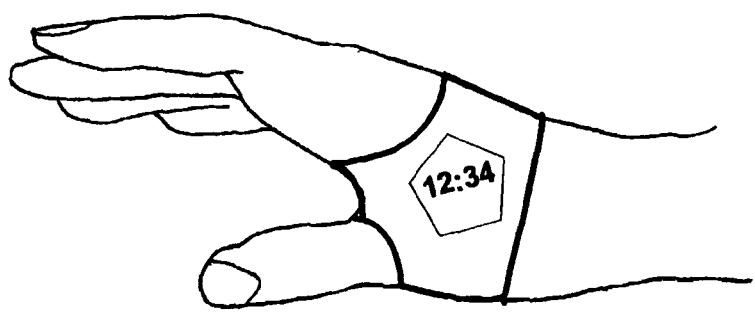

FIGS. 23A through 23F show how a display INC may be worn on the side of a hand, and may be configured with various orientations. For example, in FIGS. 23A through 23C, the display INC may be configured to be oriented toward the back of the hand, toward the fingertips, or at an angle between them, respectively. In these FIGs., the display is shown on the left hand. Alternatively, the display may be configured to be worn on the right hand, as shown in FIGS. 23D through 23F. Different users with different needs may desire displays worn on opposite hands, in different positions on the hand or wrist, and at different orientations. Some, for example, may wish to wear the display in the traditional wristwatch position and orientation on the back of the wrist. Others, for example athletes, may desire a display that can be quickly viewed on the side of the hand without having to twist the arm. The preferred orientation may depend on the user's activity.

A display may be provided in which the user may configure the position and/or orientation. For example, a user may wish to switch the display between the left wrist/hand and the right wrist/hand. A user may also be allowed to change the orientation of the display. For example, if the display is implemented using a dot-matrix liquid crystal display (LCD), the software within the MPN may support multiple orientations. A display may also be provided with multiple mounts—e.g., wristbands, partial gloves, and the like.

FIG. 24A shows flow chart 2400 of an illustrative process for providing a display as an INC in an MPN. All steps are optional and may be performed in any suitable order. In step 2410, a display may be provided as an INC. The INC may include a wireless communications device for communicating with other INCs in the MPN. If desired, the display may be combined with one or more other functions into a single INC, sharing a single wireless communications device. In step 2415, the display INC may be configured to be worn, for example on a wristband, partial glove, or the like. In step 2420, the display INC may be configured to be mounted on an item of personal equipment. That may include, for example, a car in substep 2424, a bicycle in substep 2422, or a piece of exercise equipment in substep 2426. In step 2430, the user may be allowed to change the mounting of the display INC. For example, multiple mounts may be provided so that the display INC may be moved from one part of the body to another, or from the wrist to a piece of exercise equipment.

Figure 24B:
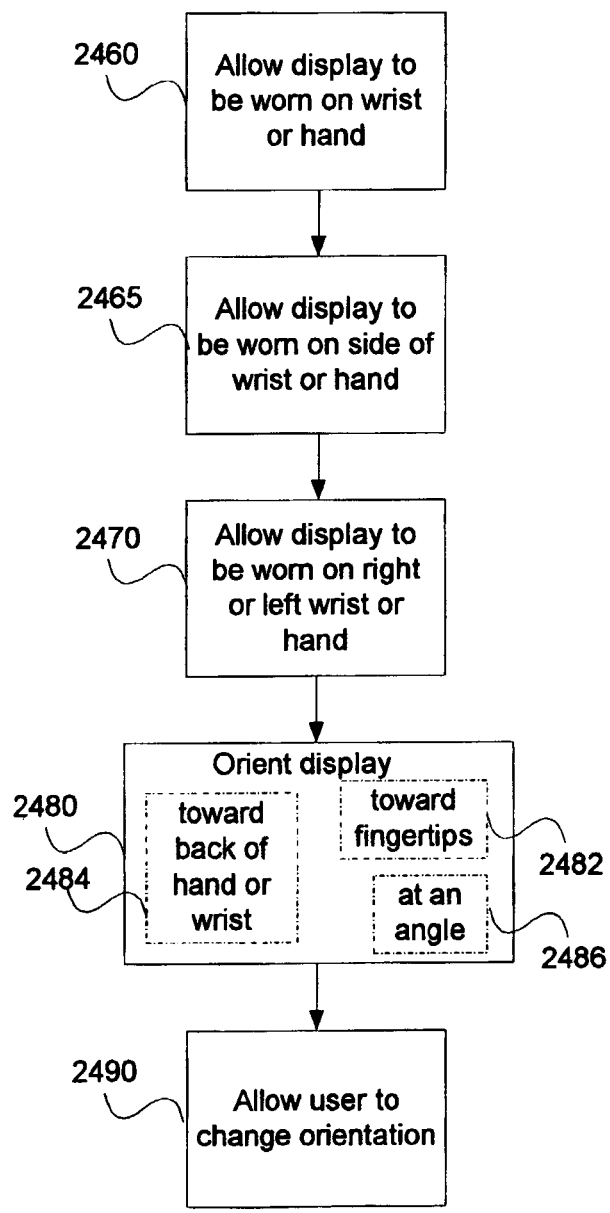

FIG. 24B shows a flow chart with illustrative expanded detailed of step 2415, in which the display INC may be worn by the user. All steps are optional and may be performed in any suitable order. In step 2460, the display may be configured to be worn on a hand or wrist. For example, a wristband or partial glove may be provided. If desired, the display may be worn on other parts of the body instead of the hand or wrist. In step 2465, the display may be configured to be worn on the side of the hand or wrist, allowing the display to be viewed more easily, for example by an athlete. In step 2470, the display and mount may be configured to allow the display to be worn on either the left or right hand or wrist.

In step 2480, the display may be oriented in a direction desirable to the user. For example, in substep 2482, the display may be oriented toward the fingertips. In substep 2484, the display may be oriented toward the back of the hand or wrist. In substep 2486, the display may be oriented at an angle between those two options. In step 2490, the orientation of the display may be configurable by a user, allowing the user to select from one or more orientation options.

Figure 25:
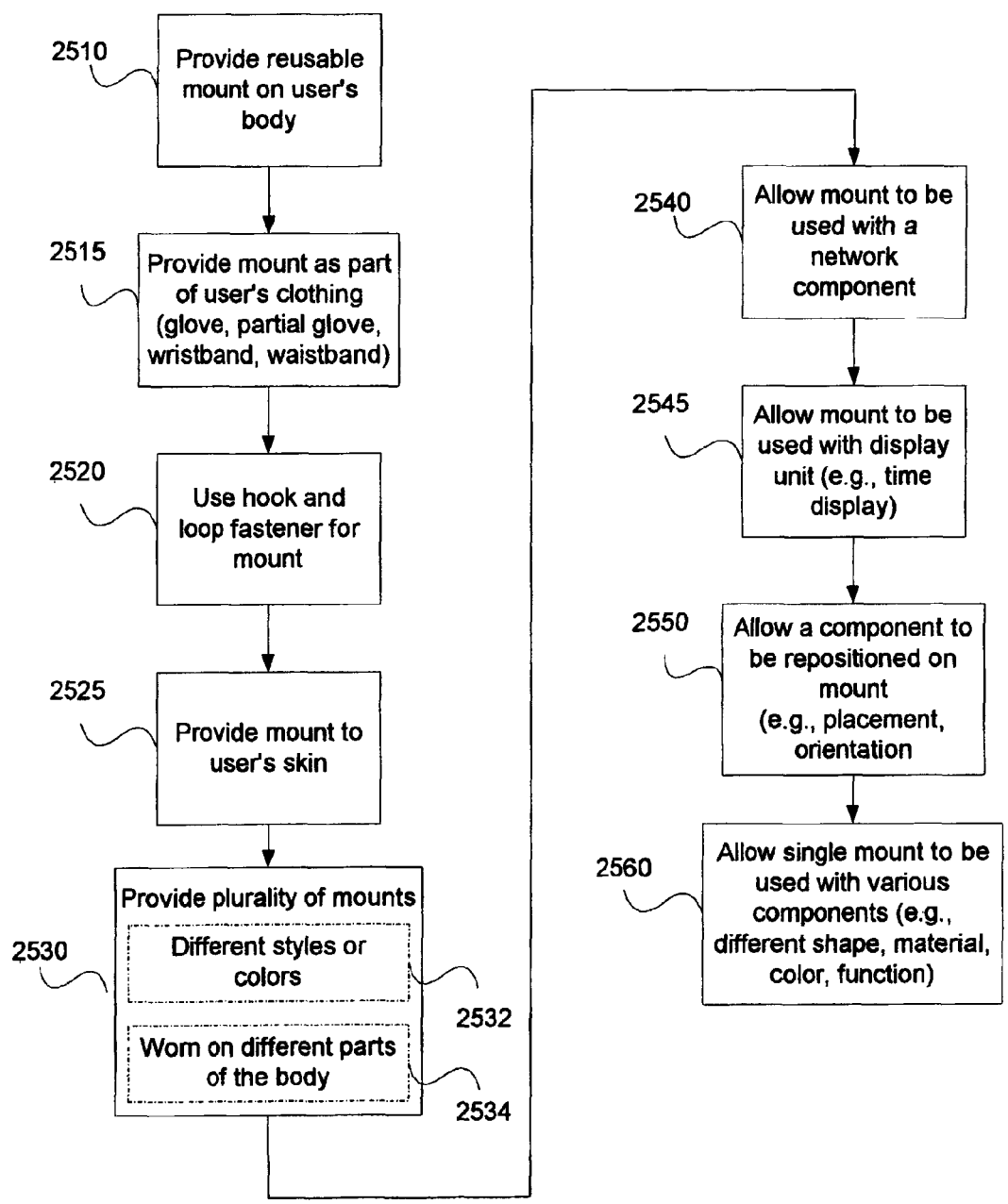
FIG. 25 is a flow chart of an illustrative process for providing a reusable wearable mount for use with various INCs of an MPN.

FIG. 25 shows illustrative flow chart 2500 of an illustrative process for providing a reusable wearable mount that may be used with various INCs, such as a display INC. This method may allow the user to use different mounts or displays to match clothing, to use displays with different functions, and to quickly and easily change the position and orientation of the display.

All steps are optional and may be performed in any suitable order. In step 2510, a reusable mount may be provided that may be worn on the user's body. In step 2515, the mount may be provided as part of an article of clothing, such as a glove, partial glove, wristband, waistband, shirt, or any other suitable article of clothing. In step 2520, the mount may use a hook and loop type of fastener. If desired, any other suitable type of fastener may be used on the article of clothing. In step 2525, the mount may be made directly to the user's skin. For example, a non-toxic adhesive may be used on the back of the INC to be mounted.

In step 2530, a plurality of mounts may be provided. For example, in substep 2532, mounts may be manufactured in different styles or colors. In substep 2534, mounts may be manufactured to be worn on different parts of the body. A user may choose one of the mounts based on style, whim, convenience, function, or for any other reason.

In step 2540, the mount may be used with an INC. The user may temporarily attach the INC to the mount. If desired, the mount may also be configured to allow devices that are not INCs to be attached. In step 2545, the INC attached to the mount may be a display INC. The display INC may be used to display current time and other information that may be provided by the MPN. In step 2550, the user may be allowed to reposition the INC on the mount. For example, the user may be allowed to change the placement and orientation of a display INC to make it more convenient to read the displayed information. In step 2560, the user may be allowed to mount various INCs onto a single mount. The INCs may be manufactured with different shapes, materials, colors, styles, functions, or otherwise may be of different value to a user at different times.

Figure 26A:
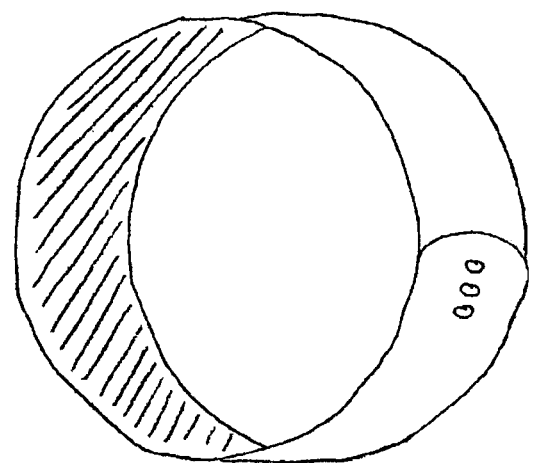
FIGS. 26A through 26C show illustrative mounts that may be used with various INCs of an MPN.
Figure 26B:
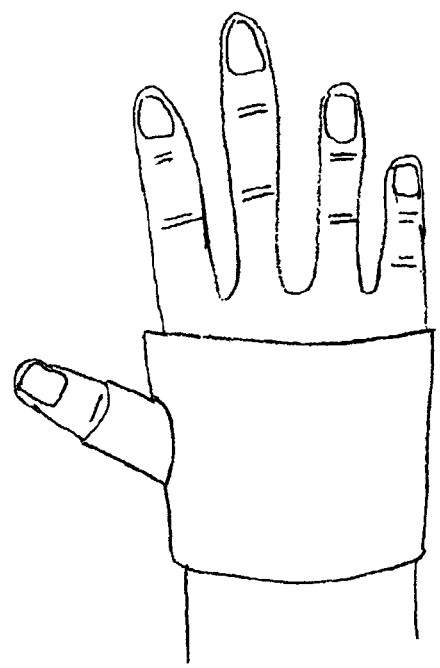
Figure 26C:
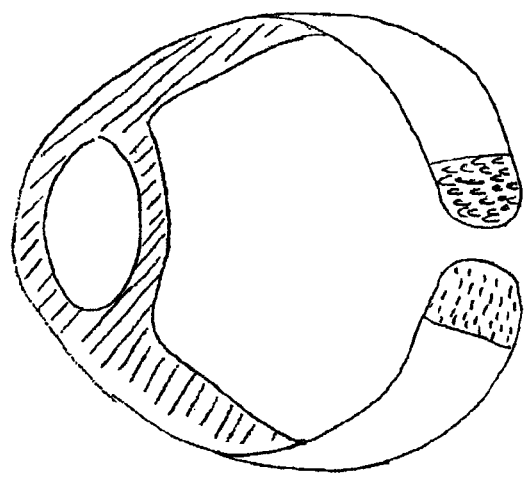
Figure 27A:
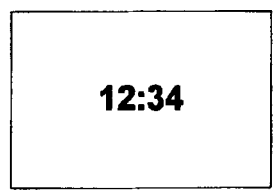
FIGS. 27A through 27D show illustrative display devices that may be used as INCs in an MPN.
Figure 27B:
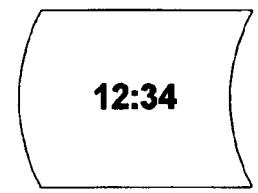
Figure 27C:
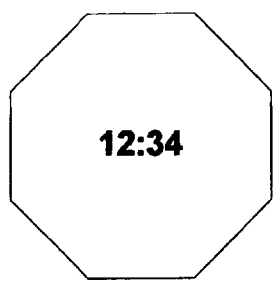
Figure 27D:
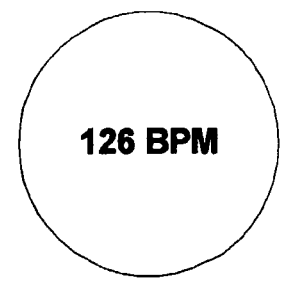

FIGS. 26A through 26C show various examples of reconfigurable wearable mounts that may be provided. FIG. 26A shows a wristband with a buckle. FIG. 26B shows a partial glove. FIG. 26C shows a stretchable band that may be looped around the hand and over the thumb. Each of these mounts may be manufactured with an area of hook and loop fasteners, where the mount includes, for example, the hook portion, and the loop portion is on the back of the INC to be mounted.

FIGS. 27A through 27D show various display INCs that may be used with the mounts of FIGS. 26A through 26C. These displays may have different shapes, different materials, different functions (for example showing either time or heart rate), or may otherwise differ. Each of the INCs may provide the means to fasten to the mount, for example the loop portion of a hook and loop fastener.

An INC may function as an audio output INC. An audio output INC may be worn or carried by the user or mounted on a piece of personal equipment. The audio output INC may be combined with other functions, such as user controls, display, or a control unit, or the INC may function solely as an audio output INC. A single audio output INC may be used to output different types of information at different times, depending on the other INCs in the MPN. The audio output INC may not need to be changed to provide new types of information output. Rather this may be accomplished by adding a new INC with a new function, downloading new software into the audio output INC or a control unit, or otherwise modifying other parts of the MPN. In addition, the user may switch to a different style of audio output INC without changing any other part of the MPN, and maintain all preexisting MPN functions.

The audio output INC may include a wireless communications device for communicating with other INCs in the MPN. For example, the audio output INC may receive digital audio data from one of the other INCs, such as a control unit. The audio output INC may include a digital-to-analog converter (DAC) for converting the digital audio data to an analog audio signal. Alternatively, the audio output INC may receive an analog audio signal from another INC. It may include one or more amplifiers and one or more speakers. It may also include means for mounting the INC to the user's body. If desired, the audio output INC may also include more advanced audio processing capabilities, including speech synthesis, recognition of various audio file formats, decryption of secure data formats, the ability to generate any of a predefined set of tones or audio segments, or other suitable circuits and algorithms.

Figure 28A:
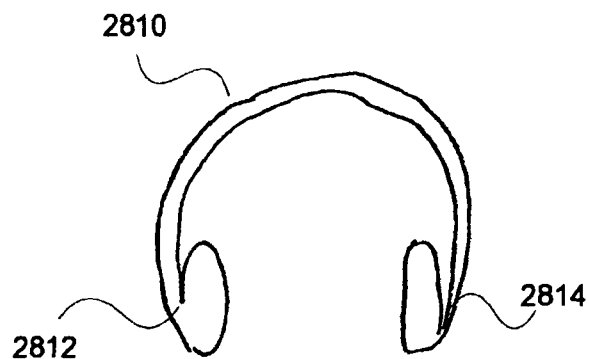
FIGS. 28A through 28D show illustrative audio output devices that may be used as INCs in an MPN.

FIGS. 28A through 28D show various types of audio output INC that may be used with an MPN. FIG. 28A shows an audio output INC configured as a pair of headphones 2810. It may include two speakers 2812 and 2814. A wireless communications device, DAC, and amplifiers may also be included. The headphones may also be configured as two separate INCs, which may each communicate wirelessly with control unit and other INCs. Each INC may have its own DAC, amplifier, and speaker. Headphones may be provided with connecting bar, or they may be configured as small modules to be inserted inside the ear and worn independently.

Figure 28B:
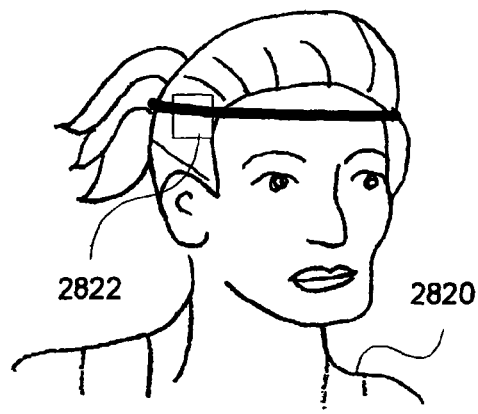
Figure 28C:
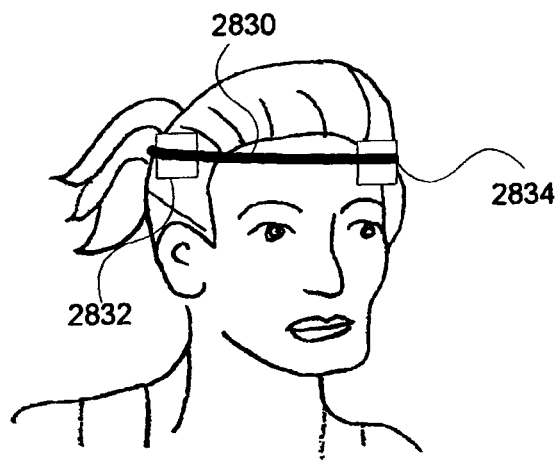
Figure 28D:
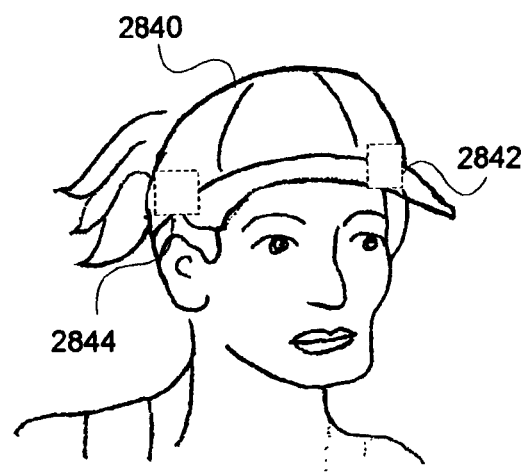

FIG. 28B shows audio output INC 2822 that may be configured to be worn with a headband 2820. The audio output INC may be worn near the ear so that minimal power is needed to drive its speaker. Sound from the speaker may be provided via conduction through the skull. FIG. 28C shows two independent audio output INCs 2832 and 2834, which may be worn with a headband 2830, to provide stereo sound. In FIG. 28D, audio output INC 2844 may be configured to be worn with hat 2840. If desired, hat 2840 may be configured to function with two audio output INCs (not shown). The audio output INC of FIGS. 28B through 28D may be configured to fit into the ear, or to lie flat across the skin near the ear. The headband or hat may be designed to hold the audio output INC or INCs in place in the ear, or to hold the audio output INC in place against the skin where sound may be conducted through the skull. If desired, the headband or hat and the audio output INC may be jointly designed so that the audio output INC may be repositioned to best meet the user's needs, and so that alternate designs of audio output INCs may be used with the same mount.

Figure 29:
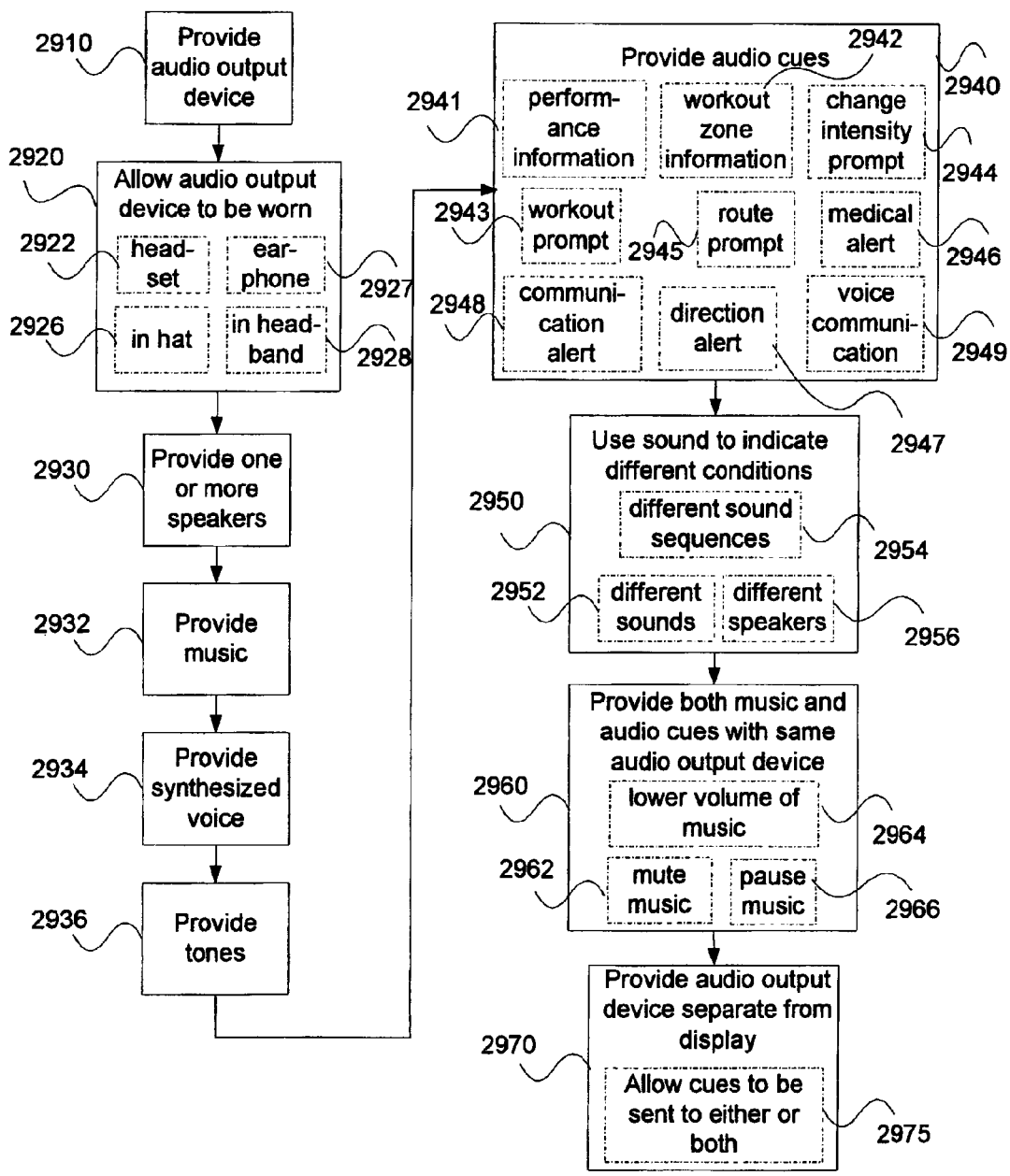
FIG. 29 is a flow chart of an illustrative process for providing an audio output device as an INC in an MPN.

FIG. 29 shows flow chart 2900 of an illustrative process for providing an audio output INC in an MPN. All steps are optional and may be performed in any suitable order. In step 2910 an audio output INC may be provided. Audio output INC may include a wireless communications device for receiving audio data and other audio commands from one or more other INCs in the MPN. It may include DAC, one or more amplifiers, and one or more speakers. It may also include speech synthesis circuitry, tone generation circuitry, digital audio file processing capability, decryption circuitry, a library of audio segments, or other suitable subsystems.

In step 2920, the audio output INC may be configured to be worn. For example, in substep 2922, it may be configured as a headset. In substep 2924, it may be configured as one or more independent earphones, for example to be inserted inside an ear. In substep 2926, it may be configured to be worn with a hat. In substep 2928, it may be configured to be worn with a headband. In step 2930, the audio output INC may include one or more speakers. For example, it may be configured to provide stereo sound. Alternatively, multiple audio output INCs may be included as separate INCs in a single MPN, and may be controlled independently.

In step 2932, audio output INC may provide music. Music may be provided in stereo. In step 2934, synthesized voice may be provided. The synthesized voice may be provided to the audio output INC as digital or analog audio. Alternatively, the voice may be provided to the INC in another form, such as text or phonemes, and the audio output INC may create the synthesized voice. In step 2936, tones may be output. The tones may be provided to the audio output INC as digital or analog audio. Alternatively, the tones may be provided to the INC in another form, such as waveform descriptions or indexes into a table of predefined audio segments, and the audio output INC may create the tones.

In step 2940, the audio output INC may be used by the MPN to provide audio cues to the user. The audio cues may be for any purpose appropriate to the functions provided by the MPN and its other INCs. For example, cues may be provided to an athlete with performance information 2941, workout zone information 2942, workout prompt 2943, or change intensity prompt 2944. Route prompt 2945 or direction alert 2947 may be provided by an MPN that provides route guidance. Medical alert 2946 may be provided by an MPN that monitors medical conditions. Communication alert (e.g., notification of an incoming telephone call or message) 2948 and voice communication 2949 may be provided by an MPN that provides communication services.

In step 2950, sound may be used to indicate different conditions or different audio cues. For example, in substep 2952, different sounds (e.g., different tones) may be used to indicate different conditions. In substep 2954, different sound sequences may be used to indicate different conditions. In substep 2956, sound may be sent to different speakers or audio output INCs to indicate different conditions.

In step 2960, the audio output INC may be used for multiple purposes simultaneously. For example, in a system that provides both music and audible athletic workout feedback, both may be sent to the same audio output INC or INCs. When an audio cue, such as workout feedback, is output, the music may be muted in substep 2962 or the volume of the music may be lowered in substep 2964. Alternatively, the music may be paused in substep 2966 while the audio cue is presented. The volume changing or pausing of the music may be controlled, for example, by a control unit. For example, the control unit may send both music and audio cues to the audio output INC, and may send commands to the audio output INC to control the volume of both. To pause the music, which may be stored in digital form in memory in the control unit, the control unit may temporarily stop reading music data from its memory while the audio cue is presented, and then resume reading the music data from where it was left off. If desired, the pausing, muting, or volume reduction of the music itself may constitute the audio cue, with no additional sound generated. For example, the system may pause the music once for two seconds as one type of cue, and pause the music three times for one half second each time as a second type of cue.

In step 2970, an audio output INC may be provided separately from a display INC. This may be an advantage over many existing systems in which these two functions are combined into a single unit worn on the wrist. In these prior art devices, either the sound volume is so loud that it disturbs other nearby people, or it is too soft to be heard by the user at all times. In this invention, the audio output INC can be provided close to the ear, and the volume can be kept low while still allowing the user to hear the audio even in poor environmental conditions. If desired, the MPN may include the ability for a user to control the volume of audio output. The system may also allow a user to independently control the volume of different types of audio output. For example, the volume of the music may be controlled separately from the volume of the audio cues, and both of those may be controlled separately from the volume of voice communications.

In substep 2975, cues may be sent to either the audio output INC as audio cues, or to the display INC as visual cues, or both. The user may be allowed to configure where different types of cues are sent.

An INC may function as a user input INC. A user input INC may be worn or carried by the user or mounted on a piece of personal equipment. The user input INC may be combined with other functions, such as a display or control unit, or the INC may function solely as a user input INC. A single user input INC may be used to input different types of information at different times, depending on the other INCs in the MPN. The user input INC may not need to be changed to provide new types of information input. Rather this may be accomplished by adding a new INC with a new function, downloading new software into the user input INC or a control unit, or otherwise modifying other parts of the MPN. In addition, the user may switch to a different style of user input INC without changing any other part of the MPN, and maintain all preexisting MPN functions. An MPN may include multiple user input INCs, which may be of similar types or of different types.

The user input INC may include a wireless communications device for communicating with other INCs in the MPN. For example, the user input INC may send digital commands or data to one of the other INCs, such as a control unit. The user input INC may include an analog-to-digital converter (ADC) for converting analog inputs to digital data. It may also include means for mounting the INC to the user's body. If desired, the user input INC may also include more advanced input processing capabilities, including voice recognition, tensile, audible, or visual feedback of input commands, anticipation of likely commands, grouping and combining of similar inputs, or other suitable circuits and algorithms.

Figure 30:
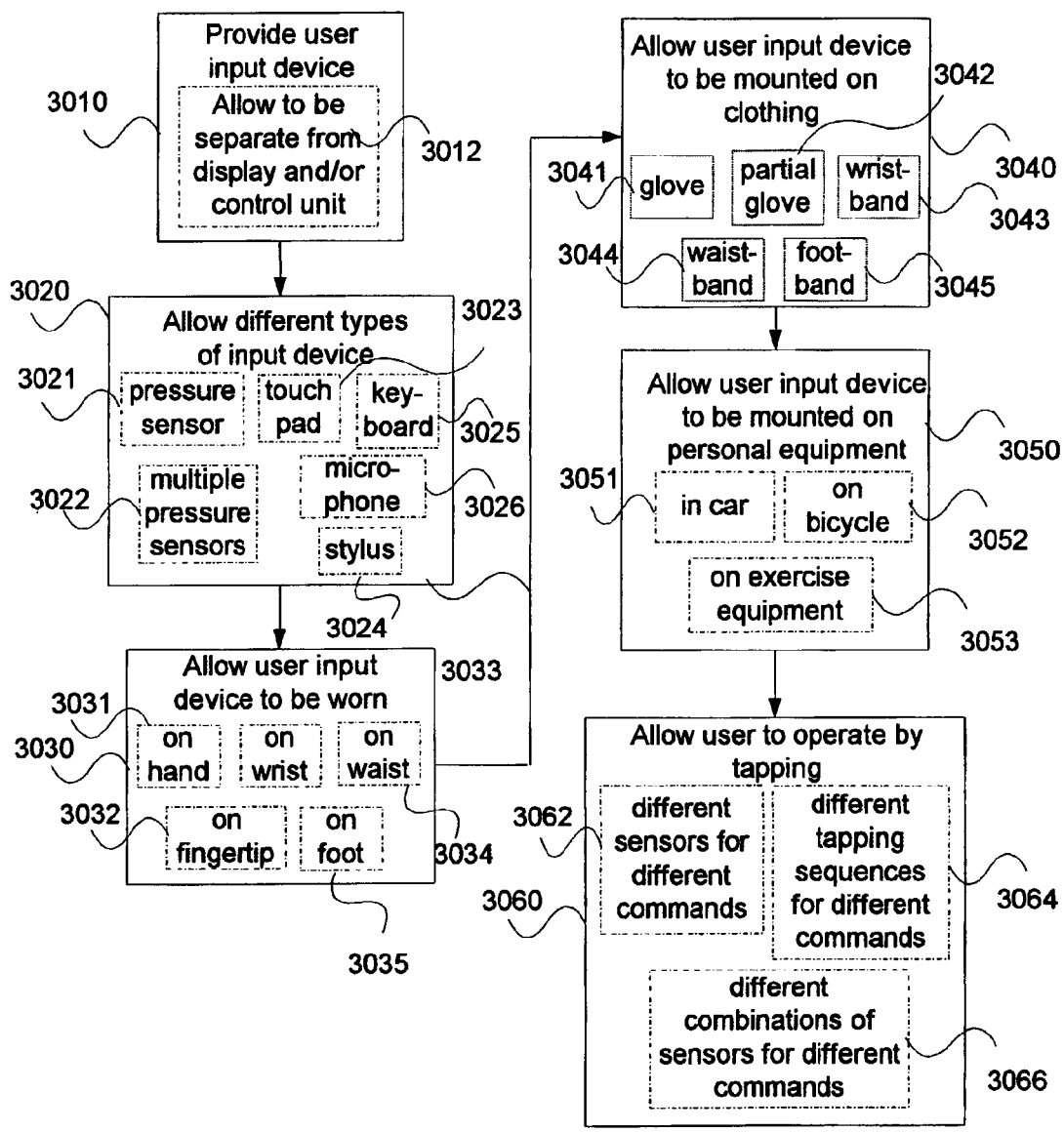
FIG. 30 is a flow chart of an illustrative process for providing a user input device as an INC in an MPN.

FIG. 30 shows flow chart 3000 of an illustrative process for providing a user input INC in an MPN. All steps are optional and may be performed in any suitable order. In step 3010, a user input INC may be provided. In step 3020, the user input INC may be separate from other INCs, such as a display INC or a control unit. This may be an advantage to some users. For example, in many prior art systems the user controls are mounted on a display device worn on the wrist. Controls may be small and close together, and may require the user to look at the display device to operate it. This requires to user to twist the arm, to look and find the controls, and to reach one hand over to the other. These actions may not be convenient for all users at all times. For example, an athlete may need to operate a system using the minimum possible motions, and without having to change the direction he or she is looking. If desired, user controls may be combined with any other INC.

In step 3020, any suitable type of user input INC may be used. Preferably, the INC is one that may be used in a mobile environment. For example, a computer keyboard and mouse may not be appropriate except as attached to a personal computer or base station that may be used at times with the MPN. Appropriate types of input INC may include a pressure sensor or button 3021, multiple pressure sensors or buttons 3022, a touch pad 3023, a stylus 3024 used for example with a touch pad, a portable keyboard 3025, and a microphone 3026. Microphone 3026 may be used to capture audio data, or it may include speech recognition circuitry. If desired, an MPN may include multiple user input INCs. For example, one system may include several buttons, a microphone with speech recognition, and a touch pad with a stylus.

In step 3030, the user input INC may be configured to be worn or carried. For example, a pressure sensor may be attached to a fingertip 3032, hand 3031, foot 3035, or waist 3034. A touch pad or microphone may be worn at the waist 3034. A microphone may be worn on the wrist 3033 or other part of the arm, or may be configured as part of a headset. If desired, the user input INC may be designed to be mounted on an item of clothing in step 3040, such as glove 3041, partial glove 3042, wristband 3043, waistband 3044, or footband 3045, shoe, or sock. The user input INC may also be mounted on an item of personal equipment in step 3050, such as on a car 3051, bicycle 3052, or exercise equipment 3053.

In step 3060, if user input INC includes one or more pressure sensors or buttons, it may be operated by tapping. For example, the user may mount a pressure sensor on one or more fingertips, and they may be operated by tapping the fingertip against the palm of the hand, the thumb, other part of the body, or another surface. The user may mount a pressure sensor on the palm of the hand and operate it by tapping it with a fingertip, with the other hand, hitting another part of the body, or striking another surface. The user may mount a pressure sensor on a waistband and operate it by tapping it. The user may mount a pressure sensor on the foot and operate it by tapping an object with the toe or by pushing off the wall while swimming laps in a swimming pool. In substep 3062, the user may tap different sensors for different commands. For example, an athlete may tap with the sensor on one finger to start and stop a stopwatch function, and tap with the sensor on a different finger to capture a single lap split time. In substep 3064, the user may tap different sequences to indicate different commands. For example, the user may tap once, twice in quick succession, or other suitable sequences. In substep 3066, the user may tap a specific combination of sensors simultaneously to input a specific command.

Figure 31A:
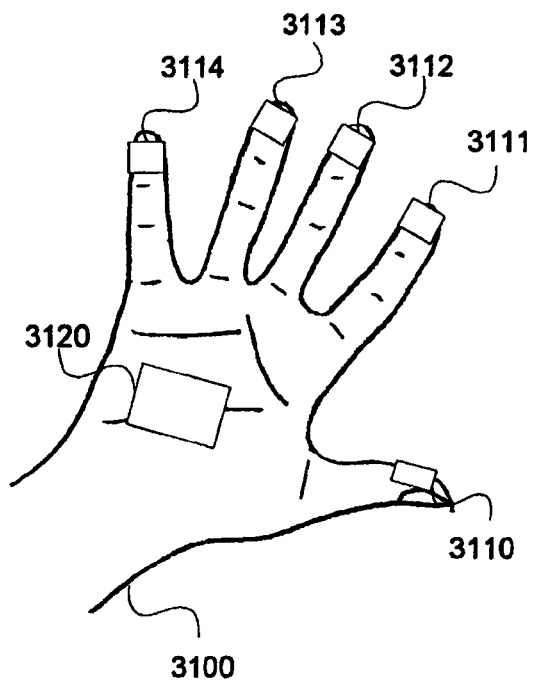
FIGS. 31A through 31C show illustrative means for mounting a user input device which is an INC in an MPN.
Figure 31B:
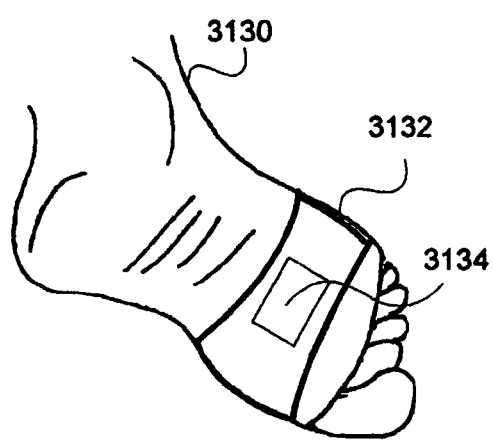
Figure 31C:
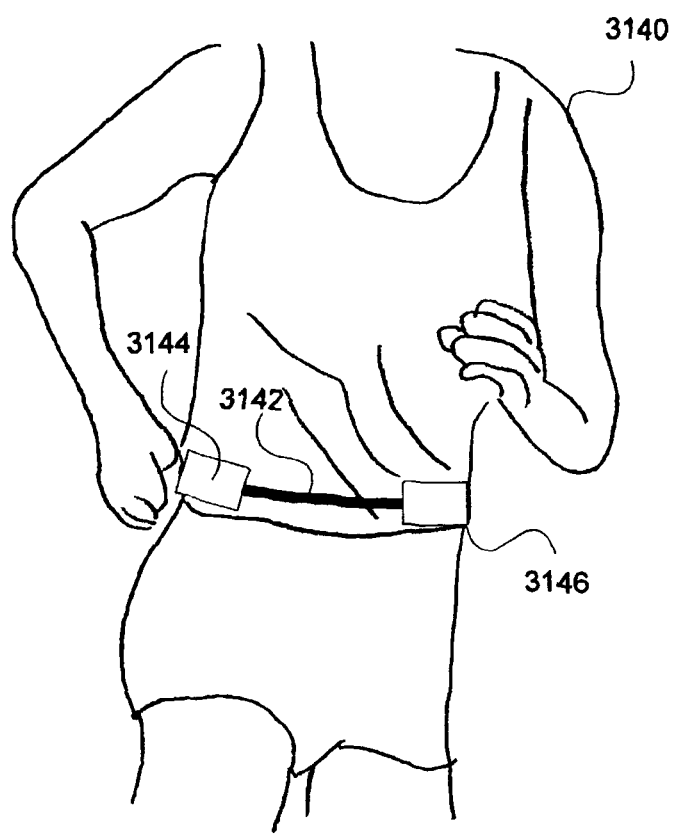

FIGS. 31A through 31C show several illustrative methods for mounting a user input INC. In FIG. 31A, pressure sensors 3110, 3111, 3112, 3113, 3114, and 3120 are mounted on a user's hand 3100. If desired, they may also be mounted on a glove or partial glove worn by the user. In this configuration, any single sensor may be operated independently. In addition, combinations of sensors may be operated simultaneously. For example, a user may tap the thumb with the forefinger and simultaneously operate both sensor 3110 and sensor 3111. The user may also simultaneously strike a surface with one, two, or more sensors to provide various input commands.

FIG. 31B shows pressure sensor 3134 mounted to a user's foot 3130 using footband 3132. This configuration may be useful to a swimmer, who may tap the wall of a swimming pool to count laps, and may tap the bottom of the pool to indicate other commands.

FIG. 31C shows user 3140 who has mounted two input INCs 3144 and 3146 on waistband 3142. These input INCs may be pressure sensors and may be operated by tapping. Alternatively, these INCs may include a microphone, portable keyboard, touchpad and stylus, or other input INC carried on the waist and retrieved for use. Any suitable combination of input INCs and mounts may be used.

An MPN may be used for many purposes. A single MPN may be used for a single purpose, or it may be used for multiple purposes. The uses of the MPN may change over time, as the user adds and removes INCs, downloads or removes software, changes configuration parameters, or just changes how he or she interacts with the system. A single INC may have a single purpose, or it may be used for multiple purposes. Some types of INCs, such as control units INCs, display INCs, audio output INCs, and user input INCs, may be general purpose.

Figure 32:
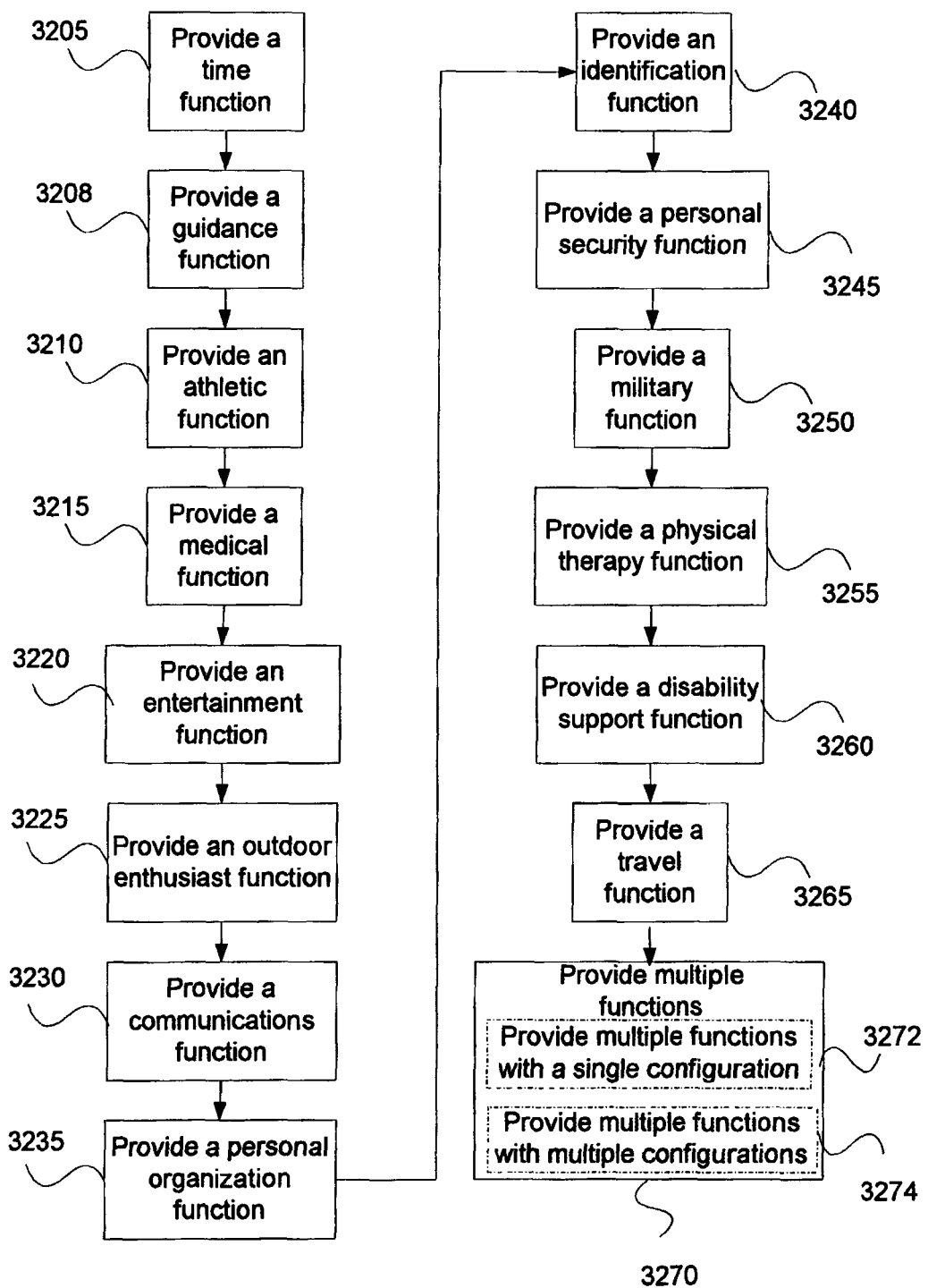
FIG. 32 is a flow chart of an illustrative process for using an MPN for multiple purposes.

FIG. 32 shows a flow chart of an illustrative process for using an MPN for multiple purposes. All steps are optional and may be performed in any suitable order. In step 3205, the MPN may be used to provide a time-related function. In step 3208, the MPN may be used to provide a guidance function. In step 3210, the MPN may be used to provide an athletic function. In step 3215, the MPN may be used to provide a medical function. In step 3220, the MPN may be used to provide an entertainment function. In step 3225, the MPN may be used to provide an outdoor-related function. In step 3230, the MPN may be used to provide a communications function. In step 3235, the MPN may be used to provide a personal organization function. In step 3240, the MPN may be used to provide an identification function. In step 3245, the MPN may be used to provide a personal security function. In step 3250, the MPN may be used to provide a military function. In step 3255, the MPN may be used to provide a physical therapy function. In step 3260, the MPN may be used to provide a disability-related function. In step 3265, the MPN may be used to provide a travel-related function. In step 3270, the MPN may be used to provide multiple functions. This may include substep 3272 of providing multiple functions with a single MPN configuration. It may also include substep 3274 of providing multiple functions with multiple MPN configurations. The functions shown in FIG. 32 are merely illustrative. Other functions may be provided if desired.

Figure 33:
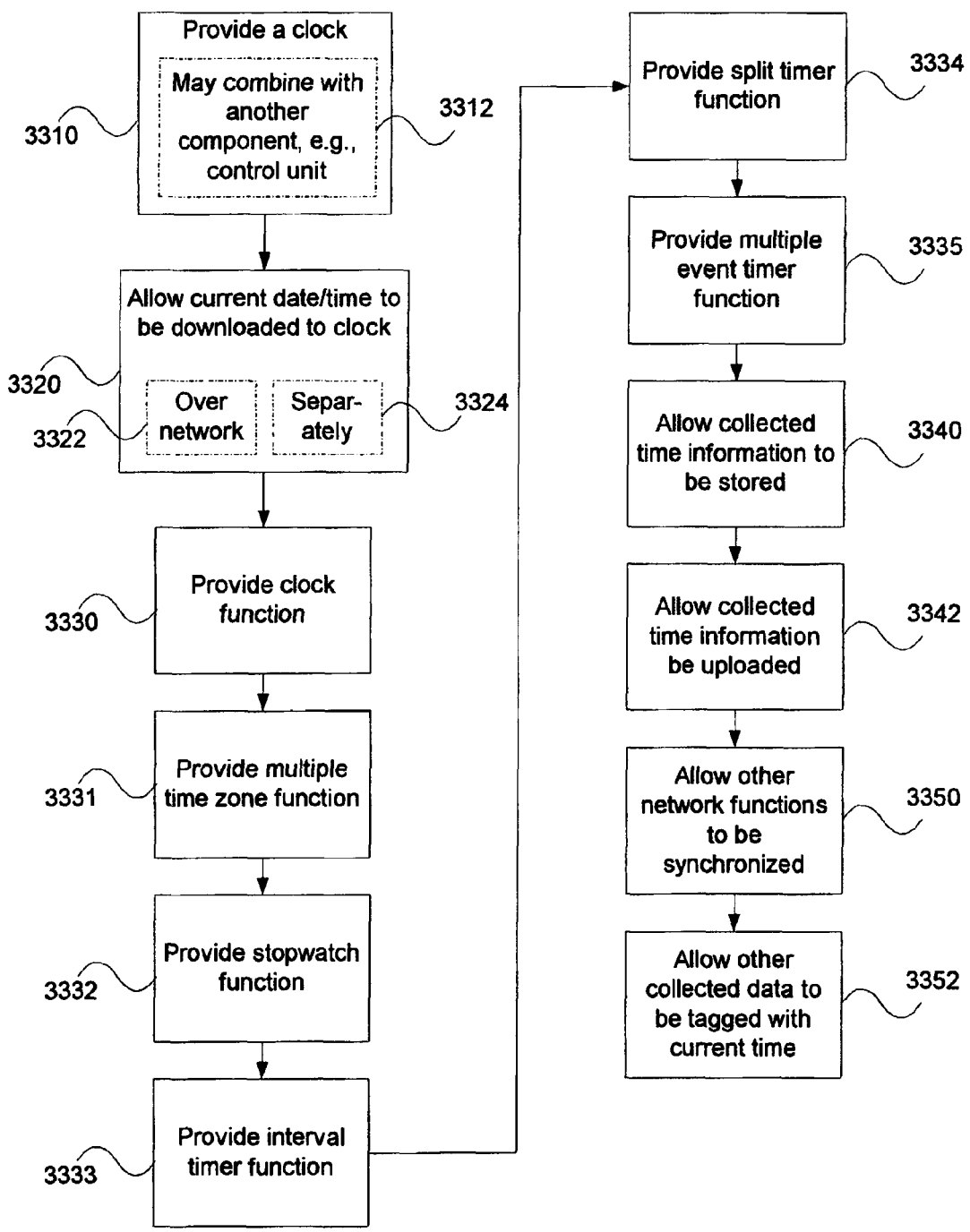
FIG. 33 is a flow chart of an illustrative process for using an MPN for time-related purposes.

Step 3205, providing time-related functions, is shown in more detail in FIG. 33. All steps are optional and may be performed in any suitable order. In step 3310, a clock may be provided as part of an MPN. This may include substep 3312 in which the clock is provided as part of another INC, such as a control unit or display INC. In step 3320, the current date and time may be downloaded into the INC. This may include substep 3322 in which the current time is downloaded over the wireless network, for example from a personal computer. Alternatively, it may include substep 3324 in which the INC include a radio receiver to acquire the current time from station WWV time of day radio broadcast.

In step 3330, the INC may provide a clock function. This may include displaying the current day and time on a display INC. The INC may include a time zone function in step 3331. This may include displaying the current time in multiple time zones, or converting a time from one time zone to another. In step 3332, the INC may provide a stopwatch function. This may include allowing the user to time individual events. It may include step 3334 of providing a split timer function, in which the user is allowed to time individual portions of an event. It may also include step 3335 in which the user is allowed to time multiple events. In step 3333, the system may provide an interval timer function, allowing the user to mark one or more recurring intervals of specific durations.

In step 3340, the system may store collected time information. This may include collected stopwatch, split, and event times. This collected data may be tagged with the date and time on which it was stored. The user may also be allowed to input descriptive data related to the collected time data. The stored data may also include time zone settings, intervals settings, or other settings. In step 3342, the collected time information may be uploaded, for example to a base station or personal computer.

In step 3350, the clock functions may be used to synchronize other MPN functions. For example, a control unit may collect data from a particular INC on a regular interval, or update a display once per second. The control unit may be allowed to read the current time from the clock. The clock may also be configured to provide an unsolicited interrupt to the control unit or other INC at a regular interval. In step 3352, data collected from other INCs may be tagged with the current time retrieved from the clock.

Figure 34:
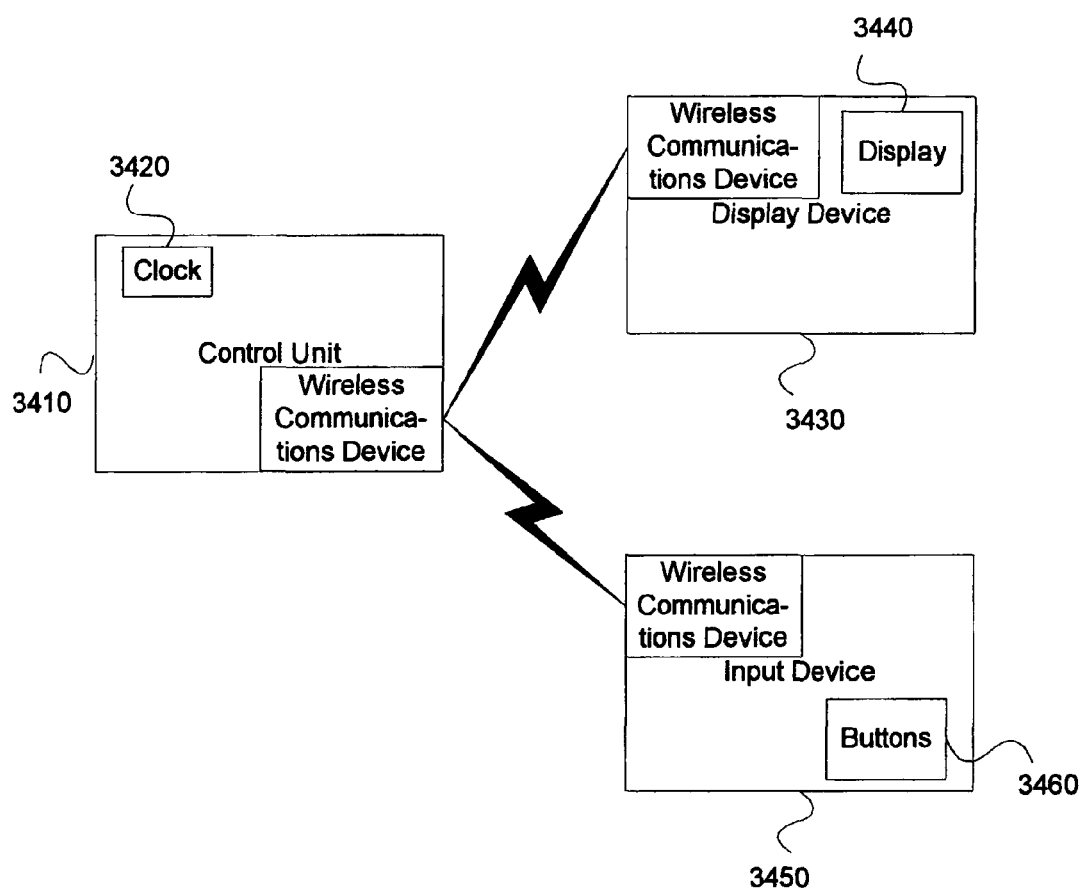
FIG. 34 is a block diagram of an illustrative MPN with a clock function.

FIG. 34 shows a block diagram of an illustrative MPN 3400 with a clock function. In this system, the clock 3420 is embedded in the control unit 3410. Clock information is sent to a separate display INC 3430, which may output the information on display 3440. User commands, such as changing clock mode and starting and stopping the stopwatch, are provided by buttons 3460 on a separate input INC 3450. The input INC 3450 may be worn on the hand, the control unit/clock 3410 may be worn on the waist, and the display INC 3440 may be worn on the wrist.

Figure 35:
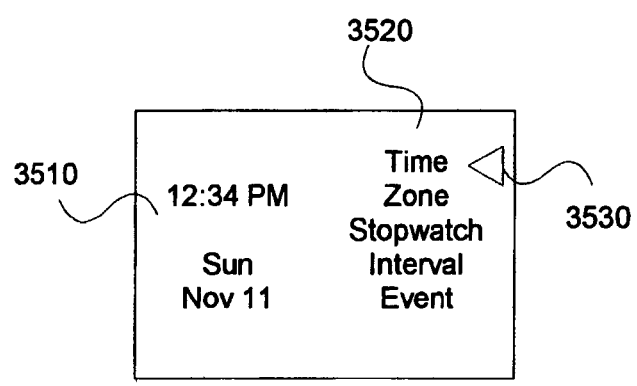
FIG. 35 is an illustrative display screen that may be shown with the MPN of FIG. 34.

FIG. 35 shows an illustrative screen 3500 that may be shown on display 3440 (FIG. 34). Mode list 3520 may list the available clock modes. In this case, the system may support a time mode, a zone mode (e.g., time zone), a stopwatch mode, an interval timer mode, and an event timer mode. Indicator 3530 may show the currently active mode, in this case the time mode. The user may change to a different mode by pressing one of buttons 3460 (FIG. 34). The current time 3510 may be displayed while in time mode.

Figure 36:
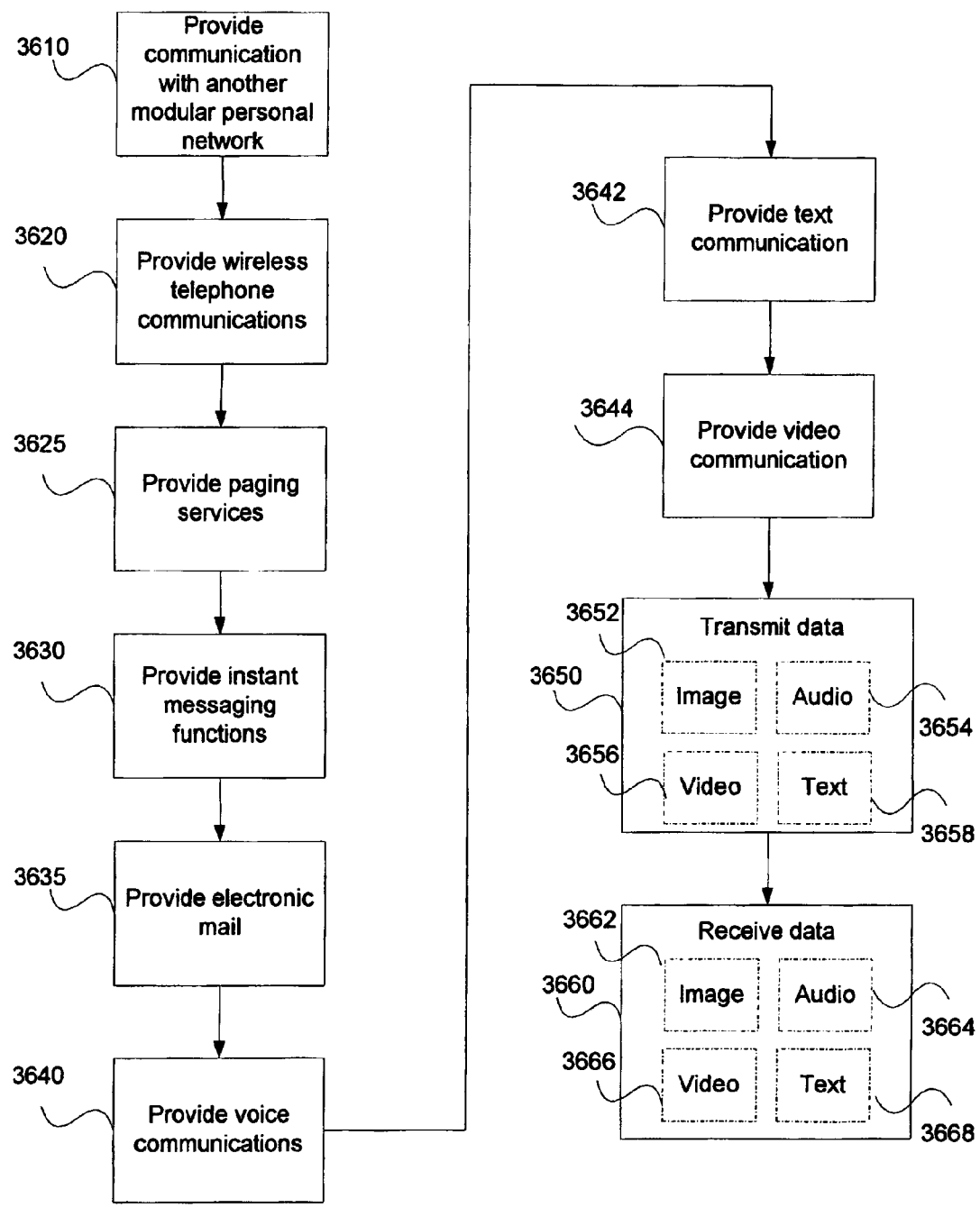
FIG. 36 is a flow chart of an illustrative process for using an MPN with a communication function.

More details of step 3230 (FIG. 32), providing a communication function in an MPN, are shown in FIG. 36. All steps are optional and may be performed in any suitable order. In step 3610, communication may be provided with another MPN. This may be accomplished if one of the INCs in the MPN includes a communications device capable of communicating with an INC of another MPN. The wireless communications device used for communicating among the INCs within an MPN may also be used for communicating with another MPN, if the user of that MPN is in close proximity. The system may be configured to accept messages with the specific network identifier associated with the other MPN, while the communications are in progress.

In step 3620, wireless telephone communications may be provided, if one of the INCs includes a wireless telephone. The audio output INC for the MPN may output the incoming audio from a telephone call, and a microphone used as a user input INC for the MPN may be used to provide the outgoing audio for the telephone call. This allows the telephone INC itself to be smaller and less costly, since it does not require a built-in speaker or microphone.

In step 3625, paging services may be provided. For example, one of the INCs may include a paging receiver. Text pages may be shown on the display INC. Audio alerts and voice pages may be sent to the audio output INC. Two-way paging may be provided if desired. An instant messaging function may be provided in step 3630, with one INC receiving text messages for display on the display INC, and another INC allowing text messages to be composed and sent to another person elsewhere. Electronic mail messages may also be composed and received in a similar manner in step 3635.

Different types of communication may be provided as appropriate. For example, voice communications may be provided in step 3640. Text communication may be provided in step 3642. Video communication may be provided in step 3644. Other formats of communication may also be supported if desired.

In step 3650, data may be transmitted by a communications device in one of the INCs in the MPN. This may include substep 3652 transmitting image data, substep 3654 transmitting audio data, substep 3656 transmitting video data, and substep 3658 transmitting text data. The data to be transmitted may be provided by the user with a user input INC, may be stored in memory within the MPN, and may be transmitted among INCs in the MPN prior to sending.

In step 3660, data may be received by a communications device in one of the INCs in the MPN. This may include substep 3662 receiving image data, substep 3664 receiving audio data, substep 3666 receiving video data, and substep 3668 receiving text data. The data received may be transmitted among INCs in the MPN and stored in memory within the MPN, prior to its being provided to the user on one or more of the INCs, such as a display INC or audio output INC. If desired, a communications alert may be provided to the user on the display or audio output INC to let the user know that a message has been received.

If desired, input and output INCs in the MPN may be shared between a communications function and another function of the MPN. For example, music may be paused or muted while voice communications or communications alerts are being provided to the audio output INC.

Figure 37:
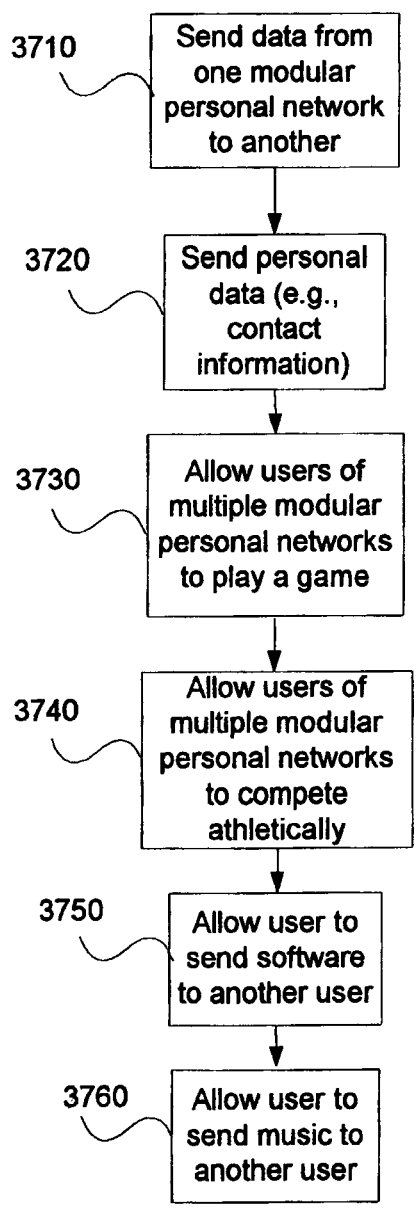
FIG. 37 is a flow chart of an illustrative process for communicating between MPNs.

FIG. 37 shows more detail of step 3610 (FIG. 36), communicating between MPNs. All steps are optional and may be performed in any suitable order. As described above, one of the INCs of the MPN may include a communications device for exchanging data with an INC of another MPN. Alternatively, the communications device used for exchanging data among INCs of a single MPN may also be used to exchange data with another MPN that may be in proximity. For example, the user may have downloaded software into the control unit or other INC that allows such communication. The user may use the user input INC to notify the MPN that these communications are to begin. The MPN may then begin to send messages to an INC of the other MPN, and may listen for incoming messages from the other MPN. In this manner, each MPN may determine the network identifier of the other user's MPN. In step 3710 of FIG. 37, data may be sent from one MPN to another. For example, the control unit or other INC may tag an outgoing message with the network identifier of the other MPN.

The data may include personal data in step 3720. For example, if the two MPNs are configured to provide personal organization features, the data sent from one to the other may include contact information, such as a name, phone number, electronic mail address, or other suitable information.

In step 3730, the data sent between MPNs may include game data. This may allow the users to play a game that requires two or more players, if both users have the same game software installed.

In step 3740, the data may allow two users to compete athletically. For example, the two users may each be on a stationary bicycle, and performance data may be exchanged between them. The two MPNs may determine who wins the competition based on data gathered from the two stationary bicycles or other sensors.

In step 3750, one user may send software to another user. This may include, for example, software that enables an MPN to perform a specific feature or provide a specific function. In step 3760, one user may be allowed to send a digital music file, or other recorded media, to another.

Any other suitable type of data may be exchanged between MPNs. If desired, data may be exchanged between more than two MPNs simultaneously, for example allowing a game with more than two players.

Figure 38:
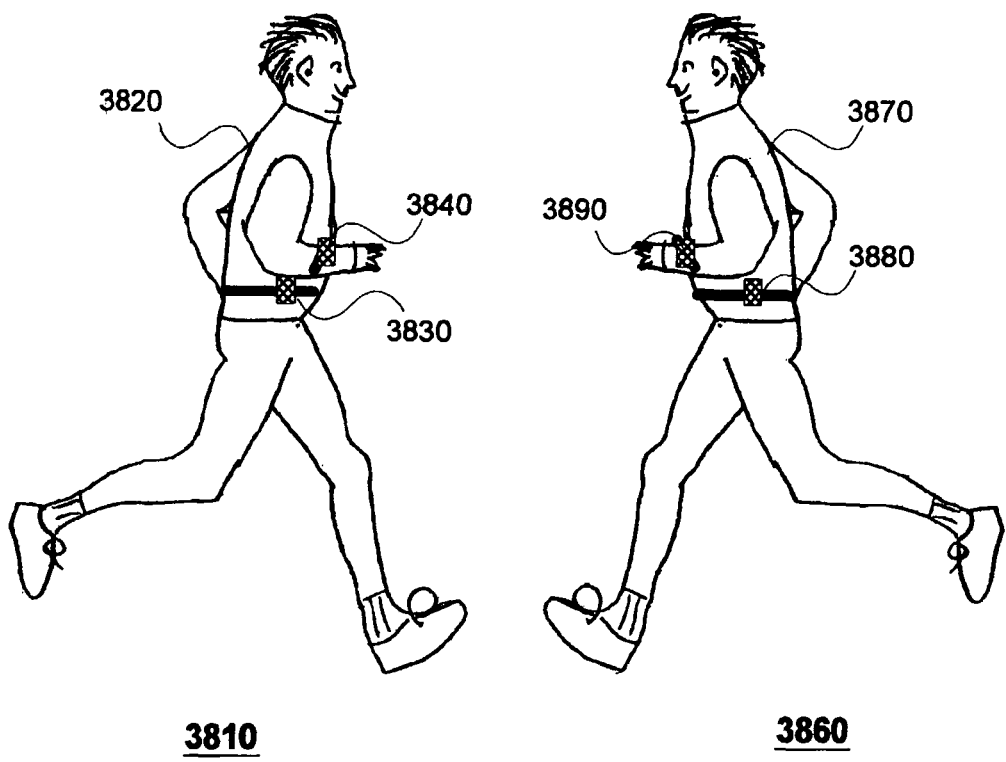
FIGS. 38 and 39 are illustrations of communications between multiple MPNs.

FIG. 38 shows two users with MPNs that are communicating. First user 3820 is wearing first MPN 3810. First MPN 3810 includes control unit 3830 and display INC 3840. User controls may be incorporated into either INC. Second user 3870 is wearing second MPN 3860, consisting of control unit 3880 and display INC 3890. Either of these two INCs may have user controls as well. Data may be exchanged between control unit 3830 and control unit 3880. Exchanged data may be displayed on display INC 3840 and display INC 3890. User 3820 and user 3870 may, for example, exchange personal contact information or may play a game. The INCs shown are merely illustrative.

Figure 39:
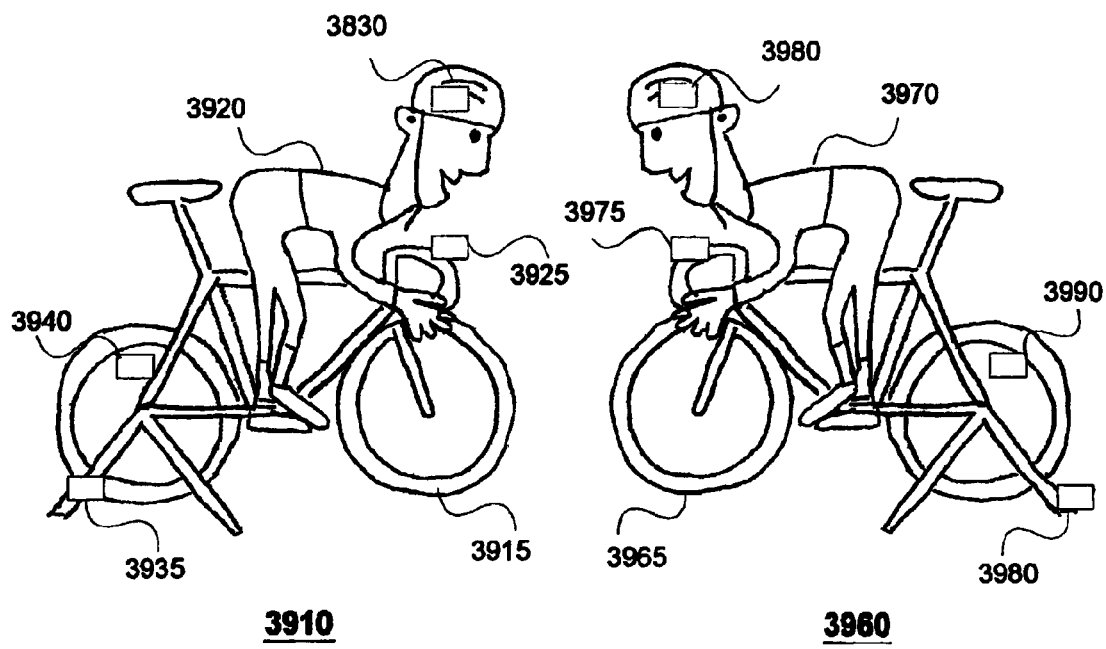

Another example of two users with communicating MPNs is shown in FIG. 39. First user 3920 is on first bicycle 3915, mounted on a stationary training stand. Second user 3970 is on second bicycle 3965, also mounted on a stationary training stand. First MPN 3910 may include INC 3925 which may combine display functions and user controls with a control unit and which may be mounted on bicycle 3915. First MPN 3910 may include audio output INC 3930 worn by first user 3920 inside a helmet or headband. It may include INC 3935 that controls the difficulty setting of the training stand. It may also include INC 3940 that measures the speed of the rear wheel of bicycle 3915. Second MPN 3960 may similarly include user input/display/control unit 3975, audio output INC 3980, difficulty setting INC 3985, and speed sensor 3990. The two control units may control the difficulty for the two riders to simulate a specific race course, and may compare the speeds of the two riders. The display INCs may be used to provide feedback on the comparative progress on the simulated course of the two riders, for example notifying each rider of the comparative position of the other. The INCs shown are merely illustrative.

FIG. 40 shows more detail of step 3220 (FIG. 32), providing entertainment functions. All steps are optional and may be performed in any suitable order. In step 4010, recorded music may be played. For example, songs may be stored in digital format (e.g., MP3 format) in memory in the control unit or other INC with storage capabilities. The storage INC may read the digital audio data and send it to the audio output INC, which may play the audio for the user. If desired, the system may provide audio control functions, such as volume control, playing and stopping, skipping songs, repeating a song, random play, etc. In step 4015, broadcast music (e.g., radio) may be played by the MPN. A radio receiver may be included in one of the INCs. The radio signal may be received and sent to the audio output INC to allow the user to listen. If desired, the audio signal may be digitized for processing within the system. If desired, the system may include volume changing and station selection functions, and other desired radio-related features.

In step 4020, the system may allow audio to be recorded. For example, one of the INCs may include a microphone. The audio may be digitized and stored into memory in one of the INCs, such as a control unit. The recorded audio may be replayed by the user, using the audio output INC. Similarly, video segments may be captured in step 4022 and still video images may be captured in step 4024 by an INC with a video input. The video segments may be digitized and stored in memory in one of the INCs. If desired, the captured video segments and images may be viewed by the user on the display INC.

If desired, any stored music or any recorded media may be shared with a user of another MPN, as described above in conjunction with FIG. 37. Any recorded audio, video, or image data may be uploaded to a personal computer, if desired.

In step 4030, the user may be allowed to play a game. The game may involve only the user of the MPN. Alternatively it may involve a user of another MPN, if one of the INCs in each MPN includes a communication device capable of communicating with the other MPN. For example, the wireless communications device within each of the INCs may be used to transfer game-related information between MPNs if the two users are in close proximity. An INC of the MPN may also be configured to communicate with an external game device.

Music and audio cues may both be provided by a single MPN, as described previously in conjunction with FIG. 29.

FIG. 41 shows more details of step 3235 (FIG. 32), providing personal organization features with an MPN. All steps are optional and may be performed in any suitable order. In step 4110, the MPN may support scheduling of appointments. The user input INC and display INC may be used for entering new appointments, modifying appointments, and viewing upcoming schedules. The display INC and audio output INC may be used to inform the user of imminent appointments. In step 4120, the MPN may manage contact information. This may include names, phone numbers, addresses, electronic mail addresses, and other information about contacts. In step 4130, the MPN may be used to manage a task list. For example, the user may be allowed to enter and prioritize tasks, and to track their completion. In step 4140, the MPN may allow the user to keep a journal. The user may be able to create text, audio, video, and other types of entries.

In step 4150, the personal organizer data stored by the MPN may be synchronized with another system, such as a software application running on a personal computer. Appointments, contacts, tasks, and journal entries created on either system may be copied to the other system. This may allow the user to keep a permanent or backup copy of data created in the mobile system, and may also allow the user to take advantage of the keyboard, mouse, and full-sized monitor on the personal computer to enter significant amounts of information. In step 4160, information may be shared with another MPN, as described above in conjunction with FIG. 37.

Figure 42:
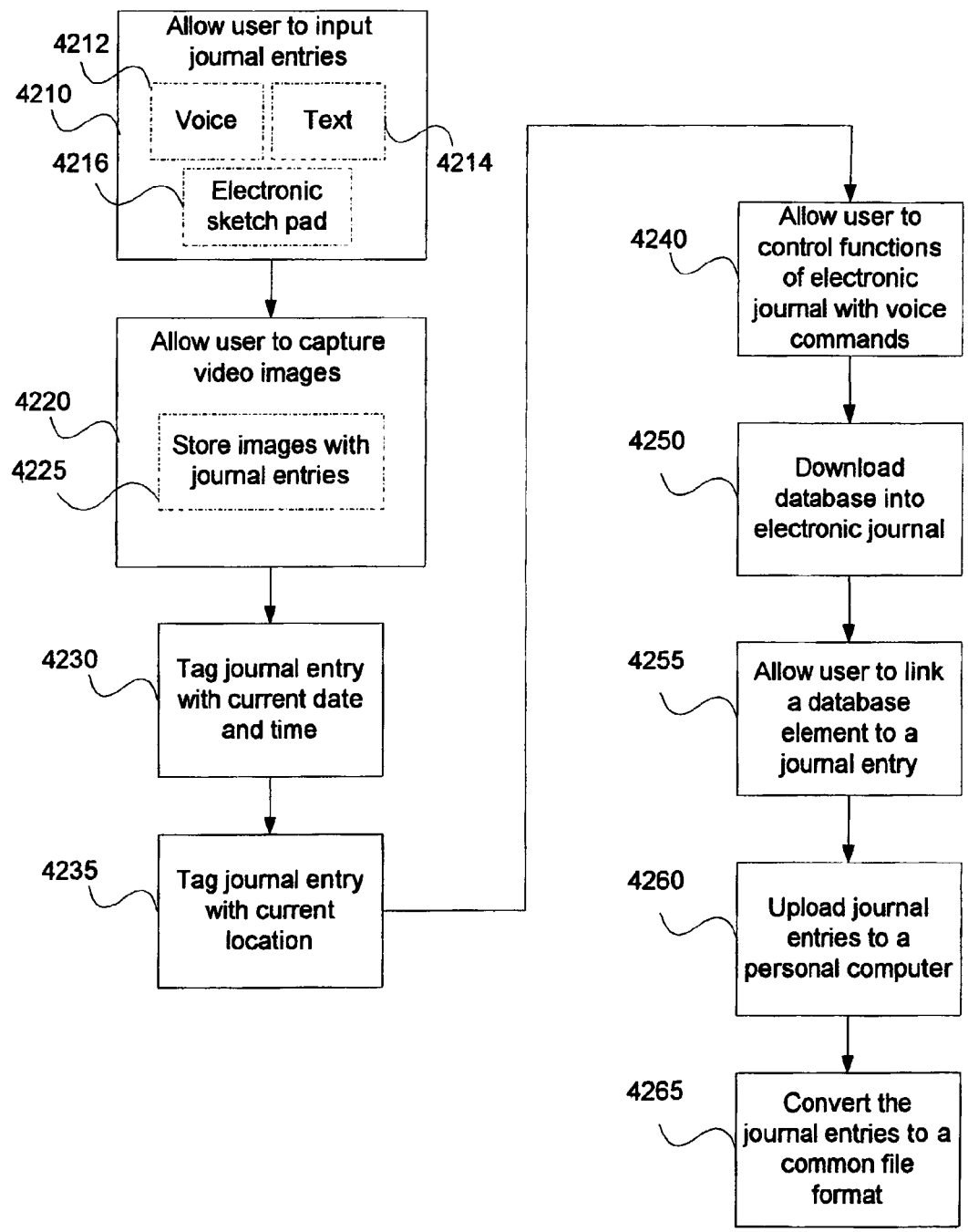
FIG. 42 is a flow chart of an illustrative process for using an MPN to provide a mobile electronic journal.

FIG. 42 shows more detail of step 4140 (FIG. 41), allowing the user to maintain a mobile electronic journal. All steps are optional and may be performed in any suitable order. In step 4210, a user may be allowed to enter journal entries. Entries may include voice in substep 4212, text in substep 4214, input from an electronic sketchpad in substep 4216, or any other suitable type of entry or combination of entries. In step 4220, the user may be allowed to capture a video image, for example using an INC that has digital camera hardware. If desired, the user may capture a video clip. In substep 4225, the captured video image may be stored with a journal entry. For example, it may be stored in the same memory, and there may be a link from one to the other. In step 4230, the journal entry may be automatically tagged with the current date and time if one of the INCs in the MPN includes a clock. In step 4235, the journal entry may be automatically tagged with the current location, if one of the INCs in the MPN includes a position monitor such as a global positioning system (GPS) monitor. In step 4240, the user may be allowed to control functions of the journal using the audio input, if the MPN includes a speech recognition function. In step 4250, a database may be downloaded into memory in the MPN. The database may include data of interest to the user, and may relate to topics to which the user may refer in the journal. For example, the database may include travel-related information, music-related information, school-related information, work-related information, or any other suitable data. In step 4255, the user may be allowed to link a journal entry to a database element.

In step 4260, any journal entries stored in the MPN may be uploaded to a personal computer. This may include the voice, text, and drawing parts of the entries, as well as any linked images and time and location tags. It may also include links to any database elements that may be linked to the journal entries, or it may include the data from the database elements themselves. In step 4265, the uploaded journal may be converted into a standard file format, so that it may be easily viewed or printed with the personal computer. The file format may include HTML, PDF, or any other suitable format. Images and audio segments may also be stored in a common file format. The data may be loaded into a database on the personal computer if desired.

Figure 43A:
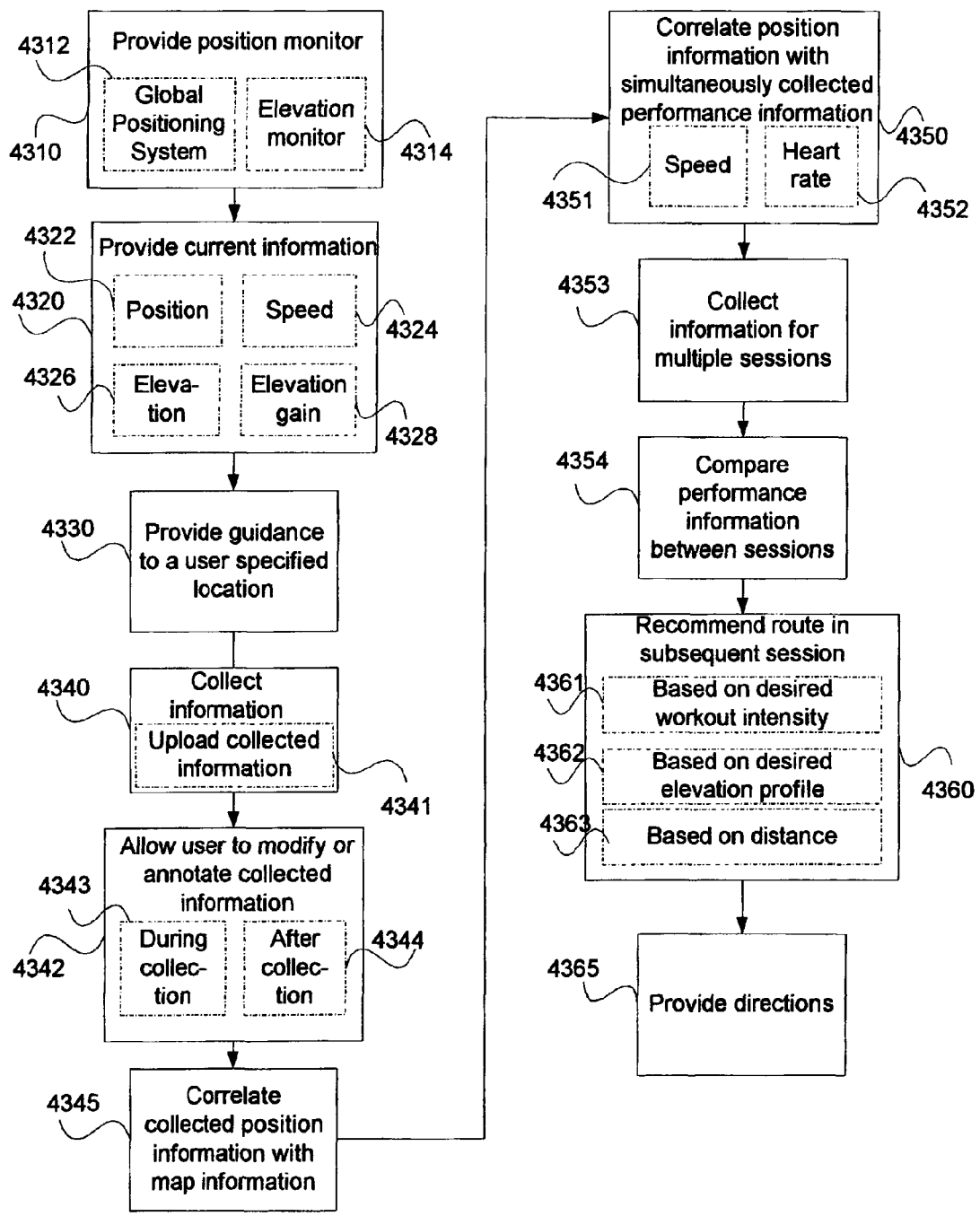
FIGS. 43A and 43B are flow charts of illustrative processes for using an MPN to provide a guidance function.

FIG. 43A shows more detail of step 3208 (FIG. 32), providing a guidance function using an MPN. In step 4310, the MPN may include a position monitor INC. This may be a GPS monitor in substep 4312. The system may also include an elevation monitor in substep 4314, which may, for example, use barometric pressure readings. In step 4320, the position monitor may be used to provide current user information. This may include current position in substep 4322, current speed in substep 4324, current elevation in substep 4326, and current elevation gain in substep 4328. If desired, the system may also collect direction information, for example from a compass, and provide direction information.

Figure 43B:
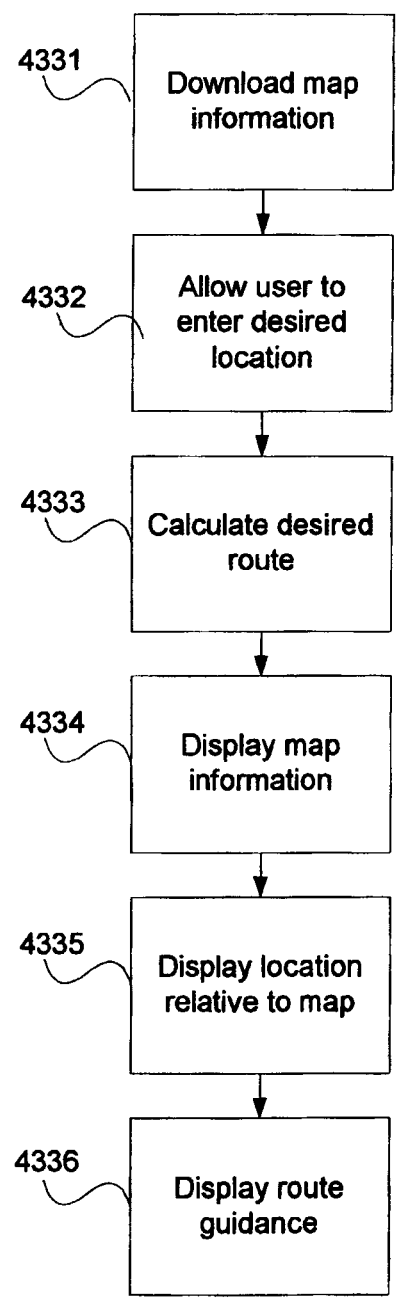

In step 4330, route guidance may be provided to a user. Turning to FIG. 43B for greater detail of step 4330, route guidance may include step 4331, in which map information may be downloaded into memory in the MPN. The map information may be downloaded using the wireless communications device in one of the INCs. Alternatively, it may be loaded from a memory device, such as a CD-ROM. In step 4332, the user may be allowed to enter a desired location. For example, the user may enter an address or the name of a destination, the user may choose a destination from a list, the user may point to a destination on a map displayed on a touch screen, or the user may speak the desired location. In step 4333, an INC in the MPN may calculate a route from the current location to the desired location. This may be done using any suitable algorithm or combination of algorithms that may compare various routes based on distance, estimated time, traffic, road conditions, or any other suitable criteria. If desired, the user may be allowed to enter criteria for choosing a route, or may be allowed to choose from multiple routes. In step 4334, map information may be displayed. The map information may include the current location, the desired location, and/or all or part of the route between them. In step 4335, the user's current location may be displayed on the map. This may also include other information, such as the user's direction and speed. In step 4336, route guidance may be displayed. In addition to displaying the chosen route on the map, the system may provide, either visually or audibly, prompts informing the user of turns and other actions. The system may also make corrections to the route if the user misses a turn or otherwise does not follow the guidance.

Returning to FIG. 43A, in step 4340, the system may collect and store position information as the user moves. This may include, for example, location, speed, and elevation, along with the time at which each measurement was taken. This step may also include substep 4341, uploading the collected data to a base station or personal computer. The collected data may be saved in a database, displayed, or analyzed, by an INC of the MPN, by a base station, by a personal computer, by a computer accessed over a wide area network such as the Internet, or in any other suitable location. In step 4342, the user may be allowed to annotate the collected position data, or otherwise modify it. For example, the user may enter text, create a voice annotation, or capture a video image or segment. Annotations may include information about a location, about the route, personal notes, images or video clips of sights seen, or any other information. If desired, the system may have a number of predefined annotations that may be quickly and easily entered by the user at any point. The system may store the annotation with the position information, and may create a link between the data items. The user may also be allowed to modify the collected data itself. The annotation or modification may be created as the position information is collected in substep 4343, for example using an input device that may be an INC in the MPN. The annotation or modification may also be created after the position information has been collected in substep 4344, for example using an input device connected to a personal computer. In step 4345, the collected information may be correlated with map data. This may be done in the MPN, using map data stored in memory in an INC of the MPN, or on a personal computer after the position information has been uploaded. The position information, along with any annotations, may be displayed on a map, for example showing the route taken by the user.

In step 4350, position information may be correlated with simultaneously collected performance information. This may be useful in an MPN that is also used to support athletic workouts. For example, the route may be an athletic training route or an athletic competition route. The performance information may, for example, be speed in substep 4351, heart rate in substep 4352, cadence, or any other suitable performance data. The personal data may be stored with the position data, and the system may also store links between the two data items. This collected performance data may be displayed during the session. It may also be displayed or printed on a personal computer at a later time. It may be displayed in a table, in a graph, on a map, on an elevation profile, or any other suitable format. In step 4353, performance data may be collected during multiple sessions. In step 4354, the performance data may be compared between sessions. The comparison may be for the entire sessions, or for portions of the sessions following the same route. For example, a table or graph may be used to show the performance differences between two sessions. Summary information, such as averages, may also be provided. Information may be displayed on an INC of the MPN, on a personal computer after being uploaded, to a computer accessed via a wide area network such as the Internet, or at any other suitable location.

The collected position information may be used to recommend a route for a later session in step 4360. For example, the MPN may store position information from one or more sessions, and may construct map data of routes that are available to the user. Prior to or during a later session, the constructed map data may be used to plan a route for the user. The system may also use the collected performance data to plan the route. If desired, the route may be that of an upcoming athletic competition, and the system may be used to collect information about the route, such as elevation profile, distance of individual segments, landmarks, or other information of interest. In substep 4361, a route may be recommended based on a desired workout intensity. For example, the system may use collected heart rate data or an elevation profile to choose a route with the desired difficulty. In substep 4362, a user may specify a desired elevation profile, and the system may choose a route that most closely matches the user's preference. In substep 4363, the system may recommend a route based on a desired distance chosen by the user. If desired, the system may allow the user to specify any other suitable criteria, or combination of criteria, for route selection. In step 4365, the MPN may provide directions or other guidance to the user during a session, based on the selected route. If desired, the guidance may be based on a route chosen ahead of time and downloaded. Alternatively, the directions may be made dynamically, as specific decision points are reached. For example, a prompt to take a specific turn may be shown on the display INC or played through the audio output INC. The system may also make modifications to the recommended route if the user does not follow the prompts. If desired, the chosen route may be based on map and elevation information loaded from a CD-ROM or other memory device or loaded from the Internet or other network, rather than using position information collected by the user.

Position data collected in one session may also be used to simulate the same route in a later session. For example, a user may travel the route of an upcoming competition in one or more sessions and collect position and elevation information. This collected position and elevation information may be used to control exercise equipment in later sessions to simulate the racecourse.

Figure 44:
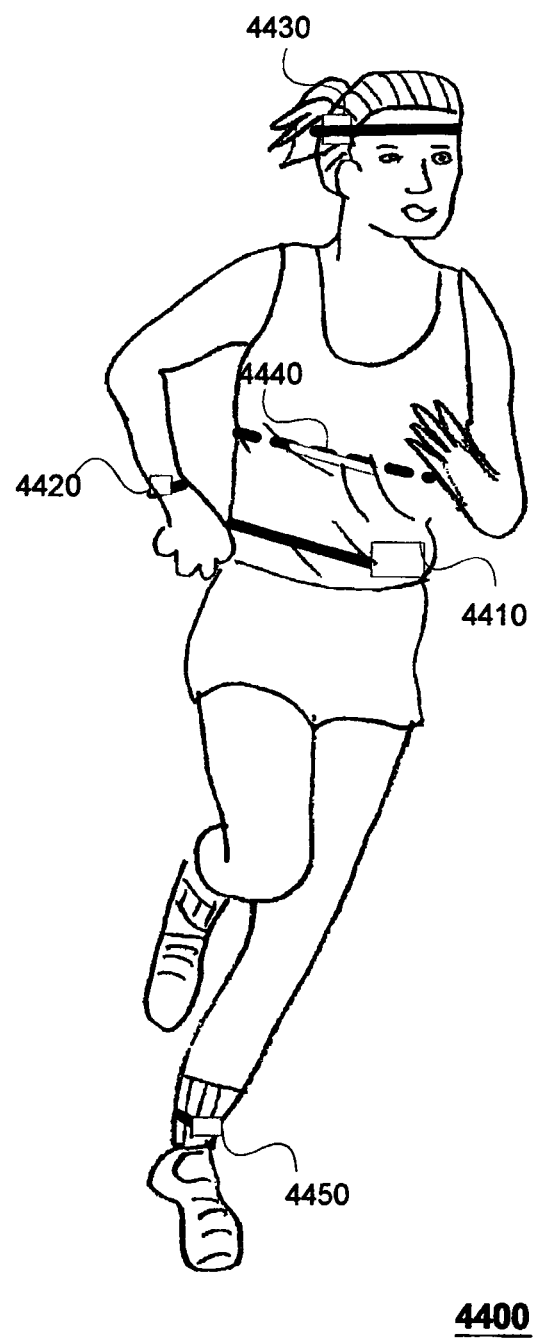
FIG. 44 is a diagram of an illustrative MPN that may be used to provide a guidance function.

FIG. 44 shows an illustrative MPN 4400 that may be used to provide guidance to an athlete. INC 4410 may be worn on a waistband, and may include a control unit, a GPS monitor, an elevation sensor, user input controls, and a clock. INC 4420 may be worn on a wristband and may include a display device and an accelerometer. INC 4430 may be worn on a headband, and may include an audio output device. INC 4440 may be worn on a chest strap and may include a heart rate sensor. INC 4450 may be worn on an ankle band and may include an accelerometer. Use of accelerometers mounted on the arm and leg to perform functions such as measuring cadence and providing form feedback is described in more detail below. INCs shown are merely illustrative, and all INCs are optional.

Figures 45A, 45B, 45C, 45D, 45E, 45F, 45G, 45H, 45I, 45J, 45K, 45L:
FIGS. 45A through 45L show illustrative screens that may be provided by an MPN in providing a guidance function.

FIGS. 45A through 45L show examples of screens that may be provided by display INC 4420 in an MPN 4400 (FIG. 44) that may be used for guidance and athletic functions. FIG. 45A provides a display of the user's current altitude. FIG. 45B provides a display of the user's current geographical location. FIG. 45C provides a display of the user's current speed. FIG. 45D provides a display of the user's current rate of elevation change. FIG. 45E provides a display of the user's heart rate. FIG. 45F provides a display of a route prompt. FIG. 45G provides a display of the user's current cadence. FIG. 45H provides a display of the user's current stride length. FIG. 45I provides a display of the current date and time. FIG. 45J provides a display of a session total time and partial time from a stopwatch function. FIG. 45K provides a display of an interval timer. FIG. 45L provides a display of a speed prompt. These screens are merely illustrative. Any suitable information may be displayed, in any suitable format. If desired, any of this information may be sent to an audio output INC in addition to or instead of the display INC.

Figure 46:
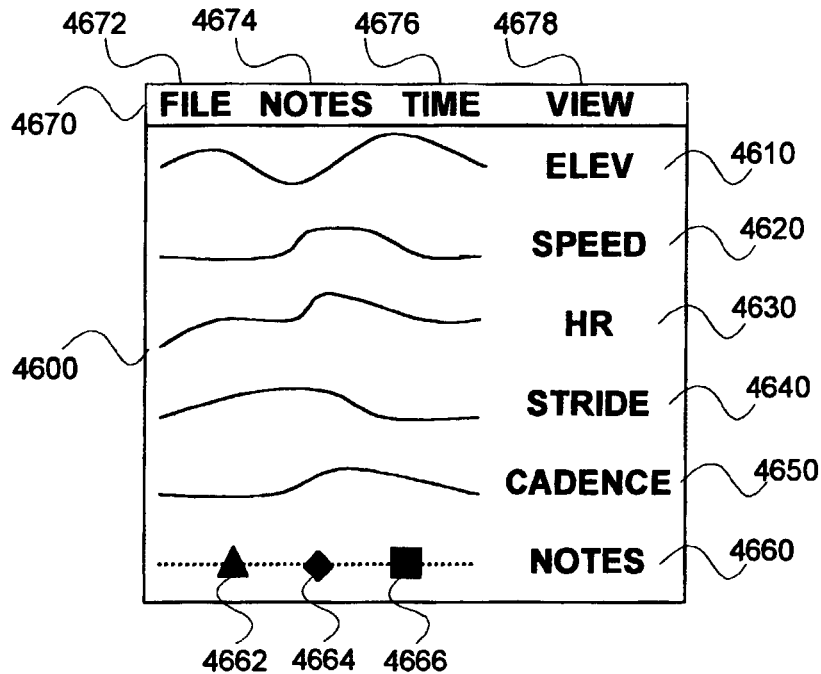
FIGS. 46 through 49 show illustrative screens that may be used with a modular personal computer that provides a guidance function.

FIGS. 46 through 49 show illustrative screens that may be displayed on a personal computer configured to interface with an MPN that provides guidance features and athletic features. FIG. 46 shows session overview screen 4600 that may display collected position, performance, and annotation data for a session. Graphs 4610, 4620, 4630, 4640, and 4650, along with note line 4660, may all be displayed relative to a common time line. Graph 4610 may display elevation vs. time for the session or portion of session. Graph 4620 may display speed vs. time for the session or portion of session. Graph 4630 may display heart rate vs. time for the session or portion of session. Graph 4640 may display stride length vs. time for the session or portion of session. Graph 4650 may display cadence vs. time for the session or portion of session. The user may be allowed to click on any graph to view more details of the graphed data (such as a chart of the data). These graphs are merely illustrative. Any suitable data may be graphed or charted. Note line 4660 may display indicator to show the link between time and each annotation. For example, indicator 4662 may indicate that an audio annotation has been linked to that first specific time during the session. Indicator 4664 may indicate that a video annotation may be linked to that second specific time during the session. Indicator 4666 may indicate that a text annotation has been linked to that third specific time during the session. The user may be allowed to point the mouse at an indicator or click on it to view the actual annotation. Menu bar 4670 may provide user access to various functions. For example, file menu 4672 may allow the user to save the session data, open a file with other session data, or perform other file related functions. Notes menu 4674 may allow the user to perform functions related to annotations, such as adding a new annotation, modifying an annotation, deleting an annotation, or viewing an existing annotation. Time menu 4676 may allow the user to perform time-related functions, such as modifying which time span from the session is graphed. View menu 4678 may allow the user to change the display to another view of the same data (such as a chart), or to any other display supported by the system. This may include, for example, allowing the user to select session comparison display 4700 of FIG. 47 or map view 4800 of FIG. 48. The menu options described here are merely illustrative. Any suitable menu options may be offered. For example, an option may be offered to allow the user to select which types of data to graph.

Figure 47:
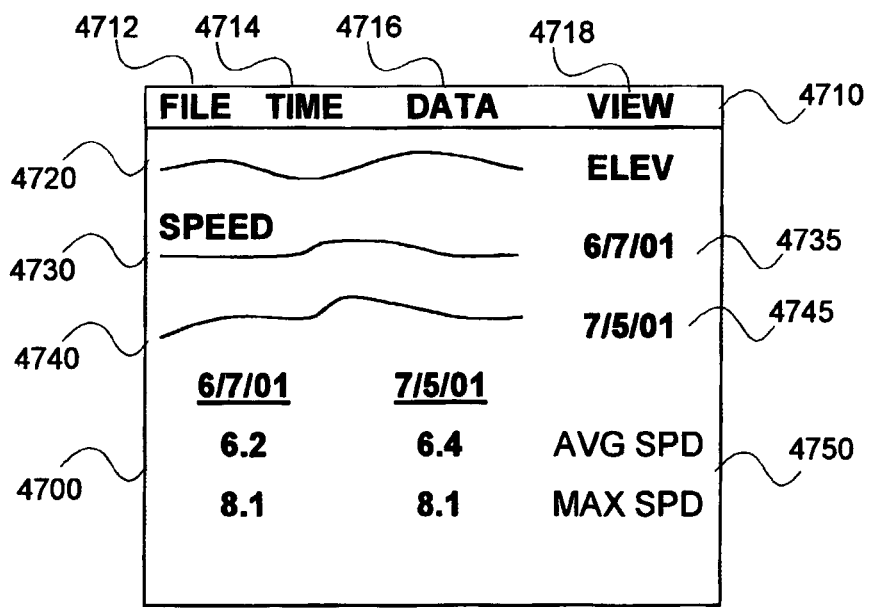

FIG. 47 shows session comparison screen 4700 that may display collected position, performance, and annotation data for multiple sessions or partial session in which the user followed the same route. Graphs 4720, 4730, and 4740 may all be displayed relative to a common distance line. Graph 4720 may display elevation vs. distance for the common route or portion of route. Graph 4730 may display speed vs. distance for the first session or portion of session on date 4735. Graph 4740 may display speed vs. distance for the second session or portion of session on date 4745. The user may be allowed to click on any graph to view more details of the graphed data (such as a chart of the data). These graphs are merely illustrative. Any suitable data may be graphed or charted. Summary region 4750 may display and compare summary data from the multiple sessions. For example, if speed data is graphed on the screen, the summary region 4750 may display average and maximum speed for the graphed segment of each session. Menu bar 4710 may provide user access to various functions. For example, file menu 4712 may allow the user to save the session data, open a file with other session data, or perform other file related functions. Time menu 4714 may allow the user to perform time-related functions, such as modifying which time span from the session is graphed. Data menu 4716 may allow the user to perform data-related functions, such as modifying which data from the session is graphed. View menu 4718 may allow the user to change the display to another view of the same data (such as a chart), or to any other display supported by the system. This may include, for example, allowing the user to select session overview display 4600 of FIG. 46 or map view 4800 of FIG. 48. The menu options described here are merely illustrative. Any suitable menu options may be offered. For example, an option may be offered to view or modify annotations.

Figure 48:
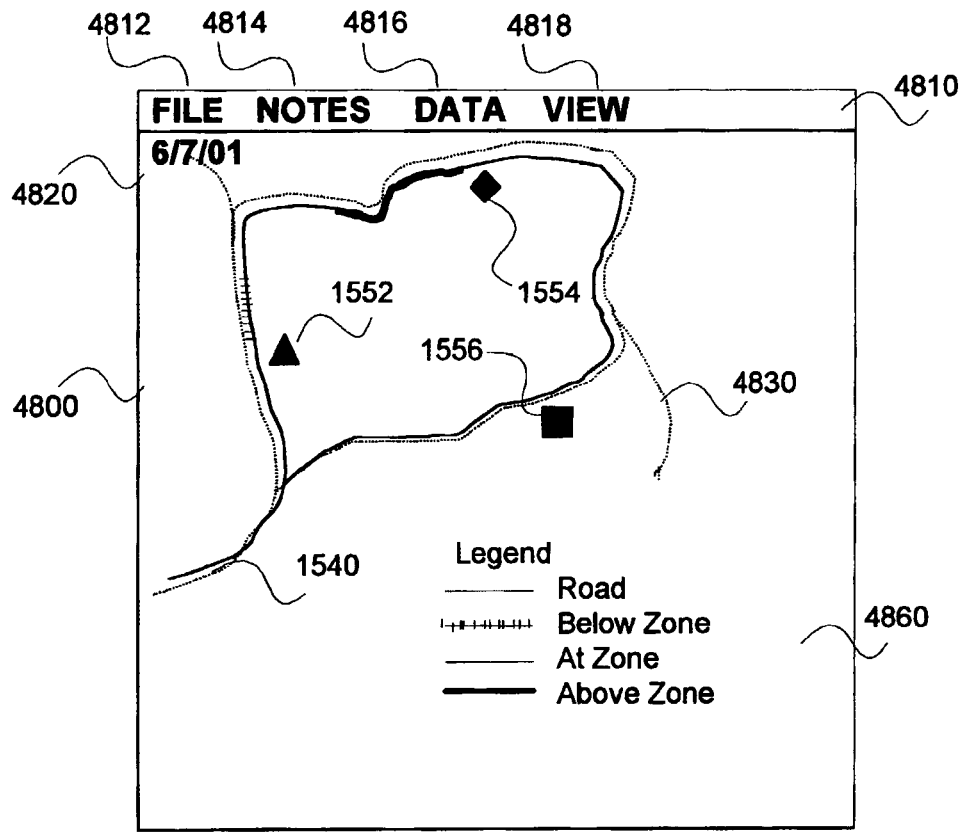

FIG. 48 shows map view screen 4800 that may display collected position, performance, and annotation data for a session or partial session in relation to a map. Date field 4820 may display the date and/or time of the session being viewed. Road indicator 4830 may show the roads, trails, and other fixed items from the region in which the session occurred. Route indicator 4840 may be used to indicate the actual route followed by the user during the session. Route indicator 4840 may have different characteristics to indicate different performance data. For example, there may be three different line styles used to indicate heart rate above a desired zone, within a desired zone, and below a desired zone. The number of line styles and the performance parameter shown are merely illustrative. Any suitable data divided into any suitable number of zones may be drawn on the map. If desired, multiple performance parameters may be shown on the same map. The user may be allowed to click on the map to view more details of the data (such as a chart or graph of the data). Note indicators may be displayed on the map to show the link between the route and each annotation. For example, indicator 4852 may indicate that an audio annotation has been linked to that first specific time during the session. Indicator 4854 may indicate that a video annotation may be linked to that second specific time during the session. Indicator 4856 may indicate that a text annotation has been linked to that third specific time during the session. The user may be allowed to point the mouse at an indicator or click on it to view the actual annotation. Legend 4860 may display a legend of the line styles used for the road indicator and route indicator, along with any other information that may be displayed on the map. For example, a legend may be provided for the different styles of annotation indicator. Menu bar 4810 may provide user access to various functions. For example, file menu 4812 may allow the user to save the session data, open a file with other session data, or perform other file related functions. Notes menu 4814 may allow the user to perform functions related to annotations, such as adding a new annotation, modifying an annotation, deleting an annotation, or viewing an existing annotation. Data menu 4816 may allow the user to perform data-related functions, such as modifying which data from the session is shown on the map. View menu 4818 may allow the user to change the display to another view of the same data (such as a chart), or to any other display supported by the system. This may include, for example, allowing the user to select session overview display 4600 of FIG. 46 or session comparison display 4700 of FIG. 47. The menu options described here are merely illustrative. Any suitable menu options may be offered. For example, an option may be offered to zoom into a portion of the route.

Figure 49:
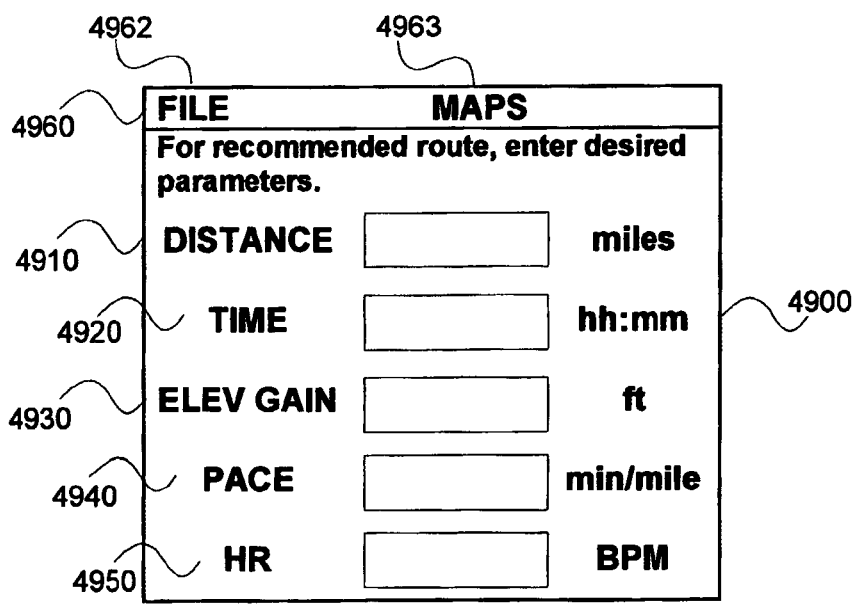

FIG. 49 shows session planning screen 4900 that may allow the user to enter desired attributes of an upcoming session, to allow the system to plan an appropriate route. For example, the user may be allowed to enter a desired total distance in screen region 4910. Screen region 4920 may allow the user to enter a desired total time for the session. Screen region 4930 may allow the user to enter a desired elevation gain for the route. Screen region 4940 may allow the user to enter a desired pace or speed for the session. Screen region 4950 may allow the user to enter a desired heart rate or heart rate range for the session. These parameters are merely illustrative. Any suitable parameters may be offered. The user may be allowed to enter a subset of desired parameters, and the system may create a route that best matches the entered parameters. Menu bar 4960 may provide user access to various functions. For example, file menu 4962 may allow the user to save the session data, open a file with other session data, or perform other file related functions. Maps menu 4964 may allow the user to perform functions related to maps, such as viewing maps of available routes, and selecting one or more preferred routes. The menu options described here are merely illustrative. Any suitable menu options may be offered. For example, an option may be offered to view data from previous sessions.

Figure 50:
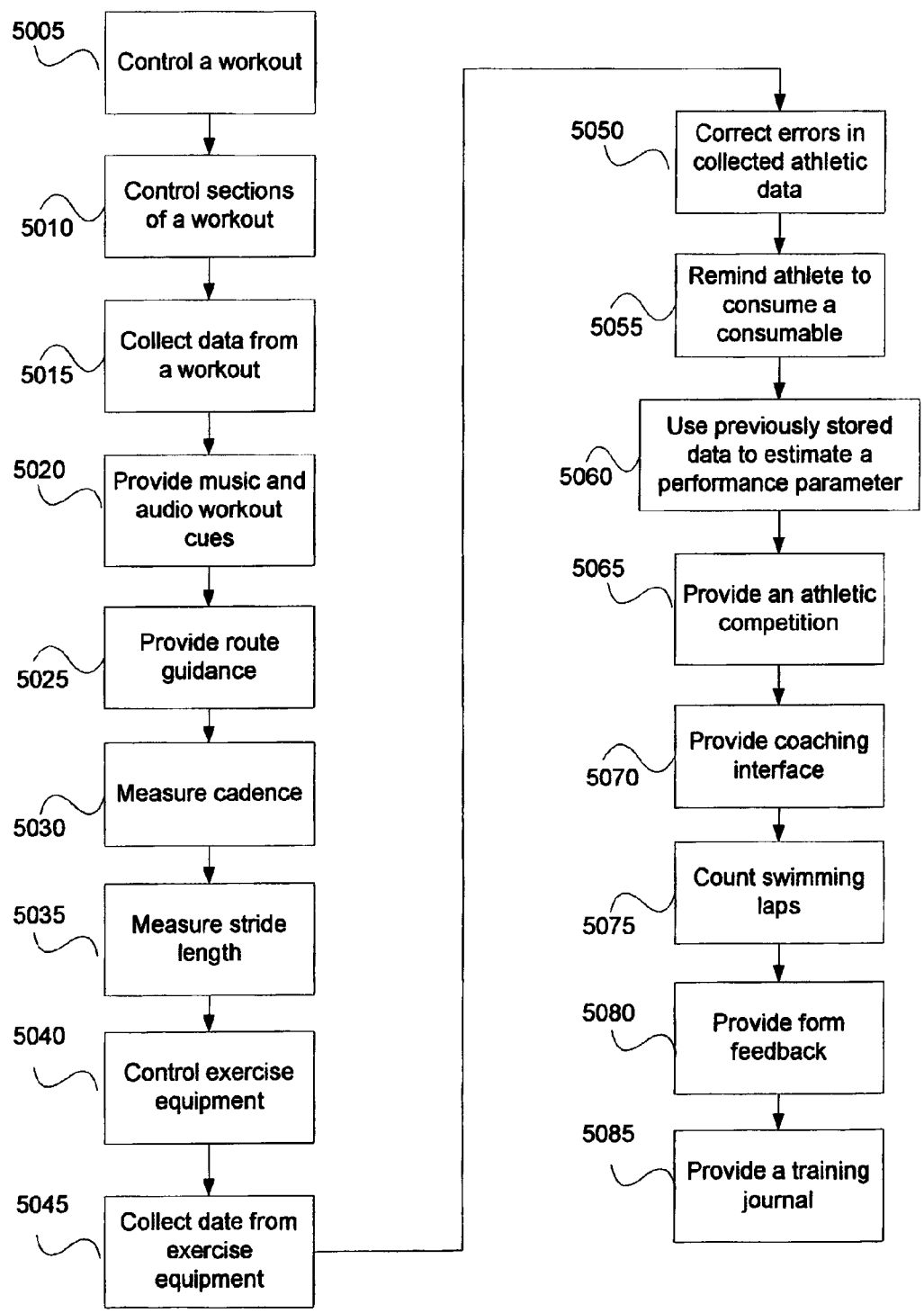
FIG. 50 is a flow chart of an illustrative process for providing an athletic function in an MPN.

FIG. 50 shows more detail of step 3210 of FIG. 32, providing an athletic function with an MPN. All steps are optional and may be performed in any suitable order. In step 5005, the MPN may be used to control a workout. In step 5010, the MPN may be used to control one or more sections of a workout. In step 5015, the MPN may be used to collect data from a workout. In step 5020, the MPN may be used to provide both music and audio workout cues, as described previously with respect to FIG. 29. In step 5025, the MPN may be used to provide route guidance during a workout, as described previously with respect to FIG. 43A. In step 5030, the MPN may measure an athlete's cadence. In step 5035, the MPN may measure an athlete's stride length. In step 5040, the MPN may be used to control a piece of exercise equipment, as described previously with respect to FIG. 21. In step 5045, the MPN may be used to collect data from a piece of exercise equipment, as described previously with respect to FIG. 21. In step 5050, the MPN may correct errors in collected athletic data. In step 5055, the MPN may remind an athlete to consume a consumable. In step 5060, the MPN may use previously stored data to estimate a performance parameter. In step 5065, the MPN may provide for an athletic competition between two or more athletes, as described previously with respect to FIG. 39. In step 5070, the MPN may provide for a coaching interface. In step 5075, the MPN may count swimming laps. In step 5080, the MPN may provide form feedback to an athlete. In step 5085, the MPN may provide a training journal. More details of these embodiments are described below. These athletic uses of the MPN are merely illustrative. Other athletic uses are possible if desired.

Figure 51:
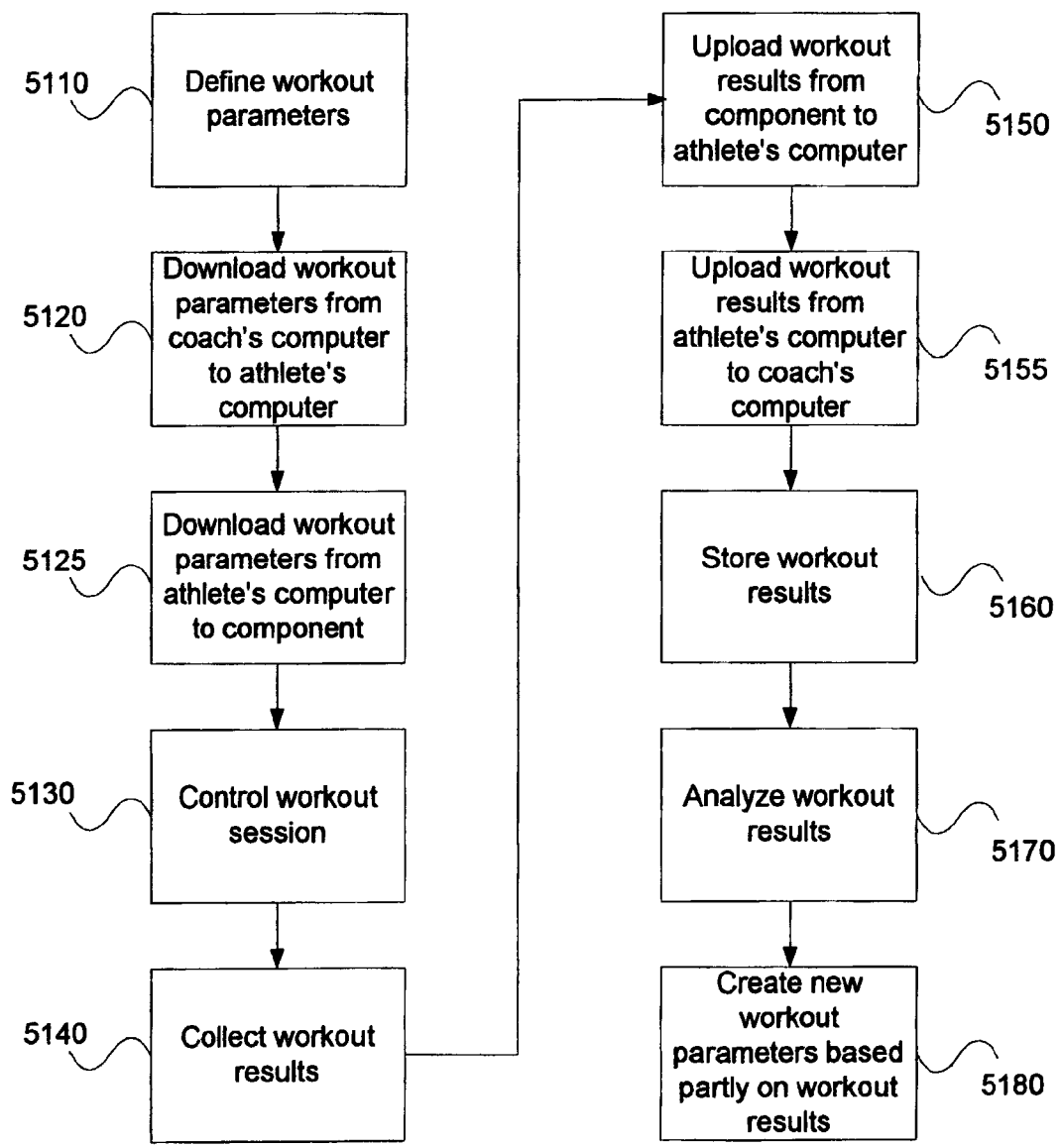
FIG. 51 is a flow chart of an illustrative process for providing workout control and feedback using an MPN.

FIG. 51 shows flow chart 5100 of an illustrative process for providing workout control and feedback. All steps are optional and may be performed in any suitable order. In step 5110, workout parameters may be defined. The parameters may be defined, for example, on a coach's computer or on an athlete's computer. The parameters may be entered by a user such as the coach or athlete, or they may be generated automatically by a coaching software application. The parameters may define aspects of a planned workout, such as its type, duration, intensity, etc. In step 5120, if the workout parameters were defined on a coach's computer, they may be downloaded to the athlete's computer. In step 5125, the parameters may be downloaded from the athlete's computer to an INC in the MPN, such as a control unit. In step 5130, the INC may control aspects of the workout session, using an output INC in the MPN. In step 5140, the INC may collect workout results from an input INC in the MPN. In step 5150, the workout results may be uploaded to the athlete's computer. In step 5155, the workout results may be uploaded to the coach's computer. In step 5160, the workout results may be stored, for example on the athlete's computer or the coach's computer. In step 5170, the workout results may be analyzed, for example on the athlete's computer or the coach's computer. For example, the workout results may be displayed, or may be compared with workout results from other workout sessions. In step 5180, the workout results may be used to determine parameters for one or more upcoming workout sessions, for example on the athlete's computer or the coach's computer.

Figure 52:
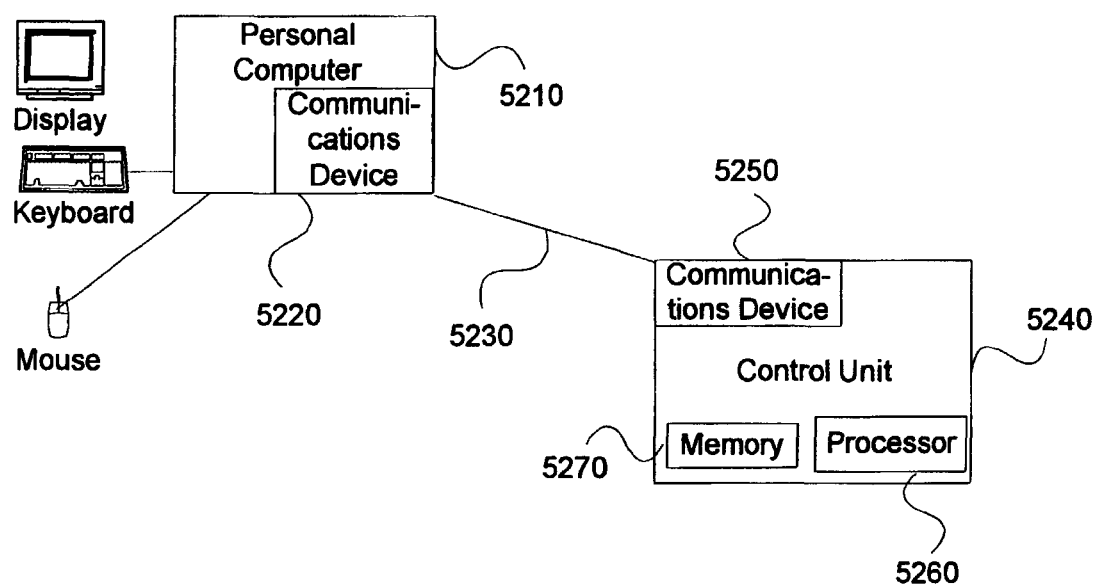
FIG. 52 is a block diagram of an illustrative system for communicating between a personal computer and an INC of an MPN.

FIG. 52 shows a block diagram of an illustrative system 5200 for communicating between a personal computer 5210 and a control unit 5240 that is an INC in an MPN. Personal computer 5210 may have communications device 5220, control unit 5240 may have communications device 5250, and they may communicate using communication path 5230. Communication path 5230 may be a wireless radio frequency link, an infrared link, a docking station link, a USB link, a serial port link, or any other suitable type of communications path. Control unit 5240 may include processor 5260 for executing software related to controlling a workout, collecting workout results, communicating with personal computer 5210, and communicating with other INCs in the MPN. Control unit 5240 may also include memory 5270 for holding software, downloaded workout parameters, and collected workout results.

Figure 53:
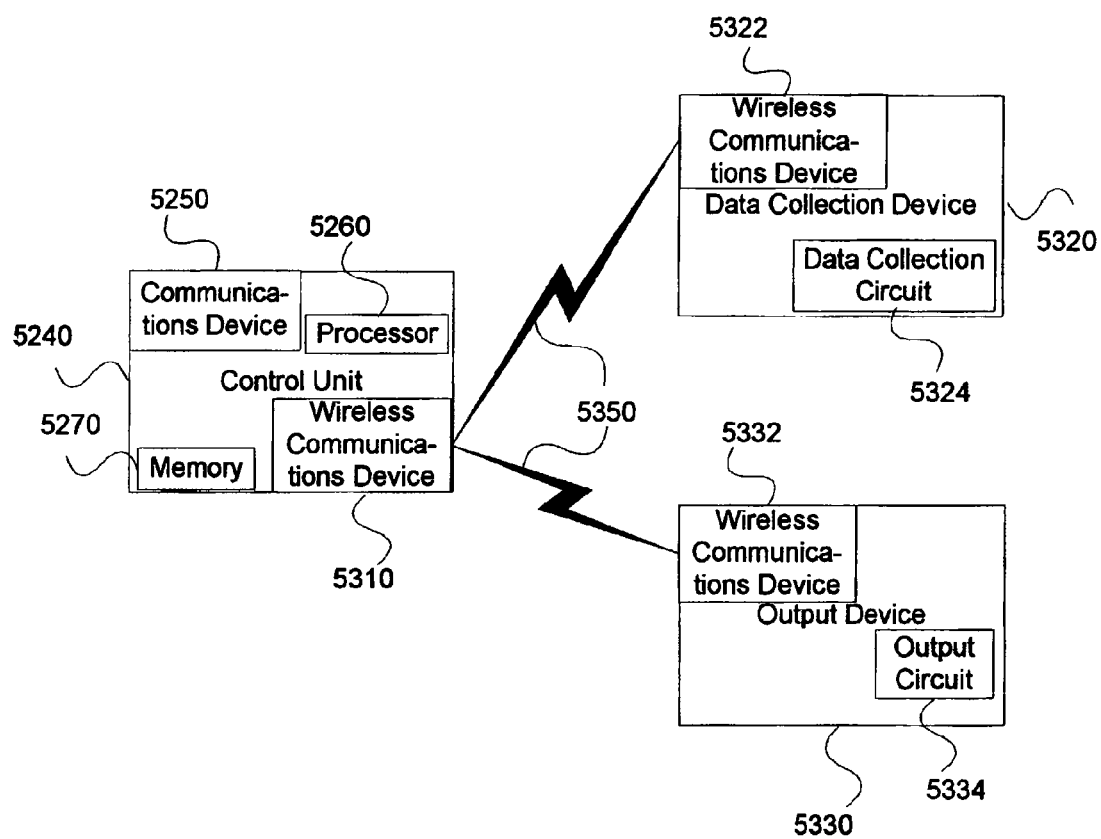
FIG. 53 is a block diagram of an illustrative MPN that controls aspects of an athletic workout and collecting results from a workout.

FIG. 53 shows a block diagram of an illustrative MPN 5300 for controlling aspects of an athletic workout and collecting results from a workout. Control unit 5240 may be the same control unit shown in FIG. 52, and may be configured to communicate with a personal computer as shown in that FIG. It may also have wireless communications device 5310 for communicating with other INCs in MPN 5300 over wireless communication path 5350, such as data collection INC 5320 and output INC 5330. If desired, wireless communications device 5310 may be the same as communications device 5250. If desired, control unit 5240 may be omitted, and its functions may be assumed by other INCs in the MPN.

Data collection INC 5320 may have wireless communication device 5322 for sending collected data to control unit 5240 or other INC having storage capabilities. It may also have data collection circuit 5324. Data collection circuit 5324 may collect any athletic data, such as speed, heart rate, power, resistance, location, cadence, or any other suitable type of athletic data. Data collection INC 5320 may be worn by the athlete. If desired, data collection INC 5320 may be mounted on a piece of athletic equipment or a bicycle and may collect data from that equipment.

Output INC 5330 may have wireless communication device 5332 for receiving control commands from control unit 5240 or other suitable INC. It may also have output circuit 5334. Output circuit 5334 may output athletic control data using any appropriate method, such as displaying a prompt to the user, outputting a prompt to the user, controlling resistance, controlling speed, or any other suitable type of athletic control. Output INC 5330 may be worn by the athlete. If desired, output INC 5330 may be mounted on a piece of athletic equipment or a bicycle and may send control commands to that equipment.

Figure 54:
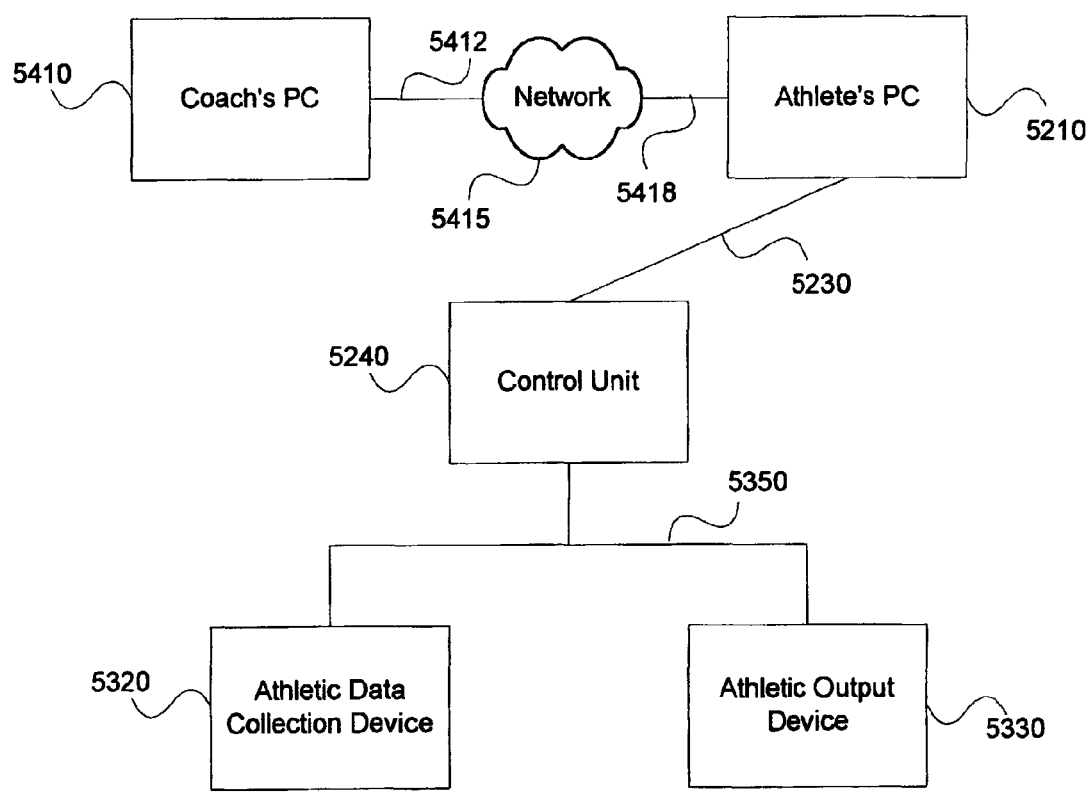
FIG. 54 is a block diagram of an illustrative system for communicating among an MPN, an athlete's personal computer, and a coach's personal computer.

FIG. 54 shows how MPN 5300 (FIG. 53) may communicate with an athlete's personal computer 5210 and a coach's personal computer 5410. Athlete's personal computer 5210 may communicate with coach's personal computer 5410 using any suitable network 5415, such as the Internet. Either computer may connect with network 5415 using connection 5412 and 5418, such as a telephone modem, a cable modem, a digital subscriber line modem, or any other suitable type of connection. As shown previously, athlete's personal computer 5210 may connect to control unit 5240, and control unit 5240 may send commands to athletic output INC 5330 and collect data from athletic data collection INC 5320. If desired, connections may not all be in place simultaneously. For example, at a first time, coach's computer 5410 may be connected to network 5415, and workout parameters may be uploaded to a web server. At a second time, athlete's computer 5210 may be connected to network 5415, and workout parameters may be downloaded from the web server. At a third time, athlete's personal computer 5210 may be connected to control unit 5240, and workout parameters may be downloaded into control unit 5240. At a fourth time, which may be during a workout session, the control unit 5240 may send control commands to athletic output INC 5330 and may receive data from athletic data collection INC 5320. At a fifth time, workout results may be uploaded from control unit 5240 to athlete's personal computer 5210. At a sixth time, workout results may be uploaded from athlete's personal computer 5210 to a web server in network 5415. At a seventh time, workout results may be downloaded from the web server in network 5415 into coach's computer 5410. If desired, data may be sent directly between coach's computer 5410 and athlete's computer 5210, rather than using a web server to store data sent from one to the other. If desired, control unit 5240 may be omitted, and athlete's personal computer 5210 may connect directly to athletic output INC 5330 and athletic data collection INC 5320 or storage INC (not shown).

Figure 55:
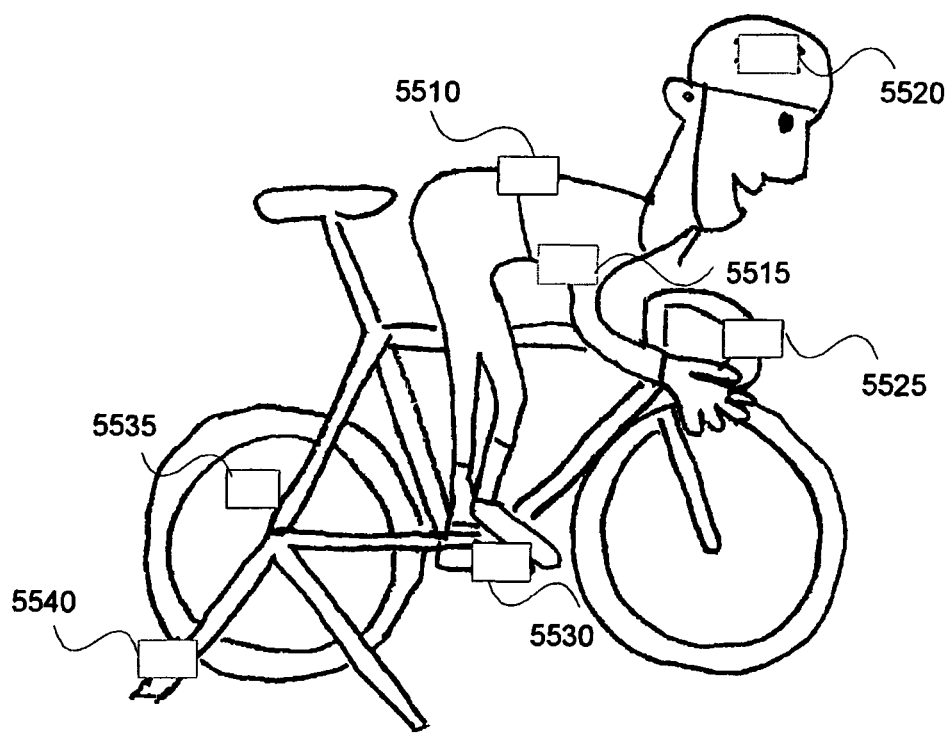
FIG. 55 is a diagram of an illustrative MPN that may be used to provide control of an athletic workout and collect workout results.

FIG. 55 shows illustrative MPN 5500 that may be used to provide control of an athletic workout and collect workout results. INC 5510 may be a control unit, and may be worn by the athlete. INC 5515 may be an athletic data collection INC worn by the athlete, and may include a heart rate sensor. INC 5520 may be an athletic output INC worn by the athlete, and may include an audio output INC. INC 5525 may be an athletic output INC mounted on a bicycle, and may include a display INC. INC 5530 may be an athletic data collection INC mounted on a bicycle, and may include a pedal cadence sensor. INC 5535 may be an athletic data collection INC mounted on a bicycle, and may include a wheel speed sensor. INC 5540 may be an athletic output INC mounted on a bicycle training stand, and may include resistance control device. During a workout, the control unit may control aspects of the workout by changing the cycling difficulty using INC 5540, and by providing prompts to the athlete using INC 5520 and INC 5525. Prompts may include, for example, prompts to pedal faster, slower, harder, or easier, to stand or sit, to pedal with one leg or both legs, or any other suitable prompts. INCs shown are merely illustrative, and each INC is optional.

Figure 56:
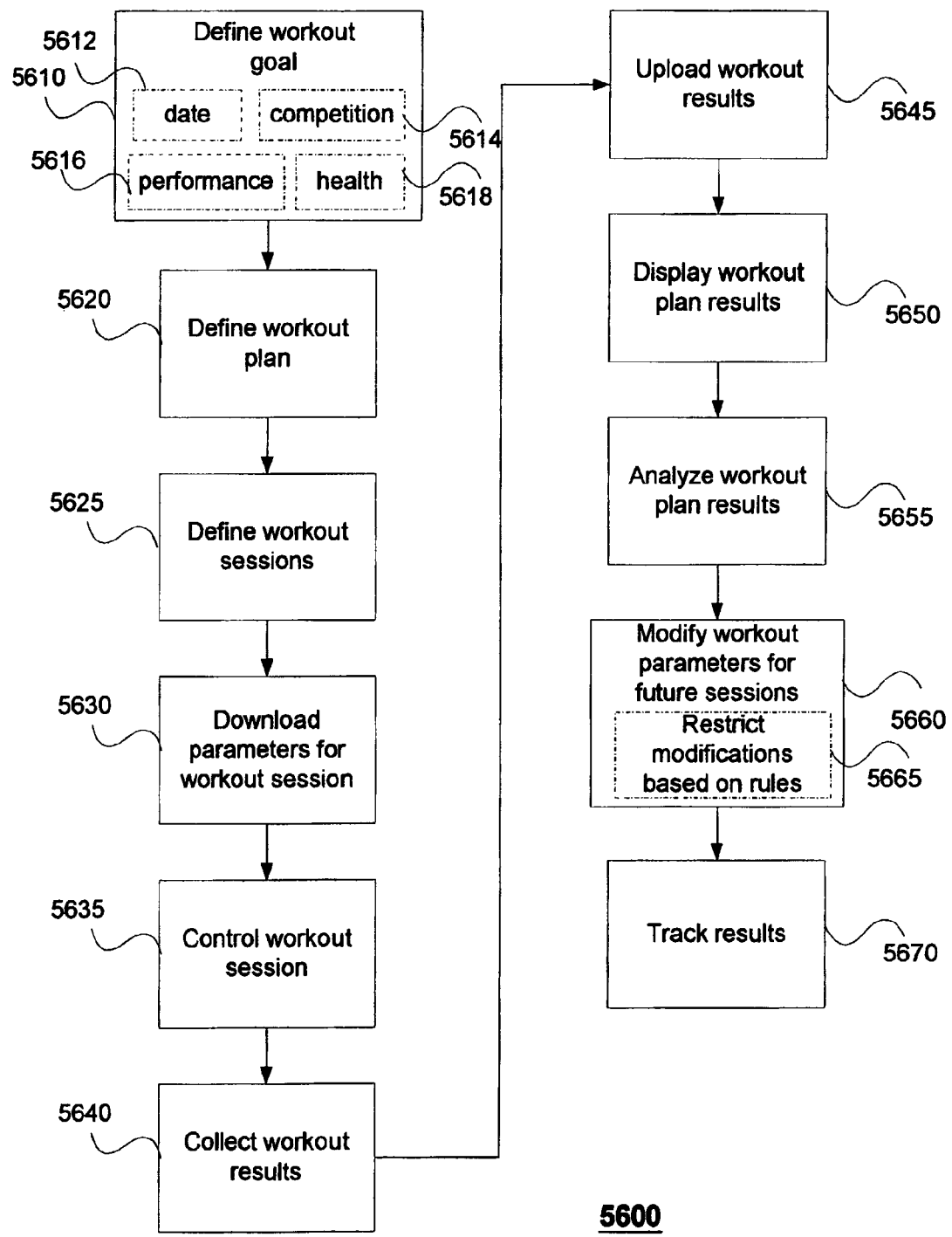
FIG. 56 is a flow chart of an illustrative process for managing a workout plan used with an MPN.

FIG. 56 shows a flow chart of an illustrative process 5600 for managing a workout plan. All steps are optional and may be performed in any suitable order. The workout plan may be managed using software on athlete's computer 5210 or coach's computer 5410 (FIG. 54). In step 5610, a workout goal may be defined. This may include a specific date in substep 5612, a specific upcoming competition in substep 5614, a specific performance goal in substep 5616, a specific health goal in substep 5618, or any other suitable type of goal. If desired, multiple goals may be defined. In step 5620, a workout plan may be defined based on the workout goal. This may include different types of workouts, different periods of time with specific sub-goals, or other suitable plan. In step 5625, a workout session may be defined. That may include a type of workout, duration, intensity, repetitions, or any other suitable parameters. As many parameters as desired may be created for each workout. The workout plan may include tracking of multiple planned workout sessions. In step 5630, the workout parameters may be downloaded from the coach's computer or athlete's computer into an INC of the MPN, such as a control unit or storage INC. In step 5635 and step 5640, during a workout session, aspects of the workout may be controlled and data may be collected. In step 5645, workout results may be uploaded. This may include storing results on the athlete's computer or the coach's computer. Results may be stored for multiple workout sessions. This may include storing the parameters that were used to define the workout sessions, as well as data collected during the sessions. In step 5650, workout results may be displayed for the athlete or coach. In step 5655, workout results may be analyzed. This may include comparing results between multiple workout sessions. In step 5660, the workout results may be used to modify one or more parameters for an upcoming workout session. Workout results may include data collected during a workout, as well as the workout parameters used during the workout session. Workout results may include information on missed workout sessions. Workout results may also include related information such as athlete health information, athlete eating and drinking records, athlete's resting heart rate, and other auxiliary information. For example, a future workout may be made easier or harder depending on the results of the workout. In another example, if the time of a workout session was changed, an upcoming session may also be moved or canceled. If desired, in substep 5665, rules may be applied to restrict how future workout modifications may be made. For example, a rule may restrict the system from scheduling two workouts of the same type on the same or consecutive days. As another example, the intensity, difficulty, or duration may not be allowed to increase more than a fixed percentage, such as ten percent. And in step 5670, the results of all workouts in a plan may be tracked as they occur. The coach or athlete may be allowed to view historical data, to view trends and improvements, or compare the results of two or more workout sessions. This may also include comparing the collected workout results to the workout plan goal or goals. If desired, other data, such as data entered by the coach or athlete, may be compared with the workout plan goal.

Figure 57:
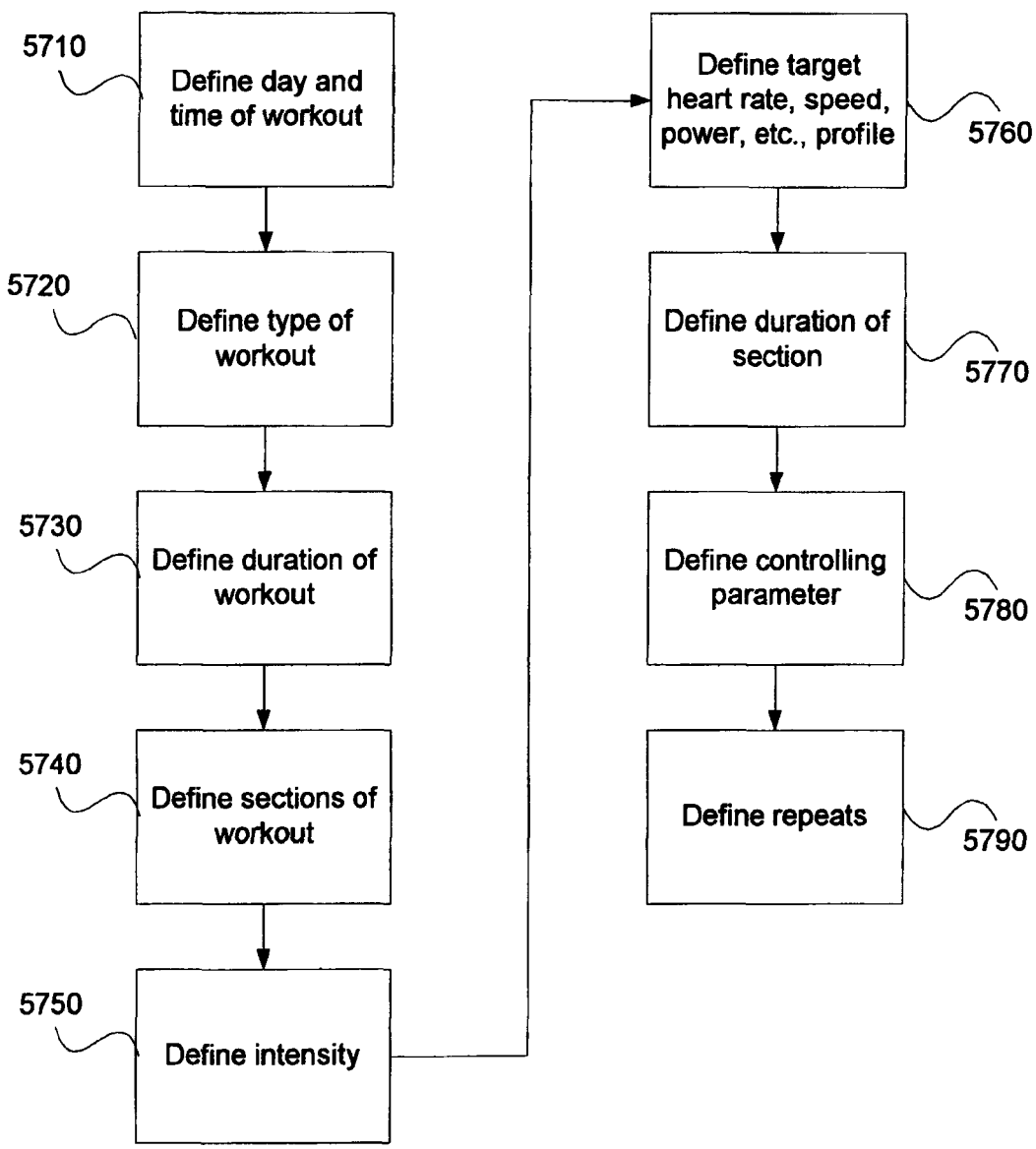
FIG. 57 is a flow chart of an illustrative process for defining workout parameters used in an MPN.

In FIG. 57, more details are shown of step 5625 (FIG. 56), defining the workout parameters. All steps are optional and may be performed in any suitable order. In step 5710, the day and time of a workout may be defined. The workout time may be defined with any suitable degree of specificity, such as any time within a week, any time within a three day period, any time on a specific day, before or after a different workout, or at a specific hour. In step 5720, the type of workout may be defined. This may include a general workout type, such as running, cycling, swimming, weightlifting, rowing, or the like. It may also include a style of workout, such as endurance, speed work, interval training, fartlek ("speed play"— bursts of speed during a training run) training, hill work, strength training, or any other suitable style. In step 5730, the duration of the workout may be defined. The duration may be measured in time, distance, or any other suitable units. The duration may be expressed as a range, if desired.

In step 5740, the workout may be divided into sections. Each section may have its own goal, such as warm up, increasing anaerobic threshold, recovery, increasing endurance, cool down, or any other suitable goal. Each section may be provided its own set of workout parameters. For example, in step 5750, target intensity may be defined for a section. In step 5760, target heart rate, speed, power, cadence, or any other parameter to be controlled may be defined for the section. If desired, multiple parameters to be controlled may be defined. If desired, the desired profile of the parameter or parameters during the section may be specified. If desired, a section may be defined with no parameter to be controlled. For example, the desired heart rate for a section may be 100 beats per minute at the start of the section, and may increase linearly to a value of 130 beats per minute at the end of the section. In step 5770, the duration of each section may be defined. The duration may be measured in units of time, units of distance, or any other suitable units. In step 5780, the controlling parameter for the section may be defined. For example, to control the heart rate, the athlete's speed may be controlled by sending audible prompts, the speed may be controlled by sending commands to a piece of exercise equipment, or the resistance may be controlled by sending commands to a piece of exercise equipment. If desired, multiple controlling parameters may be specified. If desired, limits on the values or rate of change of the controlling parameter may be specified. In step 5790, repetitions of sections may be defined. For example, two sections may be alternated, and the combination may be repeated four times. Any other suitable attributes of a section may also be defined. If desired, the definition of one section may be copied from the definition of another section.

Figure 58:
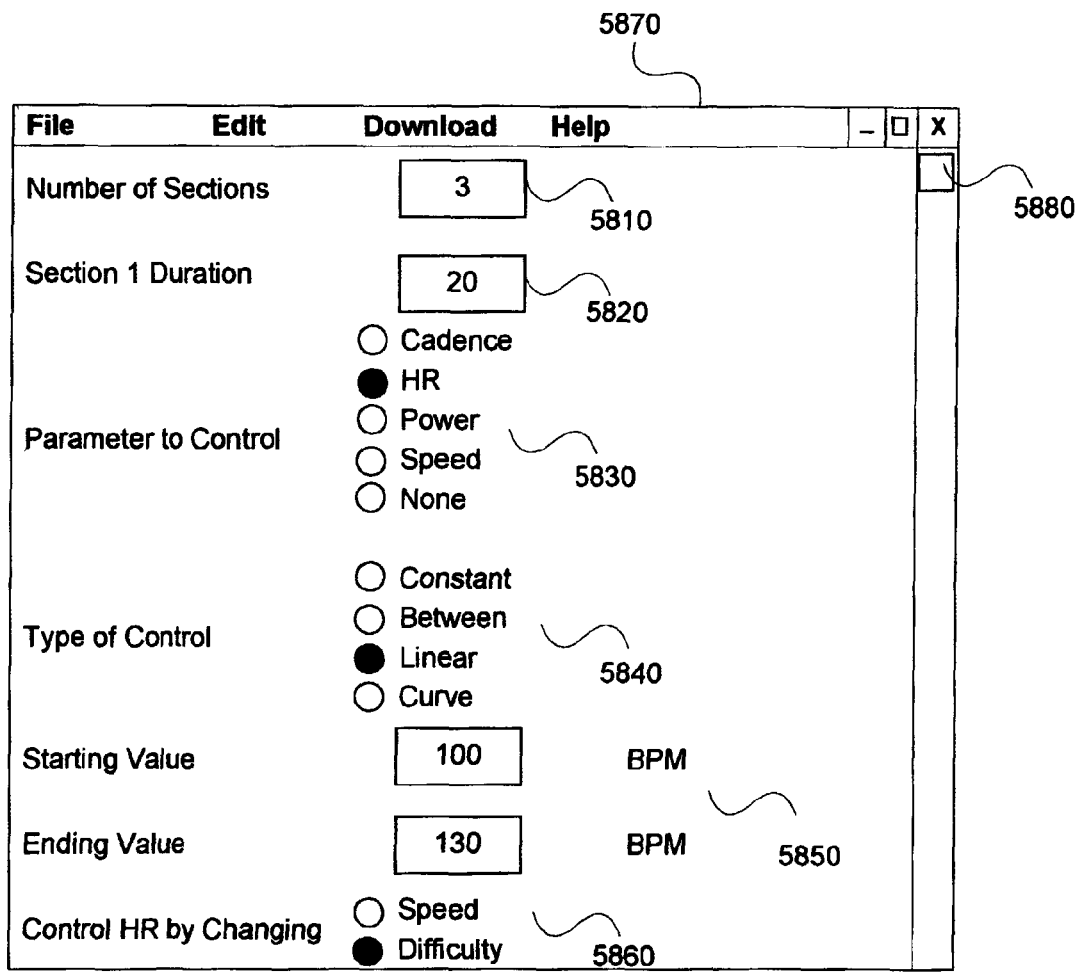
FIG. 58 is an illustrative screen that may be shown for defining a workout to be used with an MPN.

FIG. 58 shows illustrative screen 5800 that may be shown on athlete's computer or coach's computer for defining a workout. Region 5810 may be used to enter the total number of sections. Region 5820 may be used to enter the duration of a section, in this example in minutes. Selection 5830 may be used to choose the parameter to be controlled. In this example, heart rate has been chosen, and other choices are cadence, power, and speed. The user may also choose to control no parameter during the section. Selection 5840 may allow the user to specify the type of control, such as constant, between two values, linear, or on a defined curve. In this example, the user has chosen linear control. In region 5850, the user may enter the value or values at which to control the parameter. In this example, the user has entered a desired starting and ending heart rate for the section. Selection 5860 may allow the user to specify the controlling parameter, such as controlling heart rate by controlling speed or difficulty. In this example, the user has chosen difficulty as the controlling parameter. Scroll bar 5880 may allow the user to view and modify more fields, such as parameters for other sections in the workout. Menu bar 5870 may allow the user to access other features, such as file features (e.g., save and loading workout session definition files), edit features, download features (e.g., downloading workout definitions from a coach's computer or to an INC of the MPN), and help features.

FIG. 59 shows illustrative data structure 5900 that may be used to store information about a workout session. This data structure or a similar structure may be stored in a personal computer, in memory in an INC of the MPN, or in any other suitable location. If desired, similar information may be stored in multiple data structures. A workout session may consist of multiple "super sections," wherein each super section consists of one or more sections, and wherein each super section may be repeated multiple times. Data structure 5900 may include a definition of the number of super sections 5910. It may also include the definition of each super section, such as super section definition 5920, super section definition 5940, and super section definition 5960. Each super section definition may include a definition of number of sections in the super section, such as definition 5921, definition 5941, and definition 5961. Each super section definition may include a definition of number of times the super section is to be repeated during the workout session, such as definition 5922, definition 5942, and definition 5962.

Section A definition 5925 may specify that the section is to have a duration of 15 minutes in duration definition 5926. It may specify that the heart rate is to be controlled in primary parameter definition 5927, and that the heart rate is to follow a linear curve from 100 beats per minute to 125 beats per minute in curve definition 5928. It may specify a secondary parameter of cadence, which is to be kept at a rate of 90 revolutions per minute in secondary parameter specification 5929. It may specify in controlling parameter definition 5930 that the heart rate is to be controlled by user audio prompt. In this definition, section A is to occur once during the workout session.

Section B definition 5945 may specify that the section is to have a duration of 5 minutes in duration definition 5946. It may specify that the heart rate is to be controlled in primary parameter definition 5947, and that the heart rate is to be maintained in a range between 150 beats per minute and 160 beats per minute in curve definition 5948. It may specify a secondary parameter of cadence, which is to be kept at a rate of 90 revolutions per minute in secondary parameter specification 5949. It may specify in controlling parameter definition 5950 that the heart rate is to be controlled using a resistance setting output.

Section C definition 5955 may specify that the section is to have a duration of 1 minute and 30 seconds in duration definition 5956. It may specify that speed is to be controlled in primary parameter definition 5957, and that the speed is to be maintained below 15 miles per hour in curve definition 5958. It may specify a secondary parameter of resistance, which is to be kept at the easy setting in secondary parameter specification 5959. It may specify in controlling parameter definition 5960 that the speed is to be controlled by user audio prompt. In this definition, section B and section C are combined into a single super section, which is to occur twice during the workout session.

Section D definition 5975 may specify that the section is to have a duration of 15 minutes in duration definition 5976. It may specify that the heart rate is to be controlled in primary parameter definition 5977, and that the heart rate is to be maintained at a constant rate of 110 beats per minute in curve definition 5978. It may specify a secondary parameter of cadence, which is to be kept at a rate of 90 revolutions per minute in secondary parameter specification 5979. It may specify in controlling parameter definition 5980 that the heart rate is to be controlled by user audio prompt. In this definition, section D is to occur once during the workout session.

Figure 60:
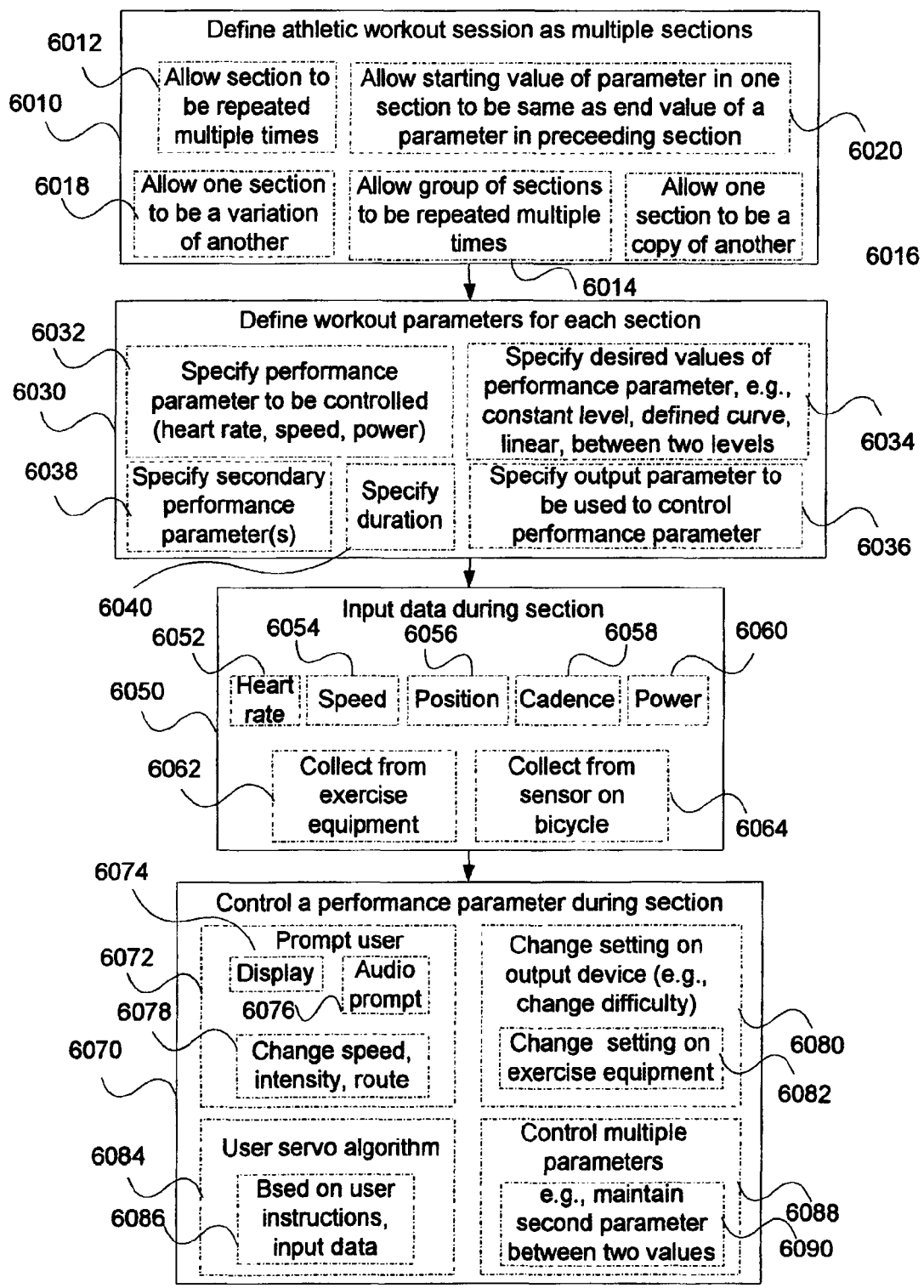
FIG. 60 is a flow chart of an illustrative process for controlling multiple sections of a workout using an MPN.

FIG. 60 shows flow chart 6000 of an illustrative process for controlling multiple sections of a workout. All steps are optional and may be performed in any suitable order. In step 6010, an athletic workout session may be defined as multiple sections. This workout definition may occur, for example, on an athlete's computer or on a coach's computer. In substep 6012, the definition may specify that a section is to be repeated multiple times during a workout session. The repetitions do not have to be consecutive. In substep 6014, groups of sections, such as super sections, may be repeated multiple times. In substep 6016, one section may be a copy of another section, in the same workout or in another workout. In substep 6018, one section may be a variation of another section, in the same workout or another workout. In substep 6020, the starting value of a parameter in one sections may be specified as the ending value of the same parameter in the previous section.

In step 6030, the workout parameters for each section may be defined. This may include substep 6032 in which a performance parameter to be controlled may be specified. This may include, for example, heart rate, cadence, power, or speed. In substep 6034, the desired value, values, or profile of the performance parameter to be controlled may be specified. This may include specifying a constant level, a defined curve, the end points of a linear variation, or two values to maintain the parameter between. If desired, a range above and below the desired curve may be defined. In substep 6036, an output parameter to be used to control the performance parameter may be specified. In substep 6038, one or more secondary performance parameters with corresponding desired values may be specified. In substep 6040, the duration of the section may be specified, for example, in time or distance. After all workout parameters have been defined, they may be downloaded from the coach's computer or athlete's computer into memory in an INC of the MPN, such as a control unit, for use during the workout. If desired, the workout parameters may be transmitted directly from the coach's computer into an INC of the MPN, or they may be transmitted over a wide area network such as the Internet to the athlete's computer, and downloaded from the athlete's computer into an INC of the MPN.

In step 6050, data may be collected during the section of the workout session. That may include heart rate data in substep 6052, speed data in substep 6054, position data in substep 6056, cadence data in substep 6058, power data in substep 6060, data from a sensor mounted on a piece of exercise equipment in substep 6062, data from a sensor mounted on a bicycle in substep 6064, or any other suitable type of input data. Data collected during a workout may be presented to the athlete during the workout, for example on a display INC. If desired, collected data may be uploaded to a base station, the athlete's personal computer or the coach's personal computer, where they may be stored, displayed as a chart or graph, compared with results from previous workouts, or otherwise analyzed. If desired, collected workout results may be used to modify workout parameters of future workout sessions.

In step 6070, a performance parameter may be controlled during the section of the workout session. This may be done by prompting the user in substep 6072. The prompt may be a visual prompt in substep 6074 or an audible prompt in substep 6076. In substep 6078, the prompt may be to change speed, change intensity or level of effort, change route, or any other suitable prompt. In substep 6080, the control may be performed by changing a setting, such as a difficulty, speed, or resistance setting, on an output INC. In substep 6082, the control may be performed by changing a setting on a piece of exercise equipment.

In substep 6084, the control may be performed using a position-integral-derivative (PID) servo algorithm, in which the value of an input parameter, the rate of change of the input parameter, and previous values of the input parameter are used to calculate a new value for the controlling parameter. The system may also include a set of limits on the output value to prevent it from exceeding a minimum value, a maximum value, and/or a maximum rate of change. In substep 6086, the input data used in the algorithm may be data that was collected in step 6050, and the definition of the input parameter and the controlling parameter may be part of the workout parameters that were defined in step 6030. The constants in the servo equation may be standard values, may be entered or downloaded by a user, or may be derived and modified with use.

In substep 6088, one or more additional parameters may be controlled during the workout section, as specified in the workout parameters. For example, a secondary parameter may be maintained between two values in substep 6090, maintained at a constant level, controlled linearly, or controlled in any other suitable fashion.

Figure 61:
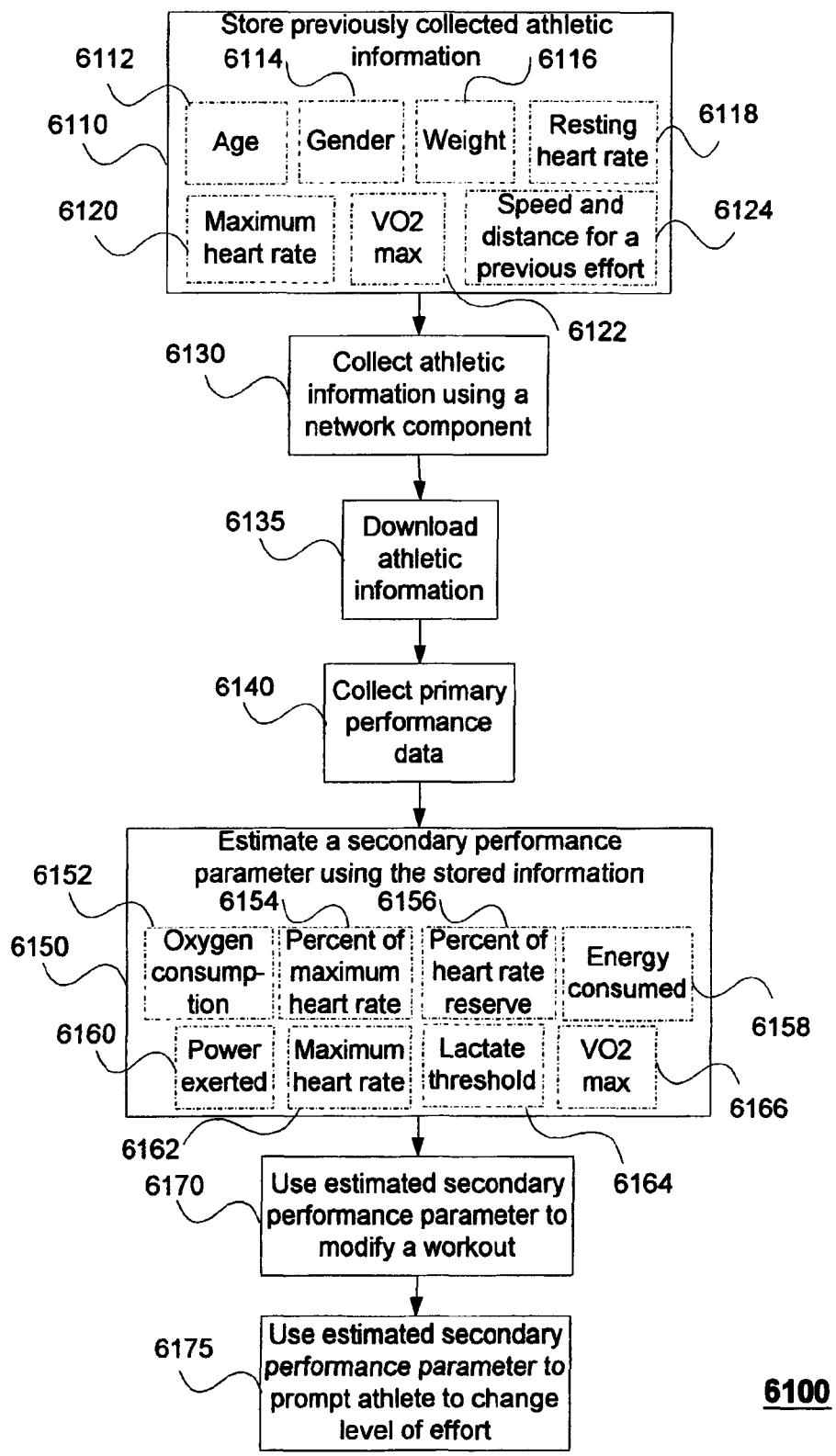
FIG. 61 is a flow chart of an illustrative process for estimating a derived performance parameter using stored information.

In addition to directly collecting data to measure a performance parameter, an MPN may use stored information along with collected information to estimate a derived performance parameter. A process for doing so is illustrated in flow chart 6100 of FIG. 61. All steps are optional and may be performed in any suitable order. In step 6110, previously collected personal data may be stored in an INC of the MPN. The personal data may be age in substep 6112, gender in substep 6114, weight in substep 6116, resting heart rate in substep 6118, maximum heart rate in substep 6120, $VO_2$ max in substep 6122, results (e.g., time and distance or speed and distance) from a previous athletic effort in substep 6124, or any other suitable personal data. The personal data may have been collected using an INC of the MPN, in step 6130. Alternatively, the personal data may have been downloaded in step 6135, for example from an athlete's computer or from a coach's computer, where it may have been entered.

In step 6140, primary performance data may be collected, for example by an INC of the MPN during an athletic effort. The data may be a single sample, or it may be many samples collected over a period of time. In step 6150, a secondary performance parameter may be estimated using the stored personal data and the collected primary performance data. In substep 6162, maximum heart rate (MHR) may be calculated. MHR is the maximum rate at which the athlete's heart can beat during a maximal effort, and is commonly measured in beats per minute. The MHR value may be entered by the user as personal data. The MHR may be estimated by the system based on the age and gender entered by the user. For example, MHR is commonly estimated as 220−age in years. Alternatively it may be estimated as 214−(age*0.8) for males and 209−(age*0.7) for females. Another method of estimating MHR is 210−(0.5*age)−(0.05*weight in pounds)+(4 if male or 0 if female). The estimate may be modified based on the specific type of activity or other factors. Alternatively, MHR may be estimated based on actual heart rate measurements in a defined athletic effort.

Resting heart rate (RHR) may be entered by the athlete as personal data or it may be measured. RHR is a measure of the rate at which the athlete's heart beats when at complete rest, and is also measured in beats per minute. RHR may be estimated based on actual heart rate measurements taken over a period of time, for example while the athlete is asleep. Regardless of how MHR was entered, measured or estimated, the percent of maximum heart rate may be estimated by dividing actual heart rate (HR) by MHR, in substep 6154. Percent of heart rate reserve may be estimated as (HR−RHR)/(MHR−RHR), in substep 6156.

Another performance parameter of interest to athletes is oxygen uptake ($VO_2$) and maximum oxygen uptake ($VO_2$ max). $VO_2$ is a measure of the amount of oxygen removed from the blood and used by the muscles during an athletic effort. $VO_2$ max is a measure of the maximum amount of oxygen that can be used by the athlete during an effort. Both are commonly measured in units of ml/kg/min. Although the actual measurement of $VO_2$ requires sophisticated equipment, there are several known methods to estimate it. For example, in "Jack Daniels, Conditioning for Distance Running—The Scientific Aspects," Wiley & Sons, 1978, the following formulas are used:

$$\text{Percent max}=0.8+0.1894393*e(-0.012778*t)+0.2989558*e(-0.1932605*t)$$

$$VO_2=-4.60+0.182258*v+0.000104*v2$$

$$VO_2\text{ max}=VO_2/\text{percent max}$$

In the above formulas, t is the time to complete a race-level effort in minutes, and v is the speed during the race in meters per minute. Oxygen uptake may be estimated during an athletic effort in substep 6152, using the above formula or any other suitable method. VO₂ max may similarly be estimated in substep 6166. The system may also estimate the speed, heart rate, or other parameter corresponding to the level of effort at which VO₂ max is reached. If desired, time and speed data may have been entered by the athlete as personal data, or may be measured by the MPN.

In substep 6158, the system may estimate energy consumed during an athletic effort. Energy consumption may be expressed in calories, and may be estimated based on age, gender, height, and weight, which may be entered as personal data. It may also be estimated based on type of activity, HR, speed, elevation gain, and other factors that may be measured during an athletic effort. Similarly, the power exerted while exercising may be estimated in substep 6160.

Lactate threshold (LT) may be estimated in substep 6164. LT represents the highest level at which exercise may be maintained for an extended period without a build-up of lactate in the blood. It may be measured, for example as a percent of VO₂ max or a percent of MHR above which lactic acid begins to accumulate in the blood. It may be estimated, for example, by using the average heart rate for a maximal athletic effort over a half hour. Alternatively, it may be estimated by measuring heart rate during a series of progressively more difficult efforts, and based on the rate of increase of heart rate between the efforts.

In step 6170, the estimated secondary parameter may be used to modify an athletic workout. For example, the intensity of a workout may be expressed as percent of LT, and during the workout the system may measure heart rate, estimate LT, and increase or decrease the speed setting of a piece of exercise equipment to maintain the proper level of effort. In step 6175, the user may be prompted to modify the level of effort based on an estimate of a secondary performance parameter. For example, the intensity of a workout may be expressed as percent of VO₂ max, and during the workout the system may measure heart rate, estimate VO₂, and prompt the user to speed up or slow down to maintain the proper level of effort. The estimated secondary parameter may also be displayed for the user by the MPN, or it may be uploaded to a base station or personal computer to be stored, displayed, or analyzed.

Figure 62:
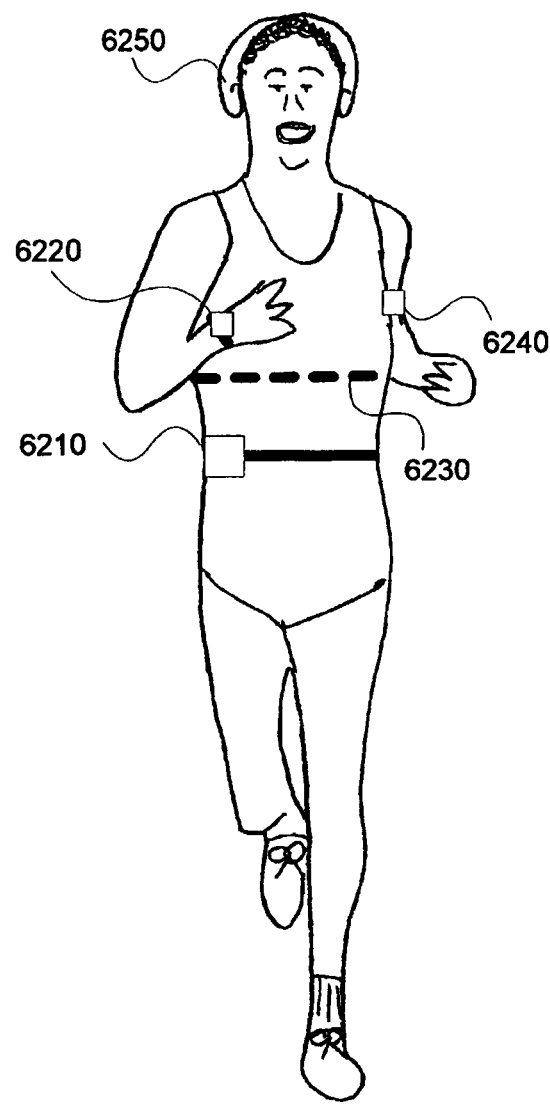
FIG. 62 is a diagram of an illustrative MPN that may be used to measure a primary performance parameter and estimate a secondary performance parameter.

FIG. 62 shows illustrative MPN 6200 that may be used to measure a primary performance parameter and estimate a secondary performance parameter. INC 6210 may be a control unit or other INC with memory and processing capabilities, and may include software to control the other INCs, as well as to perform the estimation. It may also include memory to hold software, as well as downloaded personal data such as age, gender, and weight. It may also include a communications device to download the personal data. INC 6220 may be a display INC, on which the primary and secondary performance parameters may be displayed. INC 6230 may be a heart rate sensor, used for monitoring the athlete's heart rate, which may be a primary performance parameter. INC 6240 may be an accelerometer for measuring cadence, which may also be a primary performance parameter. INC 6250 may be an audio output INC, which may be used to prompt the user to modify the level of effort based on the estimated secondary performance parameter. These INCs are merely illustrative, and all INCs are optional.

FIG. 63 shows illustrative display screen 6300 that may be displayed by the athlete's personal computer to allow the entry of personal data. It may include entry region 6310 for entering the athlete's name. It may include entry region 6320 for entering the athlete's age. It may include entry region 6330 for entering the athlete's weight. It may include selection 6340 for entering the athlete's gender. It may include entry region 6350 for entering the athlete's height. It may include entry region 6360 for entering the athlete's RHR. It may include entry region 6370 for entering the athlete's MHR. These fields are merely illustrative. Any suitable personal data may be entered on a screen such as display screen 6300. Display screen 6300 may also include menu bar 6380, which may allow the user to perform other functions. Other functions supported may include file-related functions (e.g., loading and storing personal data), device-related functions (e.g., downloading personal data to a device), system-related functions, user-related functions, security-related functions, and help-related functions. These functions are merely illustrative.

Figure 64A:
FIGS. 64A through 64F show illustrative display screens that may be displayed by a display INC in an MPN during an athletic effort.
Figure 64B:
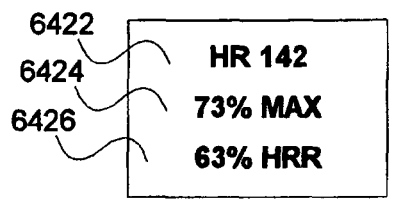
Figure 64C:
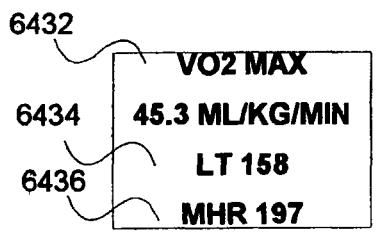
Figure 64D:
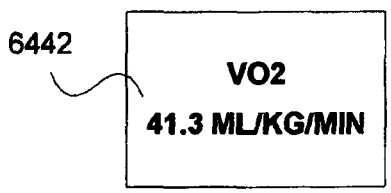
Figure 64E:
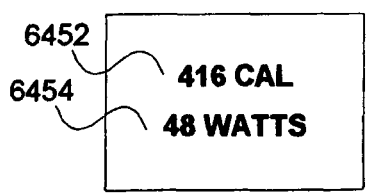
Figure 64F:
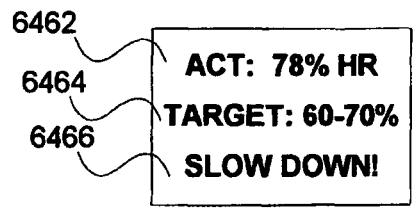

FIGS. 64A through 64F show illustrative display screens that may be displayed by a display INC in an MPN during an athletic effort. FIG. 64A shows screen 6410, which may be a prompt for the athlete to go faster, and may be based on an estimated secondary performance parameter. FIG. 64B shows screen 6420, which may display the athlete's currently measured heart rate 6422, percent of MHR 6424, and percent of HRR 6426. FIG. 64C shows screen 6430, which may display the estimated VO₂ max 6432, LT 6434, and MHR 6436 at the end of a testing effort. FIG. 64D shows screen 6440, which may display the athlete's estimated VO₂ during or after an effort. FIG. 64E shows screen 6450, which may display the athlete's cumulative energy consumption for a workout 6452 and current power exertion 6454. FIG. 64F shows screen 6460, which may show the athlete's current actual percent of HRR 6462, the target HRR range for the workout 6464, and a prompt to the athlete 6466 to modify the level of effort based on those values.

As described herein, the MPN may be used to collect data, such as heart rate and other athletic data. However, at times the data collection may be unreliable, for example because of interference with the wireless communications between INCs in the MPN. Temporary interference may be common because of nearby electro-mechanical devices, other radio frequency transmitters, poor contact between a metabolic sensor and the skin, and even static electricity between the athlete's body and clothing. One way of handling this is by including memory in the data collection INC, and retransmitting any lost data once the interference is gone. However, this may not be practical, as it may significantly increase the cost of the data collection INC. Also, at times data samples may not be collected successfully by the data collection INC, due to such factors as intermittent connections between the INC and the athlete's body. Therefore, the MPN may include algorithms to recognize invalid data samples and to estimate new values for the invalid samples.

Figure 65:
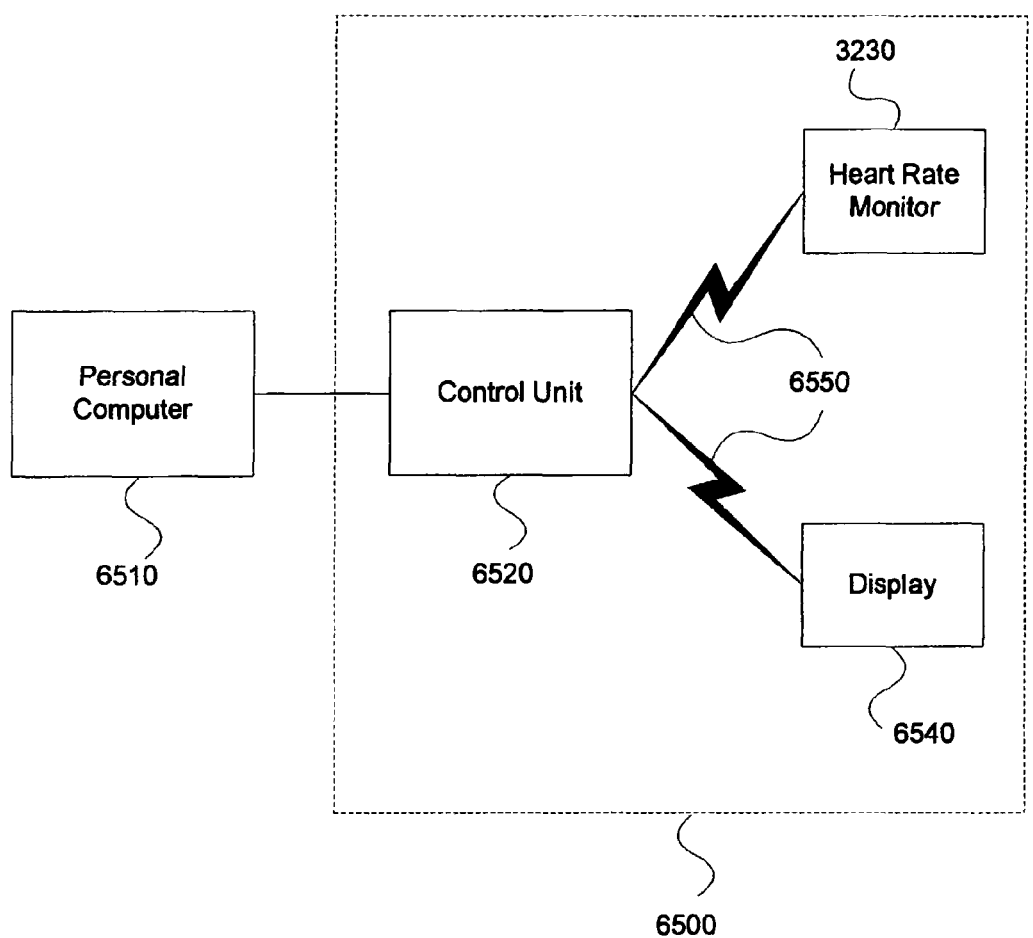
FIG. 65 is a diagram of an illustrative MPN that may be used to collect data and that may detect invalid data and estimate replacement data for the invalid data.

FIG. 65 shows illustrative MPN 6500 that may be used to collect data and that may include detection of invalid data and estimation of replacement data for the invalid data. Control unit 6520 may collect data samples from heart rate monitor 6530 using wireless communication path 6550 and store the collected heart rate data in memory in control unit 6520. Control unit may display heart rate data on display 6540. Control unit 6520 may detect invalid data received from heart rate monitor 6530, perhaps due to a failure in communication path 6550, and may estimate replacement data to store and to send to display 6540. Collected heart rate data may also be uploaded to personal computer 6510 and stored there. Personal computer 6510 may recognize invalid samples, and may estimate replacement data for the invalid data samples. The collected heart rate data, including any estimated replacement data may be displayed on a monitor attached to personal computer 6510. INCs shown are merely illustrative. All INCs are optional.

Figure 66:
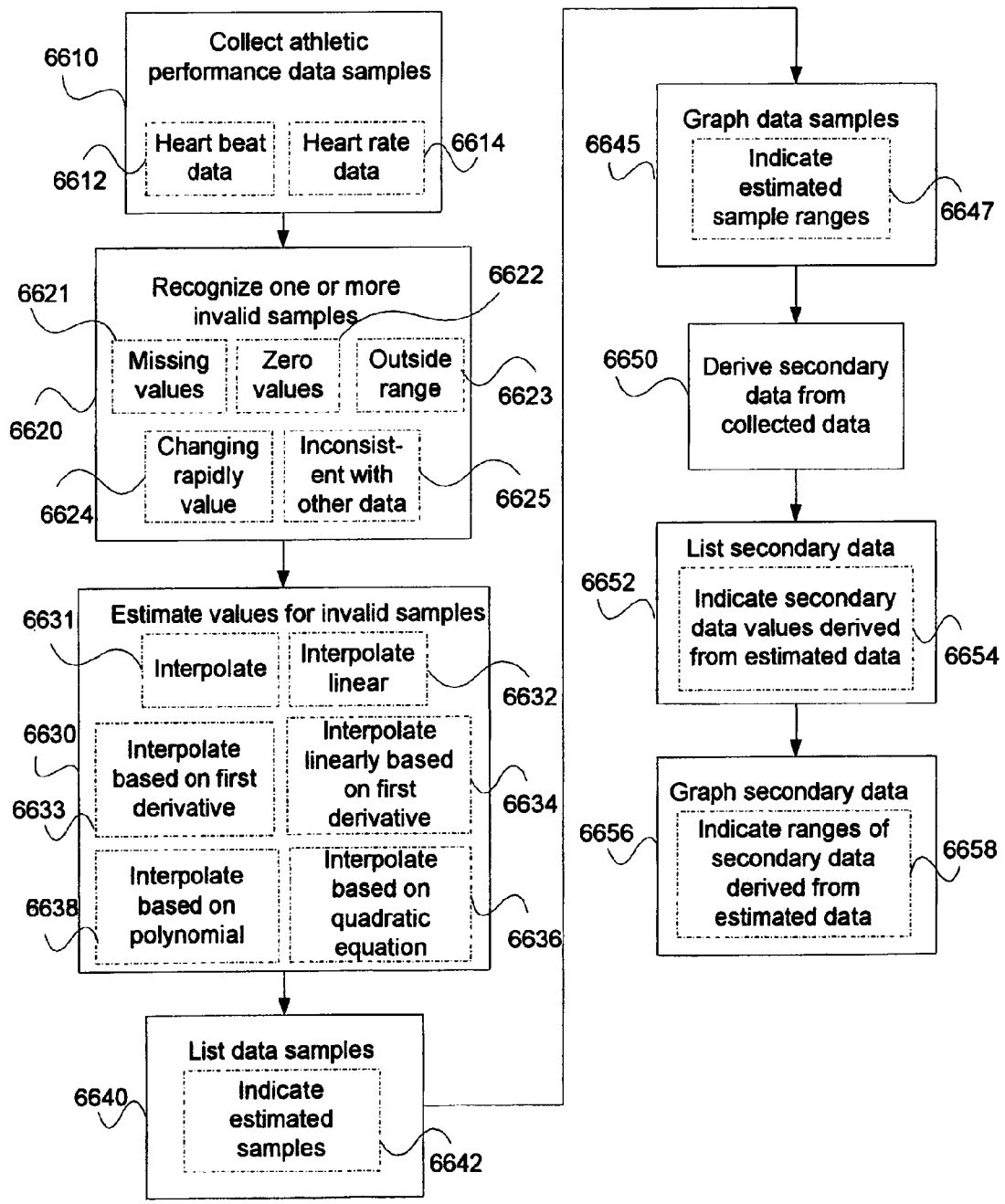
FIG. 66 is a flow chart of an illustrative process for estimating replacement data for invalid collected data.

FIG. 66 shows flow chart 6600 of an illustrative process for estimating replacement data for invalid collected data. All steps are optional and may be performed in any suitable order. In step 6610, data samples, such as athletic performance data samples, may be collected by an MPN. This may be, for example, heart beat data in substep 6612, or heart rate data in substep 6614. Any suitable type of data may be collected.

In step 6620, one or more invalid samples may be recognized. The invalid samples may be recognized, for example, by a control unit while data is being collected or by a personal computer after collected data has been uploaded. In substep 6621, invalid samples may be recognized on the basis of missing values. In substep 6622, invalid samples may be recognized on the basis of zero values, i.e., samples with the value of zero. In substep 6623, invalid samples may be recognized on the basis of values outside a defined range, for example, heart rate data lower than the resting heart rate or greater than the maximum heart rate. In substep 6624, invalid samples may be recognized on the basis of a rapid change in values, for examples values that indicate a very significant change in heart rate in a very short period of time. In substep 6625, invalid samples may be recognized on the basis of values inconsistent with other data, for example significantly different from samples collected before and after, or for example heart rate data inconsistent with collected speed and elevation data.

In step 6630, replacement values may be estimated for the invalid samples. Replacement values may be interpolated based on valid samples collected before, after, or both before and after the invalid samples in substep 6631. Replacement values may be interpolated linearly in substep 6632. Replacement values may be interpolated based on the first derivative of valid samples in substep 6633. Replacement values may be interpolated linearly based on the first derivative in substep 6634. Replacement data may be interpolated using a quadratic equation in substep 6636. Replacement data may be interpolated using a polynomial equation in substep 6638, and may match the values and/or derivatives of valid samples at the end points of the interpolation range. The data may also be estimated based on data collected in previous sessions under similar conditions, for example, the rate of change of the data may be made to match the rate of change of data collected in the similar session.

In step 6640, the data samples may be listed, for example on personal computer 6510 (FIG. 65). In substep 6642, estimated samples may be indicated in the listing. In step 6645, the data samples may be graphed, for example on personal computer 6510. In substep 6647, estimated samples ranges may be indicated in the graph. In step 6650, secondary data may be derived from the collected data. In step 6652, the secondary data may be listed, for example on personal computer 6510. In substep 6654, secondary data values derived from estimated samples may be indicated in the listing. In step 6656, the secondary data may be graphed, for example on personal computer 6510. In substep 6658, secondary data values derived from estimated samples ranges may be indicated in the graph.

FIG. 67 shows an example 6700 of heart beat data that may have been collected by an MPN. The data may include samples 6705 through 6740. It may be seen that each sample is approximately 0.5 seconds after the previous, with the exception of sample 6725. This sample was collected almost three seconds after the previous sample, indicating that samples were likely lost. By interpolation, it may be estimated that five samples were missed, and the user's heart rate may be estimated at about 122 beats per minute during this time by dividing the number of samples by the time.

FIGS. 68A and 68B illustrate how samples may be estimated to replace invalid samples. FIG. 68A shows illustrative heart rate sample data 6800 that may have been collected at a regular interval, such as every 15 seconds. In this example, heart rate data is increasing at a rate of eight beats per minute per minute in first sample range 6805. Heart rate data samples are all zero and are assumed to be invalid in second sample range 6810. Heart rate data is increasing at a reduced rate of four beats per minute per minute in third sample range 6815. Heart rate data samples are all out of range and are assumed to be invalid in fourth sample range 6820. And heart rate data is decreasing at a rate of one beat per minute per minute in fifth sample range 6825.

FIG. 68B shows how replacement values may be created for the invalid samples, creating revised heart rate sample data 6830. Range 6835, which corresponds to range 6810 in the original data, has been filled using a linear interpolation between samples collected just prior to and just after the invalid data in range 6810. Similarly, range 6840, which corresponds to range 6820 in the original data, has been filled using a linear interpolation between samples collected just prior to and just after the invalid data in range 6820.

Figure 69A:
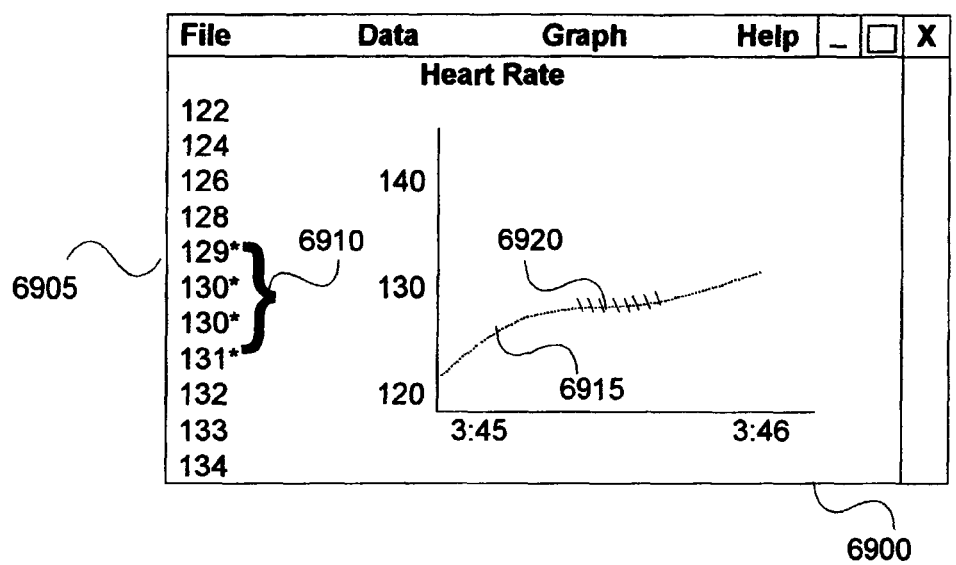
FIGS. 69A and 69B show illustrative display screen that may show collected primary and secondary data with replacement data for invalid samples.

FIG. 69A shows illustrative display screen 6900, which lists and graphs collected sample heart rate data. Sample data list 6905 may include estimated samples 6910. Estimated samples may be marked as estimated, for example with an asterisk. The sample data may also be shown in graph 6915. Range 6920 of the graph, corresponding to the estimated data, may be drawn with a different line style to indicate that the samples were estimated.

Figure 69B:
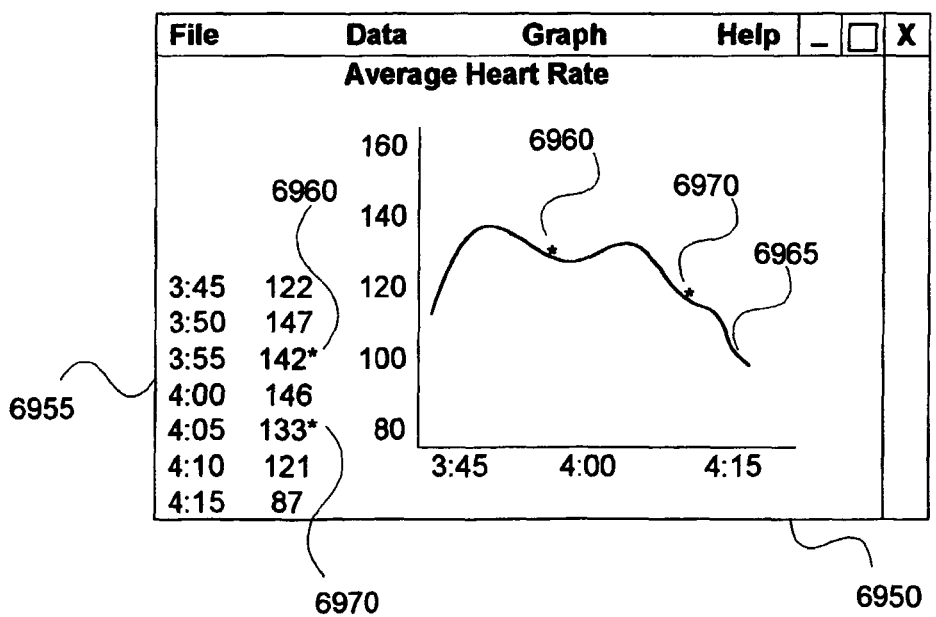

FIG. 69B shows illustrative display screen 6950, which lists and displays average heart rate data derived from the collected heart rate data samples. Data list 6955 may include data point 6960 and 6970 derived from estimated samples. Estimated data may be marked as estimated, for example with an asterisk. The derived data may also be shown in graph 6965. Values 6960 and 6970 on the graph, corresponding to the data derived from estimated samples, may be marked, for example with an asterisk, to indicate that data is estimated.

Figure 70:
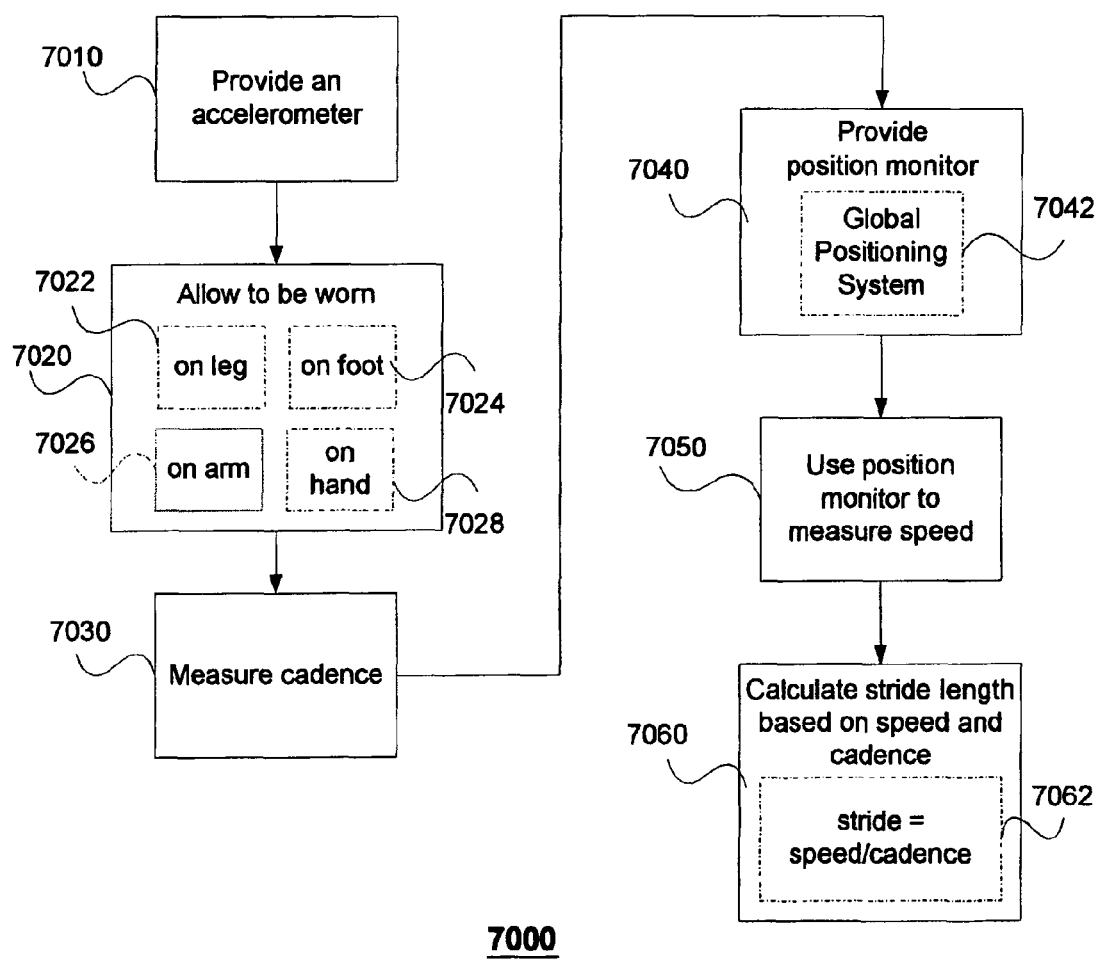
FIG. 70 is a flow chart of an illustrative process for providing an athlete with cadence and stride information using an MPN.

An MPN may also be used to provide an athlete, such as a runner or walker, with cadence information and stride length information. FIG. 70 shows flow chart 7000 of an illustrative process for providing this information. All steps are optional and may be performed in any suitable order. In step 7010, an accelerometer may be provided as an INC in the MPN. The accelerometer may send acceleration data to a control unit or other INC with storage capabilities at regular intervals. If desired, multiple accelerometers may be used to measure motion by different parts of the body, or components of motion in different directions. In step 7020, the accelerometer may be worn by the user. For example, it may be worn on the leg in substep 7022, the foot in substep 7024, the arm in substep 7026, or the hand in substep 7028. In step 7030, the accelerometer may be used to measure cadence. For example, a control unit may collect the data from the accelerometer, and measure the frequency at which the data reaches its relative maximums and minimums. This may correspond to the rate at which the user is swinging his or her arms or moving his or her legs, which translates directly to cadence.

In step 7040, a position monitor may be provided as an INC in the MPN. The position monitor may be a GPS monitor in substep 7042. The position monitor may send position data to a control unit or other component with storage capabilities at regular intervals. The position monitor may also be worn by the user. In step 7050, the position monitor may be used to measure the user's speed, which can be calculated as distance traveled divided by time. In step 7060, stride length may be calculated based on the speed and cadence of the user. In substep 7062, the stride length may be calculated as speed divided by cadence. If desired, the units of stride length displayed to the user may be converted to feet, meters, or other appropriate units. If desired, any of speed, cadence, and stride length may be displayed for the user. FIG. 45G shows an example of how cadence may be displayed on a display INC in the MPN. FIG. 45H shows an example of how stride length may be displayed on a display INC in the MPN. If desired, any of speed, cadence and stride length may be recorded for the duration of a session, and uploaded to a personal computer or base station for storage, display, or analysis. FIG. 44 shows illustrative MPN 4400 that may be used to calculate and display cadence and stride length.

Figure 71:
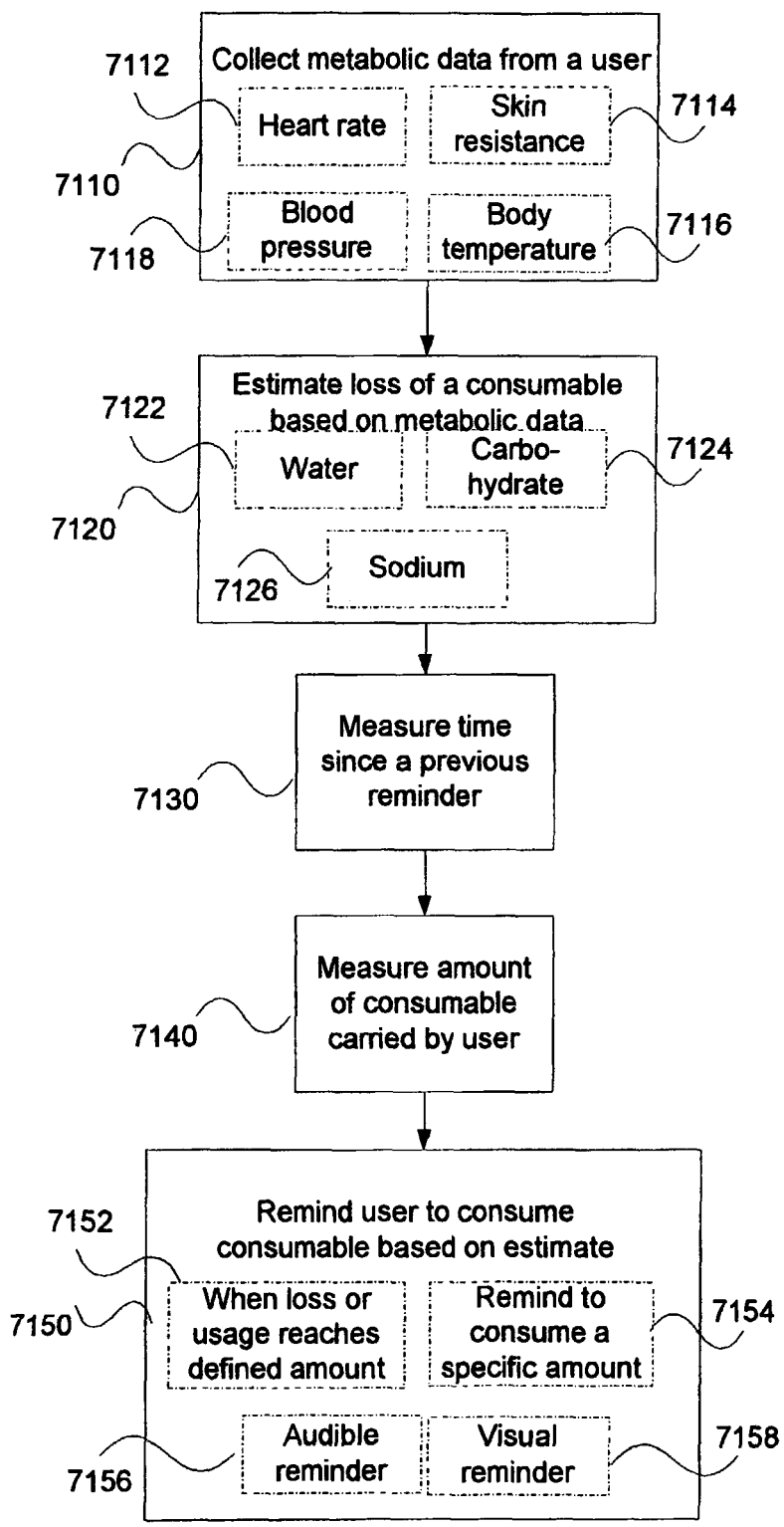
FIG. 71 is a flow chart of an illustrative process for providing consumption reminders to an athlete.

A significant impact on athletic performance is the loss of certain valuable consumables by the athlete during a training or competition event. For example, as the user continues at a high level of exertion, levels of water, sodium, carbohydrates, and other nutrients will decrease, and performance will correspondingly decrease. As levels decrease further, performance levels will decrease at an even higher rate, until the athlete is no longer able to continue. However, if the athlete consumes too much of any of these consumables, performance will also suffer, with conditions such as stomach distress and cramping, hyponatremia, and hypernatremia. The MPN can be used to measure the usage or loss of such consumables, and provide the athlete with reminders to take in specific amounts of one or more of them. FIG. 71 shows flow chart 7100 of an illustrative process for providing consumption reminders to an athlete. All steps are optional and may be performed in any suitable order.

In step 7110, metabolic data may be collected from a user such as an athlete. For example, an INC in an MPN may include a sensor to measure a specific metabolic value. In substep 7112, heart rate data may be collected. In substep 7114, skin resistance data may be collected. In substep 7116, body temperature data may be collected. In substep 7118, blood pressure data may be collected. In step 7120, the loss of a consumable may be estimated based on the metabolic data. For example, water may be estimated in substep 7122, carbohydrates in substep 7124, and sodium in substep 7126. A rate of loss of each consumable based on level of effort indicated by heart rate may be used. Skin resistance may be used to measure the amount of sweat, which translates to water and sodium loss. An increasing body temperature or blood pressure may indicate a significant loss of water. Need may also be estimated based on information stored about the athlete, such as weight or gender. In step 7130, time may be measured since the most recent reminder, and the time may be used to refine the estimate of lost consumables. In step 7140, the MPN may include an INC to measure the amount of consumable, such as energy drink or water, carried by the user. The measured amount may be reported to the user. Additionally, the measured amount may be used to calculate the amount previously consumed by the user, and may be used to refine the estimate of needed consumables. In step 7150, the user may be reminded to consume a consumable based on the estimated loss. In substep 7152, the reminder may be presented when the loss or usage reaches a defined amount. In substep 7154, the user may be told a specific amount of the consumable to consume. In substep 7156, the user may be given an audible reminder. In substep 7158, the user may be given a visual reminder.

Figure 72:
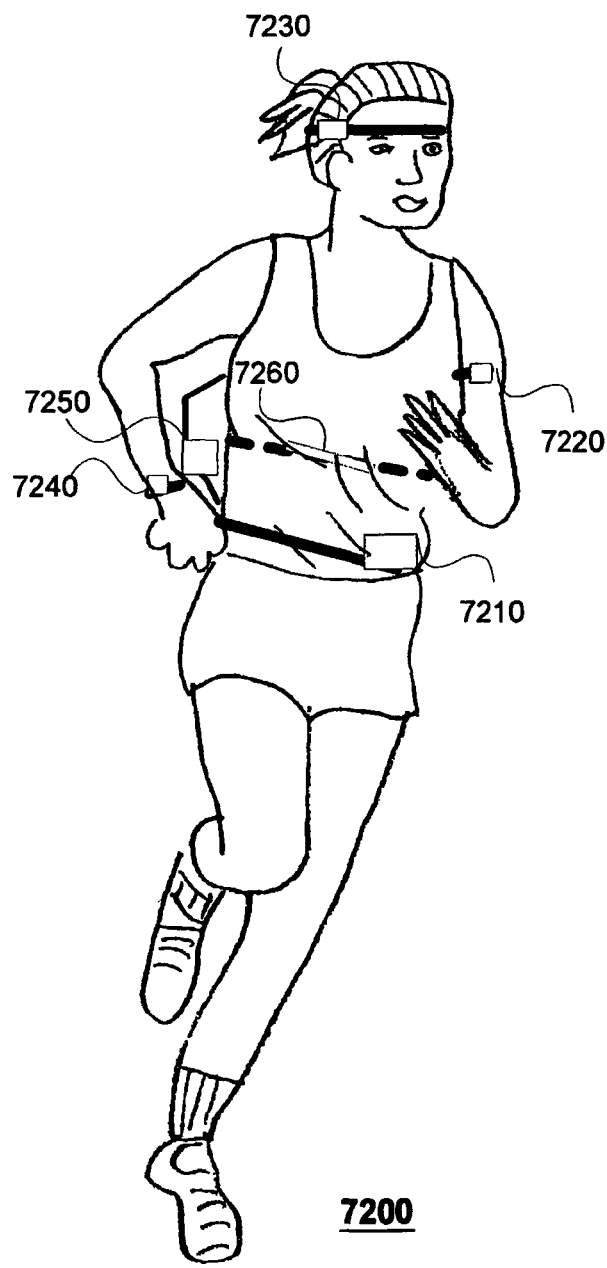
FIG. 72 is a diagram of an illustrative MPN that may be used to provide consumable reminders to an athlete.

FIG. 72 shows illustrative MPN 7200 that may be used to provide consumable reminders to an athlete. INC 7210 may be a control unit, which may include memory for storing input data samples, a processor for estimating consumable loss, and a wireless communications device for receiving metabolic data and sending reminders to the user. INC 7220 may be a metabolic data monitor, such as a skin resistance monitor, body temperature monitor, or blood pressure monitor. INC 7230 may be an audio output INC for providing audible reminders. INC 7240 may be a display INC for providing visual reminders. INC 7250 may be a device capable of measure the volume of consumable in, for example, a bladder worn by the user. INC 7260 may be a heart rate monitor. INCs shown are merely illustrative and are optional in practice.

Figure 73:
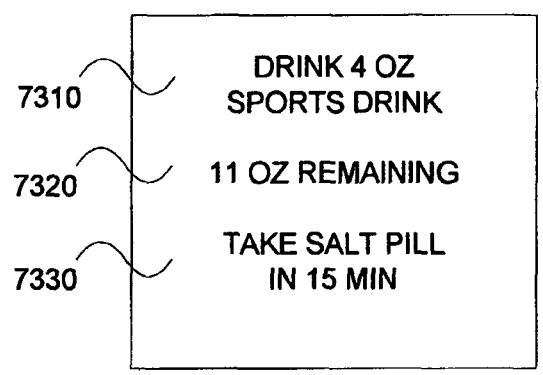
FIG. 73 is an illustrative display screen that may be used by an MPN to provide a consumable reminder.

FIG. 73 shows illustrative display screen 7300 that may be provided on display INC 7240 (FIG. 72). Prompt 7310 may tell the user to consume a specific amount of consumable, in this case four ounces of sports drink. Information display 7320 may tell the user how much sports drink is remaining. Display 7330 may inform the user that a salt pill should be taken in 15 minutes.

Figure 74:
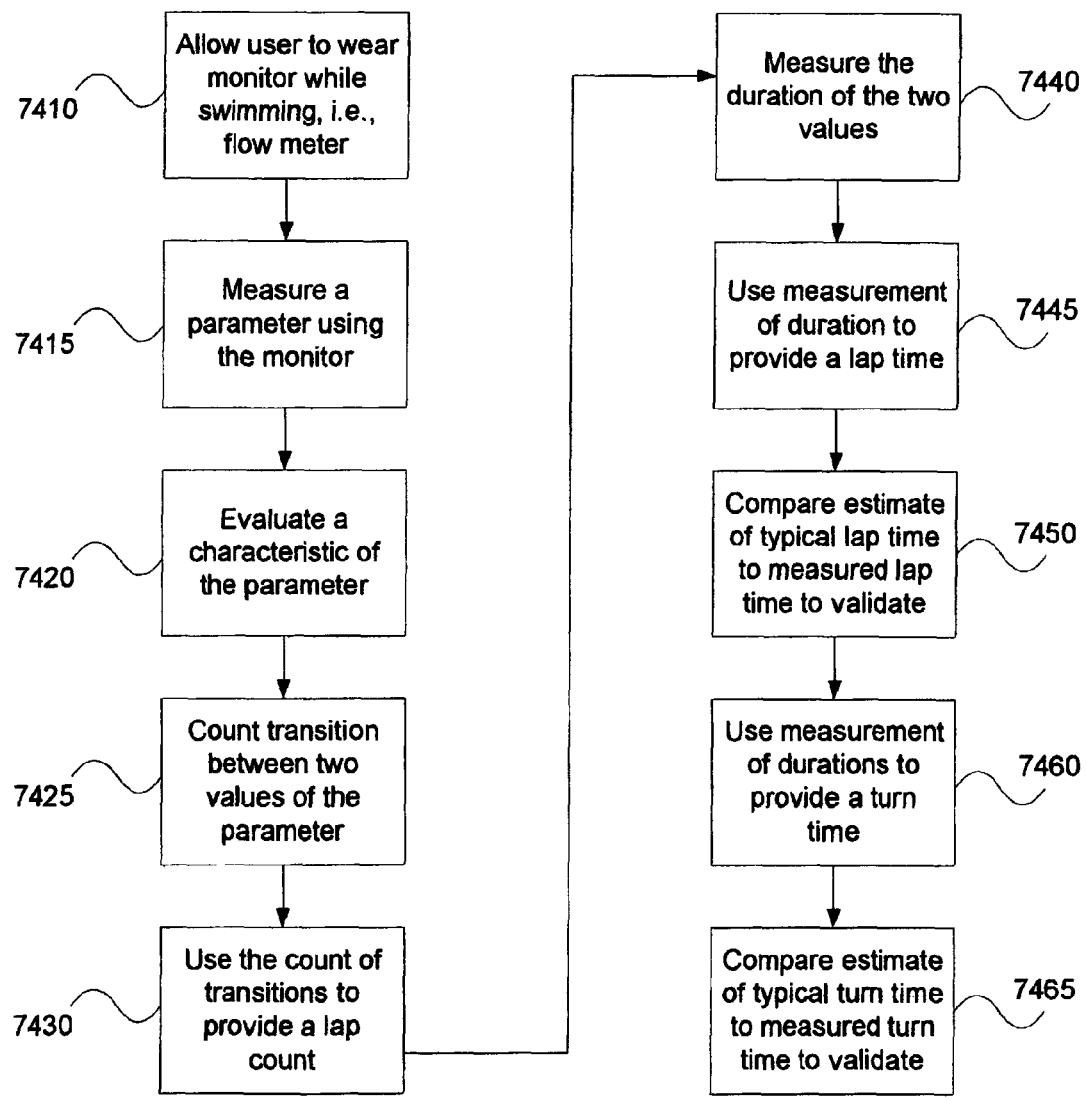
FIG. 74 is a flow chart of an illustrative process for providing swimming-related information using an MPN.

An MPN may be used by a swimmer to provide swimming-related information, such as lap counts. This is illustrated in flow chart 7400 of FIG. 74. All steps are optional and may be performed in any suitable order. In step 7410, the MPN may include a monitor, such as a flow meter, which may be worn by the swimmer in a swimming pool. Other examples of monitors that may be used include a turbulence meter, or an accelerometer to measure arm or leg movements. Preferably, the monitor should provide data with one characteristic while swimming and another characteristic while turning. If desired, multiple monitors may be worn, of the same or different types. In step 7415, the monitor may be used to measure a parameter, such as rate of flow of water past the user's body, amount of water turbulence near the user's body, arm movements, or leg movements. In step 7420, a characteristic of the parameter may be evaluated. For example, one characteristic of the flow may be the irregular readings during the turbulence of the turn at the end of the pool, as opposed to the more cyclical readings seen while swimming. Water flow may maintain a fairly constant positive value while swimming, and may vary in rate and direction while turning. Arm or leg movements may have different characteristics while swimming various strokes, while kicking, while turning, or while resting. Arm or leg movements may be regular and cyclical while swimming, and irregular while turning or resting. If desired, multiple characteristics of the measurement may be evaluated to determine which of several strokes is being used. In step 7425, transitions between the two values or characteristics may be counted. In step 7430, the count of transitions may be used, to provide a lap count. If desired, more than two characteristics of the parameter may be measured. For example, a third characteristic may be seen while the swimmer rests at the end of the pool. Also, different characteristics may be seen when the swimmer performs different strokes. For example, a system in which an athlete wears a water flow meter and a single accelerometer on one wrist can be used to detect the difference between swimming the crawl, breaststroke, backstroke, butterfly, and kicking.

In step 7440, the duration of the two or more characteristics may be measured, and this measurement may be used to provide a lap time in step 7445. If desired, the measured lap time may be compared with a typical lap time in step 7450, and validated that it falls within a normal range. For example, if two consecutive measured lap times are much less than the typical lap time, the user may have paused in the middle of a lap. Similarly, the turn time may be measured in step 7460, and may be validated in step 7465. Typical lap times and typical turn times may be standard values, they may be entered by the swimmer, they may be measured during a calibration swim, or they may be entered in any other suitable way. In a calibration swim, for example, the swimmer may swim a small number of laps of each stroke, while the system measures the characteristics of the data collected by the monitor and measures the typical lap times. Based on the data collected during a swim workout, the system may construct a model of the entire workout, including each swim, with type of stroke, speed, and distance for each swim, duration of rest periods, and other data. The data from the model may be stored, displayed, graphed, analyzed, or processed in any other suitable manner.

Figure 75:
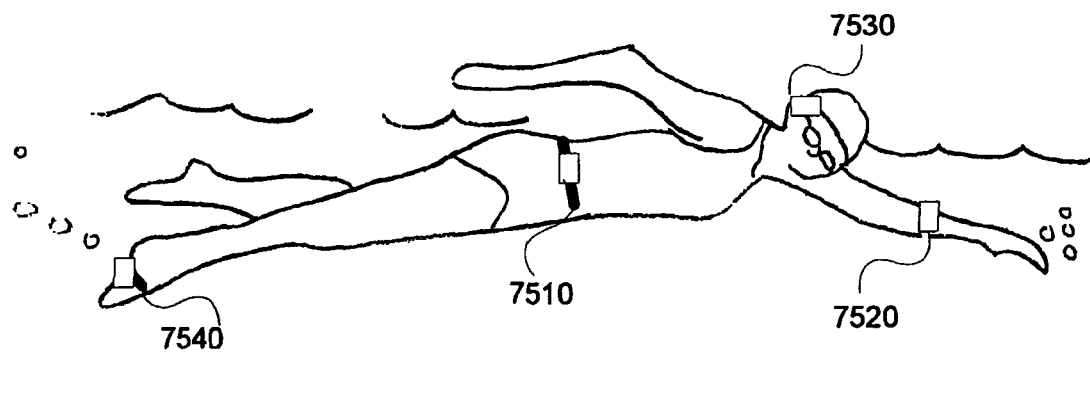
FIG. 75 is a diagram of an illustrative MPN that may be used to provide lap swimming information.

FIG. 75 shows illustrative MPN 7500 that may be used to provide lap swimming information. INC 7510 may combine the functions of a control unit and a flow meter, and may be configured to be worn attached to the swimsuit. INC 7520 may combine the functions of a display and an accelerometer and may be configured to be worn on the wrist. INC 7530 may be an audio output INC, and may be configured to be worn attached to a goggle strap or swim cap. INC 7540 may be an input INC worn on the foot, and it may be operated by tapping the end or bottom of the pool. INCs shown are merely illustrative and are optional in practice.

Figure 76A:
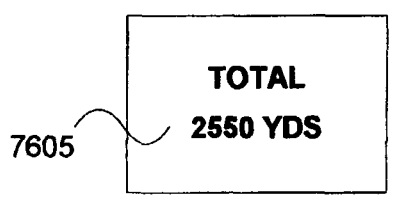
FIGS. 76A and 76B are illustrative display screens that may be used by an MPN to provide lap swimming information.
Figure 76B:
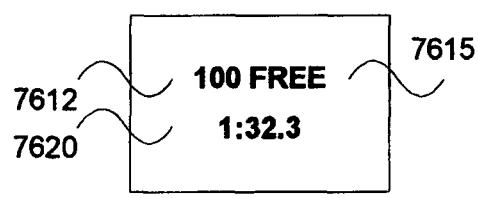

FIG. 76A shows an example of a screen 7600 that may be displayed on display INC 7520 (FIG. 75) to provide distance information to the swimmer. For example, the swimmer may have configured the system with the length of the pool, and the MPN may convert a lap count into a total distance 7605 for display. Screen 7610 of FIG. 76B may be provided on display INC 7520 at the conclusion of a swim. It shows the distance of the swim 7612 which may have been derived from the measured lap count. It shows the swim stroke 7615, which may be determined automatically based on the characteristic of data measured by input INC 7510 and 7520 (FIG. 75). Screen 7610 also includes total swim time 7620, which may be measured by the system.

Figure 77:
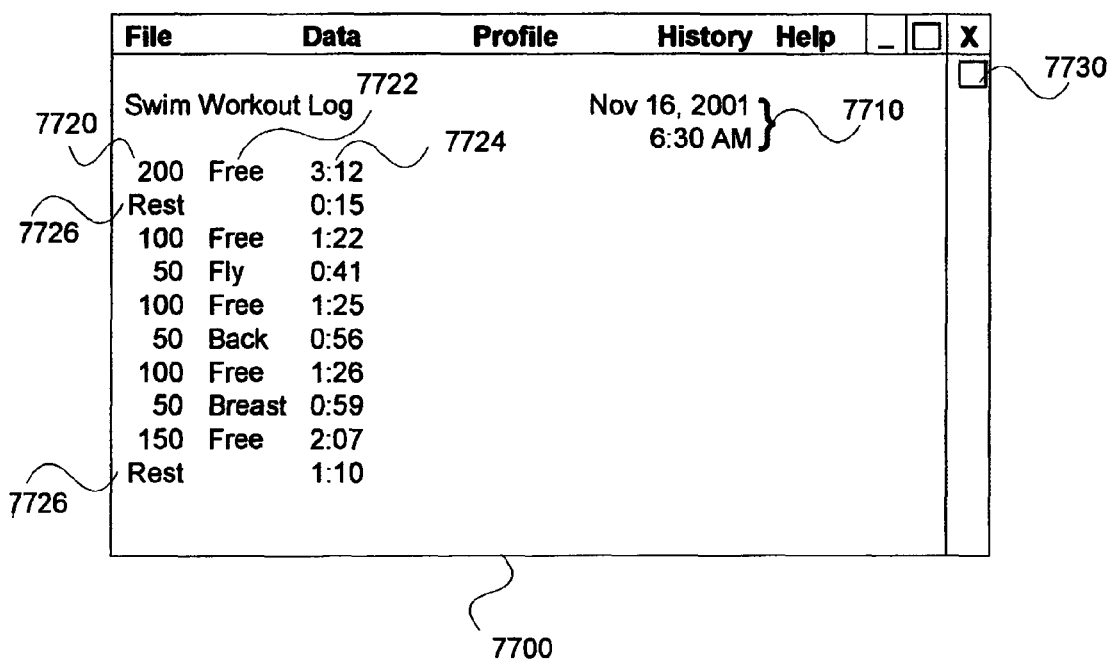
FIG. 77 is an illustrative display screen that may be shown in conjunction with an MPN used for collecting swimming-related information.

FIG. 77 shows illustrative display screen 7700 which may be shown on a monitor attached to a personal computer, after data has been uploaded from INC 7510 (FIG. 75) of the MPN. Date and time of workout 7710 may be displayed, and may have been determined automatically by a clock embedded in INC 7510. Distance 7720 may be listed for each swim, along with stroke 7722 and time 7724. Rest times 7726 may also be listed. The user may be allowed to scroll through more data, using scroll bar 7730. Other functions may be available using menu bar 7740. Other functions may include file-related functions (e.g., loading and saving data sets), data-related functions (e.g., viewing different subsets of data, or viewing the data in different formats or units), profile-related data (e.g., defining the length of the pool, typical swim times, etc.), history-related functions (e.g., comparing performance between swim sessions), and help-related functions.

Figure 78:
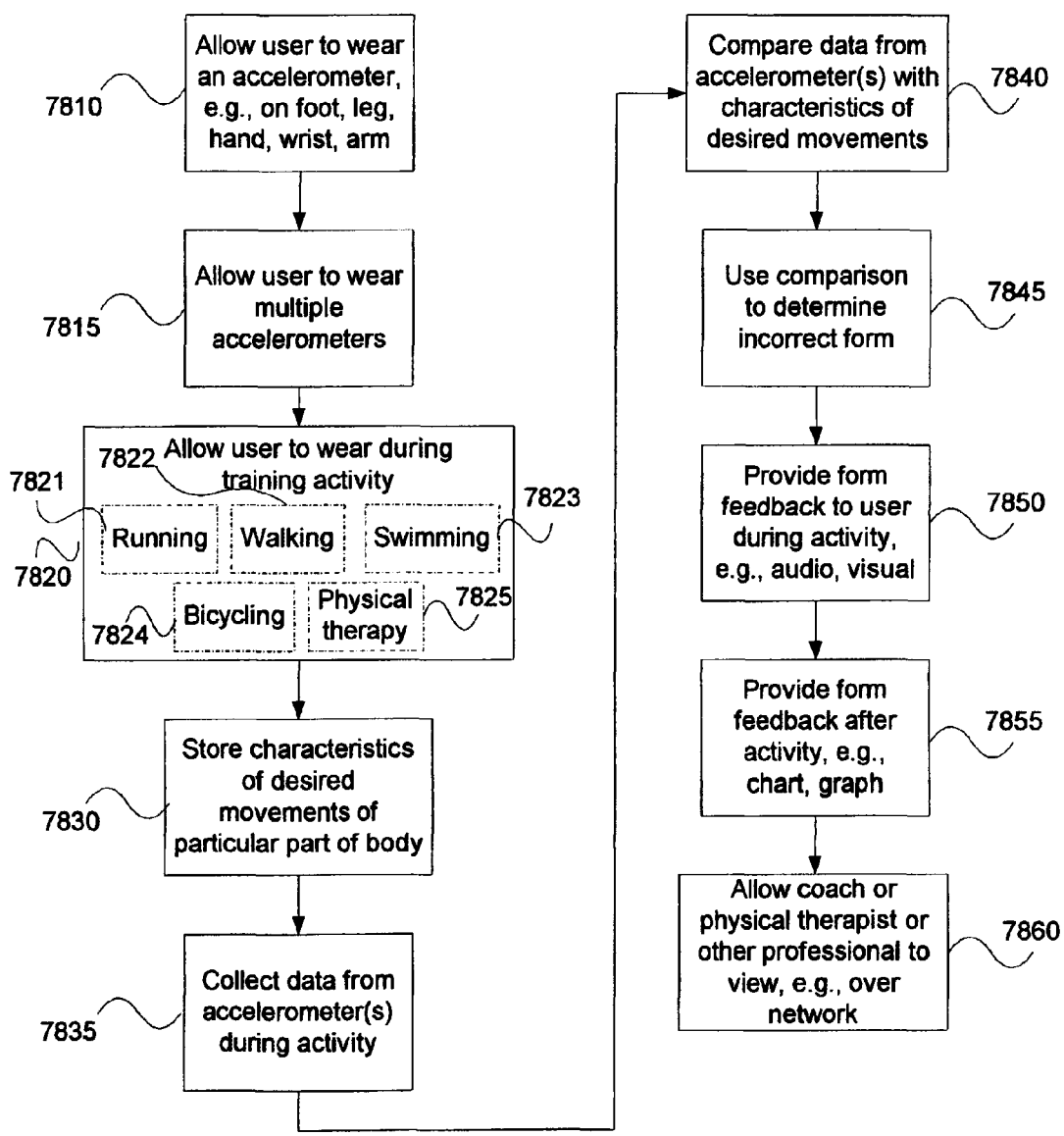
FIG. 78 is a flow chart of an illustrative process for providing gait or form feedback using an MPN.

An MPN may be used to provide form or gait feedback to an athlete or other user. Through the use of one or more accelerometers mounted on a part of the body that is moved during a particular activity, the system may compare the measured movements with ideal movements, and provide feedback to the user. An example of such a process is shown in flow chart 7800 of FIG. 78. All steps are optional and may be performed in any suitable order. In step 7810, a user may be allowed to wear an accelerometer, which may be included in an INC of an MPN. It may be worn on a part of the body that is moved, intentionally or unintentionally, during an activity for which the user desired form feedback. For example, it may be worn on a foot, leg, hand, arm, or wrist. Any other suitable part of the body may also be monitored. In step 7815, multiple accelerometers may be worn by the user. Multiple accelerometers may be worn on a single part of the body, for example to provide validation of readings, or to provide readings of different components of motion in different directions. Accelerometers may be worn on corresponding parts of the body, on opposite sides, such as opposite arms or legs, for example to monitor symmetry of motion. Accelerometers may be worn on different parts of the body, such as an arm and a leg, for example to monitor different motion aspects of an activity.

In step 7820, the user may be allowed to wear the accelerometer or accelerometers during a training activity. For example, one or more accelerometers may be worn while running in substep 7821, walking in substep 7822, swimming in substep 7823, bicycling in substep 7824, rowing, during a physical therapy activity in substep 7825, or during any other suitable activity. In step 7830, characteristics of desired movements of the monitored part or parts of the body may be stored. For example, the characteristics may have been captured by an expert in the activity wearing one or more accelerometers in the same location or locations. Alternatively, the characteristics may have been generated by monitoring multiple users and averaging the results, or by calculating optimum characteristics theoretically. If desired, the characteristics of desired motions may be stored in a personal computer, or they may be downloaded into memory in an INC of the MPN. If desired, a coach or physical therapist may wear the accelerometer or accelerometers and demonstrate the motion, while the MPN captures the characteristics of the coach's motions or therapist's motions.

In step 7835, data from the accelerometer or accelerometers may be collected during the training activity. If desired, the collected accelerometer data may be uploaded from the MPN into a personal computer. In step 7840, the system may compare the collected accelerometer data with the stored characteristics of desired motion. This comparison may be performed in the MPN, for example using a control unit, or it may be performed using a personal computer to which the data was uploaded. In step 7845, the comparison may be used to evaluate the user's form during the training activity, for example to determine incorrect aspects of the user's form. For example, while running, incorrect form may include over-striding, under-striding, lifting the feet too high, crossing the arms excessively in front of the body, or any other suitable type of incorrect form. Feedback on incorrect form may be provided to the user during the activity in step 7850. This may be audible feedback, for example using an audio output INC, and may be synthesized voice. The feedback may be visual feedback, for example using a display INC. In step 7855, feedback may be provided to the user after the training activity has been completed, for example using a personal computer. The raw data may be collected and uploaded to the personal computer, which may provide the comparison to create the feedback. Alternatively, the comparison may be performed in an INC of the MPN, and the results of the comparison may be collected and uploaded to the personal computer. The feedback may be in the form of a chart, table, or graph, it may be displayed or printed, or it may be presented in any other suitable form. Form feedback data may be combined with other suitable data when displayed, such as time, speed, or percent grade uphill or downhill. In step 7860, the collected data or the form feedback may be transmitted to a coach or physical therapist, for example over a network such as the Internet, and the coach or physical therapist may view the data or feedback.

Figure 79:
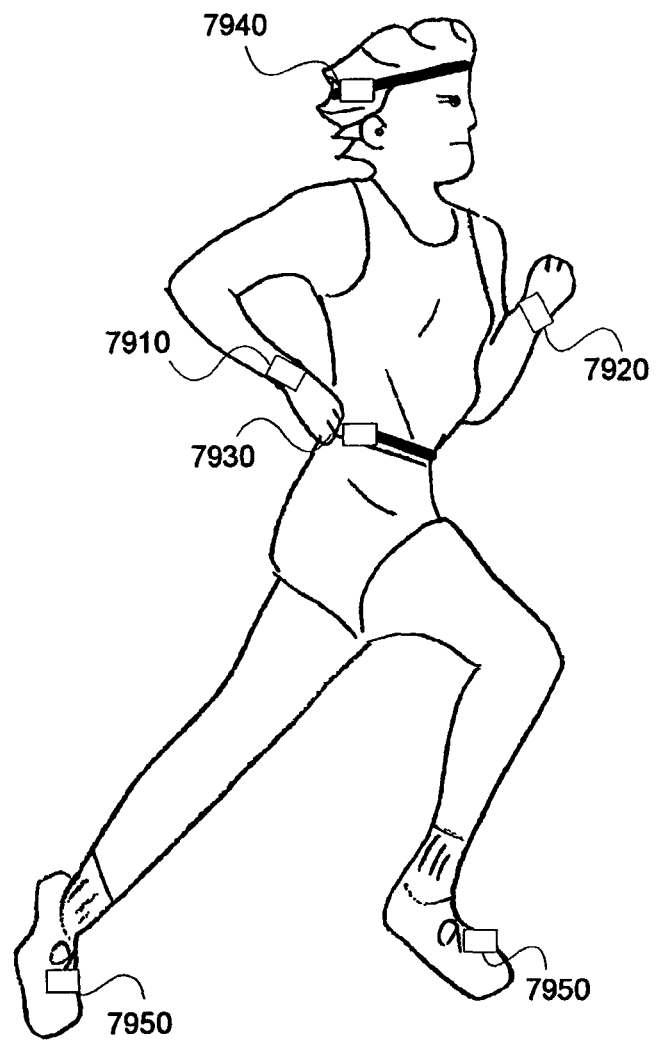
FIG. 79 is a diagram of an illustrative MPN that may be used to provide form feedback during a training activity.

FIG. 79 shows an example of an MPN 7900 that may be used to provide form feedback based on accelerometer data collected during a training activity. INC 7930 may be a control unit. The control unit may include a processor to control the data collection and to perform the form comparison. It may also include memory to store desired form characteristics and collected data. It may also include a wireless communications device for collecting accelerometer data and for providing form feedback. INC 7920 may be an accelerometer mounted on the left wrist, for measuring movements of the left arm. INC 7910 may be a display INC for providing visual feedback to the user. If desired, a display INC and an accelerometer may be combined into a single INC. INC 7940 may be an audio output INC, for providing audible form feedback. INCs 7950 may be accelerometers worn on the feet for measuring movements of the legs and feet. If desired, accelerometers may be worn on any part of the body, and may be combined with any other INC. If desired, an accelerometer may be worn on a part of the body that is not expected to move, and the system may use it to detect incorrect motions by that part of the body. INCs shown are merely illustrative and are optional in practice.

Figure 80A:
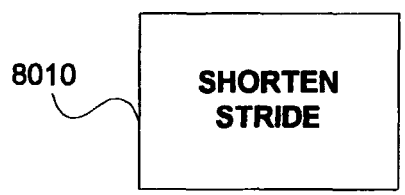
FIGS. 80A through 80C are illustrative display screens that may be shown to a user by an MPN to provide form feedback during a training activity.
Figure 80B:
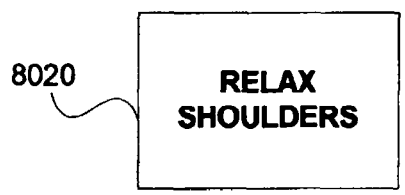
Figure 80C:
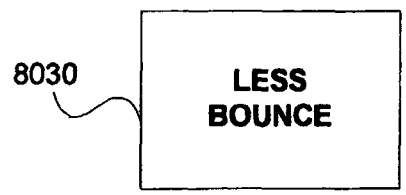

FIGS. 80A through 80C show examples of screens that may be shown on display INC 7910 (FIG. 79) during a training activity such as running or walking, to provide form feedback to a user. Screen 8010 of FIG. 80A may suggest that the user shorten his or her stride, if the collected data indicates a stride length longer than the desired stride length. Screen 8020 of FIG. 80B may suggest that the user relax his or her shoulders. Tightly held shoulders may be inferred, for example, based on the range of motion measured from the arms. Screen 8030 of FIG. 80C may suggest that the user run with less bounce, for example if the collected data indicates too much vertical motion. Any suitable type of feedback may be provided for any suitable characteristic of the training activity. Any suitable training activity may be monitored. Feedback may be provided audibly during the training activity if desired, for example using audio output INC 7940 (FIG. 79).

Figure 81:
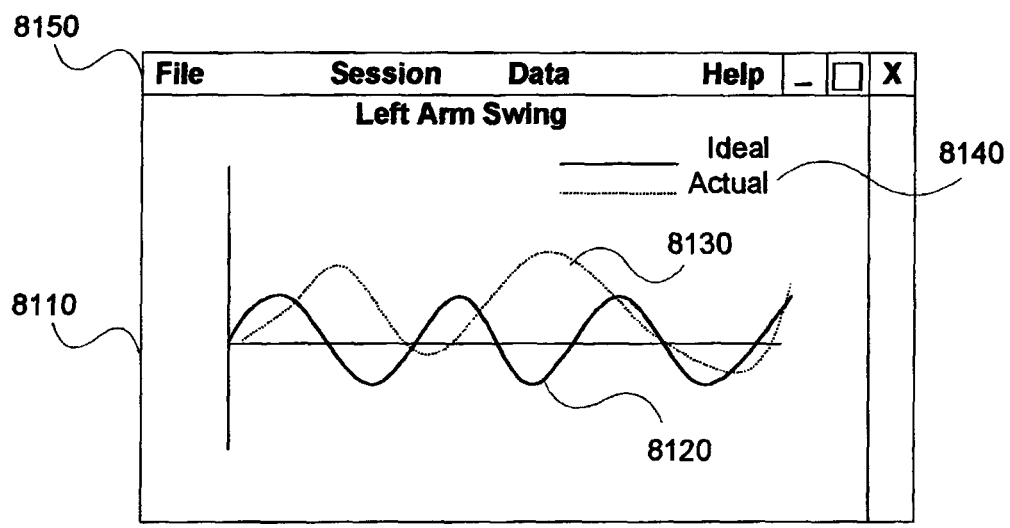
FIG. 81 is an illustrative display screen that may be shown in conjunction with an MPN used for providing gait or form feedback.

Screen 8100 of FIG. 81 is an illustrative example of a display screen that may be displayed after a training activity on a personal computer, to provide form feedback on the training activity. The screen may be displayed for the user (e.g., athlete or physical therapy patient) or may be displayed for a coach, physical therapist or other interested party. Graph 8110 may include curve 8120 of ideal motions, and curve 8130 of actual motions. This type of graph may illustrate the parts of the user's motions that vary from the ideal motions. If desired, multiple types of curves may be shown on the same graph. For example, the forward component of the motion may be represented using one curve, and the side-to-side component of the motion may be represented using a second curve. As another example, motions of both legs or of both arms may be shown on a single graph, or motions of an arm and a leg may be shown on the same graph. Legend 8140 may illustrate the line styles of the various curves. Menu bar 8150 may provide access to various functions, such as file-related functions (e.g., saving or loading collected data files or loading a file with a different set of ideal characteristics), session-related functions (e.g., looking at data from different training sessions), data-related functions (e.g., looking at data collected using different accelerometers during a single session), or help-related functions.

Figure 82:
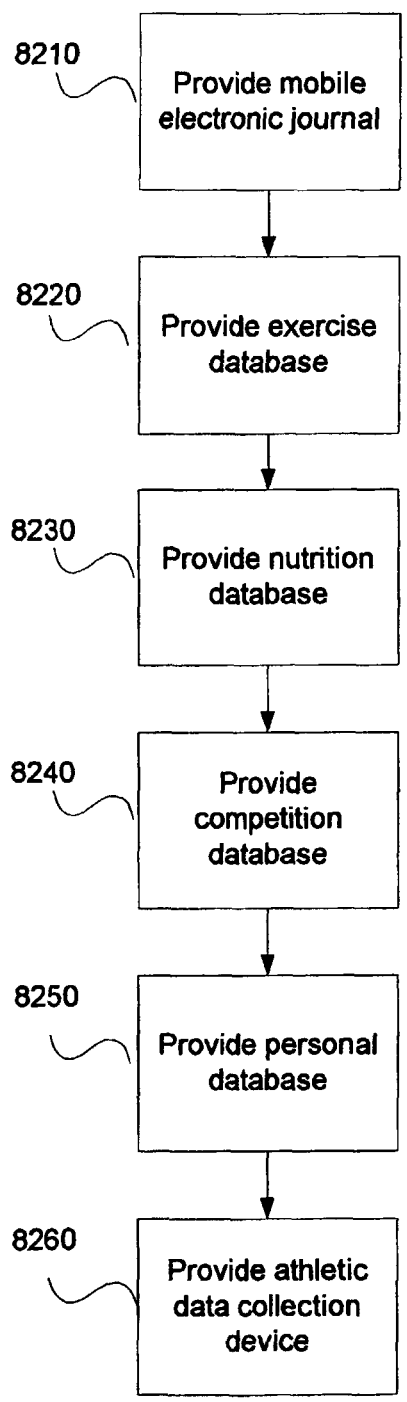
FIG. 82 is a flow chart of an illustrative process for providing an athletic training journal using an MPN.

An MPN may be used to provide an athletic training journal. FIG. 82 shows flow chart 8200 of an illustrative process for providing an athletic training journal. All steps are optional and may be performed in any suitable order. In step 8210, a mobile electronic journal may be provided, for example as described earlier in connection with FIG. 42. In step 8220, the journal may include an exercise database. For example, the exercise database may include a list of different types of exercises, and may include characteristics of each, such as calories burned per hour at different intensities or muscle groups trained. The exercise database may also include data on recommended levels, types, and amounts of exercise. In step 8230, the journal may include a nutrition database. For example, the nutrition database may include a list of different types of foods, and characteristics of each, such as calories, amount of fat, carbohydrates, protein, and other nutrients. The nutrition database may also include data on recommended amounts of various types of nutrients. In step 8240, the journal may include a competition database. The competition database may include lists of competitions of various types of activities, results, times, and other information. In step 8250, the journal may include a personal database. The personal database may include data on the user's own exercise needs or plans, the user's own nutrition needs, the user's own competition history or goals, or other suitable user data. It may include data on the user's weight, body fat percentage, waist measurement, and other suitable health measurements. In step 8260, the journal may include an athletic data collection INC. For example, it may include a heart rate monitor, a blood pressure monitor, a stopwatch, or other INC that may be used to measure athletic performance. In practice, the user may enter journal entries related to exercise, nutrition, competition, health, and other related items. For example, the user may log foods eaten, exercises performed, competitions entered, and other items of interest. If desired, journal entries may be linked to suitable database entries. The journal may make automatic calculations related to the journal entry and the database, such as calories consumed or burned, nutrition taken in or needed, etc. Journal entries may also be linked to audio or video media files, clock data, position data, or other suitable information.

Figure 83:
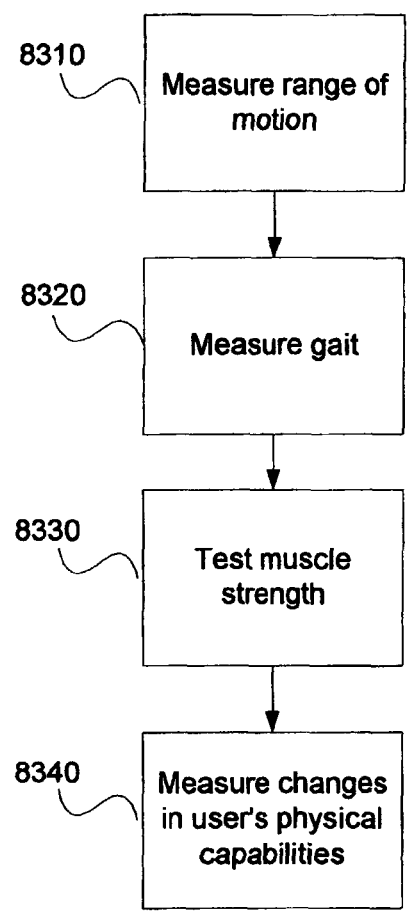
FIG. 83 is a flow chart of an illustrative process for providing physical therapy functions using an MPN.

As described in step 3255 of flow chart 3200 of FIG. 32, an MPN may be used to provide physical therapy functions. This is illustrated in more detail in FIG. 83. All steps are optional and may be performed in any suitable order. In step 8310, the MPN may be used to measure range of motion. For example, a range of motion monitor may be one of the INCs in the MPN. In step 8320, the MPN may be used to measure gait or do gait analysis. For example, the form feedback functions described previously in conjunction with FIG. 78 may be used. In step 8330, the MPN may be used to test muscle strength. For example, a muscle-strength tester may be incorporated into an INC of the MPN. In step 8340, the MPN may be used to measure changes in a user's physical capabilities. This may be done, for example, using the functions of the mobile electronic journal described in conjunction with FIG. 42. If desired, the mobile electronic journal used for physical therapy purposes may include a patient database, a treatment database, an insurance database, a diagnostic database, a range of motion sensor, accelerometers to be used for form feedback, a muscle strength tester, or other appropriate INCs.

Figure 84:
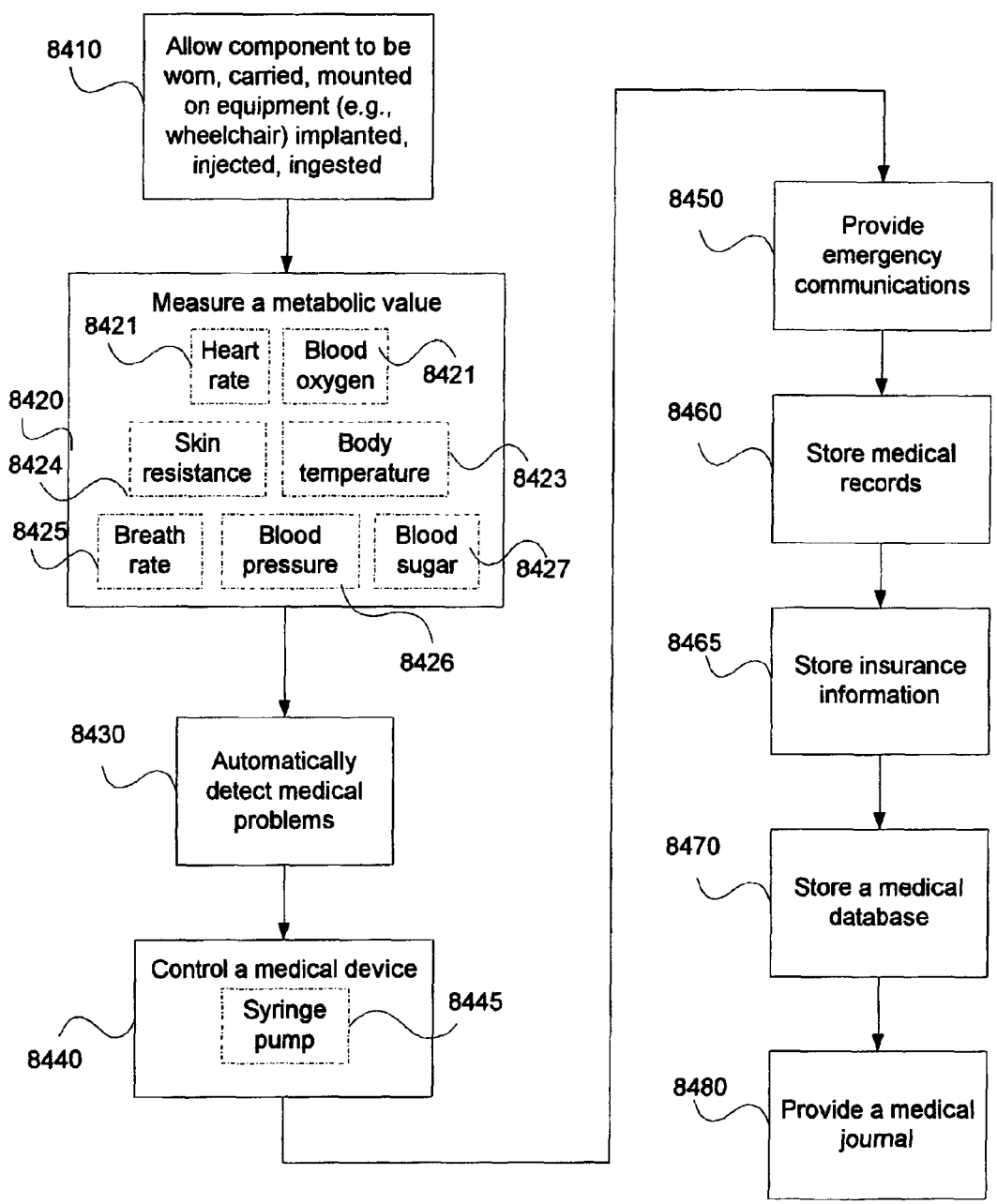
FIG. 84 is a flow chart of an illustrative process for providing medical functions using an MPN.

As described in step 3215 of flow chart 3200 of FIG. 32, an MPN may be used to provide medical functions. This is illustrated in more detail in FIG. 84. All steps are optional and may be performed in any suitable order. In step 8410, an INC may be worn or carried by a doctor, patient or nurse, mounted on equipment such as a wheelchair, or implanted, ingested, or injected into a patient. Any suitable method of providing a portable medical INC may be used. In step 8420, an INC of the MPN may be used to measure a metabolic value of a patient. This may include heart rate in substep 8421, blood oxygen level in substep 8422, body temperature in substep 8423, skin resistance in substep 8424, breath rate in substep 8425, blood pressure in substep 8426, blood sugar level in substep 8427, or any other suitable metabolic parameter. In step 8430, the MPN may be used to automatically detect a medical problem. In step 8440, the MPN may control a medical device, such as a treatment device. The medical device may be an INC in the MPN, or an INC in the MPN may send commands to the device. In substep 8445, the MPN may control a syringe pump. In step 8450, the MPN may provide emergency communications, such as an alert to emergency medical personnel. In step 8460, the MPN may provide storage of medical records. In step 8465, the MPN may provide storage of insurance information. In step 8470, the MPN may store a medical database, such as a treatment database, diagnostic database, pharmaceutical database, medical instrument database, or health alert database. In step 8480, the MPN may provide a medical journal.

Figure 85:
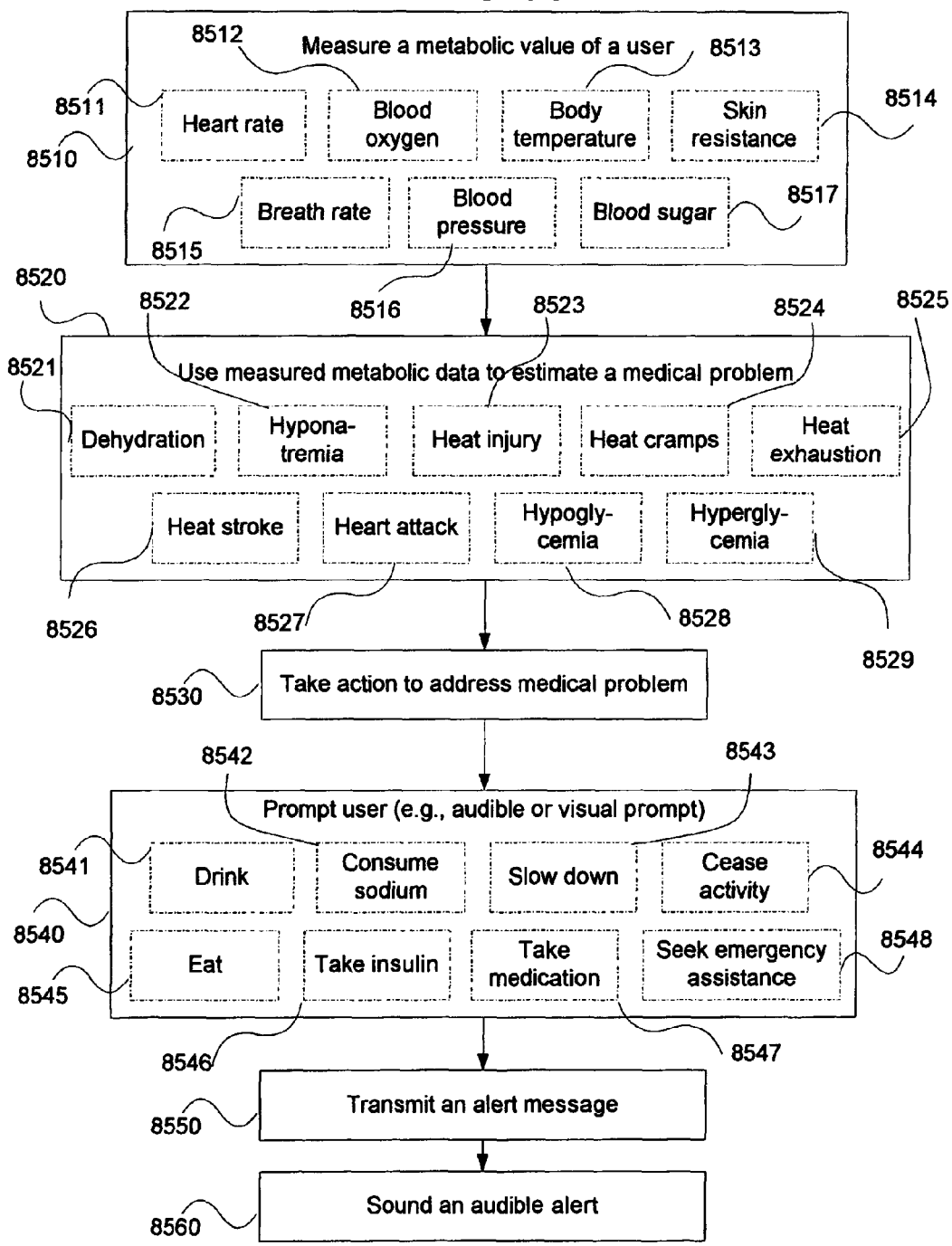
FIG. 85 is a flow chart of an illustrative process for estimating a medical problem using an MPN.

FIG. 85 shows flow chart 8500 of an illustrative process for using a measured metabolic parameter to detect a medical problem. All steps are optional and may be performed in any suitable order. In step 8510, a metabolic parameter of the user may be measured, for example by an INC of the MPN. This may include measuring heart rate in substep 8511, blood oxygen level in substep 8512, body temperature in substep 8513, skin resistance in substep 8514, breath rate in substep 8515, blood pressure in substep 8516, blood sugar level in substep 8517, or any other suitable metabolic parameter that may be measured using a portable system. In step 8520, the system may use the measured metabolic parameter to estimate a medical problem. Other factors may also be used to estimate the medical problem, such as information stored about the user, level and time of exertion, water and other substances consumed, or other suitable data. Estimating a medical problem may include detecting a medical problem, predicting a medical problem, or estimating the likelihood that the medical problem exists or will occur. For example, the system may estimate the likelihood that the user is affected with dehydration in substep 8521, hyponatremia in substep 8522, a heat injury in substep 8523, heat cramps in substep 8524, heat exhaustion in substep 8525, heatstroke in substep 8526, heart attack in substep 8527, hypoglycemia in substep 8528, hyperglycemia in substep 8529, insulin shock, diabetic coma, or any other medical problem.

The system may take an action to address the estimated medical problem in step 8530. For example, a prompt may be provided to the user, visually or audibly, in step 8540. That may include a prompt to drink in substep 8541, a prompt to consume sodium in substep 8542, a prompt to slow down in substep 8543, a prompt to cease activity in substep 8544, a prompt to eat in substep 8545, a prompt to take insulin in substep 8546, a prompt to take medication in substep 8547, a prompt to seek emergency medical attention in substep 8548, or any other suitable prompt. If desired, the system may send an alert message in step 8550. For example, a radio frequency message may be sent to emergency medical personnel. In step 8560, an audible alert may be sounded. If desired, the action may include control of a medical treatment device, such as a portable syringe pump, an implanted defibrillator, or other suitable device.

Figure 86:
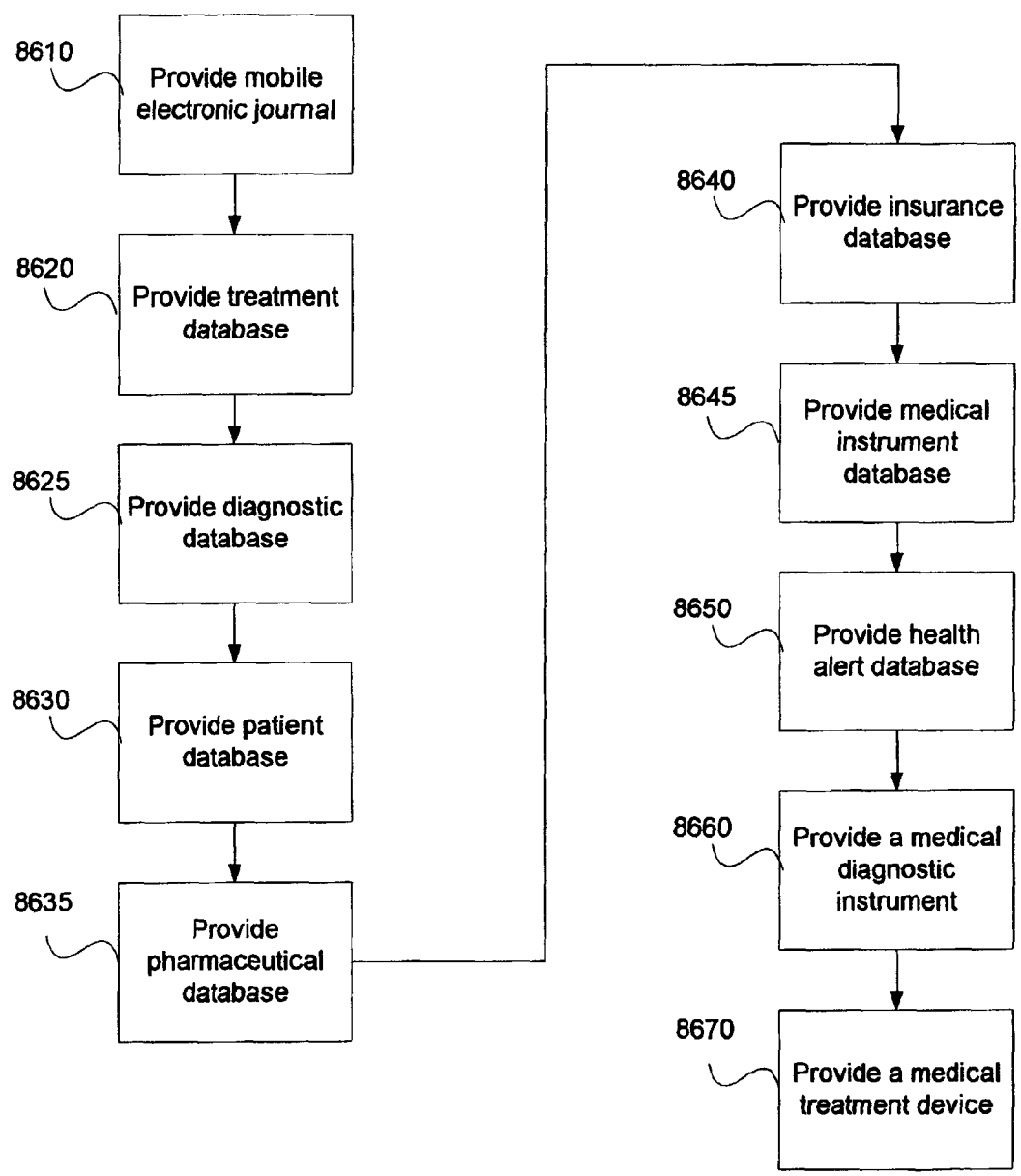
FIG. 86 is a flow chart of an illustrative process for providing a mobile electronic medical journal using an MPN.

FIG. 86 shows more detail of step 8480 (FIG. 84), providing a mobile electronic medical journal. All steps are optional and may be performed in any suitable order. In step 8610, a mobile electronic journal may be provided as described earlier with reference to FIG. 42. In step 8620, a treatment database may be provided, which may provide information about different types of medical treatments. A diagnostic database may be provided in step 8625, and may contain information about different medical diagnoses. A patient database may be provided in step 8630, and may include information about patients of a medical provider, such as medical history, previous diagnoses, previous treatments, family medical history, risk factors, insurance and payment information or other suitable types of information. In step 8635, a pharmaceutical database may be provided, and may include information about various drugs, including indications for use, recommended dosage, side effects, availability, and other suitable drug information. In step 8640, an insurance database may be provided, and may include information about different insurance providers, such as types of policies, payment histories, covered expenses, and other suitable information. A medical instrument database may be provided in step 8645, and may include information about various medical instruments, their uses, risks, and other related data. A health alert database may be provided in step 8650, and may include information about current and recent health alerts, such as may be issued by public agencies like the Centers for Disease Control. Any journal entry may be linked to one or more elements from one or more of the included databases. Each journal entry may have one or more linked images or video clips. Medical images such as x-rays, CAT scans, MRIs, bone scans and the like, may also be input and linked to journal entries. Each journal entry may also have one or more audio clips, such as a doctor's dictation. The dictation may be translated into text using voice recognition software if desired. The journal may include a medical diagnostic instrument in step 8660, and a journal entry may be linked to one or more readings from the instrument. The journal may include a medical treatment device in step 8670. Any journal entry may be linked to a usage report of the treatment device.

Figure 87:
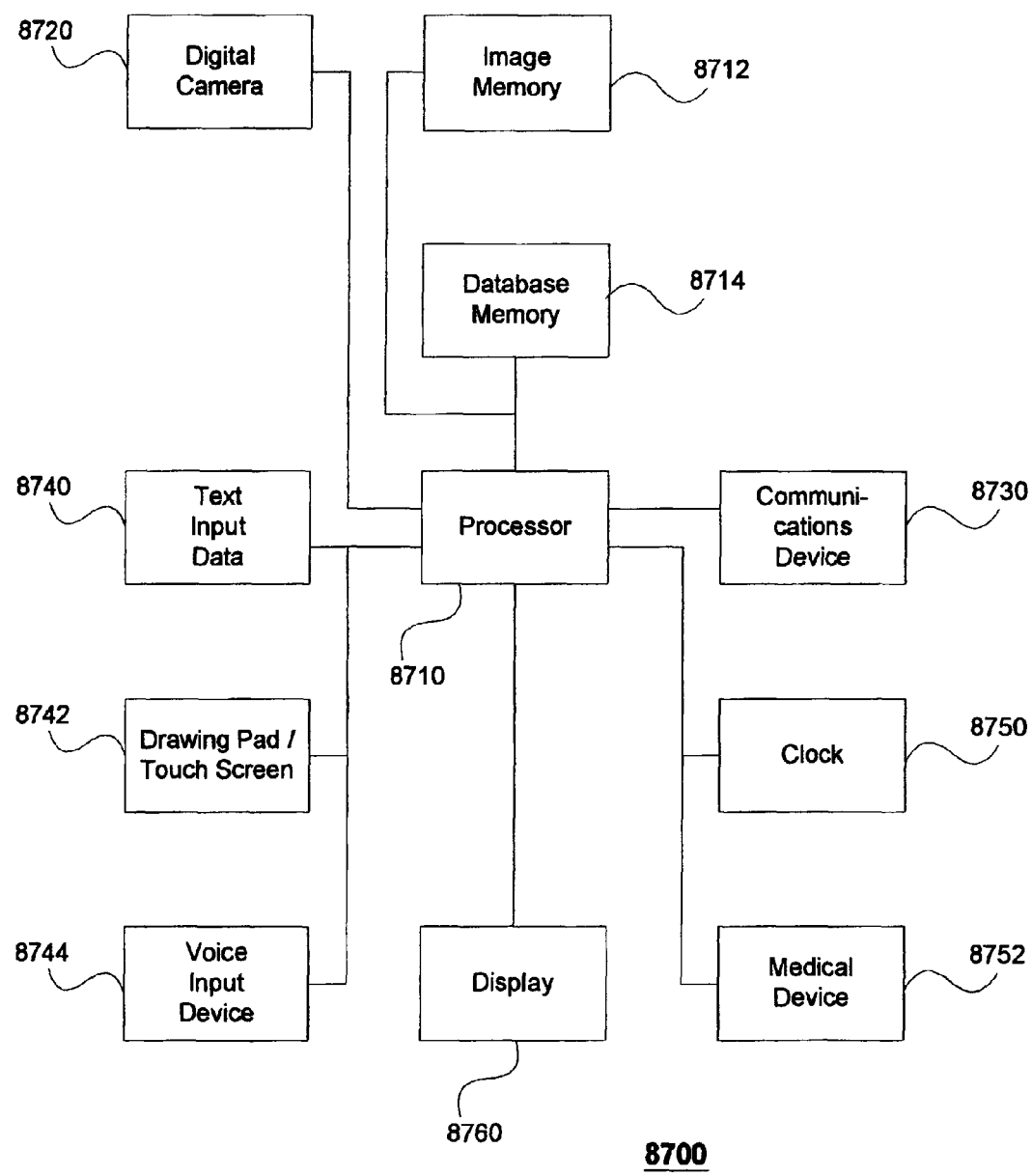
FIG. 87 is an illustrative block diagram of a mobile electronic medical journal.

FIG. 87 shows an illustrative block diagram of a mobile electronic medical journal 8700. Journal 8700 may include processor 8710, which may, for example, be in a control unit. Image memory 8712 for holding images and other user data and library memory 8714 for holding one or more databases may also be included in the control unit if desired, and if desired may be the same memory. Digital camera 8720 may be provided. It may be capable of capturing video still images to link to journal entries. If desired it may also be capable of capturing video clips for the journal entries. Communications device 8730 may be used for downloading database information and uploading journal entries. Text input INC 8740, drawing pad/touch screen input 8742, and voice input INC 8744 may be provided to allow text, drawing, and voice portions of a journal entry respectively. If desired, voice input INC 8744 may also include a voice recognition capability. A device such as a scanner may also be included to input medical images. Clock 8750 may be provided to tag journal entries with the current time. Medical device 8752 may be included to perform a medical function, and may be either a medical diagnostic/input device or a medical treatment device. If desired, multiple medical devices may be included. Display 8760 may also be provided to view journal entries, database information, and other data. If desired, an audio output INC, not shown, may be provided. INCs may be separate devices, or may be combined in any suitable fashion. All INCs shown are merely illustrative and are optional.

Figure 88:
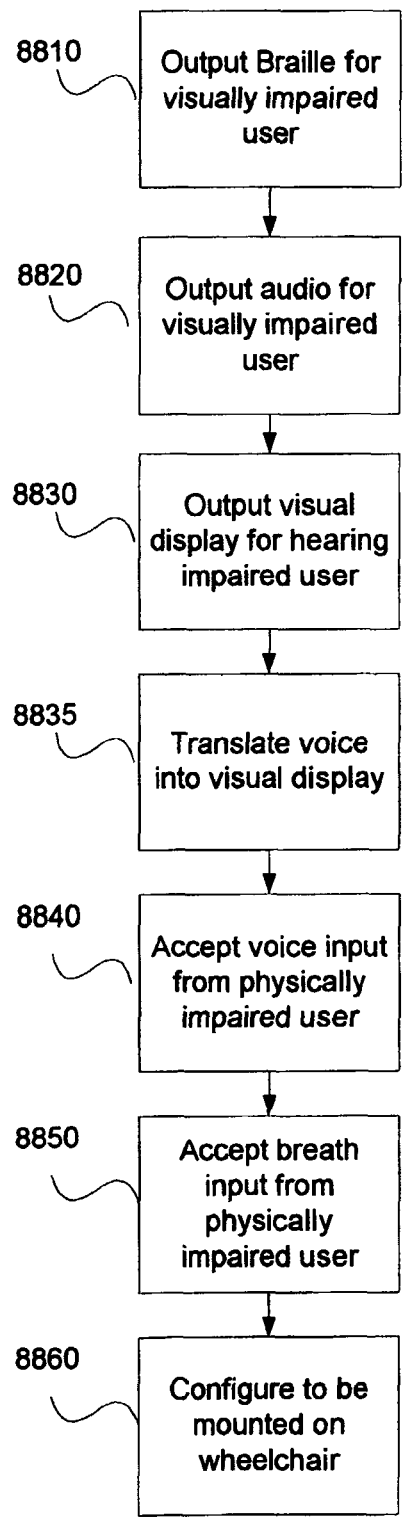
FIG. 88 is a flow chart of an illustrative process for providing features for a disabled user with an MPN.

FIG. 88 shows more detail of step 3260 of FIG. 32, providing features for a disabled user. All steps are optional and may be performed in any suitable order. In step 8810, Braille may be output for a visually impaired user. For example, an INC may include an output device capable of generating Braille characters. In step 8820, audio may be output for a visually impaired user, in addition to or instead of a visual output. This may include speech generation. In step 8830, information may be output visually for a hearing impaired user, in addition to or instead of an audible output. In step 8835, voice input may be translated into a visual input for a hearing impaired user. For example, the MPN may include an audio input INC to accept a voice input that the user wishes to have translated. The system may use voice recognition to provide a visual display, which may be, for example, text or sign language. In step 8840, voice input may be accepted from a physically impaired user. In step 8850, breath input may be accepted from a physically impaired user. This may include allowing a user to input commands to the MPN by blowing into a tube. In step 8860, one or more INCs may be configured to be mounted on a wheelchair or other device used by a disabled user.

Figure 89:
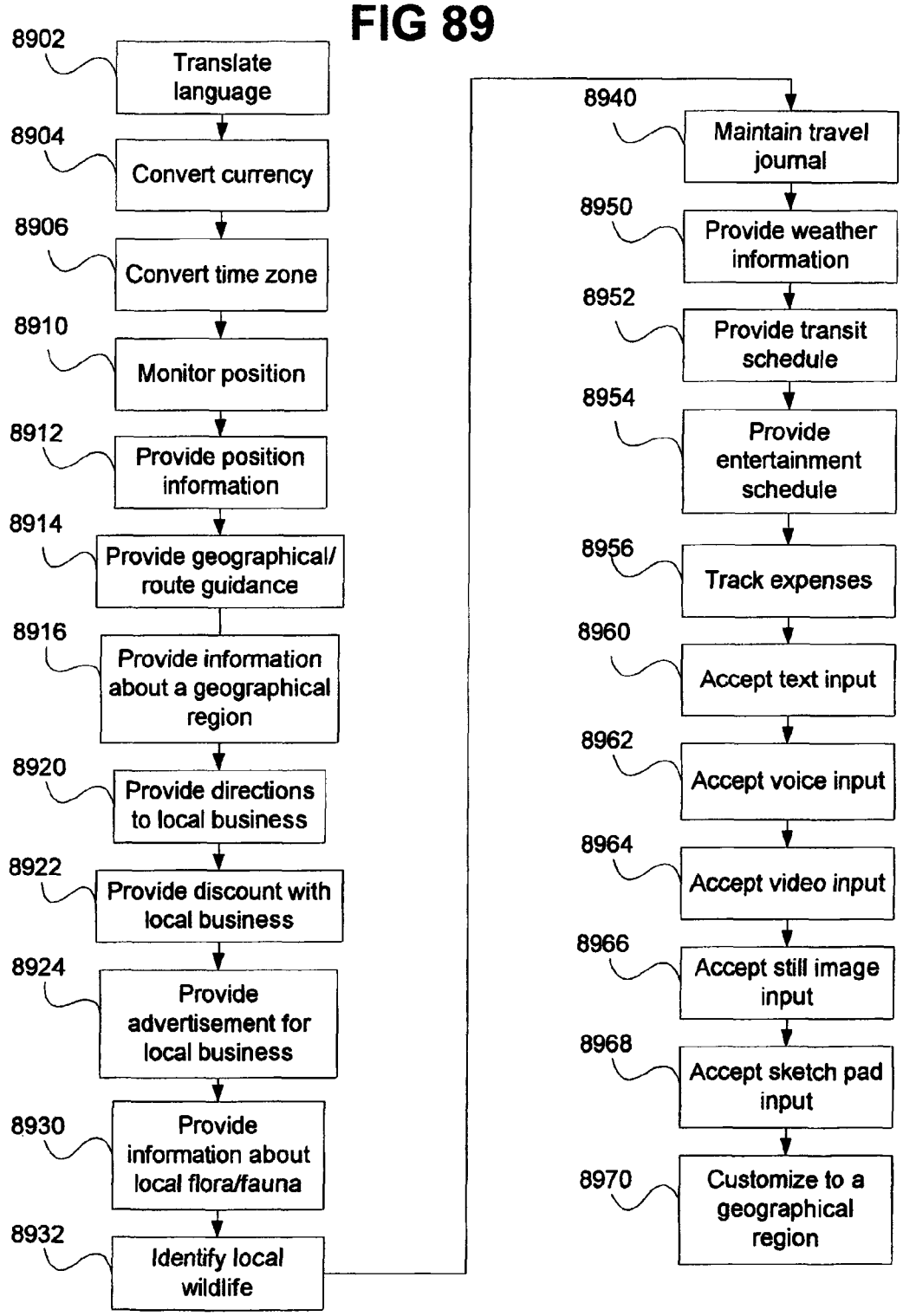
FIG. 89 is a flow chart of an illustrative process for providing travel-related functions using an MPN.

As described in step 3265 of FIG. 32, an MPN may be used by a traveler to provide travel-related functions. This is illustrated in more detail in FIG. 89. All steps are optional and may be performed in any suitable order. In step 8902, the system may provide language translation. It may translate from the user's language to a second language, or from a second language to the user's language. Input may be text or it may be spoken with voice recognition. Output may be text, spoken with speech generation, or both. Translation may be based on a local dialect or local slang. In step 8904, the system may provide currency conversion. It may convert home currency to travel currency, or travel currency to home currency. In step 8906, the system may provide time zone conversion. It may allow the display of time in the local time zone, in the home time zone, or any other time zone. In step 8910, the MPN may monitor the user's position, for example using a GPS monitor. Information on the user's position may be provided to the user in step 8912. In step 8914, the system may provide guidance to the user based on the user's location. In step 8916, the system may provide the user with information about a geographical region. This may include geographical information, local customs, laws, tipping guidelines, and other suitable local information. In step 8920, the system may provide directions to a local business or attraction, which may be based on the user's location. In step 8922, a discount with a local business may be provided. In step 8924, an advertisement for a local business may be provided to the user. In step 8930, information may be provided about local flora and/or fauna. In step 8932, the system may assist the user in identifying local wildlife. In step 8940, the system may allow the user to maintain a travel journal. In step 8950, the system may provide weather information, such as a local weather forecast. In step 8952, the system may provide a transit schedule, such as an airline schedule to or from a travel location, local train and bus schedules, and the like. In step 8954, the system may provide a local entertainment schedule. In step 8956, the system may allow the user to track expenses, for example in either local or home currency. The system may accept text input in step 8960, voice input in step 8962, video input in step 8964, still image input in step 8966, sketch pad input in step 8968, or any other suitable form of user input. In step 8970, the system may be customized to a specific geographical region. For example, prior to a trip, a user may enter the destination or destinations into a software application running on a personal computer. Suitable information for the specific region or regions may be downloaded over a network such as the Internet, and may be downloaded into an INC of the electronic travel journal, such as a control unit. Suitable information may include local language and dialect translation dictionaries, currency exchange rates, time zone information, information about a location, businesses, customs, laws, geography, wildlife, flora, climate information and weather forecasts, local transit schedules, local entertainment schedules, and any other suitable local information. If desired, local information may be updated while traveling, for example by connecting one of the INCs to a connection such as an Internet connection.

Figure 90:
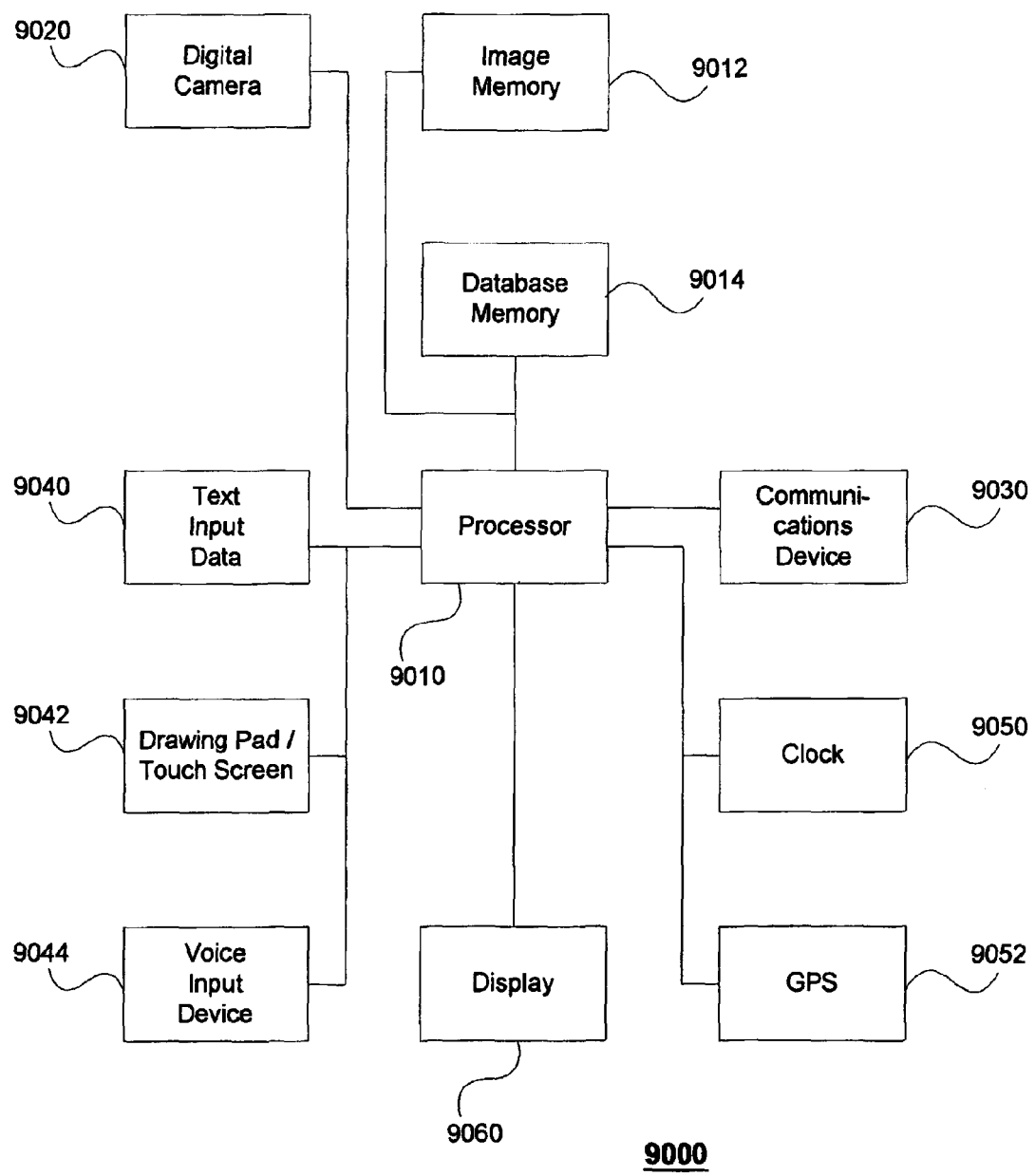
FIG. 90 is an illustrative block diagram of an MPN that may be used to provide travel-related functions.

FIG. 90 shows a block diagram of illustrative MPN 9000 that may be used while traveling. MPN may include processor 9010, which may, for example, be part of a control unit. Image memory 9012 may be used for storing video images and other user inputs. Database memory 9014 may be used to store downloaded data. Image memory 9012 and database memory 9014 may be the same memory, and may be part of a control unit. Digital camera 9020 may be provided. It may be capable of capturing video still images. If desired it may also be capable of capturing video clips. Communications device 9030 may be used for downloading data into database memory 9014, and for uploading user data form image memory 9012. Text input INC 9040, drawing pad/touch screen input 9042, and voice input INC 9044 may be provided to allow text, drawing, and voice input for travel features, respectively. If desired, voice input INC 9044 may also include a voice recognition capability. Clock 9050 may be provided to tag user entries with the current time, and to provide a user time display. GPS monitor 9052 may be included to provide location information in support of travel features. Display 9060 may also be provided to view information. If desired, an audio output INC, not shown, may be provided. INCs may be separate devices, or may be combined in any suitable fashion.

Figure 91:
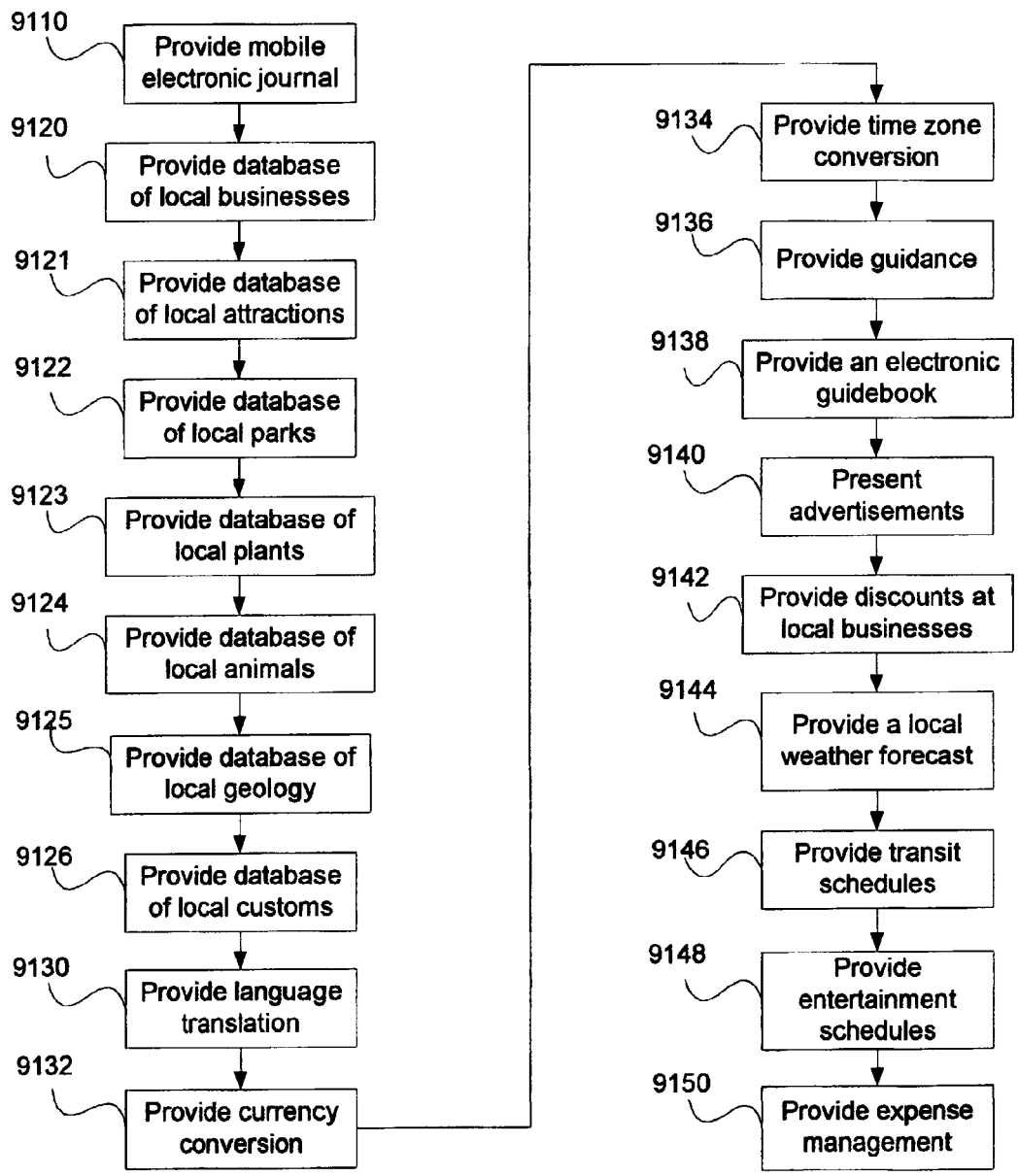
FIG. 91 is a flow chart of an illustrative process for providing a mobile electronic travel journal using an MPN.

Step 8940 (FIG. 89), providing a travel journal, is described in more detail in FIG. 91. All steps are optional and may be performed in any suitable order. In step 9110, a mobile electronic journal may be provided, for example as described in conjunction with FIG. 42. The travel journal may be configured, for example, as the MPN shown in FIG. 90. Any suitable travel database or databases may be included and stored in database memory 9014. For example, a database of local businesses may be provided in step 9120. A database of local attractions may be provided in step 9121. A database of local parks may be provided in step 9122. A database of local plants may be provided in step 9123. A database of local animals may be provided in step 9124. A database of local geology may be provided in step 9125. A database of local customs may be provided in step 9126. Any other suitable travel data may also be included. The database or databases may be downloaded into the database memory prior to a trip, based on the planned destination or destinations. If desired, any database may be updated during a trip, for example using communications device 9030 to connect to a network such as the Internet. Any journal entry may be allowed to link to one or more database elements from any of the supported databases. The travel journal may also provide any other suitable travel function or functions, such as language translation in step 9130, currency conversion in step 9132, time zone conversion in step 9134, route guidance in step 9136, electronic guidebook features (e.g., information about local customs, businesses, attractions, etc.) in step 9138, advertisements in step 9140, a discount at a local business in step 9142, a local weather forecast in step 9144, transit schedules in step 9146, entertainment schedules in step 9148, or expense management in step 9150. If desired, any journal entry may be linked to an element from another travel feature.

Figure 92:
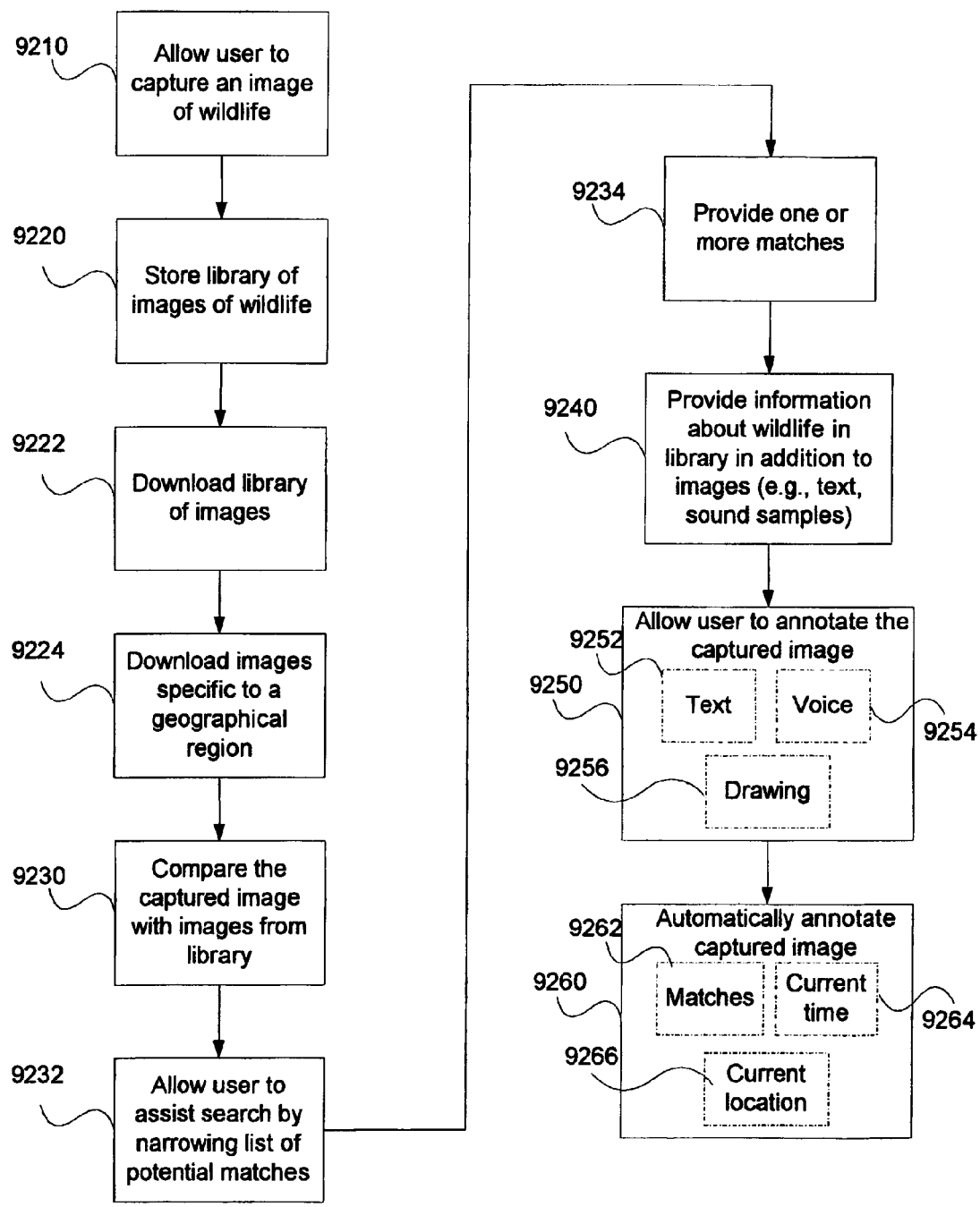
FIG. 92 is a flow chart of an illustrative process for assisting a user in identifying wildlife using an MPN.

Step 8932 (FIG. 89), assisting a user in identifying local wildlife, is described in more detail in FIG. 92. All steps are optional and may be performed in any suitable order. The MPN may be configured, for example, as shown in FIG. 90. In step 9210, the user may be allowed to capture an image of wildlife, for example using digital camera 9020, and it may be stored in image memory 9012. In step 9220, a library of images of wildlife may be stored, for example in database memory 9014. The library of images may be downloaded into database memory 9014 in step 9222 for example using communications device 9030. The images downloaded may be specific to a geographical region in step 9224. In step 9230, the captured image may be compared with the images from the library, using, for example, processor 9010. In step 9232, the system may allow the user to assist the search, for example by using a user input INC to narrow a list of potential matches. In step 9234, one or more potential matches may be presented to the user, for example using display 9060. In step 9240, additional information may be provided for the wildlife in the library. For example, there may be text descriptions, descriptions of habitat and habits, sound samples characteristic of the wildlife, etc. In step 9250, the user may be allowed to annotate the captured image. For example, the user may be allowed to add text in substep 9252, voice or other captured audio in substep 9254, a drawing in substep 9256, or any other suitable type of user annotation. In step 9260, the captured image may be automatically annotated. That may include an annotation with a link to any match or matches from the wildlife library in substep 9262, the time the image was captured determined for example using clock 9050 in substep 9264, the location at which the image was captured in substep 9266 determined for example using GPS monitor 9052, or any other suitable automatic annotation.

Figure 93:
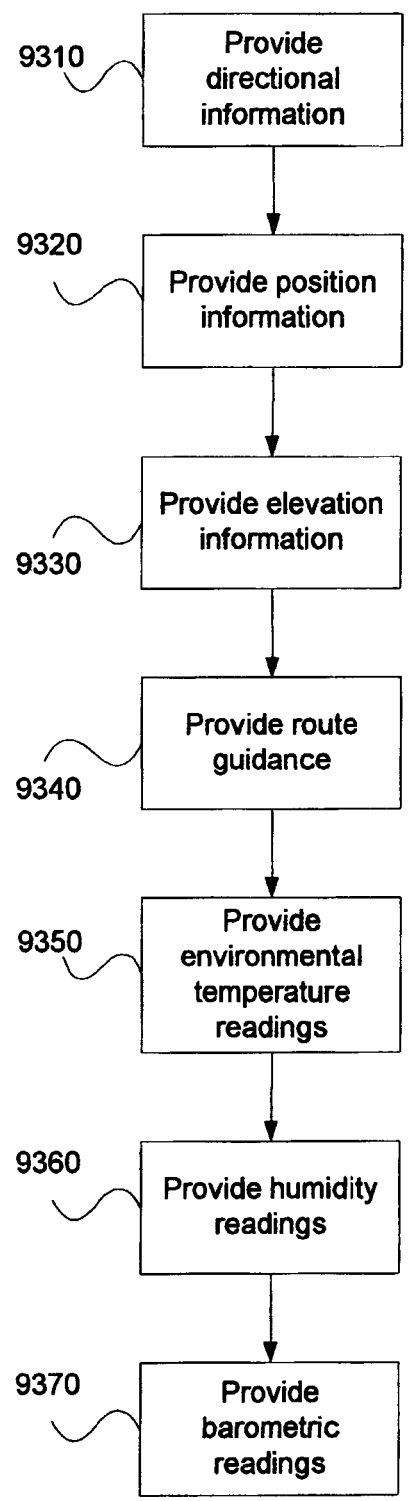
FIG. 93 is a flow chart of an illustrative process for providing outdoor-related functions using an MPN.

FIG. 93 shows more detail of step 3225 of FIG. 32, supporting outdoor enthusiast features with an MPN. All steps are optional and may be performed in any suitable order. In step 9310, the MPN may provide directional information. For example, one of the INCs may include a compass. In step 9320, the MPN may provide position information, if for example one of the INCs contains a position monitor. In step 9330, the MPN may provide elevation information, using an INC that may include an elevation monitor. In step 9340, the MPN may provide route guidance. Guidance may be based on, for example, topographical information, trail maps, visual landmarks, and other items useful to a hiker, skier, snowshoer, or other outdoor enthusiast. The MPN may also provide weather related information, such as environmental temperature readings in step 9350, humidity readings in step 9360, or barometric readings in step 9370. Other suitable outdoor features may also be included if desired.

Figure 94:
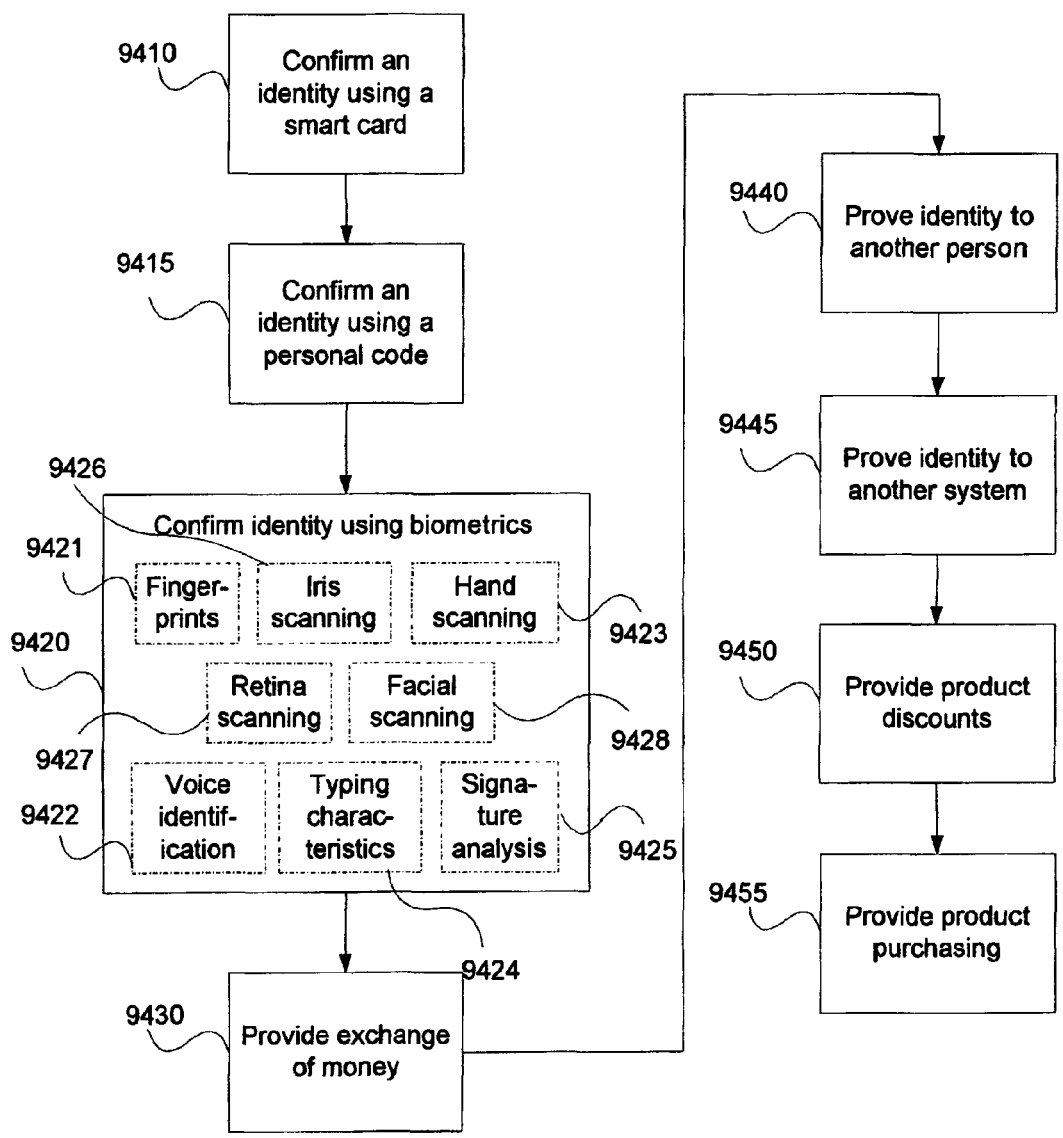
FIG. 94 is a flow chart of an illustrative process for providing identification functions using an MPN.

FIG. 94 shows more detail of step 3240 of FIG. 32, providing an identification function with an MPN. All steps are optional and may be performed in any suitable order. In step 9410, the MPN may confirm an identity using a smart card, with an INC that may include a smart card reader. In step 9415, the MPN may confirm an identity using a personal code or password, for example if one of the INCs allows numeric or text entry. In step 9420, an identity may be confirmed using biometrics. The biometric may be any suitable technique adapted to a portable INC in the MPN, and may include fingerprint analysis in substep 9421, voice identification in substep 9422, hand or finger scanning in substep 9423, analysis of typing characteristics in substep 9424, signature analysis in substep 9425, iris scanning in substep 9426, retina scanning in substep 9427, or facial scanning in substep 9428. If desired, other physical characteristics may be used for identification, such as athletic performance data or metabolic data.

In step 9430, exchange of money may be provided based on the confirmed identity. In step 9440, the identity may be proven to another person. In step 9445, the identity may be proven to another system, such as another MPN. In step 9450, a product discount may be provided based on the confirmed identity. In step 9455, product purchasing may be provided based on the confirmed identity. If desired, the system may store purchasing information, such as a credit card number, a bank account number, a bank balance, or any other suitable information. If desired, the personal identification may also be used to prevent unauthorized use of the MPN or any of its INCs. The personal identification may also be used to provide secure access to restricted areas, features, and the like.

Figure 95:
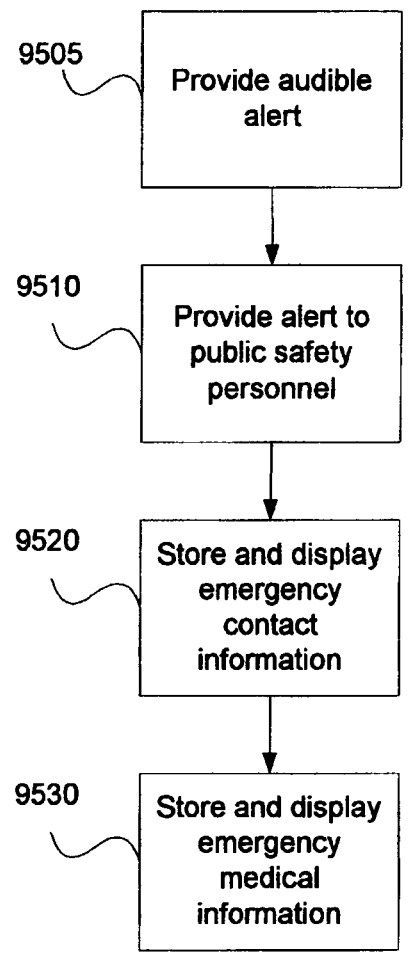
FIG. 95 is a flow chart of an illustrative process for providing security functions using an MPN.

FIG. 95 shows more detail of step 3245 of FIG. 32, providing a personal security function with an MPN. All steps are optional and may be performed in any suitable order. In step 9505, the MPN may be capable of providing an audible alert, such as a whistle or other alarm. In step 9510, the MPN may be configured to provide an alert to public safety personnel. For example, an INC may be provided that includes a communication INC configured to transmit a message to an emergency dispatch facility, a police department, a fire department, or an emergency medical facility. The audible alert or emergency message may be triggered by a specific user input, or by any other suitable input or lack of input that may arise in the event of a personal or public emergency. In step 9520, the MPN may store emergency contact information for the user, and may be configured to display or otherwise provide that information with suitable authorization. In step 9530, the MPN may be configured to store emergency medical information, such as preexisting conditions, allergies, current prescriptions, etc., and may be configured to display or otherwise provide that information with suitable authorization.

Figure 96:
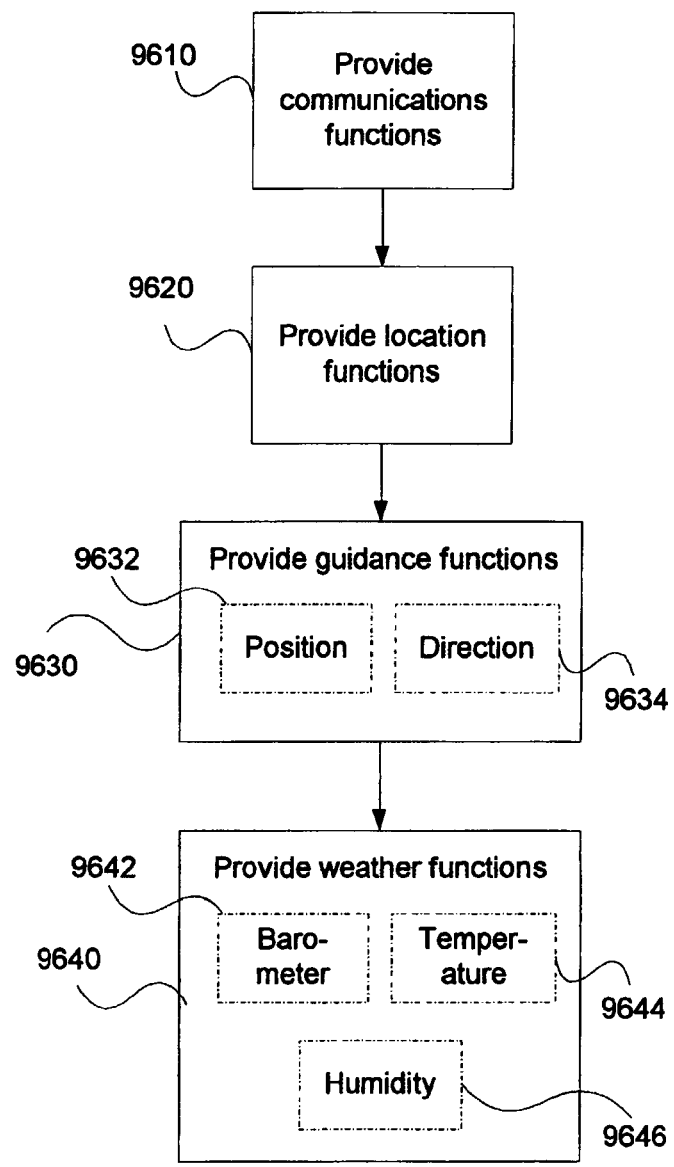
FIG. 96 is a flow chart of an illustrative process for providing military functions using an MPN.

FIG. 96 shows more detail of step 3250 of FIG. 32, providing a military function in an MPN. All steps are optional and may be performed in any suitable order. For example, individual military members involved in ground support may each be equipped with an MPN having suitable INCs and functions. The MPN may provide a communications function in step 9610, such as instant message, and voice, data, text, or video communications. The MPN may provide location functions in step 9620, such as providing the current location using a GPS monitor. The MPN may include guidance functions in step 9630. That may include guidance to specific position in substep 9632, and directional information in substep 9634. The MPN may provide weather functions in step 9640. This may include barometric readings in substep 9642, environmental temperature readings in substep 9644, humidity readings in substep 9646, or any other suitable weather function.

As described in step 3270 of FIG. 32, an MPN may support multiple functions. Some combinations have been described above. For example, providing both athletic and guidance functions was described in conjunction with FIG. 43A. Providing both music and other audio cues was described in conjunction with step 2960 of FIG. 29.

Figure 97:
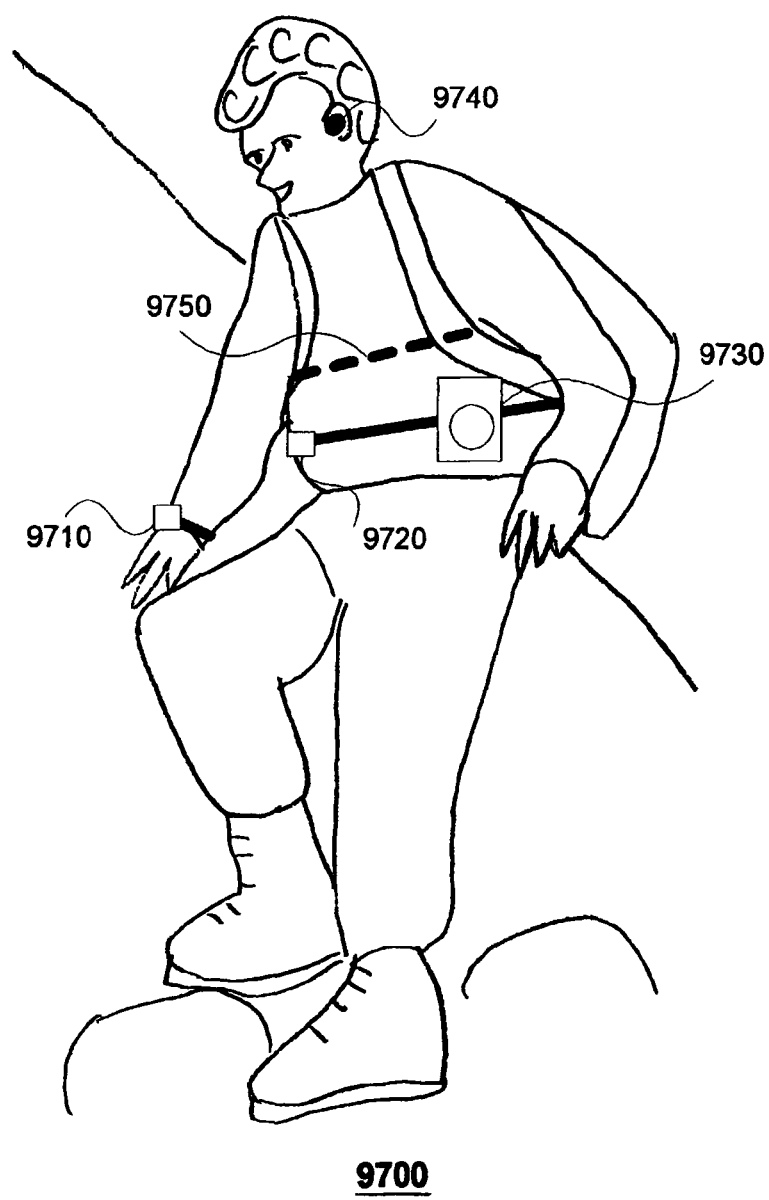
FIG. 97 is an illustrative diagram of an MPN that may be used to provide multiple functions.

Another example of an MPN 9700 that may be used for multiple purposes is shown in FIG. 97. MPN 9700 may include INC 9710, configured to be worn on the wrist. INC 9710 may include a display INC, user controls, and a microphone. MPN 9700 may include INC 9720, configured to be worn on a waistband. INC 9720 may include control unit functions, clock functions, storage of audio and video media, and a GPS monitor. MPN 9700 may include INC 9730, which may be a video/still camera configured to be worn on a waistband. MPN 9700 may include INC 9740, which may be an audio output INC. MPN 9700 may include INC 9750, which may be a heart rate sensor configured to be worn on the chest. These INCs are merely illustrative. Any suitable INCs and method of carrying may be used.

Figure 98:
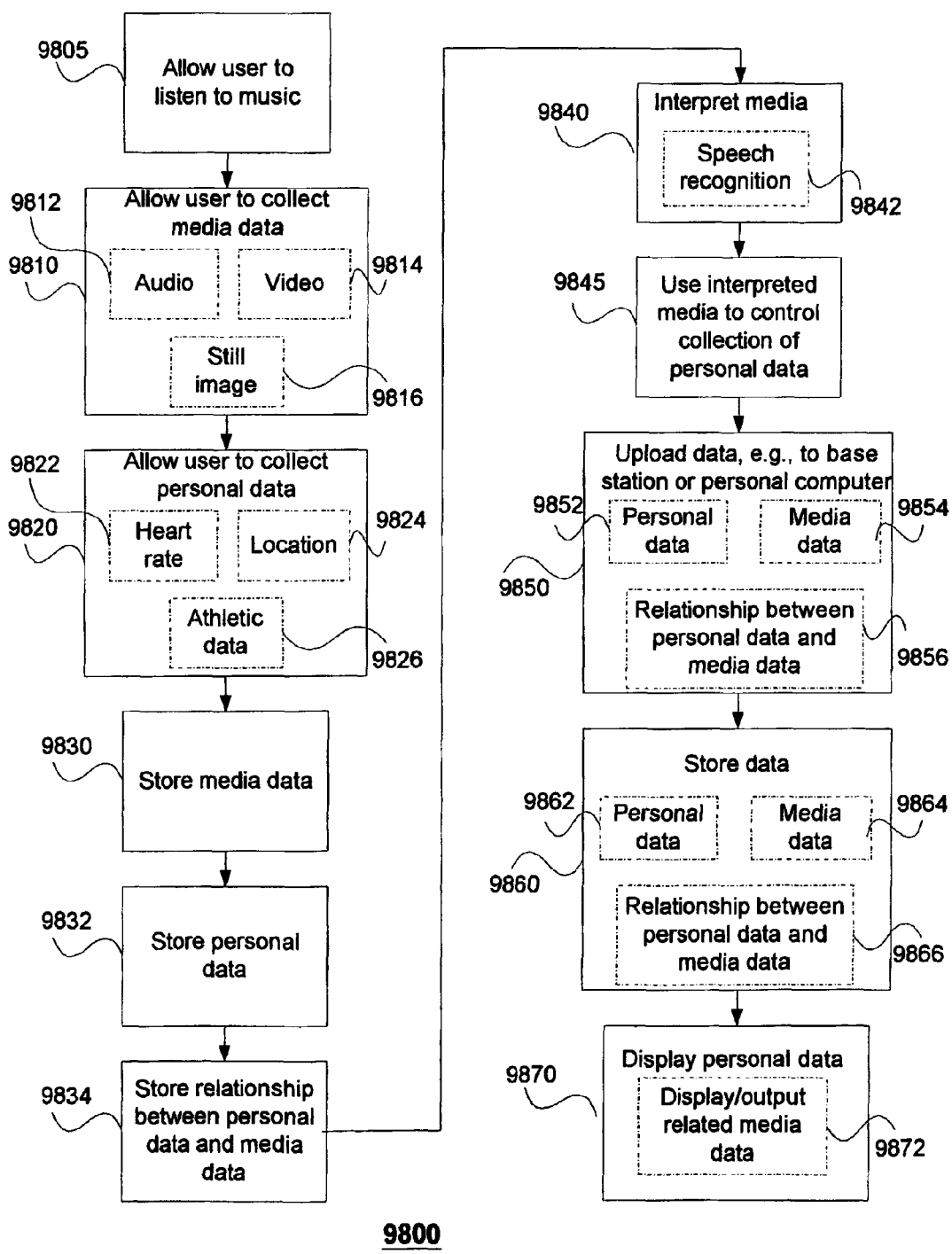
FIG. 98 is a flow chart of an illustrative process for providing music, media collection, and personal data collection using an MPN.

FIG. 98 shows flow chart 9800 of an illustrative process for allowing multiple uses of MPN 9700 (FIG. 97). All steps are optional and may be performed in any suitable order. In step 9805, the user may be allowed to listen to music. Music may be stored digitally in INC 9720 and sent to INC 9740 to be heard. In step 9810, the user may be allowed to collect media data. For example, using the microphone in INC 9710 and using INC 9730, the user may collect audio data in substep 9812, video data in substep 9814, and still images in substep 9816. In step 9820, the MPN may collect personal data. That may include, for example, heart rate data 9822 collected from INC 9750 or other suitable athletic data 9826, and speed, location 9824, and elevation data collected from the GPS monitor in INC 9720. In step 9830, the media data may be stored, for example in memory in INC 9720. In step 9832, the personal data may be stored, for example in memory in INC 9720. In step 9834, a relationship may be stored between the media data and the personal data. For example, the personal data may be stored at a regular interval with a time stamp, and the collected media data may use the same time stamp. In step 9840, the MPN may interpret collected media. That may include speech recognition in substep 9842. The interpreted media may be used to control the functions of the MPN in step 9845, for example controlling the collection of personal data. Alternatively, the interpreted media may be stored as text or in another suitable format. In step 9850, data may be uploaded, for example to a base station or personal computer. That may include uploading the personal data in substep 9852, the media data in substep 9854, and the relationship between them in step 9856. In step 9860, the uploaded data may be stored. This may include storing the personal data in substep 9862, the media data in substep 9864, and the relationship data in substep 9866. In step 9870, the personal data may be displayed. In step 9872, the media data may be displayed or output based on its relationship to the personal data. See the description of FIGS. 46 and 48 for examples of the display of personal data and the related media data.

FIG. 99 shows illustrative data structure 9900 that may be used to store personal data and their relationships to media data. In this example, personal data samples are stored every second. First sample 9920 has time stamp 9910 and has no linked media. Second sample 9940 has time stamp 9930, and has related media link 9950. In this case, the media link is the name of a file containing a still image captured by the user. The MPN has automatically named the file based on the type of content and date and time of capture. Third sample 9970 with stamp 9960 in this example has no linked media.

Figure 101A:
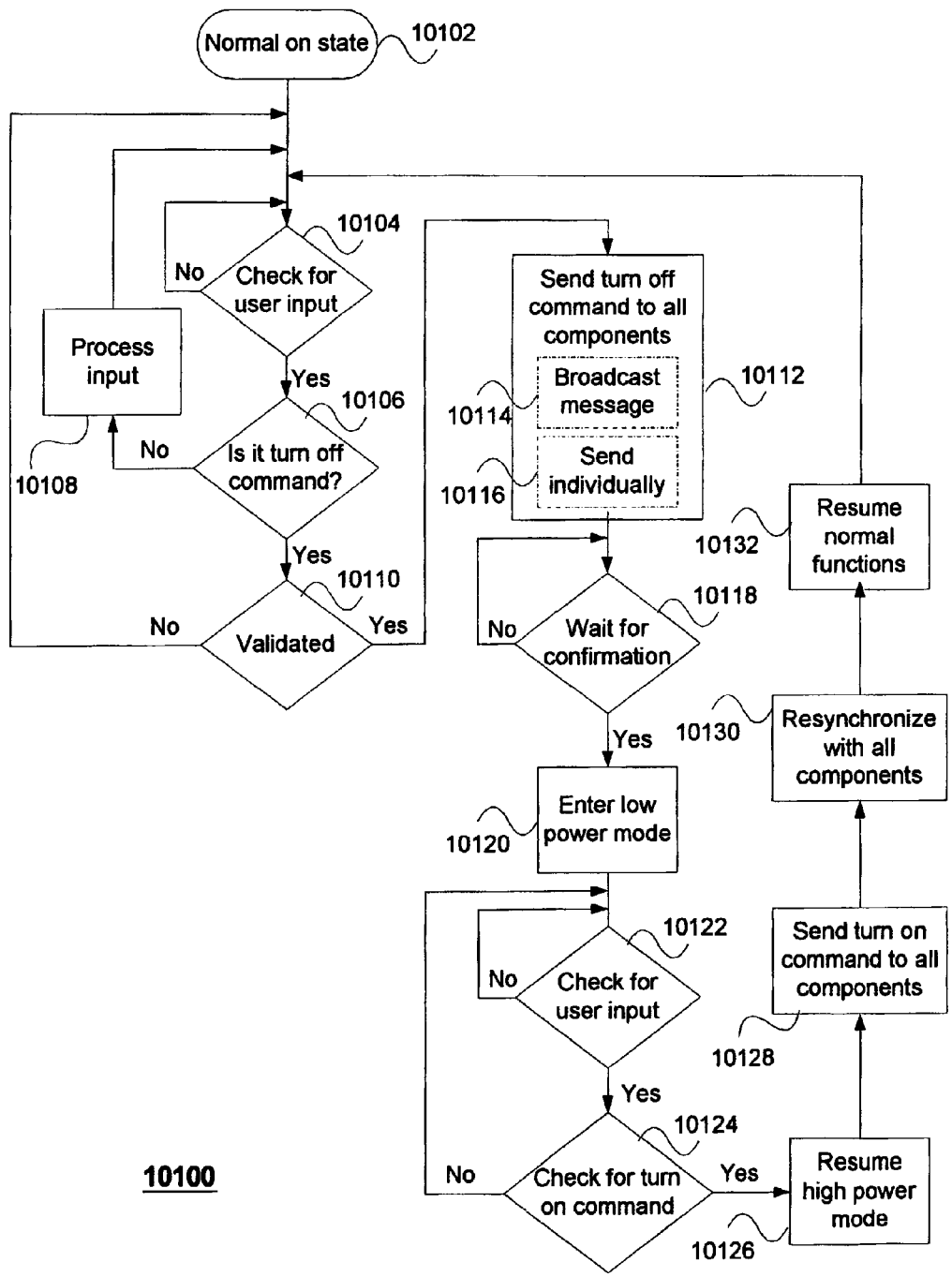

The ability to easily turn off all INCs in an MPN may be useful to conserve power. It may also be useful to terminate radio frequency transmission in an environment in which they may cause unwanted interference, such as on a commercial airliner. One of the commands received by the user input INC may be a turn on command, or a turn off command. These may be global commands applying to all INCs in the MPN. A process for handling a global turn on command and a global turn off command is shown in FIG. 101A and FIG. 101B. All steps are optional and may be performed in any suitable order. Flow chart 10100 of FIG. 101A shows an illustrative process that may be performed by a user input INC, or by an INC such as a control unit that receives commands from a user input INC. In step 10102, the INC may be in its normal "on" state, in which it processes commands and data normally. The INC may check for user input in step 10104. If no user input is received, the INC may remain in its normal "on" state and continue with normal functions. If user input is received, the INC may check to see if it is a turn off command in step 10106. Any appropriate type of user input may be used, such as a voice input, a key press, etc. If the user input is not a turn off command, the INC may process the user input normally in step 10108 and continue with normal functions. If the user input is a turn off command, the INC may check to see if the command is validated in step 10110. Validation may consist of a second input, holding the key down for an extended period, the entry of a personal code, or any other suitable user validation. If desired, the INC may not require validation. If the turn off command is not validated within a defined period of time, the INC may return to its normal "on" state. If the turn off command is validated, the INC may proceed with the turn off sequence.

In step 10112, the INC may send a turn off command to all of the INCs in the MPN. This may be a single message that is broadcast to all INCs with the same network identifier in substep 10114. Alternatively, individual messages may be sent addressed to each INC in substep 10116. In step 10118, the INC may wait for confirmation from each other INC. If confirmation is not received, the INC may resend the turn off command, display an error message, or perform another suitable action. If desired, the wait for confirmation step may be optional. Once all confirmations have been received, the INC may enter a low power mode, in step 10120. For example, if a processor with a sleep mode is used in the INC, it may enter the sleep mode, and it may configure an interrupt to be generated when a user input is received.

While in the low power turned off state, the INC may check for user input, in step 10122. For example, an interrupt may be generated when a user input is received. If no user input is received, the INC may remain in the turned off state. If user input is received, the INC may check to see if it is a turn on command, in step 10124. If not, the user input may be ignored and the INC may remain in the turned off state. If the turn on command is confirmed, the INC may resume its high power mode, in step 10126. Turn on messages may be sent to all components in step 10128, either as a single broadcast message or as individually addressed messages. The INC may resynchronize with the other components in step 10130. This may include waiting for acknowledgement from the turn on message, resending the turn on message if required, or synchronizing functions that may have been in progress prior to the turn off command. In step 10132, normal functioning may resume.

Flow chart 10150 of FIG. 101B shows an illustrative process that may be performed by an INC that does not receive user input. The INC may start in its normal "on" state, in step 10152. It may be performing its normal functions, such as data collection, output, control, storage, or other functions or combination of functions. In step 10154, the INC may check for a message, such as a wireless message from another INC in the MPN. This may include checking to see if the message has the correct network identifier, component identifier, or other address. If no message is received, the INC may continue its normal functions. When a message is received, the INC may check to see if it is a turn off message, in step 10156. If not, the message may be handled normally, in step 10158, and the INC may remain in its normal "on" state. When a turn off message is received, the INC may acknowledge the message in step 10160. The acknowledgement may be optional. In step 10162, the INC may stop its normal functions. This may include stopping any data collection, output, or control functions. The INC may stop sending any information using its wireless transmitter. Preferably, the INC will retain any stored information in memory, including information about any processes that may have been underway, and any other information required to later resume normal functions. In step 10164, the INC may enter a low power mode. For example, if a processor with a sleep mode is used in the INC, it may enter the sleep mode, and it may configure an interrupt to be generated when a wireless message is received.

While in low power mode, the INC may check for incoming messages, in step 10166. If no message is received, it may remain in low power mode. When a message is received, the INC may check to see if it is a turn on message, in step 10168. If the message is not a turn on message, the INC may ignore it and remain in the low power off state. When the turn on message is received, the INC may resume its high power mode in step 10170. An optional acknowledgement message may be sent in step 10172. Optionally, the INC may resynchronize with other INCs in the MPN, in step 10174. This may include synchronizing any functions that were in progress when the power off message was received. In step 10176, the INC may resume normal functions, and return to its normal "on" state.

Although various embodiments have been described herein in terms of an MPN, many of them are possible without all of the features and aspects of an MPN. For example, components may be designed specifically for a single purpose, and may not support dynamic configuration of a wireless network.

Although our present invention has been described in considerable detail with reference to certain preferred embodiments thereof, other embodiments are possible. This includes uses, functions, components, and combinations thereof that may not be fully described. Therefore, the spirit and scope of the appended claims should not be limited to the description of the preferred embodiments contained herein.

What is claimed is:

1. A method of determining a workout plan for an individual, the method comprising:
    receiving an input from the individual;
    determining a first type of workout based on the input from the individual;
    determining a plurality of workout sessions for the first type of workout for the workout plan;
    determining a second type of workout that is different than the first type of workout based on the input from the individual;
    determining a plurality of workout sessions for the second type of workout for the workout plan; and
    storing data describing the workout plan in a memory accessible by a server computer system, wherein the data describing the workout plan includes data describing the plurality of workout sessions for the first type of workout and data describing the plurality of workout sessions for the second type.

2. The method of claim 1, further comprising storing the input in the memory accessible by the server computer system.

3. The method of claim 1, wherein the input comprises personal data of the individual.

4. The method of claim 3, wherein the personal data comprises one of the age, the gender, and the weight of the individual.

5. The method of claim 1, wherein the input comprises performance data of the individual.

6. The method of claim 5, wherein the performance data comprises data associated with the individual's performance during a previously completed workout session.

7. The method of claim 1, wherein the first type of workout comprises cardiovascular workouts.

8. The method of claim 7, wherein the cardiovascular workouts comprise running workouts.

9. The method of claim 1, wherein the first type of workout comprises strength training workouts.

10. The method of claim 9, wherein the strength training workouts comprise weightlifting workouts.

11. The method of claim 1, wherein the first type of workout comprises cardiovascular workouts and wherein the second type of workout comprises strength training workouts.

12. The method of claim 1, wherein determining the plurality of workout sessions for the first type of workout is carried out by the server computer system.

13. The method of claim 1, wherein determining the plurality of workout sessions for the first type of workout comprises assigning days for the plurality of workout sessions for the first type of workout.

14. The method of claim 1, wherein determining the plurality of workout sessions for the first type of workout comprises assigning durations for the plurality of workout sessions for the first type of workout.

15. The method of claim 1, wherein determining the plurality of workout sessions for the first type of workout comprises assigning intensities for the plurality of workout sessions for the first type of workout.

16. The method of claim 15, wherein assigning the intensities comprises defining one of target speeds, paces, heart rates, resistance levels, or numbers of repetitions.

17. The method of claim 1, further comprising transmitting one of the plurality of workout sessions for the first type of workout or one of the plurality of workout sessions for the second type of workout from the server computer system to a portable performance monitoring device of the individual.

18. The method of claim 1, further comprising instructing the individual to engage in the workout plan by prompting the individual to engage in one of the plurality of workout sessions for the first type of workout or one of the plurality of workout sessions for the second type of workout.

19. A method of determining a workout session for an individual, the method comprising:
    receiving an input from the individual;
    determining a first workout section for the workout session based on the input from the individual;
    determining a second workout section for the workout session that is different than the first workout section based on the input from the individual;
    storing data describing the workout session in a memory accessible by a server computer system, wherein the data describing the workout session includes data describing the first workout section and the second workout section; and
    instructing the individual to engage in the workout session.

20. The method of claim 19, further comprising storing the input in the memory accessible by the server computer system.

21. The method of claim 19, wherein the input comprises personal data of the individual.

22. The method of claim 21, wherein the personal data comprises one of the age, gender, or weight of the individual.

23. The method of claim 19, wherein the input comprises performance data of the individual.

24. The method of claim 23, wherein the performance data comprises data associated with the individual's performance during a previously completed workout session.

25. The method of claim 19, wherein determining the first workout section comprises determining a first workout section type.

26. The method of claim 25, wherein the first workout section type comprises a cardiovascular workout.

27. The method of claim 25, wherein the first workout section type comprises a strength training workout.

28. The method of claim 25, wherein the second workout section comprises a second workout section type, wherein the first workout section type comprises a cardiovascular workout, and wherein the second workout section type comprises a strength training workout.

29. The method of claim 19, wherein determining the first workout section comprises determining a duration for the first workout section.

30. The method of claim 19, wherein determining the first workout section comprises determining an intensity for the first workout section.

31. The method of claim 30, wherein determining the intensity for the first workout section comprises determining one of a target speed, pace, heart rate, resistance level, or number of repetitions.

32. The method of claim 19, wherein determining the first workout section and determining the second workout section are carried out by the server computer system.

33. The method of claim 19, further comprising assigning a day for the workout session.

34. The method of claim 19, further comprising transmitting the workout session from the server computer system to a portable performance monitoring device of the individual.

35. The method of claim 19, wherein instructing the individual to engage in the workout session comprises providing the individual with a prompt to begin the first workout section.

* * * * *